United States Patent
Tatani et al.

(10) Patent No.: US 7,795,236 B2
(45) Date of Patent: Sep. 14, 2010

(54) PURINE NUCLEOSIDE DERIVATIVE MODIFIED IN 8-POSITION AND MEDICAL USE THEREOF

(75) Inventors: Kazuya Tatani, Nagano (JP); Yoshinori Nonaka, Nagano (JP); Norihiko Kikuchi, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 666 days.

(21) Appl. No.: 11/717,741

(22) Filed: Mar. 13, 2007

(65) Prior Publication Data
US 2007/0179115 A1    Aug. 2, 2007

Related U.S. Application Data

(63) Continuation of application No. PCT/JP2005/016894, filed on Sep. 14, 2005.

(51) Int. Cl.
*A01N 43/04* (2006.01)
*A61K 31/70* (2006.01)
*C07H 19/00* (2006.01)
*C07H 19/16* (2006.01)

(52) U.S. Cl. .................. 514/45; 514/46; 536/27.2; 536/27.21; 536/27.22; 536/27.23; 536/27.3

(58) Field of Classification Search .............. None
See application file for complete search history.

(56) References Cited

U.S. PATENT DOCUMENTS

| | | | |
|---|---|---|---|
| 6,727,231 B1 | 4/2004 | Page et al. | |
| 2003/0008841 A1 * | 1/2003 | Devos et al. | 514/45 |

OTHER PUBLICATIONS

Schutze, Dietrich et al., "Synthesis and Quantification of DNA Adducts of 4,4'-Methylenedianiline", Chem. Res. Toxicol., 1996, vol. 9, pp. 1103-1112.

Talaska, Glenn et al., "Detection and Characterization of Carcinogen", Carcinogenesis, vol. 11, No. 4, pp. 639-646, 1990.

Shivakumar D. Patil, et al., "Structure-Inhibitory Profiles of Nucleosides for the Human Intestinal N1 and N2 Na+-Nucleoside Transporters", Cancer Chemother Pharmacol, 2000, vol. 46, pp. 394-402.

Mabel W.L. Ritzel, et al., "Molecular Identification and Characterization of Novel Human and Mouse Concentrative Na+-Nucleoside Cotransporter Proteins (hcNT3 and mcNT3) Broadly Selective for Purine and Pyrimidine Nucleosides (Systems cib)", The Journal of Biological Chemistry, vol. 276, No. 4, pp. 2914-2927, 2001.

* cited by examiner

Primary Examiner—Traviss C McIntosh, III
(74) Attorney, Agent, or Firm—Frenkel & Associates, PC

(57) ABSTRACT

The present invention provides an 8-modified purinenucleoside derivative which is useful for diseases associated with an abnormality of plasma uric acid level. An 8-modified purinenucleoside derivative represented by the following formula (I), a prodrug thereof or a pharmaceutically acceptable salt thereof, or a hydrate or solvate thereof, is useful for the prevention or treatment of gout, hyperuricemia, urinary lithiasis, hyperuricemic nephropathy or the like.

In the formula, n is 1 or 2; $R^A$ is a hydrogen atom or a hydroxyl group; $R^1$ is a hydrogen atom, a hydroxyl group, a thiol group, an amino group or a chlorine atom; ring J represents an optionally substituted 2-naphthyl group, or a group represented by the following general formula (II) wherein Y represents a single bond or a connecting group; ring Z represents an optionally substituted aryl group or heteroaryl group or the like; and $R^2$ to $R^4$, $P^1$ and Q represents a halogen atom, a cyano group or the like.

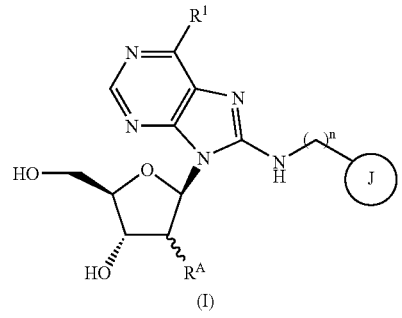

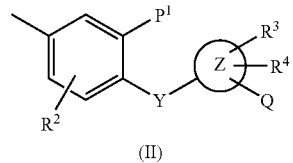

14 Claims, 1 Drawing Sheet

PURINE NUCLEOSIDE DERIVATIVE MODIFIED IN 8-POSITION AND MEDICAL USE THEREOF

CROSS-REFERENCE TO RELATED APPLICATIONS

This application is a continuation of PCT/JP2005/016894, filed Sep. 14, 2005. Further, this application claims priority to Japanese Application No. 270740/2004, filed Sep. 17, 2004.

TECHNICAL FIELD

The present invention relates to 8-modified purinenucleoside derivatives which are useful as medicaments.

More particularly, the present invention relates to 8-modified purinenucleoside derivatives or pharmaceutically acceptable salts thereof, or prodrugs thereof which are useful as agents for the prevention or treatment of a disease associated with an abnormality of plasma uric acid level.

BACKGROUND ART

Uric acid is the end product of purine bodies in human. The upper limit of normal uric acid concentration solved in plasma is 7.0 mg/dL independently from sex and age, and the condition with higher concentration is clinically defined as hyperuricemia. Hyperuricemia affects mostly in adult men and is considered to result from combination of a genetic factors involved in metabolism of purine bodies and secondary factors such as consumption of a high-energy food, nucleic acid rich food or the like. Conditions of persistent hyperuricemic increase a risk of developing arthritis following to urate crystal deposition in intra- or peri-joints. The condition with such developed arthritis is called gout, and the arthritis is called gouty attack. Hyperuricemia is classified broadly into types consisting of a uric acid overproduction-type wherein the uric acid production increases, a uric acid underexcretion-type wherein the uric acid excretion in urine decreases, and a mixed type of them (for example, see Non-patent References 1 and 2).

In the prevention or treatment of hyperuricemia or gout, the basis is to control the plasma uric acid level under a certain level to prevent the incidence of gouty arthritis, and the incidence of the gouty arthritis is considered the lowest in the case to control plasma uric acid level within the range from 4.6 to 6.6 mg/dL. So far, for the treatment of hyperuricemia or gout, allopurinol of a uric acid synthesis inhibitor or probenecid, bucolome, benzbromarone of uricosuric drugs or the like have been used for the improvement of the plasma uric acid level. In addition, in the treatment of gouty attacks, an agent for the pain attack such as colchicine, a nonsteroidal anti-inflammatory agent such as indometacin, naproxen, fenbufen, pranoprofen, oxaprozin, and an adrenocortical steroid are used (for example, see Non-patent Reference 1).

Allopurinol of a uric acid synthesis inhibitor has side effects such as poisoning syndrome (hypersensitivity angiitis), Stevens-Johnson syndrome, exfoliative dermatitis, a plastic anemia, hepatic insufficiency or the like. In addition, a uricosuric drug has a restriction not to be used for a patient with renal failure, and probenecid, bucolome and benzbromarone have side effects such as gastrointestinal disorder, urinary lithiasis, and especially, benzbromarone sometimes causes fulminant hepatic failure in a patient with idiosyncrasy (for example, see Non-patent Reference 1).

It has been desired to develop a new preventative or therapeutic drug having few side effects which can solve such problems of these existing drugs, especially one with a different mechanism compared with existing drugs from the viewpoint of broadening the choices of treatment methods.

Since hyperuricemia is brought on by life style such as overeating, food preference for high purine, high fat or high protein, habitual drinking, insufficient exercise or the like and highly correlated with obesity, hypertension, abnormality in the metabolism of sugar or lipid or the like, life style guidance plays an important role as a non-drug therapy in order to correct the life style. In particular, dietary therapy to avoid excessive intake of purine has a major rule. However, it is difficult to continue such diet therapy and improvement of the life style, and they often fail.

On the digestion and absorption pathway of nucleic acid in human, nucleic acids which are released in the intestine from a nucleic acid or nucleoproteins ingested are broken down into mononucleotides by ribonucleases, deoxyribonucleases and polynucleotidases, furthermore, it is considered that the pathway wherein mononucleotide is degraded into nucleoside by nucleotidases and phosphatase and then the nucleosides are absorbed is the main pathway. In the pathway, it is considered that the absorbed purine nucleoside is changed to uric acid (for example, see Non-patent Reference 3). As other pathways, it can be suspected that nucleoside is broken down to form purine base and then absorbed, or purine base contained in food is directly absorbed. However, these pathways have not been yet unexplained in detail.

Membrane proteins called nucleoside-transporter relate to the nucleoside uptake in the intestine. As such transporters, there are Equilibrative transporters which have transport process of nucleoside into the cell by the concentration gradient of nucleoside (hereinafter referred to as ENT) and sodium-dependent nucleoside transporters which are driven by the concentration gradient of ion between in and out of the cell (hereinafter referred to as CNT) in mammalian cells (for example, see Non-patent Reference 4). As human nucleoside transporters, two types of ENT, Type 1 (hereinafter referred to as ENT1) and Type 2 (hereinafter referred to as ENT2), have been identified and cloned so far (for example, see Non-patent References 5 and 6). In addition, three types of CNT, Type 1 (hereinafter referred to as CNT1), Type 2 (hereinafter referred to as CNT2) and Type 3 (hereinafter referred to as CNT3) have been identified and cloned (for example, see Non-patent References 7 to 9).

The distribution and characteristics of these transporters have been confirmed to some extent. Regarding ENTs, both ENT1 and ENT2 are expressed broadly in human normal tissues and transport both purine and pyrimidine nucleosides. In terms of function, their sensitivities to nitrobenzylthioinosine (hereinafter referred to as NBMPR) are different, that is, ENT1 is markedly inhibited by a low concentration of NBMPR ($IC_{50}$<5 nM), while ENT2 is hardly inhibited by NBMPR, but is inhibited only by a high concentration of NBMPR ($IC_{50}$>1 μM) (for example, see Non-patent Reference 10).

On the other hand, regarding CNTs, CNT1 transports pyrimidine nucleoside and adenosine, and the messenger RNA (hereinafter referred to as mRNA) has been confirmed to be expressed in the jejunum and kidney in rats. CNT2 transports purine nucleoside and uridine, and various kinds of mRNA have been confirmed to be expressed in organs including the heart, liver, skeletal muscles, kidney, intestines or the like in human. CNT3 has been recently cloned and transports, both purine and pyrimidine nucleosides, and the mRNA has been confirmed to be expressed in the bone marrow, pancreas, intestines and mammary gland in human. In addition, in terms of function, it has been confirmed that all of these CNTs are not influenced by NBMPR (for example, see Non-patent References 9 and 11).

In addition, in the previous studies on transport mechanism in the intestines, it is shown that purine bodies are absorbed through CNT from mucosal side in small intestinal epithelial cells and transported to blood side through ENT exiting in serosal side (for example, see Non-patent Reference 12). However, the contribution of nucleoside transporters to purine absorption in the human intestines, especially in the human small intestine has been not clarified in detail.

On the other hand, in Patent References 1 and 2, it has been reported that plasma uric acid level is lowered by inhibiting purine absorption. Additionally, it was confirmed that plasma uric acid level is lowered by restriction on eating dietary sources of purine in human. Therefore, uric acid synthesized from purine nucleosides absorbed in the intestine reflects plasma uric acid concentration (for example, see Non-patent Reference 13), plasma uric acid level can be controlled by effective inhibition of the purine nucleoside absorption through the intestines.

By the way, it was reported that regarding an 8-modified purinenucleoside derivative, that is useful for the treatment of hepatitis C virus (see Patent Reference 3), and 8-bromoadenosine exhibits a weak inhibitory activity against CNT (for example, see Non-patent Reference 14). However, any 8-modified purinenucleoside derivative has not been reported. Furthermore, it has not ever been reported or suggested that an 8-modified purinenucleoside derivative of the present invention has an inhibitory activity against CNT and is useful for the prevention or treatment of a disease associated with an abnormality of plasma uric acid level such as gout, hyperuricemia or the like.

Patent Reference 1: Japanese Patent Publication 2001-163788;
Patent Reference 2: Japanese patent no. 2632577; Patent Reference 3: International Publication WO2002/18404;
Non-patent Reference 1: Edited by the committee drafting Guideline for the management of hyperuricemia and gout, Guideline for the management of hyperuricemia and gout, Digest version, published by Jananse Society of Gout and Nucleic Acid Metabolism, Sep. 1, 2002 pp. 1-9;
Non-patent Reference 2: Astuo Taniguchi and 1 person, Shindan to Chiryo (Diagnosis and Treatment), 2002, Vol. 90, No. 2, pp. 186-191;
Non-patent Reference 3: Harper's Biochemistry, the original edition 25, translated by Yoshito Kajiro, published by MARUZEN CO., LTD. Jan. 30, 2001, p. 417;
Non-patent Reference 4: Carol E. Cass and 11 persons, Membrane Transporters as Drug Targets, 1999, PP 318-321;
Non-patent Reference 5: Mark Griffiths and 10 persons, NATURE MEDICNE, January 1997, Vol. 3, No. 1, PP. 89-93;
Non-patent Reference 6: Charles R. Crawford and 3 persons, The Journal of Biological Chemistry, 1998, Vol. 273, No. 9, PP. 5288-5293;
Non-patent Reference 7: Mabel W. L. Ritzel and 5 persons, American Journal of Physiology, 1997, Vol. 272, Cell Physiology, Vol. 41, PP. C707-C714;
Non-patent Reference 8: Juan Wang and 5 persons, American Journal of Physiology, 1997, Vol. 273, Renal Physiology, Vol. 42, PP. F1058-F1065;
Non-patent Reference 9: Mabel W. L. Ritzel and 14 persons, The Journal of Biological Chemistry, 2001, Vol. 276, No. 4, pp. 2914-2927;
Non-patent Reference 10: Carol E. Cass and 11 persons, Membrane Transporters as Drug Targets, 1999, pp. 316-318;
Non-patent Reference 11: Carol E. Cass and 11 persons, Membrane Transporters as Drug Targets, 1999, pp. 327-332;
Non-patent Reference 12: James D. Young and 4 persons, Gastrointestinal transport, molecular physiology, 2001, pp. 334-337;
Non-patent Reference 13: N. Zollner, Proceedings of the Nutrition Society, 1982, Vol. 41, pp. 329-342;
Non-patent Reference 14: Patil S. D. and 2 persons, Cancer Chemotherapy Pharmacology, 2000, Vol. 46, No. 5, pp. 394-402.

DISCLOSURE OF THE INVENTION

Problem to be Solved by the Invention

The object of the present invention is to provide 8-modified purinenucleoside derivatives useful as agents for the prevention or treatment of a disease associated with an abnormality of plasma uric acid level.

Means of Solving the Problems

To solve the above-mentioned object, the present inventors have studied earnestly on the nucleoside absorption in the human intestines. First of all, the present inventors performed cDNA cloning of human CNTs and analyzed distribution patterns of CNTs in human tissues, and confirmed that CNT1 is hardly expressed, and CNT2 is abundantly expressed in the human small intestines. Furthermore, as the result of analysis of distribution patterns in the portions of digestive tract, it was confirmed that CNT1 is expressed mostly in jejunum and ileum of the lower small intestines, and CNT2 was expressed mostly in the duodenum of the upper small intestines and follows expressed in the jejunum, and CNT3 was expressed comparable to CNT2 in ileum, though the expression is weak appearance overall.

The present inventors further studied to find a compound which inhibits the increase of plasma uric acid level, and finally confirmed that an 8-modified purinenucleoside derivative represented by the general formula (Ic) described below has a strongly inhibitory activity on the uptake of adenosine in an experiment by using COS-7 cells transfected with a human CNT2 gene. In addition, in a purine load test in rats, these compounds inhibited the increase of plasma uric acid level significantly. Therefore, it was found that since a 8-modified purinenucleoside derivative represented by the general formula (I) or (Ic) described below or a prodrug thereof or a pharmaceutically acceptable salt thereof, or a hydrate or solvate thereof, inhibits the increase of plasma uric acid level markedly, the same is useful as a drug for the prevention or treatment of a disease associated with an abnormality of plasma uric acid level, thereby-forming the bases of the present invention.

That is, the present invention relates to:

[1] an 8-modified purinenucleoside derivative represented by the following general formula:

[Chem. 1]

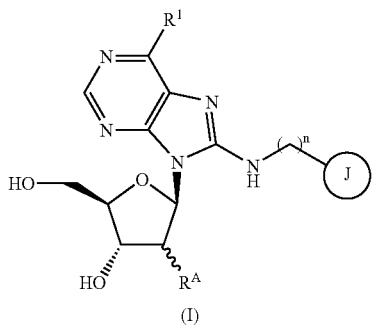

(I)

in the formula,
n represents 1 or 2;
A represents a hydrogen atom or a hydroxyl group;
$R^1$ represents a hydrogen atom, a hydroxyl group, a thiol group, an amino group or a chlorine atom;
ring J represents an optionally substituted 2-naphthyl group, or a group represented by the general formula:

[Chem. 2]

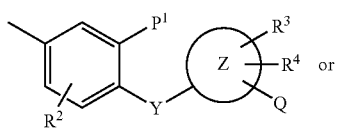

[Chem. 3]

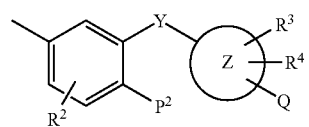

Y represents a single bond or a connecting group;
ring Z represents an aryl group, a heteroaryl group, a cycloalkyl group or a heterocycloalkyl group;
$R^2$ to $R^4$, $P^1$, $P^2$ and Q independently represents a halogen atom, a cyano group, -AH group or -A-D-E-G group,
in which
A represents a single bond, —O—, —S—, —$NR^5$—, —COO—, —$CONR^6$—, —$NR^7CO$— or —$NR^8COO$— wherein $R^5$ to $R^8$ independently represents a hydrogen atom or a lower alkyl group;
D represents an optionally substituted lower alkylene group, an optionally substituted lower alkenylene group or an optionally substituted lower alkynylene group;
E represents a single bond, —O—, —S—, —$NR^9$—, —COO—, —$CONR^{10}$, —$NR^{11}CO$—, —$NR^{12}COO$—, an optionally substituted lower cycloalkylene group, an optionally substituted heterocycloalkylene group, an optionally substituted arylene group or an optionally substituted heteroarylene group in which $R^9$ to $R^{12}$ independently represents a hydrogen atom or a lower alkyl group;
G represents a hydrogen atom, an optionally substituted lower alkyl group, an optionally substituted lower alkenyl group or an optionally substituted lower alkynyl group or an aryl(lower alkyl) group;

or a prodrug thereof, or a pharmaceutically acceptable salt thereof, or a hydrate or solvate thereof;

[2] an 8-modified purinenucleoside derivative as defined in the above [1] represented by the following general formula:

[Chem.4]

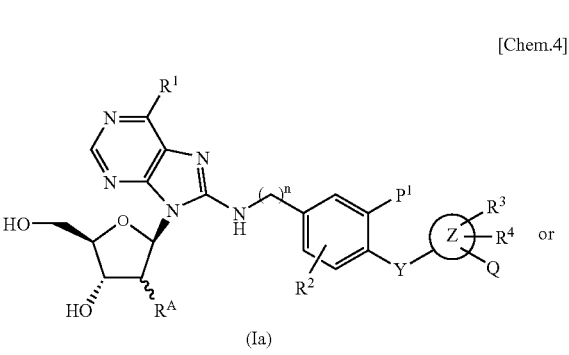

(Ia)

[Chem.5]

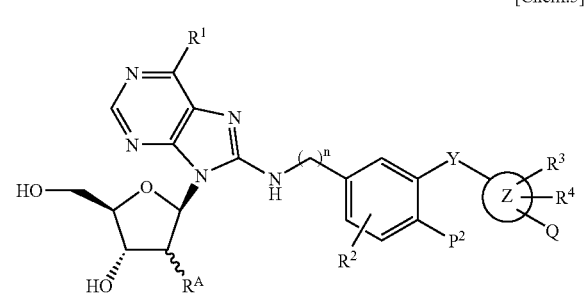

(Ib)

in which ring Z represents an aryl group or a heteroaryl group;
$R^2$ to $R_4$ independently represents a hydrogen atom, a halogen atom, a hydroxyl group, a cyano group, a lower alkyl group, a a lower alkylthio group, a lower alkoxy group which may have an aryl group, an amino group or a mono- or di-(lower alkyl) amino group; or a prodrug thereof, or a pharmaceutically acceptable salt thereof, or a hydrate or solvate thereof;

[3] an 8-modified purinenucleoside derivative as defined in the above [1] or [2] wherein the substituent:

[Chem. 6]

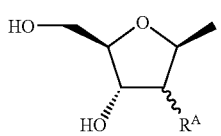

represents a D-ribosyl group, or a prodrug thereof, or a pharmaceutically acceptable salt thereof, or a hydrate or solvate thereof;

[4] an 8-modified purinenucleoside derivative as defined in any one of the above [1] to [3] wherein $R^1$ represents a hydrogen atom, a hydroxy group or an amino group, or a prodrug thereof, or a pharmaceutically acceptable salt thereof, or a hydrate or solvate thereof;

[5] an 8-modified purinenucleoside derivative as defined in any one of the above [1] to [4] wherein n represents 1, or a prodrug thereof, or a pharmaceutically acceptable salt thereof, or a hydrate or solvate thereof;

[6] an 8-modified purinenucleoside derivative as defined in any one of the above [1] to [5] wherein Y represents a single bond, or a prodrug thereof, or a pharmaceutically acceptable salt thereof, or a hydrate or solvate thereof;

[7] a pharmaceutical composition comprising as an active ingredient a 8-modified purinenucleoside derivative derivative as defined in any one of the above [1] to [6], or a prodrug thereof, or a pharmaceutically acceptable salt thereof, or a hydrate or solvate thereof;

[8] a pharmaceutical composition as defined in the above [7], which is an agent for the prevention or treatment of a disease associated with an abnormality of plasma uric acid level;

[9] a pharmaceutical composition as defined in the above [8] wherein the disease associated with an abnormality of plasma uric acid level is a disease selected from a group consisting of gout, hyperuricemia, urinary lithiasis, hyperuricemic nephropathy and acute uric acid nephropathy;

[10] a pharmaceutical composition as defined in the above [9] wherein the disease associated with an abnormality of plasma uric acid level is gout;

[11] a pharmaceutical composition as defined in the above [9] wherein the disease associated with an abnormality of plasma uric acid level is hyperuricemia;

[12] a pharmaceutical composition as defined in the above [7] which is an agent to reduce plasma uric acid level;

[13] a pharmaceutical composition as defined in any one of the above [7] to [12] comprising in combination as an active ingredient at least one agent selected from a group consisting of colchicine, a nonsteroidal anti-inflammatory agent, a steroid, a uric acid synthesis inhibitor, a uricosuric drug, a urinary alkalinizer and a uric acid oxidase.

[14] a method for the prevention or treatment of a disease associated with an abnormality of plasma uric acid level, which comprises administering an effective amount of an 8-modified purinenucleoside derivative as defined in any one of the above [1] to [6], or a prodrug thereof, or a pharmaceutically acceptable salt thereof, or a hydrate or solvate thereof;

[15] a method for the prevention or treatment as defined in the above [14] wherein the disease associated with an abnormality of plasma uric acid level is a disease selected from a group consisting of gout, hyperuricemia, urinary lithiasis, hyperuricemic nephropathy and acute uric acid nephropathy;

[16] a method for the prevention or treatment as defined in the above [15] wherein the disease associated with an abnormality of plasma uric acid level is gout;

[17] a method for the prevention or treatment as defined in the above [15] wherein the disease associated with an abnormality of plasma uric acid level is hyperuricemia;

[18] a method for the prevention or treatment as defined in the above[14], which comprises administering in combination an effective amount of at least one agent selected from a group consisting of colchicine, a nonsteroidal anti-inflammatory agent, a steroid, a uric acid synthesis inhibitor, a uricosuric drug, a urinary alkalinizer and a uric acid oxidase;

[19] a use of an 8-modified purinenucleoside derivative as defined in any one of the above [1] to [6], or a prodrug thereof, or a pharmaceutically acceptable salt thereof, a hydrate or solvate thereof, for the manufacture of a pharmaceutical composition for the prevention or treatment of a disease associated with an abnormality of plasma uric acid level;

[20] a use as defined in the above [19] wherein the disease associated with an abnormality of plasma uric acid level is a disease selected from a group consisting of gout, hyperuricemia, urinary lithiasis, hyperuricemic nephropathy and acute uric acid nephropathy;

[21] a use as defined in the above [20] wherein the disease associated with an abnormality of plasma uric acid level is gout;

[22] a use as defined in the above [20] wherein the disease associated with an abnormality of plasma uric acid level is hyperuricemia;

[23] a use of a 8-modified purinenucleoside derivative as defined in any one of the above [1] to [6], or a prodrug thereof, or a pharmaceutically acceptable salt thereof, or a hydrate or solvate thereof, and at least one agent selected from a group consisting of colchicine, a nonsteroidal anti-inflammatory agent, a steroid, a uric acid synthesis inhibitor, a uricosuric drug, a urinary alkalinizer and a uric acid oxidase for the manufacture of a pharmaceutical composition for the prevention or treatment of a disease associated with an abnormality of plasma uric acid level;

[24] a sodium-dependent nucleoside transporter 2 inhibitor comprising as an active ingredient an 8-modified purinenucleoside derivative represented by the following general formula:

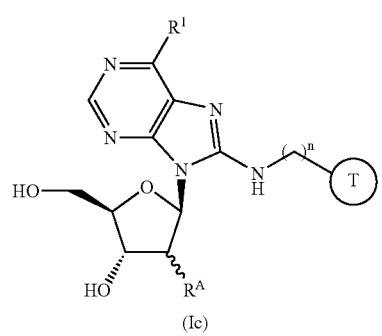

[Chem.7]

(Ic)

wherein n represents 1 or 2, $R^A$ represents a hydrogen atom or a hydroxyl group, $R^1$ represents a hydrogen atom, a hydroxyl group, a thiol group, an amino group or a chlorine atom, ring T represents an optionally substituted aryl group or heteroaryl group; or a prodrug thereof, or a pharmaceutically acceptable salt thereof, or a hydrate or solvate thereof; and the like.

In the compounds represented by the above general formula (I) of the present invention, as substituents which a 2-naphthyl group may have are, for example, a halogen atom, a hydroxy group, a thiol group, an amino group, a carboxyl group, a cyano group, a carbamoyl group, a phthalimide group, a lower alkyl group, a lower alkoxy group, a lower alkylthio group, a mono- or di-(lower alkyl) amino group, a lower alkoxycarbonyl group, or a mono- or di-N-(lower alkyl)carbamoyl group or the like can be illustrated.

In the case that Y is a connecting group, as a connecting group, for example, —$CH_2$—, —O—, —$OCH_2$—, —S— and —$SCH_2$— can be illustrated, as a preferable group, —$CH_2$—, —O—, —$OCH_2$— and —S— can be illustrated.

The term "aryl group" means an aromacyclic hydrocarbon group having 6 or 10 carbon atoms such as a phenyl group, a naphthyl group or the like, and the term "arylene" means a divalent group derived by removing one hydrogen atom on other than adjacent atoms having free valence of the above aryl group.

The term "heteroaryl group" means a 5 or 6-membered mono cyclic aromatic heterocyclic group containing any 1 to 4 hetero atoms selected from a group consisting of an oxygen atom, a sulfur atom and a nitrogen atom in the ring, which is derived from thiazole, oxazole, isothiazole, isooxazole, pyridine, pyrimidine, pyrazine, pyridazine, pyrrole, furan, thiophene, imidazole, pyrazole, oxadiazole, thiadiazole, triazole, tetrazole, furazan or the like or a 5 or 6-membered fused aromatic heterocyclic group fused with a 6-membered ring, containing any 1 to 4 hetero atoms selected from a group consisting of an oxygen atom, a sulfur atom and a nitrogen atom in the ring, which is derived from indole, isoindole, benzofuran, isobenzofuran, benzothiophene, benzoxazole, benzothiazole, benzisoxazole, benzisothiazole, indazole, benzimidazole, quinoline, isoquinoline, phthalazine, quinoxaline, quinazoline, sinoline, indolizine, naphthyridine, pteridine or the like, and the term "heteroarylene group" means a divalent group derived by removing one hydrogen atom on other than adjacent atoms having free valence of the above heteroaryl group.

The term "halogen atom" means a fluorine atom, a chlorine atom, a bromine atom or an iodine atom.

The term "lower" means a straight-chained or branched hydrocarbon group having 6 or less carbon atoms, for example, as "lower alkyl group", a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like can be illustrated, as "lower alkenyl group", a vinyl group, an allyl group, a 1-propenyl group, an isopropenyl group, a 1-butenyl group, a 2-butenyl group, a 2-methylallyl group or the like can be illustrated, as "lower alkynyl group", an ethynyl group, a 2-propynyl group or the like can be illustrated, as "lower alkoxy group", a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like can be illustrated, and as "lower alkoxycarbonyl group", a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like can be illustrated.

The term "optionally substituted" means optionally having the same or different 1 to 3 substituents, as the optional substitutents, a halogen atom, a cyano group; $—OW^1$, $—NW^2W^3$, $—OCOW^4$, $—OCOOW^5$, $—NW^6COW^7$, $—NW^8COOW^9$, $—NHC(=NH)—NH^2$, $—CONW^{10}W^{11}$, $—NW^{12}CONW^{13}W^{14}$, $—SO_2NW^{15}W^{16}$ or $—N^+W^{17}W^{18}W^{19}$ can be illustrated, wherein $W^1$ to $W^3$ independently represent a hydrogen atom, a lower alkyl group, a hydroxy (lower alkyl) group or an aryl (lower alkyl) group; $W^4$ and $W^5$ independently represent a lower alkyl group, a hydroxy (lower alkyl) group or an aryl (lower alkyl) group; $W^6$ to $W^{16}$ independently represent a hydrogen atom, a lower alkyl group, a hydroxy (lower alkyl) group or an aryl (lower alkyl) group; or $W^6$ and $W^7$, $W^8$ and $W^9$, $W^{10}$ and $W^{11}$, $W^{12}$ and $W^{13}$, $W^{13}$ and $W^{14}$, and $W^{15}$ and $W^{16}$ may form an aliphatic cyclic amino group which contains the nitrogen atom at the binding position; $W^{17}$ to $W^{19}$ independently represent a lower alkyl group, a hydroxy (lower alkyl) group or an aryl (lower alkyl) group; or $W^{17}$, $W^{18}$ and $W^{19}$ may form a ring structure which contains the nitrogen atom at the binding position can be illustrated.

The term "cycloalkyl group" means an aliphatic monocyclic hydrocarbon group having 3 to 8 carbon atoms such as a cyclopropyl group, a cyclobutyl group, a cyclopentyl group, a cyclohexyl group, a cycloheptyl group, a cyclooctyl group or the like, and the term "cycloalkylene group" means a divalent group derived by removing one hydrogen atom on other than adjacent atoms having free valence of the above cycloalkyl group. The term "heterocycloalkyl group" means a 3 to 8-membered aliphatic monocyclic hydrocarbon group having 1 or 2 hetero atoms selected from a group consisting of an oxygen atom, a sulfur atom and a nitrogen atom in the ring, which may have 1 or 2 oxo group such as an aziridino group, an azetidino group, a morpholino group, a 2-morpholinyl group, a thiomorpholino group, a 1-pyrrolidinyl group, a piperidino group, a 4-piperidinyl group, a 1-piperazinyl group, a 1-pyrrolyl group or the like, or a 5 to 6-membered aliphatic monocyclic hydrocarbon group as defined above fused with a benzene ring, for example, a 1,3-dioxoisoindolin-2-yl group or the like, and the term "heterocycloalkylene group" means a divalent group derived by removing one hydrogen atom on other than adjacent atoms having free valence of the above heterocycloalkyl group.

The term "hydroxyl (lower alkyl) group" means the above lower alkyl group substituted by a hydroxy group at any position, and for example, a hydroxymethyl group, a 1-hydroxyethyl group, a 2-hydroxyethyl group, a hydroxypropyl group, a 2-hydroxypropyl group, a 3-hydroxypropyl group, a 1,1-dimethyl-2-hydroxypropyl group or the like can be included.

The term "aryl (lower alkyl) group" means the above lower alkyl group substituted by the above aryl group at any position, and for example, a benzyl group, a 1-phenylethyl group, a 2-phenylethyl group, a phenylpropyl group, a phenylbutyl group, a phenylpentyl group, a phenylhexyl group, a naphthylmethyl group, a naphthylethyl group, a naphthylpropyl group, a naphthylbutyl group, a naphthylpentyl group, a naphthylhexyl group or the like can be included.

The term "mono- or di-(lower alkyl) amino group" means an amino group mono- or di-substituted by the above lower alkyl group, the term "mono- or di-N-(lower alkyl)carbamoyl group" means a carbamoyl group mono- or di-substituted by the above lower alkyl group, and in the case of di-substituted, each lower alkyl may be different.

The term "aliphatic cyclic amino group" means a 3 to 8-membered cyclic amino group which may contain any hetero atom other than the nitrogen atom at the binding position selected from a group consisting of an oxygen atom, a sulfur atom and nitrogen atom in the ring such as an aziridino group, an azetidino group, a morpholino group, a thiomorpholino group, a 1-pyrrolidinyl group, a piperidino group, a 1-piperazinyl group, a 1-pyrrolyl group or the like, and which may have 1 or 2 oxo group (for example, 2-oxo-1-pyrrolidinyl group or the like)

The compounds represented by the above general formula (I) of the present invention can be prepared, for example, in the following methods or similar methods, or known or similar methods described in literatures or the like. In addition, in case that a protective group is necessary, introduction and removal procedures can be optionally combined in the usual way (for example, see Patent Reference 3 or Synthesis, 1977, pp. 725-726).

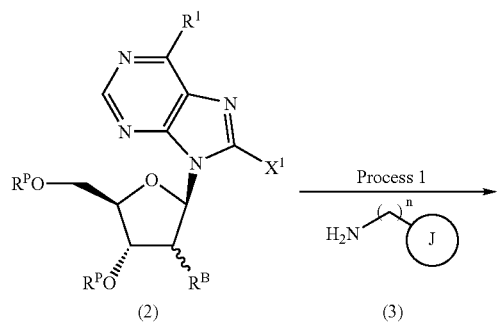

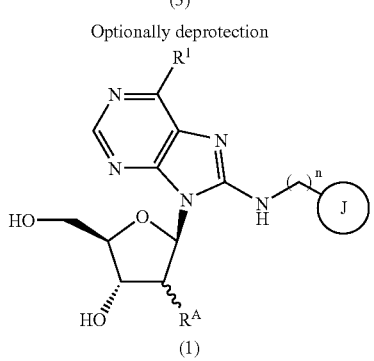

condensation with a compound represented by the above general formula (3) in the presence or absence of a base such as triethylamine, N,N-diisopropylethylamine, potassium carbonate, pyridine or the like without or in an inert solvent, and optionally by removing a protective group. As the inert solvent used in the reaction, for example, methanol, ethanol, 1-propanol, isobutanol, N,N-dimethylformamide, N,N-dimethylacetamide, tetrahydrofuran, toluene, water, a mixed solvent thereof or the like can be illustrated. The reaction temperature is usually from room temperature to reflux temperature, and the reaction time is usually from 1 hour to 3 days, varying based on a used starting material, solvent and reaction temperature.

Compounds represented by the above general formula (2) used as a starting material in the present production process are commercially available or can be prepared in a known or similar method (for examples, the methods described in J. Org. Chem., 1981, 46(13), 2819-2823., Chem. Pharm. Bull., 1977, 25(4), 575-578., Tetrahedron, 1970, 26, 4251-4259., Org. Lett., 2001, 3(26), 4221-4223 (Supporting information), Nucleic Acids Res., 1990, 18, 3339-3345., and J. Med. Chem., 1985, 28(10), 1481-1485).

Compounds represented by the above general formula (3) are commercially available or can be also prepared in a known or similar method or the following method. In addition, in case that a protective group is necessary, introduction and removal procedures can be optionally combined in the usual way.

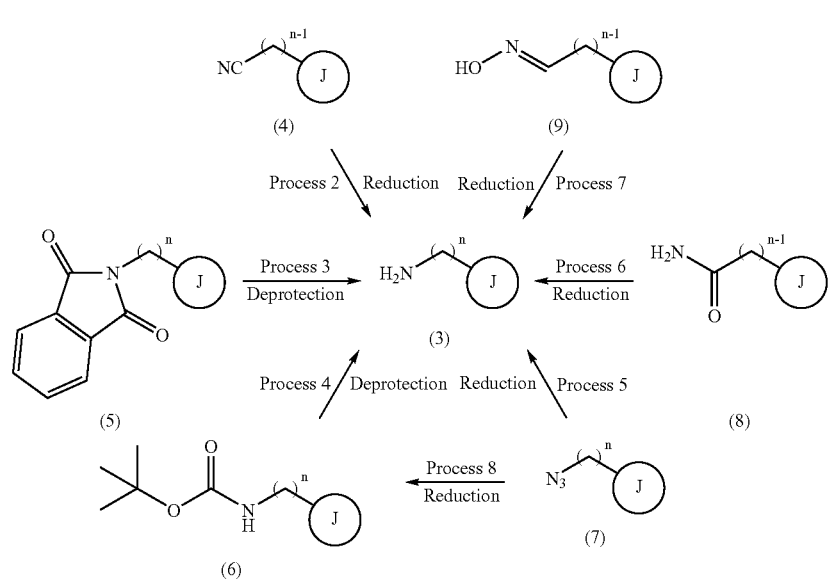

In the formula, $X^1$ represents a halogen atom, $R^P$ represents a hydrogen atom or a hydroxy-protective group wherein each $R^P$ may be different, $R^B$ represents a hydrogen atom or a protected hydroxy group, and n, $R^A$, $R^1$ and ring J have the same meanings as defined above.

Process 1

An 8-modified purinenucleoside derivative represented by the above general formula (1) can be prepared by subjecting a compound represented by the above general formula (2) to In the formula, n and ring J have the same meanings as defined above.

Process 2

A compound represented by the above general formula (3) can be also prepared by subjecting a compound represented by the above general formula (4) according to a general reduction method of a nitrile, for example, 1) to reduction using a reducing agent such as lithium aluminium hydride, diisobutylaluminum hydride or the like in an inert solvent, or 2) to catalytic reduction using a metal catalyst such as palladium on carbon, platinum oxide or the like in the presence or absence of an acid such as hydrochloric acid or the like in an inert solvent. As the inert solvent used in the reduction reaction 1), for example, tetrahydrofuran, diethylether, toluene, dichloromethane, a mixed solvent thereof or the like can be illustrated. The reaction temperature is usually from −78° C. to reflux temperature, and the reaction time is usually from 30 minutes to 1 day, varying based on a used starting material, solvent and reaction temperature. As the inert solvent used in the reduction reaction 2), methanol, ethanol, tetrahydrofuran, ethyl acetate, acetic acid, water, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 3

A compound represented by the above general formula (3) can be also prepared by subjecting a compound represented by the above general formula (5) according to a general deprotection method of a phthaloyl group, for example, to deprotection using hydrazine, methylamine or the like in an inert solvent. As the inert solvent used in the reaction, for example, dichloromethane, chloroform, methanol, ethanol, water, a mixed solvent thereof or the like can be illustrated. The reaction temperature is usually from 0° C. to reflux temperature, and the reaction time is usually from 30 minutes to 3 days, varying based on a used starting material, solvent and reaction temperature.

Process 4

A compound represented by the above general formula (3) can be also prepared by subjecting a compound represented by the above general formula (6) according to a general deprotection method of a tert-butoxycarbonyl group, for example, to deprotection using an acid such as trifluoroacetic acid, hydrochloric acid or the like in an inert solvent. As the inert solvent used in the reaction, for example, dichloromethane, chloroform, 1,4-dioxane, methanol, ethanol, water, a mixed solvent thereof or the like can be illustrated. The reaction temperature is usually from −45° C. to reflux temperature, and the reaction time is usually from 30 minutes to 1 day, varying based on a used starting material, solvent and reaction temperature.

Process 5

A compound represented by the above general formula (3) can be also prepared by subjecting a compound represented by the above general formula (7) according to a general reduction method of an azide, for example, 1) to catalytic reduction using a metal catalyst such as palladiumon carbon, Lindlar's catalyst or the like in the presence or absence of an acid such as hydrochloric acid or the like in an inert solvent, or 2) to reduction using a reducing agent such as lithium aluminum hydride or the like. As the inert solvent used in the reduction reaction 1), for example, methanol, ethanol, tetrahydrofuran, ethyl acetate, acetic acid, water, a mixed solvent thereof or the like can be illustrated. The reaction temperature is usually from 0° C. to reflux temperature, and the reaction time is usually from 30 minutes to 1 day, varying based on a used starting material, solvent and reaction temperature. As the inert solvent used in the reduction reaction 2), for example, tetrahydrofuran, diethylether, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 6

A compound represented by the above general formula (3) can be also prepared by subjecting a compound represented by the above general formula (8) according to a general reduction method of an amide, for example, to reduction using a reducing agent such as lithium aluminum hydride, diborane or the like in an inert solvent. As the inert solvent used in the reaction, for example, tetrahydrofuran, diethylether, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 7

A compound represented by the above general formula (3) can be also prepared by subjecting a compound represented by the above general formula (9) according to a general reduction method of an oxime, for example, 1) to catalytic reduction using a metal catalyst such as palladium on carbon, platinum oxide or the like in the presence or absence of an acid such as hydrochloric acid or the like in an inert solvent, or 2) to reduction using a reducing agent such as lithium aluminum hydride or the like in an inert solvent. As a solvent used in the reduction reaction 1), for example, methanol, ethanol, tetrahydrofuran, ethyl acetate, acetic acid, water, a mixed solvent thereof or the like can be illustrated. The reaction temperature is usually from 0° C. to reflux temperature, and the reaction time is usually from 30 minutes to 1 day, varying based on a used starting material, solvent and reaction temperature. As the inert solvent used in the reduction reaction 2), for example, tetrahydrofuran, diethylether, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 8

A compound represented by the above general formula (6) can be prepared by subjecting a compound represented by the above general formula (7), to catalytic reduction using a metal catalyst such as palladium-on carbon, Lindlar's catalyst or the like in the presence of di-tert-butyl dicarbonate in an inert solvent. As the inert solvent used in the reaction, for example, methanol, ethanol, tetrahydrofuran, ethyl acetate, water, a mixed solvent thereof or the like can be illustrated. The reaction temperature is usually from 0° C. to reflux temperature, and the reaction time is usually from 30 minutes to 3 days, varying based on a used starting material, solvent and reaction temperature.

Compounds represented by the above general formulas (4) to (9) used as a starting material in the above processes 2 to 8 are commercially available or can be also prepared in a known or similar method or the like, for example, and the following method can be illustrated. In addition, in case that a protective group is necessary, introduction and removal procedures can be optionally combined in the usual way.

The compounds represented by the above general formulas (4), (8) and (9) used as a starting material in each of the above processes 2, 6 and 7 can be also prepared in the following method.

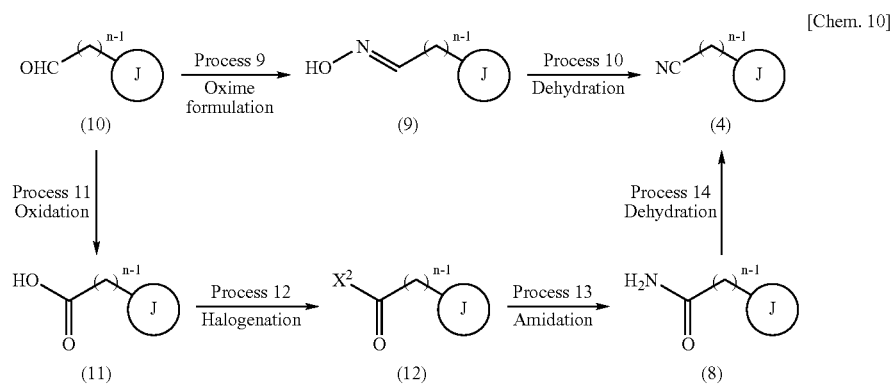

[Chem. 10]

In the formula, $X^2$ represents a halogen atom, and n and ring J have the same meanings as defined above.

Process 9

A compound represented by the above general formula (9) can be also prepared by allowing a compound represented by the above general formula (10) to react with hydroxylamine in an inert solvent. As the inert solvent used in the reaction, for example, methanol, ethanol, pyridine, water, a mixed solvent thereof or the like can be illustrated. The reaction temperature is usually from room temperature to reflux temperature, and the reaction time is usually from 1 hours to 1 day, varying based on a used starting material, solvent and reaction temperature.

Process 10

A compound represented by the above general formula (4) can be also prepared by subjecting a compound represented by the above general formula (9) to dehydration with thionyl chloride, p-toluenesulfonyl chloride, acetic anhydride, phthalic anhydride in the presence or absence of a base such as triethylamine, pyridine, triethylenediamine, sodium acetate, or the like without or in an inert solvent. As the inert solvent used in the reaction, for example, dichloromethane, chloroform, acetonitrile, benzene, ethyl acetate, acetic acid, pyridine, a mixed solvent thereof or the like can be illustrated. The reaction temperature is usually from 0° C. to reflux temperature, and the reaction time is usually from 1 hour to 3 days, varying based on a used starting material, solvent and reaction temperature.

Process 11

A compound represented by the above general formula (11) can be also prepared by subjecting a compound represented by the above general formula (10) according to a general oxidation method of an aldehyde, for example, 1) to oxidation using sodium chlorite in the presence of 2-methyl-2-butene and sodium dihydrogen phosphate in an inert solvent, or 2) to oxidation using an oxidizing agent (for example, OXONE (registered trade mark) or the like in an inert solvent (for example, in a method described in Org. Lett., 2003, 5(7), 1031 to 1034). As the inert solvent used in the oxidation reaction 1), tert-butylalcohol, water, a mixed solvent thereof or the like can be illustrated. The reaction temperature is usually from 0° C. to room temperature, and the reaction time is usually from 1 hour to 3 days, varying based on a used starting material, solvent and reaction temperature. As the inert solvent used in the oxidation reaction 2), for example, N,N-dimethylformamide, N-methyl-2-pyrrolidone, hexamethylphosphoric triamide, tert-butylalcohol, acetonitrile, acetone, water, a mixed solvent thereof or the like can be illustrated. The reaction temperature is usually from 0° C. to reflux temperature, and the reaction time is usually from 30 minutes to 3 days, varying based on a used starting material, solvent and reaction temperature.

Process 12

A compound represented by the above general formula (12) can be also prepared by subjecting a compound represented by the above general formula (11) to halogenation using a halogenating reagent such as thionyl chloride, oxalyl chloride, phosphorus trichloride, phosphorus pentachloride, thionyl bromide or the like optionally in the coexistence with a catalytic amount of N,N-dimethylformamide, hexamethylphosphoric triamide, pyridine or the like in an inert solvent. As the inert solvent used in the reaction, for example, diethylether, tetrahydrofuran, dichloromethane, toluene, N,N-dimethylacetamide, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 13

A compound represented by the above general formula (8) can be also prepared by allowing a compound represented by the above general formula (12) to react with ammonia, hexamethyldisilazane or the like without or in an inert solvent. As the inert solvent used in the reaction, for example, toluene, dichloromethane, chloroform, hexane, water, a mixed solvent thereof or the like can be illustrated. The reaction temperature is usually from −78° C. to reflux temperature, and the reaction time is usually from 10 minutes to 1 day, varying based on a used starting material, solvent and reaction temperature Process 14

A compound represented by the above general formula (4) can be also prepared by subjecting a compound represented by the above general formula (8) to dehydration with trifluoroacetic anhydride, thionyl chloride, methanesulfonyl chloride, p-toluenesulfonyl chloride, N,N'-dicyclohexycarbodiimide in the presence or absence of a base such as triethylamine, N,N-diisopropylethylamine, pyridine, or the like in an inert solvent. As the inert solvent used in the reaction, for example, dichloromethane, chloroform, benzene, toluene, pyridine, a mixed solvent thereof or the like can be illustrated. The reaction temperature is usually from room temperature to reflux temperature, and the reaction time is usually from 30 minutes to 1 day, varying based on a used starting material, solvent and reaction temperature.

Furthermore the compounds represented by the above general formulas (5) and (7) used as a starting material in each of the above processes 3 and 5 can be also prepared in the following method.

[Chem. 11]

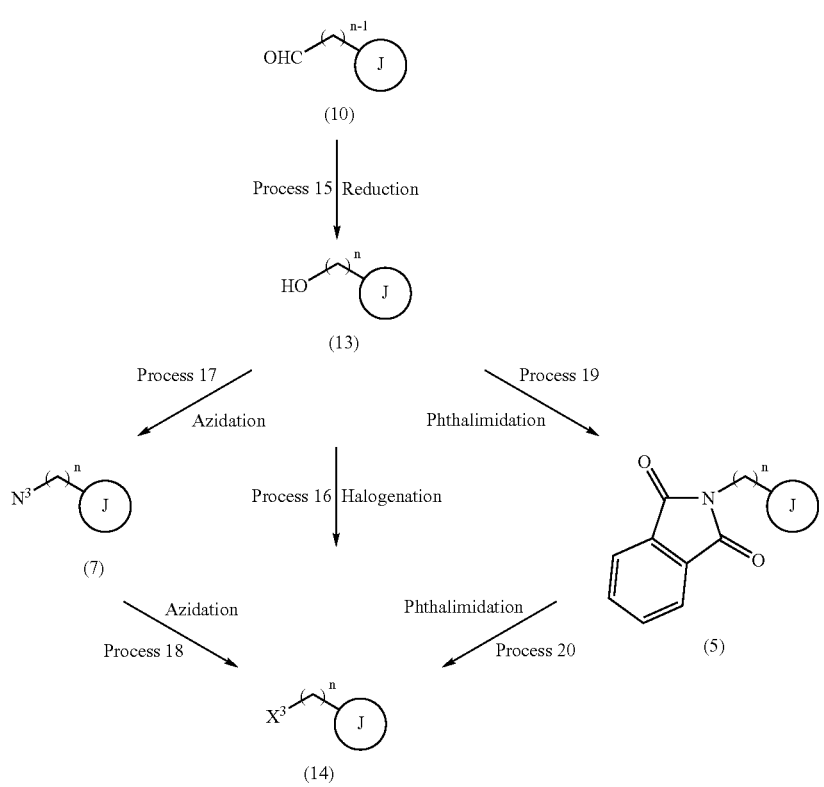

In the formula, $X^3$ represents a halogen atom, and n and ring J have the same meanings as defined above.

Process 15

A compound represented by the above general formula (13) can be also prepared by subjecting a compound represented by the above general formula (10) according to a general reduction method of an aldehyde, for example, to reduction using a reducing agent such as sodium tetrahydroborate, lithium aluminium hydride in an inert solvent. As the inert solvent used in the reaction, for example, methanol, ethanol, diethylether, tetrahydrofuran, water, a mixed solvent thereof or the like can be illustrated. The reaction temperature is usually from 0° C. to reflux temperature, and the reaction time is usually from 10 minutes to 1 day, varying based on a used starting material, solvent and reaction temperature.

Process 16

A compound represented by the above general formula (14) can be also prepared by subjecting a compound represented by the above general formula (13) to halogenation using a halogenating reagent such as thionyl chloride, oxalyl chloride, phosphorus trichloride, phosphorus pentachloride, thionyl bromide or the like optionally in the coexistence with a catalytic amount of N,N-dimethylformamide, hexamethylphosphoric triamide, pyridine or the like in an inert solvent. As the inert solvent used in the reaction, for example, diethylether, tetrahydrofuran, dichloromethane, toluene, N,N-dimethylacetamide, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 17

A compound represented by the above general formula (7) can be also prepared by allowing a compound represented by the above general formula (13) to react with an azidating reagent such as sodium azide, lithium azide or the like in the presence of an azodicarboxylate such as diethyl azodicarboxylate, diisopropyl azodicarboxylate or the like, and an organophosphorus reagent such as triphenylphosphine or the like in an inert solvent (Mitsunobu reaction). As the inert solvent used in the reaction, for example, tetrahydrofuran, toluene, N,N-dimethylformamide, a mixed solvent thereof or the like can be used. The reaction temperature is usually from room temperature to reflux temperature, and the reaction time is usually from 10 minutes to 1 day, varying based on a used starting material, solvent and reaction temperature.

Process 18

A compound represented by the above general formula (7) can be also prepared by subjecting a compound represented by the above general formula (14) to azidation using an azidating reagent such as sodium azide, lithium azide or the like in an inert solvent. As the inert solvent used in the reaction, for example, N,N-dimethylformamide, N,N-dimethylacetamide, dimethylsulfoxide, N-methyl-2-pyrrolidone, acetonitrile, tetrahydrofuran, water, a mixed solvent thereof or the like can be used. The reaction temperature is usually from room temperature to reflux temperature, and the reaction time is usually from 30 minutes to 1 day, varying based on a used starting material, solvent and reaction temperature.

Process 19

A compound represented by the above general formula (5) can be also prepared by allowing a compound represented by the above general formula (13) to react with an phthalimide in the presence of an azodicarboxylate such as diethyl azodicarboxylate, diisopropyl azodicarboxylate or the like, and an organophosphorus reagent such as triphenylphosphine or the like in an inert solvent (Mitsunobu reaction). As the inert solvent used in the reaction, for example, tetrahydrofuran, toluene, N,N-dimethylformamide, a mixed solvent thereof or the like can be used. The reaction temperature is usually from room temperature to reflux temperature, and the reaction time is usually from 10 minutes to 1 day, varying based on a used starting material, solvent and reaction temperature.

Process 20

A compound represented by the above general formula (5) can be also prepared by allowing a compound represented by the above general formula (14) to react with potassium phthalimide in an inert solvent. As the inert solvent used in the reaction, for example, N,N-dimethylformamide, N,N-dimethylacetamide, dimethylsulfoxide, N-methyl-2-pyrrolidone, acetonitrile, tetrahydrofuran, water, a mixed solvent thereof or the like can be used. The reaction temperature is usually from room temperature to reflux temperature, and the reaction time is usually from 30 minutes to 1 day, varying based on a used starting material, solvent and reaction temperature.

Among the compounds represented by the above general formula (10) used as starting materials in the above processes 9, 11 and 15, a compound (17) wherein n is 1 can be also prepared in a method shown in processes 21 to 22.

[Chem. 12]

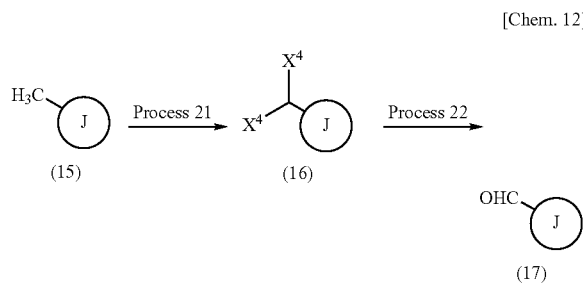

In the formula, $X^4$ represents a halogen atom, and n and ring J have the same meanings as defined above.

Process 21

A compound represented by the above general formula (16) can be also prepared by subjecting a compound represented by the above general formula (15) to halogenation using a halogenating reagent such as sulphuryl chloride, N-bromosuccinimide or the like, and optionally adding a radical initiating agent such as dibenzoyl peroxide, azobisisobutylonitrile or the like without or in an inert solvent. As the inert solvent used in the reaction, for example, dichloromethane, carbon tetrachloride, cyclohexane, benzene, a mixed solvent thereof or the like can be illustrated. The reaction temperature is usually from room temperature to reflux temperature, and the reaction time is usually from 1 hour to 3 days, varying based on a used starting material, solvent and reaction temperature.

Process 22

A compound represented by the above general formula (17) can be also prepared by allowing a compound represented by the above general formula (16) to react with a silver salt such as silver nitrate or the like in a solvent and then by hydrolyzing in the presence of an acid such as hydrochloric acid, sulfuric acid or the like. As the solvent used in the reaction, for example, methanol, ethanol, isopropanol, water, a mixed solvent thereof or the like can be illustrated. The reaction temperature is usually from room temperature to reflux temperature, and the reaction time is usually from 1 hour to 1 day, varying based on a used starting material, solvent and reaction temperature.

Among the compounds represented by the above general formula (10) used as starting materials in the above-mentioned processes 9, 11 and 15, a compound (20) wherein n is 2 can be also prepared in a method shown in processes 23 to 24.

[Chem. 13]

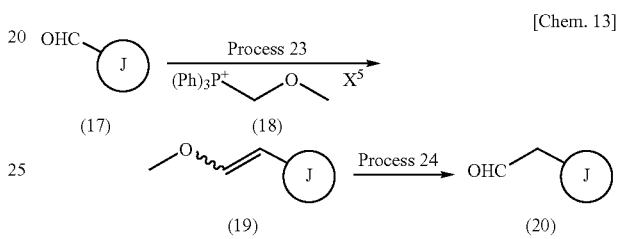

In the formula, Ph represents a phenyl group, $X^5$ represents a halide ion, and ring J have the same meanings as defined above.

Process 23

A compound represented by the above general formula (19) can be also prepared by subjecting a compound represented by the above general formula (17) to condensation with a compound represented by the above general formula (18) in the presence of a base such as sodium hydride, potassium tert-butoxide, n-butyllithium, lithium bis(trimethylsilyl)amide, sodium bis(trimethylsilyl)amide, sodium hydroxide or the like in an inert solvent. As the inert solvent used in the reaction, for example, tetrahydrofuran, dimethylsulfoxide, N,N-dimethylformamide, N,N-dimethylacetamide, N-methyl-2-pyrrolidone, 1,3-dimethyl-2-imidazolidinone, acetonitrile, a mixed solvent thereof or the like can be illustrated. The reaction temperature is usually from −78° C. to reflux temperature, and the reaction time is usually from 30 minutes to 1 day, varying based on a used starting material, solvent and reaction temperature.

Process 24

A compound represented by the above general formula (20) can be also prepared by subjecting a compound represented by the above general formula (19) to hydrolysis in the presence of an acid such as hydrochloric acid, sulfuric acid, methanesulfonic acid, p-toluenesulfonic acid, pyridinium p-toluenesulfonate or the like. As the solvent used in the reaction, for example, tetrahydrofuran, acetone, acetonitrile, water, a mixed solvent thereof or the like can be illustrated. The reaction temperature is usually from 0° C. to reflux temperature, and the reaction time is usually from 30 minutes to 1 day, varying based on a used starting material, solvent and reaction temperature.

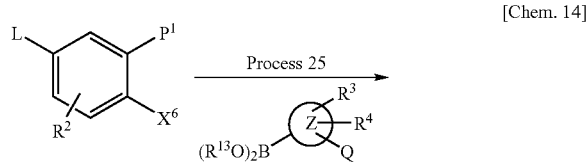

(21)    (22)

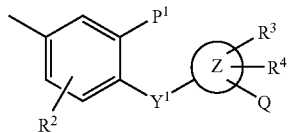

(23)

In the formula, $X^6$ represents a halogen atom or a trifluoromethanesulfonyloxy group; L represents a formyl group, a cyano group or a carbamoyl group; $R^{13}$ represents a hydrogen atom, a lower alkyl group, or two $R^{13}$ represent an ethylene or trimethylene group which forms a 5 to 6-membered ring containing a boron atom and two oxygen atoms bound to the same, and the cyclic group may have lower alkyl groups; $Y^1$ represents a single bond; and $R^2$, $R^3$, $R^4$, ring Z, $P^1$ and Q have the same meanings as defined above.

Process 25

Among the compounds represented by the above general formula (4), (8) and (10), a compound wherein n is 1 and ring J is the following general formula:

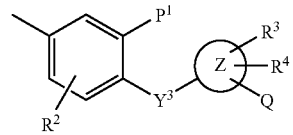

in the formula, $Y^1$ represents a single bond; and $R^2$, $R^3$, $R^4$ ring Z, $P^1$ and Q have the same meanings as defined above, can be also prepared by subjecting a compound represented by the above general formula (21) to condensation with an organoboron compound represented by the above general formula (22) in the presence of a palladium catalyst such as tetrakis(triphenylphosphine)palladium(0) or the like and a base such as sodium carbonate, potassium carbonate or the like in an inert solvent. As the inert solvent used in the reaction, for example, tetrahydrofuran, ethanol, acetonitrile, N,N-dimethylformamide, N,N-dimethylacetamide, toluene, water, a mixed solvent thereof or the like can be illustrated. The reaction temperature is usually from room temperature to reflux temperature, and the reaction time is usually from 1 hour to 3 days, varying based on a used starting material, solvent and reaction temperature. A compound represented by the above general formula (22) used as a starting material in the present process is commercially available or can be prepared in a known or similar method (for examples, in a method described in J. Org. Chem., 2000, 65(1), 164-168., J. Org. Chem., 1993, 58(8), 2201-2208., J. Med. Chem., 1997, 40(22), 3542-3550., and Synthesis, 2004, 4, 469-483).

In addition, among the compounds represented by the above general formulas (4), (8) and (10), a compound wherein n is 1 and ring J is the following general formula:

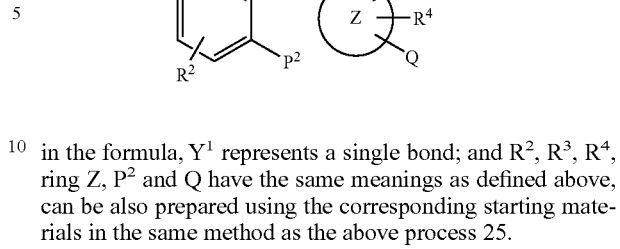

in the formula, $Y^1$ represents a single bond; and $R^2$, $R^3$, $R^4$, ring Z, $P^2$ and Q have the same meanings as defined above, can be also prepared using the corresponding starting materials in the same method as the above process 25.

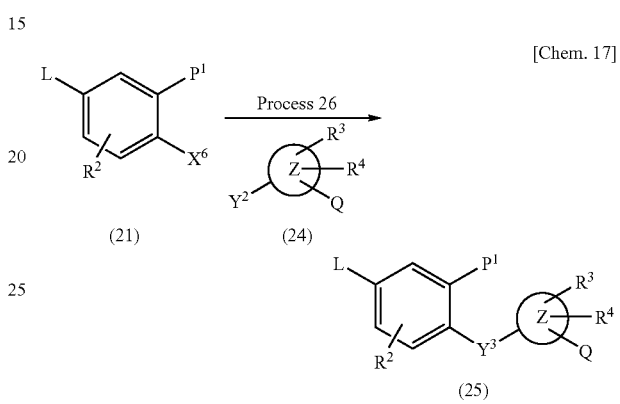

(21)    (24)

(25)

In the formula, $Y^2$ represents a hydroxy group, a hydroxymethyl group, a thiol group or a thiomethyl (—$CH_2SH$) group; $Y^3$ represents —O—, —$OCH_2$—, —S— or —$SCH_2$—; and $X^6$, L, $R^2$, $R^3$, $R^4$, ring Z, $P^1$ and Q have the same meanings as defined above.

Process 26

Among the compounds represented by the above general formula (4), (8) and (10), a compound wherein n is 1 and ring J is a group represented by the following general formula:

in the formula, $Y^3$ represents —O—, —$OCH_2$—, —S— or —$SCH_2$—; and $R^2$, $R^3$, $R^4$, ring Z, $P^1$ and Q have the same meanings as defined above, can be also prepared by subjecting a compound represented by the above general formula (21) to condensation with a compound represented by the above general formula (24) in the presence of a base such as potassium carbonate, cesium carbonate, sodium hydride, potassium tert-butoxide, sodium hydroxide or the like in an inert solvent. As the inert solvent used in the reaction, for example, N,N-dimethylformamide, N,N-dimethylacetamide, dimethylsulfoxide, N-methyl-2-pyrrolidone, 1,3-dimethyl-2-imidazolidinone, acetonitrile, tetrahydrofuran, water, a mixed solvent thereof or the like can be illustrated. The reaction temperature is usually from room temperature to reflux temperature, and the reaction time is usually from 30 minutes to 1 day, varying based on a used starting material, solvent and reaction temperature.

Among the compounds represented by the above general formula (21) used as starting materials in the above process 25 or 26, a compound (32) wherein $P^1$ is an alkoxy group and $X^6$ is a trifluoromethanesulfonyloxy group can be also prepared in the following method or a similar method.

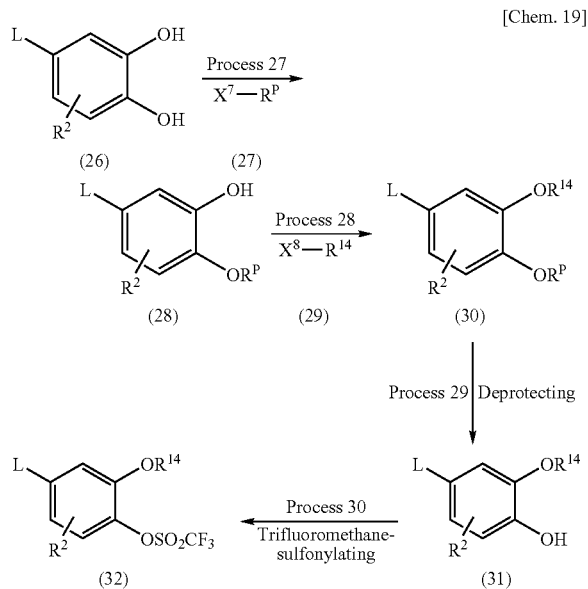

[Chem. 19]

In the formula, $X^7$ and $X^8$ independently represent a halogen atom; $R^P$ represents a hydroxy-protective group; $R^{14}$ represents an optionally substituted alkyl group; and L and $R^2$ have the same meanings as defined above.

Process 27

A compound represented by the above general formula (28) can be also prepared by subjecting a compound represented by the above general formula (26) to O-alkylation using an alkylating agent or an agent to introduce a hydroxy-protective group represented by the above general formula (27) in the presence of a base such as sodium hydroxide, potassium carbonate, triethylamine, diisopropylethylamine or the like, optionally in the coexistence with a catalytic amount of sodium iodide in an inert solvent. As an agent to introduce a hydroxy-protective group, benzyl bromide, chloromethylmethyl ether or the like can be illustrated. As the inert solvent used in the reaction, for example, methanol, ethanol, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 28

A compound represented by the above general formula (30) can be prepared by subjecting a compound represented by the above general formula (28) to O-alkylation using an alkylating agent represented by the above general formula (29) in the presence of a base such as sodium hydroxide, potassium carbonate, triethylamine, diisopropylethylamine or the like, optionally in the coexistence with a catalytic amount of sodium iodide in an inert solvent. As the inert solvent used in the reaction, for example, methanol, ethanol, tetrahydrofuran, N,N-dimethylformamide, water, a mixed solvent thereof or the like can be illustrated. The reaction temperature is usually from room temperature to reflux temperature, and the reaction time is usually from 10 minutes to 1 day, varying based on a used starting material, solvent and reaction temperature.

Process 29

A compound represented by the above general formula (31) can be also prepared by removing a hydroxy-protective group of a compound represented by the above general formula (30) wherein $R^P$ represents a hydroxy-protective group in the usual way. For example, in case that the protective group is a benzyl group, a compound represented by the above general formula (31) can be also prepared by catalytic reduction using a metal catalyst such as palladium on carbon or the like in the presence or absence of an acid such as hydrochloric acid or the like in an inert solvent. As the inert solvent used in the catalytic reduction reaction, for example, methanol, ethanol, tetrahydrofuran, ethyl acetate, acetic acid, a mixed solvent thereof or the like can be illustrated. The reaction temperature is usually from room temperature to reflux temperature, and the reaction time is usually from 30 minutes to 1 day, varying based on a used starting material, solvent and reaction temperature.

Process 30

A compound represented by the above general formula (32) can be also prepared by subjecting a compound represented by the above general formula (31) to trifluoromethanesulfonylation using a trifluoromethanesulfonylating reagent such as trifluoromethanesulfonic anhydride or the like in the presence of a base such as pyridine, triethylamine, diisopropylethylamine or the like in an inert solvent. As the inert solvent used in the reaction, for example, toluene, tetrahydrofuran, N,N-dimethylformamide, dichloromethane, a mixed solvent thereof or the like can be illustrated. The reaction temperature is usually from −78° C. to reflux temperature, and the reaction time is usually from 10 minutes to 1 day, varying based on a used starting material, solvent and reaction temperature.

On the other hand, the compounds represented by the above general formulas (Ia) and (Ib) of the present invention can be prepared, for example, in the following or similar method or in the combination with the same. In case that a protective group is necessary, introduction and removal procedures can be optionally combined in the usual way.

[Chem. 20]

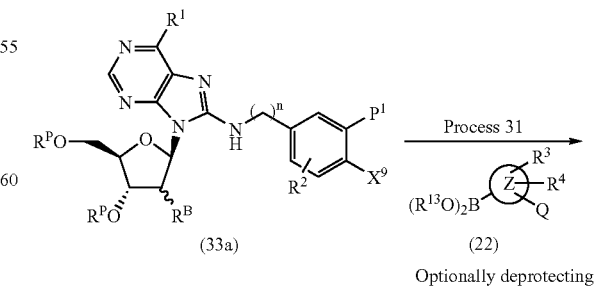

Optionally deprotecting

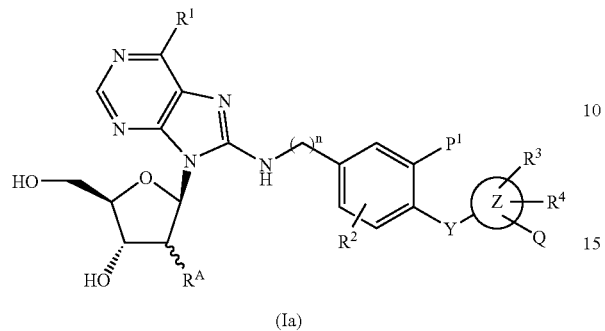

(Ia)

In the formula, $X^9$ represents a halogen atom or a trifluoromethanesulfonyloxy group; $Y^9$ represents a single bond; and n, $R^4$, $R^1$, $R^2$, $R^3$, $R^4$, $R^{13}$, $R^P$, ring Z, $P^1$ and Q have the same meanings as defined above.

Process 31

Among the compounds represented by the above general formula (Ia), a compound wherein Y is a single bond can be also prepared by subjecting a compound represented by the above general formula (33a) to condensation with an organoboron compound represented by the above general formula (22) in the presence of a palladium catalyst such as tetrakis(triphenylphosphine)palladium(0) or the like and a base such as sodium carbonate, potassium carbonate or the like in an inert solvent and optionally by removing a protective group. As the inert solvent used in the reaction, for example, tetrahydrofuran, ethanol, acetonitrile, N,N-dimethylformamide, N,N-dimethylacetamide, toluene, water, a mixed solvent thereof or the like can be illustrated. The reaction temperature is usually from room temperature to reflux temperature, and the reaction time is usually from 1 hour to 3 days, varying based on a used starting material, solvent and reaction temperature.

Among the compounds represented by the above general formula (Ib), a compound wherein Y is a single bond can be also prepared using the corresponding starting materials in the same method as the above process 31.

In compounds of the present invention, a compound wherein $R^1$ is a hydroxy group, a chlorine atom, a thiol group or a hydrogen atom can be also prepared, for example, in the following or similar method or a known method (for examples, the method described in J. Chem. Soc. Perkin Trans. 1, 1990, 2937-2942., Chem. Pharm. Bull., 1989, 37(2), 336-339., and J. Org. Chem., 1962, 3279-3283) or a similar method or the like. In addition, in case that a protective group is necessary, introduction and removal procedures can be optionally combined in the usual way. In addition, the following process to exchange $R^1$ can be optionally conducted in either suitable manufacturing process of the above described process.

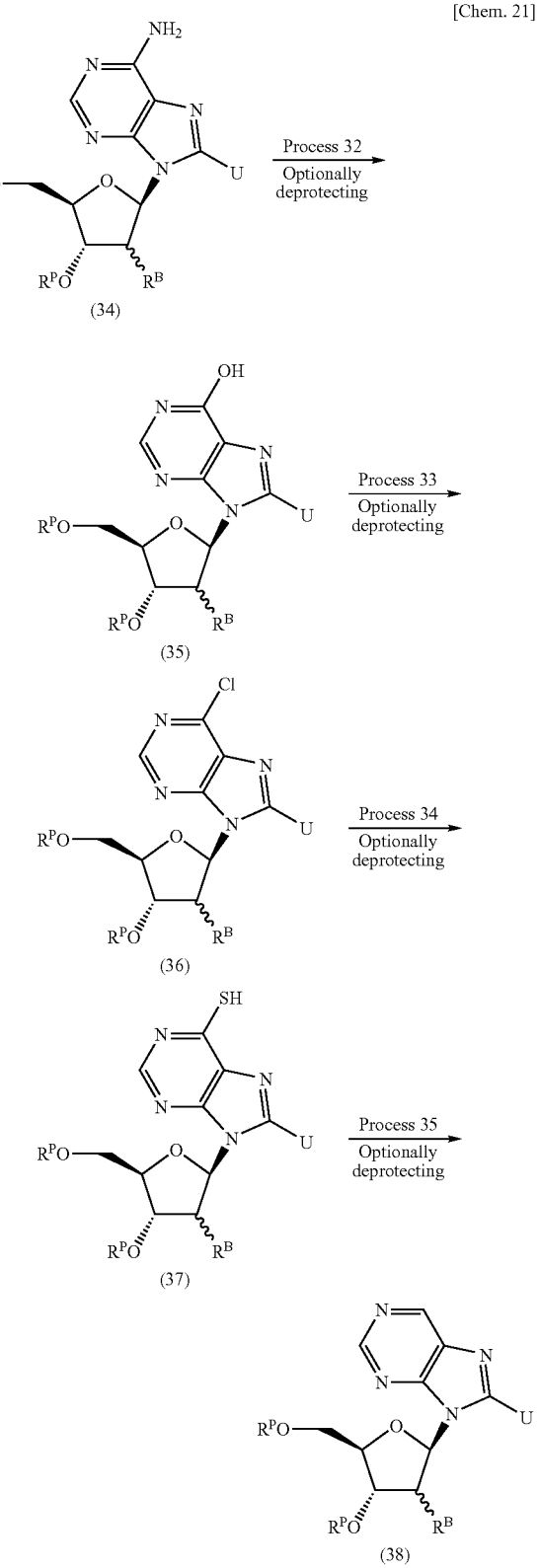

In the formula, U represents, for example, a hydrogen atom, a halogen atom or a substituted amino group; $R^P$ and $R^B$ have the same meanings as defined above.

Process 32

A compound (35) wherein $R^1$ is a hydroxy group can be also prepared by subjecting a compound (34) wherein the corresponding group is an amino group to deamination using a diazotizating reagent such as sodium nitrite or the like in an inert solvent, and optionally by removing a protective group. As the inert solvent used in the reaction, for example, acetic acid, water, a mixed solvent thereof or the like can be illustrated. The reaction temperature is usually from 0° C. to reflux temperature, and the reaction time is usually from 1 hour to 3 days, varying based on a used starting material, solvent and reaction temperature.

Process 33

A compound (36) wherein $R^1$ is a chlorine atom can be also prepared by subjecting a compound (35) wherein the corresponding group is a hydroxy group, 1) to halogenation using a halogenating reagent such as thionyl chloride, phosphorus oxychloride or the like in the presence or absence of a base such as N,N-dimethylaniline, pyridine or the like optionally in the coexistence with a catalytic amount of N,N-dimethylformamide in an inert solvent, and optionally by removing a protective group, or 2) to halogenation in the presence of a carbon tetrachloride and an organophosphorus reagent such as triphenylphosphine, trimethylphosphite or the like in an inert solvent, and optionally by removing a protective group. As the inert solvent used in halogenation reaction, for example, dichloromethane, tetrahydrofuran, toluene, a mixed solvent thereof or the like can be illustrated. The reaction temperature is usually from room temperature to reflux temperature, and the reaction time is usually from 1 hour to 1 day, varying based on a used starting material, solvent and reaction temperature.

Process 34

A compound (37) wherein $R^1$ is a thiol group can be also prepared by subjecting a compound (36) wherein the corresponding group is a chlorine atom to thiolation using a thiourea in an inert solvent, and optionally by removing a protective group. As the inert solvent used in the reaction, for example, ethanol, 1-propanol, acetonitrile, water, a mixed solvent thereof or the like can be illustrated. The reaction temperature is usually from room temperature to reflux temperature, and the reaction time is usually from 1 hour to 1 day, varying based on a used starting material, solvent and reaction temperature.

Process 35

A compound (38) wherein $R^1$ is a hydrogen atom can be also prepared by subjecting a compound (37) wherein the corresponding group is a thiol group to desulfurization using a metal catalyst such as Raney nickel or the like in an inert solvent, and optionally by removing a protective group. As the inert solvent used in the reaction, for example, ethanol, 2-methoxyethanol, water, a mixed solvent thereof or the like can be illustrated. The reaction temperature is usually from room temperature to reflux temperature, and the reaction time is usually from 1 hour to 1 day, varying based on a used starting material, solvent and reaction temperature.

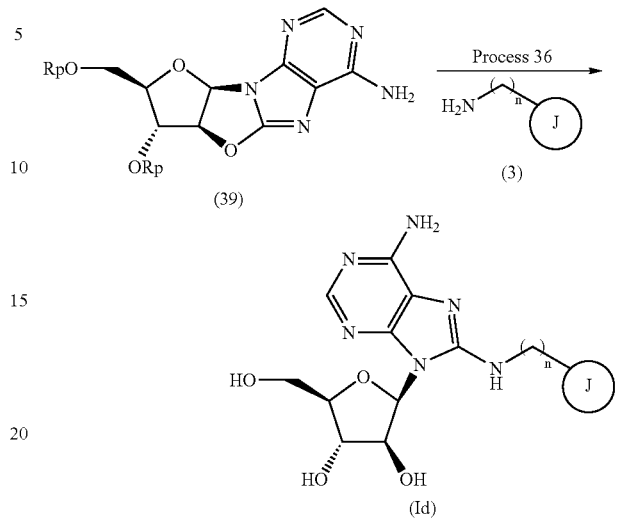

[Chem. 22]

In the formula, n, $R^p$ and ring J have the same meanings as defined above.

Process 36

An 8-modified purinenucleoside derivative represented by the above general formula (Id) can be prepared by subjecting a compound represented by the above general formula (39) to condensation with a compound represented by the above general formula (3) in the presence or absence of a base such as triethylamine, N,N-diisopropylethylamine, potassium carbonate, pyridine or the like without or in an inert solvent, and optionally by removing a protective group. As the inert solvent used in the reaction, for example, methanol, ethanol, 1-propanol, isobutanol, N,N-dimethylformamide, N,N-dimethylacetamide, tetrahydrofuran, toluene, water, a mixed solvent thereof or the like can be illustrated. The reaction temperature is usually from room temperature to reflux temperature, and the reaction time is usually from 1 hour to 3 days, varying based on a used starting material, solvent and reaction temperature.

A compound represented by the above general formula (39) used as a starting material in the present process is commercially available or can be prepared in a known method (for examples, the method described in chem. Pharm. Bull., 1977, 25, 2482-2489), or a similar method or the like.

In addition, among the compounds represented by the above general formula (Ia) or (Ib), a compound wherein at least one of $R^2$ to $R^4$, $P^1$, $P^2$ and Q is a lower alkenyl group or a lower alkynyl group can be also prepared, 1) by subjecting a compound wherein the corresponding group is a bromine atom or a iodine atom to condensation using the corresponding alkene or alkyne derivative in the presence of a palladium catalyst such as palladium acetate or the like, an organic phosphorus ligand such as triphenylphosphine or the like and a base such as cesium carbonate, sodium tert-butoxide or the like in an inert solvent or 2) by subjecting a compound wherein the corresponding group is a bromine atom or a iodine atom to condensation with the corresponding organoboron compound in the presence of a base such as sodium carbonate, cesium carbonate, sodium tert-butoxide or the like in the coexistence with a palladium catalyst such as tetrakis (triphenylphosphine) palladium(0) or the like and optionally with a ligand such as 2,2'-bis(diphenylphosphino)-1,1'-binaphthyl or the like in an inert solvent. As the inert solvent used in the reactions 1) and 2), for example, toluene, tetrahydrofuran, N,N-dimethylformamide, ethanol, acetonitrile, water a mixed solvent thereof or the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (Ia) or (Ib), a compound wherein at least one of $R^2$ to $R^4$, $P^1$, $P^2$ and Q has an alkoxy group, an alkylthio group, a mono- or di-substituted amino group or an ester group can be also prepared by subjecting a compound wherein the corresponding group is a hydroxy group, a thiol group, an amino group or a carboxy group, to alkylation using an alkylating reagent such as the corresponding halogenated alkyl compound or the like in the presence of a base such as sodium hydride, potassium carbonate, cesium carbonate, triethylamine, N,N-diisopropylethylamine, sodium hydroxide or the like in an inert solvent optionally in the coexistence with a catalytic amount of sodium iodide. As the inert solvent used in the reaction, for example, tetrahydrofuran, N,N-dimethylformamide, dichloromethane, toluene, ethanol, acetone, water, a mixed solvent thereof or the like can be illustrated. The reaction temperature is usually from 0° C. to reflux temperature, and the reaction time is usually from 10 minutes to 1 day, varying based on a used starting material, solvent and reaction temperature.

Among the compounds represented by the above general formula (Ia) or (Ib), a compound wherein at least one of $R^2$ to $R^4$, $P^1$, $P^2$ and Q has an alkoxy group or an ester group can be also prepared by subjecting a compound wherein the corresponding group is a hydroxy group or a carboxy group to condensation (Mitsunobu reaction) using with the corresponding alcohol compound in the presence of a azodicarboxylate such as diethyl azodicarboxylate, diisopropyl azodicarboxylate or the like and an organophosphorus reagent such as triphenylphosphine or the like in an inert solvent. As the inert solvent used in the reaction, for example, dichloromethane, tetrahydrofuran, benzene, toluene, N,N-dimethylformamide, a mixed solvent thereof or the like can be illustrated. The reaction temperature is usually from room temperature to reflux temperature, and the reaction time is usually from 10 minutes to 1 day, varying based on a used starting material, solvent and reaction temperature.

Among the compounds represented by the above general formula (Ia) or (Ib), a compound wherein at least one of $R^2$ to $R^4$, $P^1$, $P^2$ and Q has a carbamoyl group or amono- or di-substituted carbamoyl group can be also prepared by subjecting a compound wherein the corresponding group is a carboxy group and the corresponding amine compound to amidation using a condensing agent such as diphenylphospholylazide, dicyclohekylcarbodiimide or the like in an inert solvent, optionally in the coexistence with an activated esterifing reagent such as 1-hydroxybenzotriazole or the like. As the inert solvent used in the reaction, for example, N,N-dimethylformamide, dichloromethane, chloroform, toluene, tetrahydrofuran, a mixed solvent thereof or the like can be illustrated. The reaction temperature is usually from room temperature to reflux temperature, and the reaction time is usually from 1 hour to 3 days, varying based on a used starting material, solvent and reaction temperature.

Among the compounds represented by the above general formula (Ia) or (Ib), a compound wherein at least one of $R^2$ to $R^4$, $P^1$, $P^2$ and Q has an acylamino group can be also prepared 1) by subjecting a compound wherein the corresponding group is an amino group or a mono-substituted amino group to acylation using an acylating reagent such as the corresponding acylhalide derivative or the like in the presence or absence of a base such as triethylamine, N,N-diisopropylethylamine, pyridine, 4-dimethylaminopyridine, sodium hydroxide or the like in an inert solvent, or 2) by subjecting a compound wherein the corresponding group is an amino group to acylation using an acylating reagent such as the corresponding acylhalide derivative or the like in the presence or absence of a base such as triethylamine, N,N-diisopropylethylamine, pyridine, 4-dimethylaminopyridine, sodium hydroxide or the like in an inert solvent, and then optionally to alkylation using an alkylating reagent such as the corresponding halogenated alkyl compound or the like in the presence of a base such as sodium hydride, potassium carbonate, cesium carbonate, triethylamine, N,N-diisopropylethylamine, potassium tert-butoxide, sodium hydroxide or the like in an inert solvent optionally in the coexistence with a catalytic amount of sodium iodide. As the inert solvent used in acylation, for example, dichloromethane, chloroform, acetonitrile, toluene, pyridine, water, a mixed solvent thereof or the like can be illustrated. The reaction temperature is usually from 0° C. to reflux temperature, and the reaction time is usually from 10 minutes to 1 day, varying based on a used starting material, solvent and reaction temperature. As the inert solvent used in alkylation reaction 2), for example, tetrahydrofuran, N,N-dimethylformamide, dichloromethane, toluene, ethanol, acetone, water, a mixed solvent thereof or the like can be illustrated. The reaction temperature is usually from 0° C. to reflux temperature, and the reaction time is usually from 10 minutes to 1 day, varying based on a used starting material, solvent and reaction temperature.

As a protective group in the present invention, various protective groups generally used in organic syntheses can be used. For example, as a hydroxy-protective group, a p-methoxybenzyl group, a benzyl group, a methoxymethyl group, an acetyl group, a pivaloyl group, a benzoyl group, a tert-butyldimethylsilyl group, a tert-butyldiphenylsilyl group, an allyl group and the like, in addition, in case that there are two neighboring hydroxy groups, an isopropylidene group, a cyclopentylidene group, a cyclohexylidene group and the like can be illustrated. As a thiol-protective group, a p-methoxybenzyl group, a benzyl group, an acetyl group, a pivaloyl group, a benzoyl group, a benzyloxycarbonyl group and the like can be illustrated. As an amino-protective group, a benzyloxycarbonyl group, a tert-butoxycarbonyl group, a benzyl group, a p-methoxybenzyl group, a trifluoroacetyl group, an acetyl group, a phthaloyl group and the like can be illustrated. As a carboxyl-protective group, a benzyl group, a tert-butyldimethylsilyl group, an allyl group and the like can be illustrated.

The compounds represented by the above general formula (I) of the present invention can be isolated and purified by conventional separation means such as fractional recrystallization, purification using chromatography, solvent extraction, solid phase extraction or the like. In addition, the 8-modified purinenucleoside derivatives represented by the above general formula (Ic) which exhibit an inhibitory activity against CNT2 can be prepared, isolated and purified in the same methods as the above processes of the 8-modified purinenucleoside derivatives represented by the above general formula (I).

The 8-modified purinenucleoside derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succininc acid, tartaric acid, fumaric acid, butyric acid, oxalic acid, malonic acid, maleic acid, lactic acid, malic acid, carbonic acid, benzoic acid, glutamic acid, aspartic acid and the like, salts with inorganic bases such as sodium salt, potassium salt and the like, addition salts with organic bases such as N-methyl-D-glucamin, N,N'-dibenzylethylenediamine, 2-aminoethanol, tris (hydroxymethyl) aminomethane, arginine, lysine and the like.

Among the 8-modified purinenucleoside derivatives represented by the above general formula (I) of the present invention, there can be two geometric isomers, cis (Z)-isomer and trans (E)-isomer, in each compound having an unsaturated bond. In the present invention, either of cis (Z)-isomer, trans (E)-isomer and a mixture thereof can be employed.

Among the 8-modified purinenucleoside derivatives represented by the above general formula (I) of the present invention, there can be two optical isomers, R-isomer and S-isomer, in each compound having an asymmetric carbon atom excluding the sugar-residue moiety. In the present invention, either of R-isomer and S-isomer can be employed, and a mixture of both isomers can be also employed.

Among the 8-modified purinenucleoside derivatives represented by the above general formula (I) of the present invention, there can be tautomers. The compounds of the present invention include these tautomers.

In the present invention, the term "prodrug" means a compound obtained by modifying a parent compound with a pharmaceutically acceptable group generally used in a prodrug, and such compound can be expected, for example, to have additional characteristics such as improved stability, long action or the like and exert an efficacy after being converted into the parent compound in the intestine tract or the like. The prodrugs of the compound represented by the above general formula (I) of the present invention can be prepared by suitably introducing a group forming a prodrug into one or more group optionally selected from a group consisting of a hydroxy group, an amino group, another group acceptable to form a prodrug of a compound represented by the above general formula (I) using an agent to form a prodrug such as the corresponding halide or the like in the usual way and then optionally isolating and purifying in the usual way as an occasion demand (see "*Gekkan-yakuji*. The clinical pharmacokinetics for proper uses of pharmaceutical drugs", Extra edition, March 2000, Vol. 42, No. 4, pp. 669-707; and "New drug delivery system", issued by CMC Co. Ltd., Jan. 31, 2000, pp. 67-173). As a group forming a prodrug used in a hydroxy group or an amino group, for example, lower alkyl-CO—, lower alkyl-O— lower alkyl-CO—, lower alkyl-OCO— lower alkyl-CO—, lower alkyl-OCO—, lower alkyl-O— lower alkyl-OCO— and the like can be illustrated.

In the present invention, as a solvate with pharmaceutically acceptable solvent, for example, the solvate with the ethanol can be illustrated.

In the present invention, as the diseases associated with an abnormality of plasma uric acid level include gout, hyperuricemia, urinary lithiasis, hyperuricemic nephropathy, acute uric acid nephropathy and the like can be illustrated, and especially gout and hyperuricemia can be illustrated.

When the pharmaceutical compositions of the present invention are employed in the practical prevention or treatment, the dosage of a compound represented by the above general formula (I) or a prodrug thereof, or a pharmaceutically acceptable salt thereof, or a hydrate or solvate thereof as the active ingredient is appropriately decided depending on the age, sex, body weight and degree of symptoms and treatment of each patient, for example, which is approximately within the range of 1 to 2,000 mg per day per adult human in the case of oral administration, and the daily dose can be divided into one or several doses and administered suitably.

When the pharmaceutical compositions of the present invention are employed in the practical prevention or treatment, various dosage forms are used depending on their usages for oral or parenteral administration. As examples of the dosage forms, orally administration forms such as powders, fine granules, granules, tablets, capsules, dry syrups or the like are preferable.

These pharmaceutical compositions can be prepared by admixing with an appropriate pharmaceutical additive such as excipients, disintegrators, binders, lubricants or the like in accordance with pharmaceutically conventional methods and formulating the mixture depending on their dosage forms in the usual way.

For example, powders can be formulated by, if desired, admixing well an active ingredient with appropriate excipients, lubricants and the like. Tablets can be formulated by, if desired, admixing an active ingredient with appropriate excipients, disintegrators, binders, lubricants and the like, and compressing the mixture in accordance with conventional methods. The tablets, further if desired, can be suitably coated to provide film-coated tablets, sugar-coated tablets, enteric-coated tablets and the like. Capsules can be formulated by, if desired, admixing well an active ingredient with appropriate excipients, lubricants and the like, or formulating granules or fine-powders in accordance with conventional methods, and then filling the compositions in appropriate capsules. Such orally administration forms can be formulated as immediate release or sustained release preparations depending on the prevention or treatment methods.

A compound represented by the above general formula (I) of the present invention or prodrugs thereof, or pharmaceutically acceptable salts thereof, or hydrates or solvates thereof can be used in combination with a drug for the treatment of hyperuricemia or gout which does not substantially inhibit the absorption of nucleosides. As drugs usable for the treatment of hyperuricemia in the present invention, for example, a uricosuric drug such as probenecid, bucolome, benzbromarone or the like; a uric acid synthesis inhibitor such as allopurinol, oxypurinol, febuxostat, Y-700 or the like; a urinary alkalinizer such as sodium hydrogen carbonate, potassium citrate, sodium citrate or the like; and a uric acid oxidase such as rasburicase, uricase PEG-20, a recombinant uric acid oxidase (uricase) and the like can be illustrated. In addition, as drugs for the treatment of gout, colchicines; a nonsteroidal anti-inflammatory agent such as indometacin, naproxen, fenbufen, pranoprofen, oxaprozin, ketoprofen, etoricoxib, tenoxicam or the like; an adrenocortical steroid and the like can be illustrated. In the present invention, the active ingredient of the present invention can be used in combination with at least one of these drugs, and the pharmaceutical composition comprising in combination at least one of these drugs is not limited to a single preparation simultaneously formulated with the active ingredient of the present invention, and includes administration modes such as a combination of a separated preparation formulated separately from a pharmaceutical composition containing the active ingredient of the present invention to be administered at the same or different dosage intervals. In addition, in case of use in combination with a drug other than the active ingredient of the present invention, the dose of the compound of the present invention can be decreased according to the dosage of the other drug used in combination with, occasionally, beneficial effect more than additive effect in the prevention or treatment of the above diseases can be obtained, and adverse effects of coadministrated drugs can be avoided or declined.

EFFECT OF THE INVENTION

The 8-modified purinenucleoside derivatives represented by the above general formula (I) of the present invention, or prodrugs, or pharmaceutically acceptable salts thereof, or hydrates or solvates thereof, can remarkably suppress increase of plasma uric acid level by inhibition of the purine nucleosides absorption through the intestines to the body.

BEST MODE FOR CARRYING OUT THE INVENTION

Figure 1:
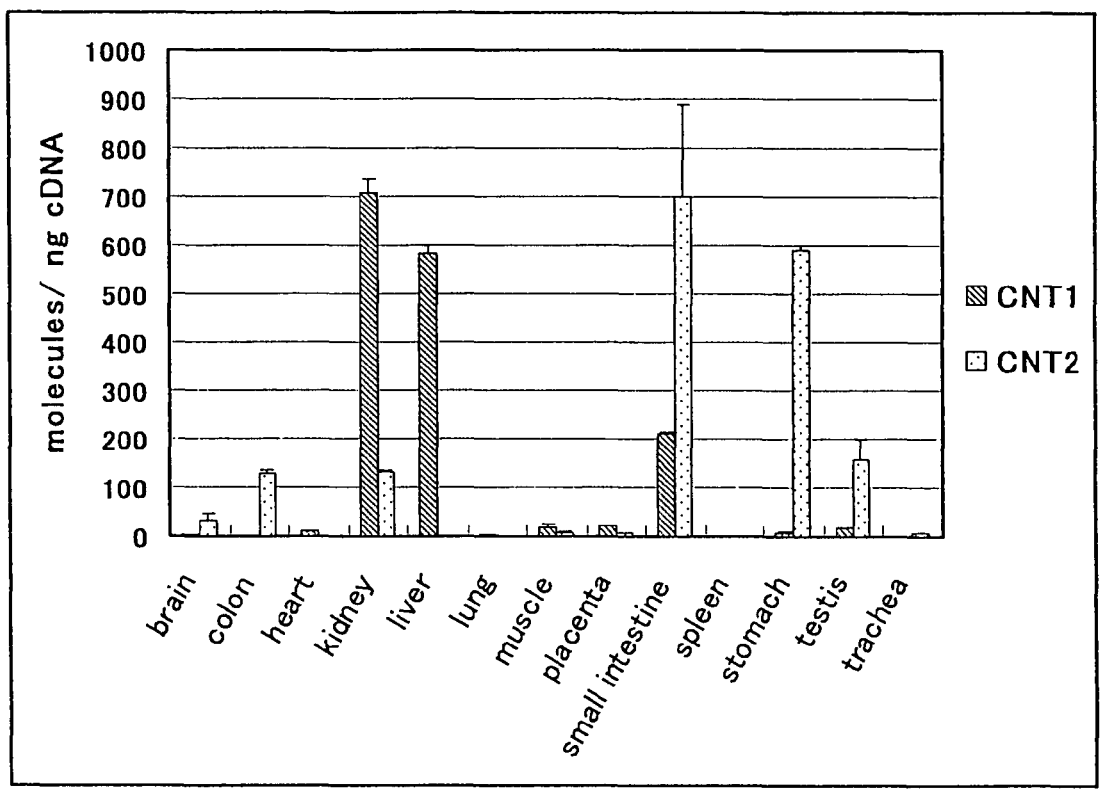
FIG. 1 is a graph showing the pattern of CNT1 and CNT2 distribution inhuman tissues. The vertical axis is the number of molecular per 1 ng cDNA (molecular number/ng cDNA). The horizontal axis is the name of tissues. The left bar graph shows CNT1 and the right bar graph shows CNT2.

The present invention is further illustrated in more detail by way of the following Reference Examples, Examples and Test Examples. However, the present invention is not limited thereto.

Reference Example 1

8-(4-Bromobenzylamino)adenosine

A mixture of 8-bromoadenosine (0.100 g), 4-bromobenzylamine hydrochloride (0.193 g) and triethylamine (0.201 mL) in ethanol (2.9 mL) was stirred under reflux for 96 hours. The reaction mixture was cooled to room temperature and concentrated under reduced pressure. The residue was purified by column chromatography on aminopropylated silica gel (eluent: dichloromethane/methanol=10/1) to give the title compound (0.118 g).

Reference Example 2 tert-Butyl N-(3'-benzyloxybiphenyl-4-ylmethyl)carbamate

To a mixture of tert-butyl N-(4-bromobenzyl)carbamate (5.00 g), 3-benzyloxyphenylboronic acid (4.38 g), sodium carbonate (3.70 g), water (14 mL) and N,N-dimethylformamide (70 mL) was added tetrakis(triphenylphosphine)palladium(0) (1.01 g), and the resulting mixture was stirred at 80° C. for 14 hours. The reaction mixture was cooled to room temperature and the insoluble material was filtered out. The filtrate was partitioned between ethyl acetate (110 mL) and water (50 mL). The organic layer was washed successively with water (50 mL) and brine (50 mL), dried over anhydrous sodium sulfate and concentrated under reduced pressure. The residue was purified by column chromatography on aminopropylated silica gel (eluent: hexane/ethyl acetate=6/1) to give the title compound (5.32 g).

Reference Example 3 tert-Butyl N-(2'-benzyloxybiphenyl-4-ylmethyl)carbamate

The title compound was prepared in a similar manner to that described in Reference Example 2 using 2-benzyloxyphenylboronic acid instead of 3-benzyloxyphenylboronic acid.

Reference Example 4 tert-Butyl N-(4'-hydroxybiphenyl-4-ylmethyl)carbamate

The title compound was prepared in a similar manner to that described in Reference Example 2 using 4-hydroxyphenylboronic acid instead of 3-benzyloxyphenylboronic acid.

Reference Example 5 tert-Butyl N-(3'-methoxycarbonylbiphenyl-4-ylmethyl)-carbamate

The title compound was prepared in a similar manner to that described in Reference Example 2 using 3-methoxycarbonylphenylboronic acid instead of 3-benzyloxyphenylboronic acid.

Reference Example 6 tert-Butyl N-[4-(4,4,5,5-tetramethyl-1,3,2-dioxaborolane-2-yl)benzyl]carbamate

To a mixture of tert-butyl N-(4-bromobenzyl)carbamate (0.500 g), bis(pinacolato)diboron (0.488 g), potassium acetate (0.514 g) and dimethylsulfoxide (10.5 mL) was added [1,1'-bis(diphenylphosphino)ferrocene]dichloropalladium (II) complex with dichloromethane (0.043 g), and the resulting mixture was stirred at 80° C. for 30 minutes. The reaction mixture was cooled to room temperature and then partitioned between ethyl acetate (40 mL) and water (15 mL). The organic layer was washed with water/brine (1/1, 10 mL), dried over anhydrous sodium sulfate and concentrated under reduced pressure. The residue was purified by column chromatography on silica gel (eluent: hexane/ethyl acetate=4/1) to give the title compound (0.579 g).

Reference Example 7

1-Bromo-3-pentyloxybenzene

To a solution of 3-bromophenol (0.500 g) in N,N-dimethylformamide (5.8 mL) was added potassium carbonate (1.20 g). Then 1-bromopentane (0.896 mL) was added, and the resulting mixture was stirred at room temperature for 18.5 hours. The reaction mixture was partitioned between diethyl ether (35 mL) and water (10 mL). The organic-layer was washed successively with water (10 mL×2) and brine (10

Reference Example 8

1-Bromo-3-isopropoxybenzene

The title compound was prepared in a similar manner to that described in Reference Example 7 using 2-iodopropane instead of 1-bromopentane.

Reference Example 9

Benzyl 3-bromobenzoate

The title compound was prepared in a similar manner to that described in Reference Example 7 using 3-bromobenzoic acid instead of 3-bromophenol and benzyl bromide instead of 1-bromopentane.

Reference Example 10

Benzyl N-(3-bromophenyl)carbamate

To a mixture of 3-bromoaniline (0.500 g), 2 mol/L aqueous sodium hydroxide (2.18 mL) and tetrahydrofuran (3.63 mL) was added dropwise benzyl chloroformate (0.498 mL), and the resulting mixture was stirred at room temperature for 3.5 hours. The reaction mixture was partitioned between ethyl acetate (35 mL) and water (10 mL). The organic layer was washed with brine (10 mL), dried over anhydrous sodium sulfate and concentrated under reduced pressure. The residue was purified by column chromatography on silica gel (eluent: hexane/ethyl acetate=8/1) to give the title compound (0.897 g).

Reference Example 11 tert-Butyl N-(3'-pentyloxybiphenyl-4-ylmethyl)carbamate

To a mixture of 1-bromo-3-pentyloxybenzene (0.365 g), tert-bytyl N-[4-(4,4,5,5-tetramethyl-1,3,2-dioxaborolane-2-yl) benzyl]carbamate (0.575 g), sodium carbonate (0.318 g), water (1.3 mL) and N,N-dimethylformamide (6.5 mL) was added tetrakis(triphenylphosphine) palladium(0) (0.087 g), and the resulting mixture was stirred at 80° C. for 11 hours. The reaction mixture was cooled to room temperature and then partitioned between ethylacetate (35 mL) and water (10 mL). The organic layer was washed successively with water/brine (2/1, 15 mL) and brine (15 mL), dried over anhydrous sodium sulfate and concentrated under reduced pressure. The residue was purified by column chromatography on aminopropylated silica gel (eluent: hexane/ethyl acetate=6/1) to give the title compound (0.437 g)

mL), dried over anhydrous sodium sulfate and concentrated under reduced pressure to give the title compound (9.728 g).

Reference Example 12 tert-Butyl N-(3'-isopropoxybiphenyl-4-ylmethyl) carbamate

The title compound was prepared in a similar manner to that described in Reference Example 11 using 1-bromo-3-isopropoxybenzene instead of 1-bromo-3-pentyloxybenzene.

Reference Example 13 tert-Butyl N-(3'-benzyloxycarbonylbiphenyl-4-ylmethyl)-carbamate

The title compound was prepared in a similar manner to that described in Reference Example 11 using benzyl 3-bromobenzoate instead of 1-bromo-3-pentyloxybenzene.

Reference Example 14 tert-Butyl N-(3'-dimethylaminobiphenyl-4-ylmethyl) carbamate

The title compound was prepared in a similar manner to that described in Reference Example 11 using 3-bromo-N,N-dimethylaniline instead of 1-bromo-3-pentyloxybenzene.

Reference Example 15 tert-Butyl N-(3'-benzyloxycarbonylaminobiphenyl-4-yl-methyl)carbamate

The title compound was prepared in a similar manner to that described in Reference Example 11 using benzyl (3-bromophenyl)carbamate instead of 1-bromo-3-pentyloxy-benzene.

Reference Example 16 tert-Butyl N-[3'-(2-hydroxyethyl)biphenyl-4-ylmethyl]-carbamate

The title compound was prepared in a similar manner to that described in Reference Example 11 using 2-(3-bromophenyl)ethanol instead of 1-bromo-3-pentyloxy-benzene.

Reference Example 17 tert-Butyl N-(4-pyridine-3-ylbenzyl)carbamate

The title compound was prepared in a similar manner to that described in Reference Example 11 using 3-bromopyridine instead of 1-bromo-3-pentyloxybenzene.

Reference Example 18 tert-Butyl N-(3'-hydroxybiphenyl-4-ylmethyl)carbamate

To a solution of tert-butyl N-(3'-bezyloxy-biphenyl-4-yl-methyl)carbamate (1.16 g) in ethanol/tetrahydrofuran (4/1, 30 mL) was added 10% palladium-on carbon (55.4 wt % $H_2O$, 0.520 g), and the resulting mixture was stirred at 30° C. for 5 hours under a hydrogen atmosphere. The insoluble material was filtered out and the filtrate was concentrated under reduced pressure. The residue was purified by column chromatography on silica gel (eluent: hexane/ethyl acetate=5/2) to give the title compound (0.731 g).

Reference Example 19 tert-Butyl N-(2'-hydroxybiphenyl-4-ylmethyl)carbamate

The title compound was prepared in a similar manner to that described in Reference Example 18 using tert-butyl N-(2'-benzyloxybiphenyl-4-ylmethyl)carbamate instead of tert-butyl N-(3'-benzyloxybiphenyl-4-ylmethyl)carbamate.

Reference Example 20 tert-Butyl N-(3'-propoxybiphenyl-4-ylmethyl)carbamate

To a solution of tert-butyl N-(3'-hydroxybiphenyl-4-ylmethyl)carbamate (0.300 g) in N,N-dimethylformamide (2.5 mL) was added potassium carbonate (0.194 g). Then 1-bromopropane (0.119 mL) was added, and the resulting mixture was stirred at room temperature for 9.5 hours. Potassium carbonate (0.180 g) and 1-bromopropane (0.110 mL) were added, and stirring was continued at room temperature for additional 14 hours. The reaction mixture was partitioned between diethyl ether (30 mL) and water (10 mL). The organic layer was washed successively with water (10 mL×2) and brine (10 mL), dried over anhydrous sodium sulfate and concentrated under reduced pressure to give the title compound (0.333 g).

Reference Example 21 tert-Butyl N-(3'-butoxybiphenyl-4-ylmethyl)carbamate

The title compound was prepared in a similar manner to that described in Reference Example 20 using 1-bromobutane instead of 1-bromopropane.

Reference Example 22 tert-Butyl N-[3'-(3-benzyloxypropoxy)biphenyl-4-ylmethyl]carbamate

The title compound was prepared in a similar manner to that described in Reference Example 20 using 3-benzyloxy-1-bromopropane instead of 1-bromopropane.

Reference Example 23 tert-Butyl N-[3'-(2-methoxyethoxy)biphenyl-4-ylmethyl]-carbamate

The title compound was prepared in a similar manner to that described in Reference Example 20 using 1-bromo-2-methoxyethane instead of 1-bromopropane.

Reference Example 24 tert-Butyl N-(2'-propoxybiphenyl-4-ylmethyl)carbamate

The title compound was prepared in a similar manner to that described in Reference. Example 20 using tert-butyl N-(2'-hydroxybiphenyl-4-ylmethyl)carbamate instead of tert-butyl N-(3'-hydroxybiphenyl-4-ylmethyl)carbamate.

Reference Example 25 tert-Butyl N-(2'-butoxybiphenyl-4-ylmethyl)carbamate

The title compound was prepared in a similar manner to that described in Reference Example 20 using tert-butyl N-(2'-hydroxybiphenyl-4-ylmethyl)carbamate instead of tert-butyl N-(3'-hydroxybiphenyl-4-ylmethyl)carbamate and 1-bromobutane instead of 1-bromopropane.

Reference Example 26 tert-Butyl N-(2'-pentyloxybiphenyl-4-ylmethyl)carbamate

The title compound was prepared in a similar manner to that described in Reference Example 20 using tert-butyl N-(2'-hydroxybiphenyl-4-ylmethyl)carbamate instead of tert-butyl N-(3'-hydroxybiphenyl-4-ylmethyl)carbamate and 1-bromopentane instead of 1-bromopropane.

Reference Example 27 tert-Butyl N-(2'-isopropoxybiphenyl-4-ylmethyl)carbamate

The title compound was prepared in a similar manner to that described in Reference Example 20 using tert-butyl N-(2'-hydroxybiphenyl-4-ylmethyl)carbamate instead of tert-butyl N-(3'-hydroxybiphenyl-4-ylmethyl)carbamate and 2-iodopropane instead of 1-bromopropane.

Reference Example 28 tert-Butyl N-[3'-(4-benzyloxybutoxy)biphenyl-4-ylmethyl]carbamate

To a solution of tert-butyl N-(3'-hydroxybiphenyl-4-ylmethyl)carbamate (0.400 g), 4-benzyloxy-1-butanol (0.313 g) and triphenylphosphine (0.456 g) in tetrahydrofuran (6.7 mL) was added dropwise diisopropyl azodicarboxylate (40% toluene solution, 0.878 g), and the resulting mixture was stirred at room temperature for 75 minutes. The reaction mixture was concentrated under reduced pressure. The residue was purified by column chromatography on silica gel (eluent: dichloromethane/ethyl acetate=6/1) to give the title compound (0.551 g).

Reference Example 29 tert-Butyl N-[3'-(2-benzyloxycarbonylaminoethoxy)-biphenyl-4-ylmethyl]carbamate

The title compound was prepared in a similar manner to that described in Reference Example 28 using benzyl N-(2-hydroxyethyl)carbamate instead of 4-benzyloxy-1-butanol.

Reference Example 30

Tert-Butyl N-[3'-(3-benzyloxycarbonylaminopropoxy)biphenyl-4-yl-methyl]carbamate The title compound was prepared in a similar manner to that described in Reference Example 28 using benzyl N-(3-hydroxypropyl)carbamate instead of 4-benzyloxy-1-butanol.

Reference Example 31 tert-Butyl N-[3'-(4-benzyloxycarbonylamionbutoxy)-biphenyl-4-ylmethyl]carbamate

To a solution of tert-butyl N-(3'-hydroxybiphenyl-4-yl-methyl)carbamate (0.300 g) in N,N-dimethylformamide (4.0 mL) was added potassium carbonate (0.346 g). Then N-(4-bromo-butyl)phthalimide (0.339 g) was added, and the resulting mixture was stirred at 50° C. for 16 hours. The reaction mixture was cooled to room temperature and then partitioned between diethyl ether (35 mL) and water (10 mL). The organic layer was washed successively with water (10 mL×2) and brine (10 mL), dried over anhydrous sodium sulfate and concentrated under reduced pressure. To a solution of the residue in chloroform (6.0 mL) was added dropwise a mixture of hydrazine monohydrate (0.251 g) and ethanol (1.2 mL), and the resulting mixture was stirred at room temperature for 67 hours. The insoluble material was filtered out, and the filtrate was partitioned between dichloromethane (35 mL) and water/brine (2/1, 15 mL). The organic layer was dried over anhydrous sodium sulfate and concentrated under reduced pressure. To a solution of the residue in tetrahydrofuran (5.0 mL) was added N-carbobenzoxysuccinimide (0.250 g), and the resulting mixture was stirred at room temperature for 32 hours. The reaction mixture was concentrated under reduced pressure. The residue was purified by column chromatography on aminopropylated silica gel (eluent: hexane/ethyl acetate=2/1) to give the title compound (0.373 g).

Reference Example 32

Benzyl 3-(4,4,5,5-tetramethyl-1,3,2-dioxaborolane-2-yl)benzoate

The title compound was prepared in a similar manner to that described in Reference Example 6 using benzyl 3-bromobenzoate instead of tert-butyl N-(4-bromobenzyl)-carbamate.

Reference Example 33 tert-Butyl 3'-[(N,N-dimethylcarbamoyl)biphenyl-4-yl-methyl]carbamate

To a mixture of tert-butyl N-(4-bromobenzyl)carbamate (0.425 g), benzyl 3-(4,4,5,5-tetramethyl-1,3,2-dioxa-borolane-2-yl)benzoate (0.553 g), sodium carbonate (0.315 g), water (1.3 mL) and N,N-dimethylformamide (6.5 mL) was added tetrakis(triphenylphosphine)palladium(0) (0.086 g), and the resulting mixture was stirred at 80° C. for 70 minutes. The reaction mixture was cooled to room temperature and then partitioned between ethyl acetate (35 mL) and water (15 mL). The organic layer was washed successively with water/brine (2/1, 15 mL×2) and brine (15 mL), dried over anhydrous sodium sulfate and concentrated under reduced pressure. To a solution of the residue (1.0 g) in ethanol (7.4 mL) was added 1 mol/L aqueous sodium hydroxide (2.23 mL), and the resulting mixture was stirred at 80° C. for 80 minutes. One mol/L aqueous sodium hydroxide (2.23 mL) was added and stirring was continued for additional 2 hours. The reaction mixture was cooled to room temperature. One mol/L hydrochloric acid (4.46 mL) was added and then the whole was partitioned between ethyl acetate (35 mL) and water (10 mL). The organic layer was washed with brine (10 mL), dried over anhydrous sodium sulfate and concentrated under reduced pressure. The residue was purified by column chromatography on silica gel (eluent: hexane/ethyl acetate=3/2-1/2) to give 4'-(tert-butoxycarbonylaminomethyl)biphenyl-3-carboxylic acid (0.388 g). To a solution of the carboxylic acid (0.330 g) in N,N-dimethylformamide (5.0 mL) were added successively dimethylamine hydrochloride (0.123 g), diphenylphosphoryl azide (0.435 mL) and triethylamine (0.422 mL), and the resulting mixture was stirred at room temperature for 67.5 hours. One mol/L hydrochloric acid (10 mL) was added and the whole was extracted with ethyl acetate (30 mL). The organic layer was washed successively with water (10 mL), saturated aqueous sodium hydrogen carbonate (10 mL) and brine (10 mL), dried over anhydrous sodium sulfate and concentrated under reduced pressure. The residue was purified by column chromatography on silica gel (eluent: dichloromethane/ethyl acetate=8/1) to give the title compound (0.246 g).

Reference Example 34

3'-Benzyloxybiphenyl-4-ylmethylamine

To an ice-cold solution of tert-butyl N-(3'-benzyloxy-biphenyl-4-ylmethyl)carbamate (0.500 g) in dichloromethane (2.6 mL) was added trifluoroacetic acid (0.976 mL), and the resulting mixture was stirred under ice-cooling for 1 hour. Saturated aqueous sodium hydrogen carbonate (15 mL) was added dropwise and the whole was extracted with dichloromethane (30 mL). The organic layer was washed with saturated aqueous sodium hydrogen carbonate/brine (1/1, 10 mL), dried over anhydrous sodium sulfate and concentrated under reduced pressure to give the title compound (0.367 g).

Reference Example 35

2'-Benzyloxybiphenyl-4-ylmethylamine

The title compound was prepared in a similar manner to that described in Reference Example 34 using tert-butyl N-(2'-benzyloxybiphenyl-4-ylmethyl)carbamate instead of tert-butyl N-(3'-benzyloxybiphenyl-4-ylmethyl)carbamate.

Reference Example 36

4'-Hydroxybiphenyl-4-ylmethylamine

The title compound was prepared in a similar manner to that described in Reference Example 34 using tert-butyl N-(4'-hydroxybiphenyl-4-ylmethyl)carbamate instead of tert-butyl N-(3'-benzyloxybiphenyl-4-ylmethyl)carbamate.

Reference Example 37

3'-Methoxycarbonylbiphenyl-4-ylmethylamine

The title compound was prepared in a similar manner to that described in Reference Example 34 using tert-butyl N-(3'-methoxycarbonylbiphenyl-4-ylmethyl) carbamate instead of tert-butyl N-(3'-benzyloxybiphenyl-4-ylmethyl) carbamate.

Reference Example 38

3'-Pentyloxybiphenyl-4-ylmethylamine

The title compound was prepared in a similar manner to that described in Reference Example 34 using tert-butyl N-(3'-pentyloxybiphenyl-4-ylmethyl)carbamate instead of tert-butyl N-(3'-benzyloxybiphenyl-4-ylmethyl)carbamate.

Reference Example 39

3'-Isopropoxybiphenyl-4-ylmethylamine

The title compound was prepared in a similar manner to that described in Reference Example 34 using tert-butyl N-(3'-isopropoxybiphenyl-4-ylmethyl)carbamate instead of tert-butyl N-(3'-benzyloxybiphenyl-4-ylmethyl)carbamate.

Reference Example 40

3'-Benzyloxycarbonylbiphenyl-4-ylmethylamine

The title compound was prepared in a similar manner to that described in Reference Example 34 using tert-butyl N-(3'-benzyloxycarbonylbiphenyl-4-ylmethyl)carbamate instead of tert-butyl N-(3'-benzyloxybiphenyl-4-ylmethyl)-carbamate.

Reference Example 41

3'-Dimethylaminobiphenyl-4-ylmethylamine

The title compound was prepared in a similar manner to that described in Reference Example 34 using tert-butyl N-(3'-dimethylaminobiphenyl-4-ylmethyl) carbamate instead of tert-butyl N-(3'-benzyloxybiphenyl-4-ylmethyl) carbamate.

Reference Example 42

3'-Benzyloxycarbonylaminobiphenyl-4-ylmethylamine

The title compound was prepared in a similar manner to that described in Reference Example 34 using tert-butyl N-(3'-benzyloxycarbonylaminobiphenyl-4-ylmethyl)carbamate instead of tert-butyl N-(3'-benzyloxybiphenyl-4-ylmethyl)-carbamate.

Reference Example 43

3'-(2-Hydroxyethyl)biphenyl-4-ylmethylamine

The title compound was prepared in a similar manner to that described in Reference Example 34 using tert-butyl N-[3'-(2-hydroxyethyl)biphenyl-4-ylmethyl] carbamate instead of tert-butyl N-(3'-benzyloxybiphenyl-4-ylmethyl) carbamate.

Reference Example 44

4-Pyridine-3-ylbenzylamine

The title compound was prepared in a similar manner to that described in Reference Example 34 using tert-butyl N-(4-pyridine-3-ylbenzyl)carbamate instead of tert-butyl N-(3'-benzyloxybiphenyl-4-ylmethyl)carbamate.

Reference Example 45

3'-Propoxybiphenyl-4-ylmethylamine

The title compound was prepared in a similar manner to that described in Reference Example 34 using tert-butyl N-(3'-propoxybiphenyl-4-ylmethyl)carbamate instead of tert-butyl N-(3'-benzyloxybiphenyl-4-ylmethyl)carbamate.

Reference Example 46

3'-Butoxybiphenyl-4-Ylmethylamine

The title compound was prepared in a similar manner to that described in Reference Example 34 using tert-butyl N-(3'-butoxybiphenyl-4-ylmethyl)carbamate instead of tert-butyl N-(3'-benzyloxybiphenyl-4-ylmethyl)carbamate.

Reference Example 47

3'-(3-Benzyloxypropoxy)biphenyl-4-ylmethylamine

The title compound was prepared in a similar manner to that described in Reference Example 34 using tert-butyl N-[3'-(3-benzyloxypropoxy)biphenyl-4-ylmethyl]carbamate instead of tert-butyl N-(3'-benzyloxybiphenyl-4-ylmethyl)-carbamate.

Reference Example 48

2'-(2-Methoxyethoxy)biphenyl-4-ylmethylamine

The title compound was prepared in a similar manner to that described in Reference Example 34 using tert-butyl N-[3'-(2-methoxyethoxy)biphenyl-4-ylmethyl]carbamate instead of tert-butyl N-(3'-benzyloxybiphenyl-4-ylmethyl)-carbamate.

Reference Example 49

2'-Propoxybiphenyl-4-ylmethylamine

The title compound was prepared in a similar manner to that described in Reference Example 34 using tert-butyl N-(2'-propoxybiphenyl-4-ylmethyl)carbamate instead of tert-butyl N-(3'-benzyloxybiphenyl-4-ylmethyl)carbamate.

Reference Example 50

2'-Butoxybiphenyl-4-ylmethylamine

The title compound was prepared in a similar manner to that described in Reference Example 34 using tert-butyl N-(2'-butoxybiphenyl-4-ylmethyl)carbamate instead of tert-butyl N-(3'-benzyloxybiphenyl-4-ylmethyl)carbamate.

Reference Example 51

2'-Pentyloxybiphenyl-4-ylmethylamine

The title compound was prepared in a similar manner to that described in Reference Example 34 using tert-butyl N-(2'-pentyloxybiphenyl-4-ylmethyl)carbamate instead of tert-butyl N-(3'-benzyloxybiphenyl-4-ylmethyl)carbamate.

Reference Example 52

2-Isopropoxybiphenyl-4-ylmethylamine

The title compound was prepared in a similar manner to that described in Reference Example 34 using tert-butyl N-(2'-isopropoxybiphenyl-4-ylmethyl)carbamate instead of tert-butyl N-(3'-benzyloxybiphenyl-4-ylmethyl)carbamate.

Reference Example 53

3'-(4-Benzyloxybutoxy)biphenyl-4-ylmethylamine

The title compound was prepared in a similar manner to that described in Reference Example 34 using tert-butyl N-[3'-(4-benzyloxybutoxy)biphenyl-4-ylmethyl]carbamate instead of tert-butyl N-(3'-benzyloxybiphenyl-4-ylmethyl)-carbamate.

Reference Example 54

3'-(2-Benzyloxycarbonylaminoethoxy)biphenyl-4-ylmethyl-amine

The title compound was prepared in a similar manner to that described in Reference Example 34 using tert-butyl N-[3'-(2-benzyloxycarbonylaminoethoxy)biphenyl-4-ylmethyl]carbamate instead of tert-butyl N-(3'-benzyloxybiphenyl-4-ylmethyl)carbamate.

Reference Example 55

3'-(3-Benzyloxycarbonylaminopropoxy)biphenyl-4-ylmethyl-amine

The title compound was prepared in a similar manner to that described in Reference Example 34 using tert-butyl N-[3'-(3-benzyloxycarbonylaminopropoxy)biphenyl-4-ylmethyl]carbamate instead of tert-butyl N-(3'-benzyloxy-biphenyl-4-ylmethyl)carbamate.

Reference Example 56

3'-(4-Benzyloxycarbonylaminobutoxy)biphenyl-4-ylmethyl-amine

The title compound was prepared in a similar manner to that described in Reference Example 34 using tert-butyl N-[3'-(4-benzyloxycarbonylaminobutoxy)biphenyl-4-ylmethyl]carbamate instead of tert-butyl N-(3'-benzyloxy-biphenyl-4-ylmethyl)carbamate.

Reference Example 57

3'-(N,N-Dimethylcarbamoyl)biphenyl-4-ylmethylamine

The title compound was prepared in a similar manner to that described in Reference Example 34 using tert-butyl N-[3'-(N,N-dimethylcarbamoyl)biphenyl-4-ylmethyl]carbamate instead of tert-butyl N-(3'-benzyloxybiphenyl-4-ylmethyl)-carbamate.

Reference Example 58

3-Methoxy-4-phenylbenzaldehyde

To an ice-cold solution of 4-hydroxy-3-methoxy-benzaldehyde (1.00 g) in dichloromethane (22 mL) was added triethylamine (1.37 mL). Then trifluoromethanesulfonic anhydride (1.40 mL) was added dropwise, and the resulting mixture was stirred under ice-cooling for 45 minutes. Ice was added and the whole was partitioned between AcOEt (60 mL) and saturated aqueous sodium hydrogen carbonate (30 mL). The organic layer was washed successively with water/brine (3/1, 40 mL) and brine (30 mL), dried over anhydrous sodium sulfate and concentrated under reduced pressure. The residue (1.98 g) was dissolved in N,N-dimethylformamide (25 mL). Phenylboronic acid (0.882 g), sodium carbonate (1.39 g), water (5 mL) and tetrakis(triphenyl-phosphine)palladium(0) (0.380 g) were added, and the resulting mixture was stirred at 80° C. for 2.5 hours. The reaction mixture was cooled to room temperature and then partitioned between ethyl acetate (70 mL) and water (30 mL). The organic layer was washed with water/brine (1/1, 30 mL×2), dried over anhydrous sodium sulfate and concentrated under reduced pressure. The residue was purified by column chromatography on silica gel (eluent: hexane/ethyl acetate=10/1 to 5/1) to give the title compound (1.12 g).

Reference Example 59

2-Methoxy-4-phenylbenzaldehyde

The title compound was prepared in a similar manner to that described in Reference Example 58 using 4-hydroxy-2-methoxybenzaldehyde instead of 4-hydroxy-3-methoxy-benzaldehyde.

Reference Example 60

2-Fluoro-4-phenylbenzaldehyde

The title compound was prepared in a similar manner to that described in Reference Example 2 using 4-bromo-2-fluoro-benzaldehyde instead of tert-butyl N-(4-bromobenzyl)carbamate and phenylboronic acid instead of 3-benzyloxyphenylboronic acid.

Reference Example 61

2-(Methylthio)-4-phenylbenzaldehyde

To a solution of 2-fluoro-4-phenylbenzaldehyde (0.400 g) in N,N-dimethylformamide (4 mL) was added sodium methane-thiolate (0.210 g), and the resulting mixture was stirred at 50° C. for 2.5 hours. The reaction mixture was cooled to room temperature and then partitioned between diethyl ether (30 mL) and water (10 mL). The organic layer was washed successively with water (10 mL×2) and brine (10 mL), dried over anhydrous sodium sulfate and concentrated under reduced pressure to give the title compound (0.387 g).

Reference Example 62

2-(Phenylthio)benzaldehyde

To a solution of 4-fluorobenzaldehyde (0.443 mL) in 1,3-dimethyl-2-imidazolidinone (6.4 mL) was added potassium carbonate (0.659 g). Then benzenethiol (0.326 mL) was added, and the resulting mixture was stirred at 120° C. for 2.5 hours. The reaction mixture was cooled to room temperature and then partitioned between diethyl ether (60 mL) and water (15 mL). The organic layer was washed successively with water (15 mL×2) and brine (15 mL), dried over anhydrous sodium sulfate and concentrated under reduced pressure to give the title compound (0.826 g).

Reference Example 63

N-(2-Methoxybiphenyl-4-ylmethyl)phthalimide

To a solution of 3-methoxy-4-phenylbenzaldehyde (0.300 g) in ethanol (2.8 mL) was added sodium borohydride (0.027 g), and the resulting mixture was stirred at room temperature for 50 minutes. Saturated aqueous ammonium chloride/water (1/1, 10 mL) was added dropwise and the whole was extracted with ethyl acetate (30 mL). The organic layer was washed with brine (10 mL), dried over anhydrous sodium sulfate and concentrated under reduced pressure. The residue (0.291 g) was dissolved in tetrahydrofuran (2.7 mL). After addition of phthalimide (0.260 g) and triphenylphosphine (0.463 g), diisopropyl azodicarboxylate (40% toluene solution, 0.893 g) was added dropwise and the resulting mixture was stirred at room temperature for 1.5 hours. The reaction mixture was concentrated under reduced pressure. The residue was purified by column chromatography on silica gel (eluent: hexane/ethyl acetate=5/1) to give the title compound (0.417 g).

Reference Example 64

N-(3-Methoxybiphenyl-4-ylmethyl)phthalimide

The title compound was prepared in a similar manner to that described in Reference Example 63-using 2-methoxy-4-phenylbenzaldehyde instead of 3-methoxy-4-phenyl-benzaldehyde.

Reference Example 65

N-(3-Benzyloxybiphenyl-4-ylmethyl)phthalimide

To an ice-cold solution of 2-methoxy-4-phenyl-benzaldehyde (0.418 g) in dichloromethane (9.8 mL) was added aluminium chloride (0.525 g), and the resulting mixture was stirred at room temperature for 19 hours. Water (15 mL) was added dropwise and the whole was extracted with ethyl acetate (45 mL) The organic layer was washed successively with 1 mol/L hydrochloric acid (15 mL), saturated aqueous sodium hydrogen carbonate (15 mL) and brine (15 mL), dried over anhydrous sodium sulfate and concentrated under reduced pressure. The residue (0.456 g) was dissolved in N,N-dimethylformamide (4.9 mL). Potassium carbonate (0.354 g) and benzyl bromide (0.281 mL) were added, and the resulting mixture was stirred at room temperature for 12.5 hours. The reaction mixture was partitioned between diethyl ether (40 mL) and water (10 mL). The organic layer was washed successively with water (10 mL×2) and brine (10 mL), dried over anhydrous sodium sulfate and concentrated under reduced pressure. The residue (0.556 g) was suspended in ethanol/tetrahydrofuran (3/1, 6.4 mL). Sodium borohydride (0.037 g) was added, and the resulting mixture was stirred at room temperature for 20 minutes. Saturated aqueous ammonium chloride/water (1/1, 10 mL) was added dropwise and the whole was extracted with ethyl acetate (35 mL). The organic layer was washed with brine (10 mL), dried over anhydrous sodium sulfate and concentrated under reduced pressure. The residue (0.580 g) was dissolved in tetrahydrofuran (6.4 mL). After addition of phthalimide (0.369 g) and triphenylphosphine (0.658 g), diisopropylazodicarboxylate (40% toluene solution, 1.27 g) was added dropwise, and the resulting mixture was stirred at room temperature for 88 hours. The reaction mixture was concentrated under reduced pressure. The residue was purified by column chromatography on silica gel (eluent: hexane/ethylacetate=6/1) to give the title compound (0.469 g).

Reference Example 66

N-(Naphthalene-2-ylmethyl)phthalimide

To a solution of 2-(bromomethyl)naphthalene (0.500 g) in N,N-dimethylformamide (11 mL) was added potassium phthalimide (0.461 g), and the resulting mixture was stirred at 50° C. for 2 hours. The reaction mixture was partitioned between ethyl acetate (50 mL) and water (15 mL). The organic layer was washed successively with water (15 mL×2) and brine (15 mL), dried over anhydrous sodium sulfate and concentrated under reduced pressure to give the title compound (0.380 g).

Reference Example 67

N-(3-Fluorobiphenyl-4-ylmethyl)phthalimide

To a solution of 2-fluoro-4-phenylbenzaldehyde (0.400 g) in ethanol/tetrahydrofuran (2/1, 6.6 mL) was added sodium borohydride (0.038 g), and the resulting mixture was stirred at room temperature for 6 hours. Saturated aqueous ammonium chloride/water (1/1, 10 mL) was added and the whole was extracted with ethyl acetate (30 mL). The organic layer was washed with brine (10 mL), dried over anhydrous sodium sulfate and concentrated under reduced pressure. The residue (0.351 g) was dissolved in chloroform (4.3 mL). Thionyl chloride (0.190 mL) was added dropwise at room temperature, and the resulting mixture was stirred at 60° C. for 3 hours. The reaction mixture was cooled to room temperature and then concentrated under reduced pressure. The residue (0.411 g) was dissolved in N,N-dimethylformamide (4.3 mL). Potassium phthalimide (0.418 g) was added, and the resulting mixture was stirred at 60° C. for 13.5 hours. The reaction mixture was cooled to room temperature and then partitioned between diethylether/ethylacetate (5/1, 60 mL) and water (10 mL) The organic layer was washed successively with water (10 mL×2) and brine (10 mL), dried over anhydrous sodium sulfate and concentrated under reduced pressure. n-Hexane was added to the residue, and then the precipitate was collected by filtration, washed with n-hexane and dried under reduced pressure to give the title compound (0.413 g).

Reference Example 68

N-[3-(Methylthio)biphenyl-4-ylmethyl]phthalimide

The title compound was prepared in a similar manner to that described in Reference Example 67 using 2-methylthio)-4-phenylbenzaldehyde instead of 2-fluoro-4-phenylbenzaldehyde.

Reference Example 69

N-(4-Benzylbenzyl)phthalimide

To a solution of 4-benzoylbenzoic acid (2.00 g) in trifluoroacetic acid (30 mL) was added dropwise triethylsilane (3.53 mL), and the resulting mixture was stirred at room temperature for 3 hours. The reaction mixture was concentrated under reduced pressure, and then n-hexane was added to the residue. The precipitate was collected by filtration, washed with n-hexane and dried under reduced pressure at 60° C. to give 4-benzylbenzoic acid (1.66 g). To an ice-cold suspension of lithium aluminium hydride (0.315 g) in tetrahydrofuran (45 mL) was added dropwise a solution of 4-benzylbenzoic acid (1.60 g) in tetrahydrofuran (30 mL), and the resulting mixture was stirred at room temperature for 4.5 hours. The reaction was quenched by sequential addition of water (0.320 mL), 15% aqueous sodium hydroxide (0.320 mL) and water (0.320 mL). The insoluble material was filtered out and the filtrate was concentrated under reduced pressure to give 4-benzylbenzyl alcohol (1.56 g). 4-Benzylbenzylalcohol (1.56 g) was dissolved in tetrahydrofuran (39 mL). After addition of phthalimide (1.39 g) and triphenylphosphine (2.68 g), diisopropylazodicarboxylate (40% toluene solution, 5.17 g) was added dropwise, and the resulting mixture was stirred at room temperature for 1 hour. The reaction mixture was concentrated under reduced pressure and the residue was purified by column chromatography on silica gel (eluent: hexane/ethyl acetate=5/1) to give the title compound (1.87 g).

Reference Example 70

N-(4-Phenoxybenzyl)phthalimide

The title compound was prepared in a similar manner to that described in Reference Example 63 using 4-phenoxybenzaldehyde instead of 3-methoxy-4-phenylbenzaldehyde.

Reference Example 71

N-(4-Benzyloxybenzyl)phthalimide

The title compound was prepared in a similar manner to that described in Reference Example 63 using 4-benzyloxybenzaldehyde instead of 3-methoxy-4-phenylbenzaldehyde.

Reference Example 72

N-[4-(Phenylthio)benzyl]phthalimide

The title compound was prepared in a similar manner to that described in Reference Example 63 using 4-(phenylthio)-benzaldehyde instead of 3-methoxy-4-phenylbenzaldehyde.

Reference Example 73

N-(3-Benzyloxybenzyl)phthalimide

The title compound was prepared in a similar manner to that described in Reference Example 63 using 3-benzyloxybenzaldehyde instead of 3-methoxy-4-phenylbenzaldehyde.

Reference Example 74

2-Methoxybiphenyl-4-ylmethylamine

To a solution of N-(2-methoxybiphenyl-4-ylmethyl)-phthalimide (0.414 g) in chloroform (5.0 mL) was added dropwise a mixture of hydrazinemonohydrate (0.241 g) and ethanol (1.0 mL), and the resulting mixture was stirred at room temperature for 31 hours. The insoluble material was filtered out, and the filtrate was partitioned between dichloromethane (40 mL) and water (15 mL). The organic layer was washed with brine (10 mL), dried over anhydrous sodium sulfate and concentrated under reduced pressure to give the title compound (0.259 g).

Reference Example 75

3-Methoxybiphenyl-4-ylmethylamine

The title compound was prepared in a similar manner to that described in Reference Example 74 using N-(3-methoxybiphenyl-4-ylmethyl)phthalimide instead of N-(2-methoxybiphenyl-4-ylmethyl)phthalimide.

Reference Example 76

3-Benzyloxybipenyl-4-ylmethylamine

The title compound was prepared in a similar manner to that described in Reference Example 74 using N-(3-benzyloxybiphenyl-4-ylmethyl)phthalimide instead of N-(2-methoxybiphenyl-4-ylmethyl)phthalimide.

Reference Example 77

Naphthalene-2-ylmethylamine

The title compound was prepared in a similar manner to that described in Reference Example 74 using N-(naphthalene-2-ylmethyl)phthalimide instead of N-(2-methoxybiphenyl-4-ylmethyl)phthalimide.

Reference Example 78

3-Fluorobiphenyl-4-ylmethylamine

The title compound was prepared in a similar manner to that described in Reference Example 74 using N-(3-fluorobiphenyl-4-ylmethyl)phthalimide instead of N-(2-methoxybiphenyl-4-ylmethyl)phthalimide.

Reference Example 79

3-(Methylthio)biphenyl-4-ylmethylamine

The title compound was prepared in a similar manner to that described in Reference Example 74 using N-[3-(methylthio)biphenyl-4-ylmethyl] phthalimide instead of N-(2-methoxybiphenyl-4-ylmethyl)phthalimide.

Reference Example 80

4-Benzylbenzylamine

The title compound was prepared in a similar manner to that described in Reference Example 74 using N-(4-benzylbenzyl)phthalimide instead of N-(2-methoxybiphenyl-4-ylmethyl)phthalimide.

Reference Example 81

4-Phenoxybenzylamine

The title compound was prepared in a similar manner to that described in Reference Example 74 using N-(4-phenoxybenzyl)phthalimide instead of N-(2-methoxybiphenyl-4-ylmethyl)phthalimide.

Reference Example 82

4-Benzyloxybenzylamine

The title compound was prepared in a similar manner to that described in Reference Example 74 using N-(4-benzyloxy-benzyl)phthalimide instead of N-(2-methoxybiphenyl-4-yl-methyl)phthalimide.

Reference Example 83

4-(Phenylthio)benzylamine

The title compound was prepared in a similar manner to that described in Reference Example 74 using N-[4-(phenylthio)-benzyl]phthalimide instead of N-(2-methoxybiphenyl-4-yl-methyl)phthalimide.

Reference Example 84

3-Benzyloxybenzylamine

The title compound was prepared in a similar manner to that described in Reference Example 74 using N-(3-benzyloxy-benzyl)phthalimide instead of N-(2-methoxybiphenyl-4-yl-methyl(phthalimide.

Reference Example 85

3-Methoxy-4-phenylbenzonitrile

The title compound was prepared in a similar manner to that described in Reference Example 58 using 4-hydroxy-3-methoxybenzonitrile instead of 4-hydroxy-3-methoxy-benzaldehyde.

Reference Example 86

3-Hydroxy-4-phenylbenzonitrile

To an ice-cold solution of 3-methoxy 4-phenyl-benzonitrile (1.42 g) in dichloromethane (27 mL) was added dropwise boron tribromide (1.27 mL). The resulting mixture was stirred at room temperature for 1 hour and then at 30° C. for 38 hours. Boron tribromide (0.634 mL) was added dropwise and stirring was continued for additional 23 hours. The reaction mixture was poured into ice (40 g) and the whole was extracted with ethyl acetate (75 mL). The organic layer was washed successively with 1 mol/L hydrochloric acid (25 mL), saturated aqueous sodium hydrogen carbonate (25 mL) and brine (25 mL), dried over anhydrous sodium sulfate and concentrated under reduced pressure to give the title compound (1.21 g).

Reference Example 87

3-Benzyloxy-4-phenylbenzonitrile

The title compound was prepared in a similar manner to that described in Reference Example 20 using 3-hydroxy-4-phenylbenzonitrile instead of tert-butyl N-(3'-hydroxybiphenyl-4-ylmethyl)carbamate and benzyl bromide instead of 1-bromopropane.

Reference Example 88

3-Methyl-4-phenylbenzonitrile

The title compound was prepared in a similar manner to that described in Reference Example 2 using 4-bromo-3-methylbenzonitrile instead of tert-butyl N-(4-bromobenzyl)carbamate and phenylboronic acid instead of 3-benzyloxyphenylboronic acid.

Reference Example 89

2-Methyl-4-phenylbenzonitrile

The title compound was prepared in a similar manner to that described in Reference Example 2 using 4-bromo-2-methylbenzonitrile instead of tert-butyl N-(4-bromobenzyl)carbamate and phenylboronic acid instead of 3-benzyloxyphenylboronic acid.

Reference Example 90

2-Benzyloxybenzonitrile

The title compound was prepared in a similar manner to that described in Reference Example 20 using 2-cyanophenol instead of tert-butyl N-(3'-hydroxybiphenyl-4-ylmethyl)-carbamate and benzyl bromide instead of 1-bromopropane.

Reference Example 91

4-(Pyridine-2-yl)benzonitrile

The title compound was prepared in a similar manner to that described in Reference Example 11 using 2-bromopyridine instead of 1-bromo-3-pentyloxybenzene and 4-cyanophenylboronic acid instead of tert-butyl N-[ 4-(4,4,5,5-tetramethyl-1,3,2-dioxaborolane-2-yl)-benzyl]carbamate.

Reference Example 92

4-(Pyridine-4-yl)benzonitrile

The title compound was prepared in a similar manner to that described in Reference Example 11 using 4-bromopyridine hydrochloride instead of 1-bromo-3-pentyloxybenzene and 4-cyanophenylboronic acid instead of tert-butyl N-[4-(4,4,5,5-tetramethyl-1,3,2-dioxaborolane-2-yl)-benzyl]carbamate.

Reference Example 93

2-Benzyloxybiphenyl-4-ylmethylamine

To a suspension of lithium alminiumhydride (0.399 g) in tetrahydrofuran (45 mL) was added dropwise a solution of 3-benzyloxy-4-phenylbenzonitrile (2.00 g) in tetrahydrofuran (25 mL) at room temperature, and the resulting mixture was stirred at 60° C. for 3 hours. The reaction mixture was cooled to room temperature and then quenched by sequential addition of water (0.399 mL), 15% aqueous sodium hydroxide (0.399 mL) and water (0.399 mL). After addition of anhydrous sodium sulfate (20 g), the mixture was stirred at room temperature for 4 hours and the insoluble material was filtered out. The filtrate was concentrated under reduced pressure to give the title compound (1.97 g).

Reference Example 94

2-Methylbiphenyl-4-ylmethylamine

The title compound was prepared in a similar manner to that described in Reference Example 93 using 3-methyl-4-phenyl-benzonitrile instead of 3-benzyloxy-4-phenylbenzonitrile.

Reference Example 95

3-Methylbiphenyl-4-ylmethylamine

The title compound was prepared in a similar manner to that described in Reference Example 93 using 2-methyl-4-phenyl-benzonitrile instead of 3-benzyloxy-4-phenylbenzonitrile.

Reference Example 96

2-Benzyloxybenzylamine

The title compound was prepared in a similar manner to that described in Reference Example 93 using 2-benzyloxybenzonitrile instead of 3-benzyloxy-4-phenylbenzonitrile.

Reference Example 97

4-(Pyridine-2-yl)benzylamine

The title compound was prepared in a similar manner to that described in Reference Example 93 using 4-(Pyridine-2-yl)-benzonitrile instead of 3-benzyloxy-4-phenylbenzonitrile.

Reference Example 98

4-(Pyridine-4-yl)benzylamine

The title compound was prepared in a similar manner to that described in Reference Example 93 using 4-(pyridine-4-yl)-benzonitrile instead of 3-benzyloxy-4-phenylbenzonitrile.

Reference Example 99

2-(4-Benzyloxybutoxy)biphenyl-4-ylmethylamine

To a solution of 3-hydroxy-4-phenylbenzonitrile (0.600 g) in N,N-dimethylformamide (4.1 mL) was added potassium carbonate (0.850 g). Then 4-benzyloxy-1-bromobutane (0.703 mL) was added, and the resulting mixture was stirred at 50° C. for 26.5 hours. The reaction mixture was cooled to room temperature and then partitioned between diethyl ether (35 mL) and water (10 mL). The organic layer was washed successively with water (10 mL×2) and brine (10 mL), dried over anhydrous sodium sulfate and concentrated under reduced pressure. The residue (1.25 g) was dissolved in tetrahydrofuran (13 mL) and added to an ice-cold suspension of lithium alminiumhydride (0.175 g) in tetrahydrofuran (18 mL), and the resulting mixture was stirred at 60° C. for 2 hours. The reaction mixture was cooled to room temperature and then quenched by sequential addition of water (0.175 mL), 15% aqueous sodium hydroxide (0.175 mL) and water (0.175 mL). After addition of anhydrous sodium sulfate (10.4 g), the mixture was stirred at room temperature for 13 hours and the insoluble material was filtered out. The filtrate was concentrated under reduced pressure to give the title compound (1.21 g).

Reference Example 100

Tert-Butyl N-(2-hydroxybiphenyl-4-ylmethyl)carbamate

To a solution of 2-benzyloxybiphenyl-4-ylmethylamine (1.87 g) in tetrahydrofuran (25.8 mL) was added dropwise di-tert-butyl dicarbonate (1.93 mL), and the resulting mixture was stirred at room temperature for 13 hours. Then 10% palladium on carbon (56.2 wt % $H_2O$, 0.854 g) was added and stirring was continued at room temperature for 10 hours under a hydrogen atmosphere. The insoluble material was filtered out and the filtrate was concentrated under reduced pressure. The residue was purified by column chromatography on silica gel (eluent: hexane/ethyl acetate=3/1) to give the title compound (1.77 g)

Reference Example 101

Tert-Butyl N-[2-(3-benzyloxycarbonylaminopropoxy)biphenyl-4-ylmethyl]carbamate A solution of tert-butyl N-(2-hydroxybiphenyl-4-yl-methyl)carbamate (0.30 g), benzyl N-(3-hydroxypropyl)-carbamate (0.273 g) and triphenylphosphine (0.342 g) in tetrahydrofuran (4.0 mL) was stirred at 50° C. for 30 minutes. Then diisopropyl azodicarboxylate (40% toluene solution, 0.701 mL) was added dropwise, and the resulting mixture was stirred at 50° C. for 3 hours. The reaction mixture was concentrated under reduced pressure. The residue was purified by column chromatography on silica gel (eluent: hexane/ethylacetate=3/1) to give the title compound (0.750 g).

Reference Example 102 tert-Butyl N-[2-(3-dimethylaminopropoxy)biphenyl-4-yl-methyl]carbamate

The title compound was prepared in a similar manner to that described in Reference Example 101 using 3-dimethylamino-1-propanol instead of benzyl N-(3-hydroxylpropyl) carbamate.

Reference Example 103

2-(3-Benzyloxycarbonylaminopropoxy)biphenyl-4-ylmethyl-amine

The title compound was prepared in a similar manner to that described in Reference Example 34 using tert-butyl N-[2-(3-benzyloxycarbonylaminopropoxy)biphenyl-4-yl-methyl] carbamate instead of tert-butyl N-(3'-benzyloxy-biphenyl-4-ylmethyl)carbamate.

Reference Example 104

2-(3-Dimethylaminopropoxy)biphenyl-4-ylmethylamine

To an ice-cold solution of tert-butyl N-[ 2-(3-dimethylaminopropoxy)biphenyl-4-ylmethyl]carbamate (0.487 g) in dichloromethane (1.7 mL) was added dropwise trifluoroacetic acid (1.29 mL), and the resulting mixture was stirred under ice-cooling for 1.5 hours. The reaction mixture was diluted with dichloromethane (30 mL), and then potassium carbonate powder (2.93 g) was added. The insoluble material was filtered out and the filtrate was concentrated under reduced pressure to give the title compound (0.340 g).

Reference Example 105

4-Benzyloxy-3-hydroxybenzaldehyde

To a mixture of 3,4-dihydroxybenzaldehyde (21.6 g), potassium carbonate (21.56 g) and N,N-dimethylformamide (200 mL) was added dropwise benzyl bromide (18.5 mL) under ice-cooling, and the resulting mixture was stirred at room temperature for 16 hours. Two mol/L hydrochloric acid (40 mL) was added to the reaction mixture and the whole was extracted with ethyl acetate. The organic layer was washed with brine, dried over anhydrous magnesium sulfate and concentrated under reduced pressure. The residue was purified by column chromatography on silica gel (eluent: ethyl acetate/hexane=1/5) to give the title compound (19.0 g).

Reference Example 106

4-Benzyloxy-3-hydroxybenzonitrile

A mixture of 4-benzyloxy-3-hydroxybenzaldehyde (19.0 g), hydroxylammonium chloride (8.6 g), sodium acetate (13.7 g), water (30 mL) and ethanol (150 mL) was stirred at 80° C. for 8 hours. Water (100 mL) was added to the reaction mixture and the whole was extracted with ethyl acetate. The organic layer was washed with brine, dried over anhydrous magnesium sulfate and concentrated under reduced pressure. The residue was dissolved in dichloromethane (100 mL), and then pyridine (20 mL) was added. Trifluoroacetic anhydride (35.3 mL) was added dropwise under ice-cooling, and the resulting mixture was stirred at room temperature for 6 hours. Two mol/L hydrochloric acid was added to the reaction mixture and the whole was extracted with ethyl acetate. The organic layer was washed with saturated aqueous sodium hydrogen carbonate and brine, dried over anhydrous magnesium sulfate and concentrated under reduced pressure. The residue was purified by column chromatography on silica gel (eluent: ethyl acetate/hexane=1/10) to give the title compound (1.0 g).

Reference Example 107

4-Benzloxy-3-(4-benzyloxybutoxy)benzonitrile

To a solution of 4-benzyloxy-3-hydroxybenzonitrile (3.4 g) in N,N-dimethylformamide (20 mL) was added potassium carbonate (6.3 g). Then benzyl 4-bromobutyl ether (3 mL) was added, and the resulting mixture was stirred at 50° C. for 16 hours. Two mol/L hydrochloric acid (40 mL) was added dropwise to the reaction mixture and the whole was extracted with ethyl acetate. The organic layer was washed with brine, dried over anhydrous magnesium sulfate and concentrated under reduced pressure. The residue was purified by column chromatography on silica gel (eluent: ethyl acetate/hexane=1/5) to give the title compound (5.9 g).

Reference Example 108

4-Hydroxy-3-(4-hydroxybutoxy)benzonitrile

4-Benzyloxy-3-(4-benzyloxybutoxy)benzonitrile (4.0 g) was dissolved in a mixed solvent of trifluoroacetic acid (9 mL), dimethyl sulfide (0.5 mL) and water (5 mL), and the resulting mixture was stirred at room temperature for 18 hours. The reaction mixture was concentrated under reduced pressure and the residue was purified by column chromatography on silica gel (eluent: ethyl acetate/hexane=1/5) to give the title compound (1.0 g).

Reference Example 109

4-(3-Benzyloxyphenyl)-3-(4-hydroxybutoxy)benzonitrile

4-Hydroxy-3-(4-hydroxybutoxy)benzonitrile (1.0 g) and pyridine (1.9 mL) were dissolved in dichloromethane (15 mL), and then trifluoromethanesulfonic anhydride (1.7 mL) was added dropwise under ice-cooling with stirring. The resulting mixture was stirred at room temperature for 30 minutes, 1 mol/L hydrochloric acid (50 mL) was added and the whole was extracted with ethyl acetate. The organic layer was washed successively with saturated sodium hydrogen carbonate and brine, dried over anhydrous magnesium sulfate and concentrated under reduced pressure. A mixture of the residue, 3-benzyloxyphenylboronic acid (1.3 g), sodium carbonate (1.0 g), tetrakis(triphenyl-phosphine)palladium(0) (0.3 g), water (2 mL) and N,N-dimethylformamide (15 mL) was stirred at 80° C. for 12 hours. One mol/L hydrochloric acid (30 mL) was added dropwise to the reaction mixture and the whole was extracted with ethyl acetate. The organic layer was washed with brine, dried over anhydrous magnesium sulfate and concentrated under reduced pressure. The residue was purified on column chromatography on aminopropylated silica gel (eluent: ethyl acetate/hexane=1/5) to give the title compound (0.8 g).

Reference Example 110

3'-Benzyloxy-2-(4-hydorxybutoxy)biphenyl-4-ylmethylamine

The title compound was prepared in a similar manner to that described in Reference Example 93 using 4-(3-benzyloxyphenyl)-3-(4-hydoxybutoxy)benzonitrile instead of 3-benzyloxy-4-phenylbenzonitrile.

Reference Example 111

2-Hydroxybiphenyl-4-ylmethylamine

The title compound was prepared in a similar manner to that described in Reference Example 34 using tert-butyl N-(2'-hydroxybiphenyl-4-ylmethyl)carbamate instead of tert-butyl N-(3'-benzyloxybiphenyl-4-ylmethyl)carbamate.

Reference Example 112

8-(3'-Benzyloxybiphenyl-4-ylmethylamino)-2',3',5'-tris-O-(tert-butyldimethylsilyl)adenosine A mixture of 8-bromo-2',3',5'-tris-O-(tert-butyl-dimethylsilyl)adenosine (0.660 g), 3'-benzyloxybiphenyl-4-ylmethylamine (0.832 g) and N,N-diisopropylethylamine (0.667 mL) in 1-propanol (9.6 mL) was heated under reflux with stirring for 62 hours. The reaction mixture was cooled to room temperature and then partitioned between ethyl acetate (35 mL) and 10% aqueous citric acid (10 mL). The organic layer was washed successively with 10% aqueous citric acid (10 mL×2), saturated aqueous sodium hydrogen carbonate (10 mL) and brine (10 mL), dried over anhydrous sodium sulfate and concentrated under reduced pressure. The residue was purified by column chromatography on aminopropylated silica gel (eluent: hexane/ethyl acetate=2/1) to give the title compound (0.716 g).

Reference Example 113

2',3',5'-Tris-O-(tert-butyldimethylsilyl)-8-(3'-hydroxy-biphenyl-4-ylmethylamino)adenosine A mixture of 8-(3'-benzyloxybiphenyl-4-ylmethylamino)-2',3',5'-tris-O-(tert-butyldimethylsilyl)adenosine (0.713 g) and 10% palladium on carbon (55.4 wt % $H_2O$, 0.480 g) in ethyl acetate (11 mL) was stirred at room temperature for 23 hours under a hydrogen atmosphere. The insoluble material was filtered out and the filtrate was concentrated under reduced pressure to give the title compound (0.615 g).

Reference Example 114

2',3',5'-Tris-O-(tert-butyldimethylsilyl)-8-(3'-methoxy-carbonylmethoxybiphenyl-4-ylmethylamino)adenosine To a solution of 2',3',5'-tris-O-(tert-butyl-dimethylsilyl)-8-(3'-hydroxybiphenyl-4-ylmethylamino)-adenosine (0.612 g) in N,N-dimethylformamide (4.0 mL) was added potassium carbonate (0.165 g). Then methyl bromoacetate (0.098 mL) was added, and the resulting mixture was stirred at room temperature for 5 hours. The reaction mixture was partitioned between diethyl ether (55 mL) and water (10 mL). The organic layer was washed successively with water (10 mL×2) and brine (10 mL), dried over anhydrous sodium sulfate and concentrated under reduced pressure. The residue was purified by column chromatography on silica gel (eluent: hexane/ethyl acetate=3/2) to give the title compound (0.423 g).

Reference Example 115

2',3',5'-Tris-O-(tert-butyldimethylsilyl)-8-(4'-hydroxy-biphenyl-4-ylmethylamino)adenosine The title compound was prepared in a similar manner to that described in Reference Example 112 using 4'-hydroxybiphenyl-4-ylmethylamine instead of 3'-benzyloxybiphenyl-4-ylmethylamine.

Reference Example 116

2',3',5'-Tris-O-(tert-butyldimethylsilyl)-8-(4'-methoxy-carbonylmethoxybiphenyl-4-ylmethylamino) adenosine The title compound was prepared in a similar manner to that described in Reference Example 114 using 2',3',5'-tris-O-(tert-butyldimethylsilyl)-8-(4'-hydroxybiphenyl-4-ylmethylamino)adenosine instead of 2',3',5'-tris-O-(tert-butyldimethylsilyl)-8-(3'-hydroxybiphenyl-4-yl-methylamino) adenosine.

Reference Example 117

8-[3'-Benzyloxy-2-(4-hydroxybutoxy)biphenyl-4-ylmethyl-amino]-2',3',5'-Tris-O-(tert-butyldimethyl-silyl)adenosine The title compound was prepared in a similar manner to that described in Reference Example 112 using 3'-benzyloxy-2-(4-hydroxybutoxy)biphenyl-4-ylmethylamine instead of 3'-benzyloxybiphenyl-4-ylmethylamine.

Reference Example 118

8-[2-(4-Azidebutoxy)-3'-benzyloxybiphenyl-4-ylmethyl-amino]-2',3',5'-Tris-O-(tert-butyldimethylsilyl) adenosine To a stirred mixture of 8-[3'-benzyloxy-2-(4-hydroxybutoxy)biphenyl-4-ylmethylamino]-2',3',5'-tris-O-(tert-butyldimethylsilyl)adenosine (0.425 g), sodium azide (0.056 g), triphenylphosphine (0.147 g) and N,N-dimethyl-formamide (4.3 mL) was added carbon tetrabromide (0.186 g), and the resulting mixture was stirred at 30° C. for 36 hours. The reaction mixture was partitioned between ethyl acetate (35 mL) and water (10 mL). The organic layer was washed successively with water/brine (2/1, 15 mL×2) and brine (10 mL), dried over anhydrous sodium sulfate and concentrated under reduced pressure. The residue was purified by column chromatography on silica gel (eluent: hexane/ethyl acetate=3/1 to 2/1) to give the title compound (0.257 g).

Reference Example 119

8-[2-(4-tert-Butoxycarbonylaminobutoxy)-3'-hydroxy-biphenyl-4-ylmethylamino]-2',3',5'-tris-O-(tert-butyl-dimethylsilyl)adenosine To a solution of 8-[2-(4-azidebutoxy)-3'-benzyloxy-biphenyl-4-ylmethylamino]-2',3', 5'-tris-O-(tert-butyl-dimethylsilyl)adenosine (0.057 g) and di-tert-butyl dicarbonate (0.017 mL) in tetrahydrofuran (1.4 mL) was added 10% palladium on carbon (56.2 wt % $H_2O$, 0.065 g), and the resulting mixture was stirred at room temperature for 17 hours under a hydrogen atmosphere. The insoluble material was filtered out and the filtrate was concentrated under reduced pressure. The residue was purified by column chromatography on silica gel (eluent: hexane/ethyl acetate=1/1 to 1/2) to give the title compound (0.049 g).

Reference Example 120

2',3',5'-Tris-O-(tert-butyldimethylsilyl)-8-(2'-hydroxy-biphenyl-4-ylmethylamino)adenosine The title compound was prepared in a similar manner to that described in Reference Example 112 using 2'-hydroxy-biphenyl-4-ylmethylamine instead of 3'-benzyloxybiphenyl-4-ylmethylamine.

Reference Example 121

8-(3-Benzyloxybiphenyl-4-ylmethylamino)-2',3',5'-tris-O-(tert-butyldimethylsilyl)adenosine The title compound was prepared in a similar manner to that described in Reference Example 112 using 3-benzyloxy-biphenyl-4-ylmethylamine instead of 3'-benzyloxybiphenyl-4-ylmethylamine.

Reference Example 122

2',3',5'-Tris-O-(tert-butyldimethylsilyl)-8-(3-hydroxy-biphenyl-4-ylmethylamino)adenosine The title compound was prepared in a similar manner to that described in Reference Example 113 using 8-(3-benzyloxy-biphenyl-4-ylmethylamino)-2',3',5'-tris-O-(tert-butyldimethylsilyl)adenosine instead of 8-(3'-benzyloxybiphenyl-4-ylmethylamino)-2',3',5'-tris-O-(tert-butyldimethylsilyl)adenosine.

Reference Example 123

8-(2-Benzyloxybiphenyl-4-ylmethylamino)-2',3',5'-tris-O-(tert-butyldimethylsilyl)adenosine The title compound was prepared in a similar manner to that described in Reference Example 112 using 2-benzyloxy-biphenyl-4-ylmethylamine instead of 3'-benzyloxybiphenyl-4-ylmethylamine.

Reference Example 124

2',3',5'-Tris-O-(tert-butyldimethylsilyl)-8-(2-hydroxy-biphenyl-4-ylmethylamino)adenosine The title compound was prepared in a similar manner to that described in Reference Example 113 using 8-(2-benzy-loxy-biphenyl-4-ylmethylamino)-2',3',5'-tris-O-(tert-butyl-dimethylsilyl)adenosine instead of 8-(3'-benzyloxybiphenyl-4-ylmethylamino)-2',3',5'-tris-O-(tert-butyldimethylsilyl) adenosine.

Reference Example 125

2',3',5'-Tris-O-(tert-butyldimethylsilyl)-8-(3'-methoxy-carbonylbiphenyl-4-ylmethylamino)adenosine The title compound was prepared in a similar manner to that described in Reference Example 112 using 3'-methoxy-carbonylbiphenyl-4-ylmethylamine instead of 3'-benzyloxy-biphenyl-4-ylmethylamine.

Reference Example 126

8-(3'-Benzyloxycarbonylbiphenyl-4-ylmethylamino)-2',3',5'-tris-O-(tert-butyldimethylsilyl)adenosine The title compound was prepared in a similar manner to that described in Reference Example 112 using 3'-benzyloxy-carbonylbiphenyl-4-ylmethylamine instead of 3'-benzyloxy-biphenyl-4-ylmethylamine.

Reference Example 127

2',3',5'-Tris-O-(tert-butyldimethylsilyl)-8-[2-(4-phthalimidebutoxy)biphenyl-4-ylmethylamino]adenosine To a solution of 2',3',5'-tris-O-(tert-butyl-dimethylsilyl)-8-(2-hydroxybiphenyl-4-ylmethylamino)-adenosine (0.200 g) in N,N-dimethylformamide (1.6 mL) was added potassium carbonate (0.103 g). Then N-(4-bromobutyl)-phthalimide (0.105 g) was added, and the resulting mixture was stirred at 50° C. for 21 hours. The reaction mixture was cooled to room temperature and then partitioned between diethyl ether (30 mL) and water (10 mL). The organic layer was washed successively with water (10 mL×2) and brine (10 mL), dried over anhydrous sodium sulfate and concentrated under reduced pressure. The residue was purified by column chromatography on aminopropylated silica gel (eluent: hexane/ethyl acetate-1/1) to give the title compound (0.216 g).

Reference Example 128

8-[2-(4-Aminobutoxy)biphenyl-4-ylmethylamino]-2', 3',5'-tris-O-(tert-butyldimethylsilyl)adenosine To a solution of 2',3',5'-tris-O-(tert-butyl-dimethylsilyl)-8-[2-(4-phthalimidebutoxy)biphenyl-4-yl-methylamino]adenosine (0.120 g) in chloroform (1.5 mL) was added dropwise a mixture of hydrazine monohydrate (0.030 g) and ethanol (0.3 mL), and the resulting mixture was stirred at 40° C. for 42 hours. Hydrazine monohydrate (0.030 mL) was more added and stirring was continued at 60° C. for 18 hours. The reaction mixture was cooled to room temperature and the insoluble material was filtered out. The filtrate was concentrated under reduced pressure. The residue was purified by column chromatography on aminopropylated silica gel (eluent: dichloromethane/methanol=50/1) to give the title compound (0.086 g).

Reference Example 129

3-Acetoxy-5-benzyloxybenzoic acid

3-Benzyloxy-5-hydroxybenzoic acid (2.16 g) and acetic anhydride (15 mL) were suspended in acetic acid (15 mL), and the resulting mixture was stirred at 120° C. for 24 hours. The reaction mixture was concentrated under reduced pressure and the residue obtained was purified by column chromatography on silica gel (eluent: ethyl acetate/hexane=1/1 to 1/0) to give the title compound (1.74 g).

Reference Example 130

3-Benzyloxy-5-hydroxy-N,N-dimethylbenzamide

3-Acetoxy-5-benzyloxybenzoic acid (1.0 g) was suspended in dichloromethane (12 mL), oxalyl chloride (0.49 g), N,N-dimethylformamide (0.01 mL), tetrahydrofuran was added sequentially, and the resulting mixture was stirred at room temperature for 2 hours. The reaction mixture was concentrated under reduced pressure and then dichloromethane was added to the residue. Dimethylamine hydrochloride (0.28 g) and pyridine (0.1 mL) were added to the reaction mixture and stirred at room temperature for 24 hours. The reaction mixture was concentrated under reduced pressure and the residue obtained was dissolved in tetrahydrofuran (15 mL). Sodium methoxide-methanol solution (5.2 mol/L, 1.02 mL) was added to the reaction mixture and stirred at room temperature for 30 minutes. One mol/L hydrochloric acid was added to the reaction mixture and the whole was extracted with ethyl acetate. The organic layer was washed with brine, dried over anhydrous sodium sulfate and concentrated under reduced pressure. The residue obtained was purified by column chromatography on silica gel (eluent: ethylacetate/hexane=1/1) to give the title compound (0.67 g).

Reference Example 131 tert-Butyl N-(3'-Benzyloxy-5'-dimethylcarbamoylbiphenyl-4-ylmethyl)carbamate

The title compound was prepared in a similar manner to that described in Reference Example 58 using 3-benzyloxy-5-hydroxy-N,N-dimethylbenzamide instead of 4-hydroxy-3-methoxybenzaldehyde and tert-butyl N-[4-(4,4,5,5-tetramethyl-[1,3,2]-dioxaborolane-2-yl)bezyl]carbamate instead of phenylboronic acid.

Reference Example 132

2-Hydroxy-3'-dimethylcarbamoylbiphenyl-4-ylmethylamine

To an ice-cold solution of tert-butyl N-(4-hydroxy-3-methoxybenzyl)carbamate (2.03 g) in dichloromethane (20 mL) was added pyridine (1.92 mL). Then trifluoromethanesulfonic anhydride (1.53 mL) was added dropwise, and the resulting mixture was stirred under ice-cooling for 1 hour. Ice was added and the whole was partitioned between ethyl acetate (60 mL) and saturated aqueous sodium hydrogen carbonate (30 mL). The organic layer was washed successively with water/brine (3/1, 40 mL) and brine (30 mL), dried over anhydrous magnesium sulfate and concentrated under reduced pressure. The residue (2.03 g) was dissolved in 1,2-dimethoxyethane (40 mL). N,N-Dimethyl-3-(4,4,5,5-tetramethyl-1,3,2-dioxaborolane-2-yl)benzamide (1.96 g), 2 mol/L aqueous sodium carbonate (8 mL) and tetrakis-(triphenylphosphine)palladium(0) (0.43 g) were added, and the resulting mixture was stirred at 80° C. for 24 hours. The reaction mixture was cooled to room temperature and then partitioned between ethyl acetate (70 mL) and water (30 mL). The organic layer was washed with water/brine (1/1, 30 mL×2), dried over anhydrous sodium sulfate and concentrated under reduced pressure. The residue was purified by column chromatography on silica gel (eluent: hexane/ethyl acetate=10/1 to 5/1) to give tert-butyl N-(3'-dimethylcarbamoyl-2-methoxybiphenyl-4-ylmethyl)carbamate (2.03 g). The compound obtained was dissolved in dichloromethane (8 mL), 1.0 mol/L boron tribromide-dichloromethane solution (15.6 mL) was added dropwise, and the resulting mixture was stirred at room temperature for 30 minutes. Methanol (10 mL) was added to the reaction mixture and concentrated under reduced pressure. The residue obtained was purified by column chromatography on aminopropylated silica gel (eluent: ethyl acetate/methanol=10/1 to 5/1) to give the title compound (0.75 g).

Reference Example 133 tert-Butyl N-(2-benzyloxy-3'-dimethylcarbamoylbiphenyl-4-ylmethyl)carbamate

2-Hydroxy-3'-dimethylcarbamoylbiphenyl-4-ylmethylamine (0.74 g) and di-tert-butyl dicarbonate (0.63 g) were suspended in tert-butanol (10 mL), 2 mol/L aqueous sodium hydroxide (2.74 mL) was added, and the resulting mixture was stirred at room temperature for 3 hours. One mol/L hydrochloric acid was added to the reaction mixture and the whole was extracted with ethyl acetate. The organic layer was washed with brine, dried over anhydrous sodium sulfate and concentrated under reduced pressure. The residue obtained and potassium carbonate (0.29 g) were suspended in N,N-dimethylformamide (5 mL), benzyl bromide (0.25 mL) was added, and the resulting mixture was stirred at room temperature for 24 hours. One mol/L hydrochloric acid was added to the reaction mixture and the whole was extracted with ethyl acetate. The organic layer was washed with brine, dried over anhydrous sodium sulfate and concentrated under reduced pressure. The residue obtained was purified by column chromatography on silica gel (eluent: ethyl acetate/hexane=1/1) to give the title compound (0.71 g).

Reference Example 134 tert-Butyl N-(2-methoxycarbonylbiphenyl-4-ylmethyl)-carbamate

Methyl 4-formylbiphenyl-2-carboxylate (1.06 g) and sodium acetate (0.73 g) were suspended in tetrahydrofuran (20 mL), 50% aqueous hydroxylamine (0.6 mL) was added, and the resulting mixture was stirred at 80° C. for 8 hours. Water was added to the reaction mixture and the whole was extracted with ethyl acetate. The organic layer was washed with brine, dried over anhydrous magnesium sulfate and concentrated under reduced pressure. The residue obtained was dissolved in ethanol (10 mL), di-tert-butyl dicarbonate (0.37 g) and 5% platinum on carbon (60 wt % $H_2O$, 0.21 g) were added, and the resulting mixture was stirred at room temperature for 4 hours under a hydrogen atmosphere. The insoluble material was filtered out and the filtrate was concentrated under reduced pressure. The residue obtained was purified by column chromatography on silica gel (eluent: ethyl acetate/hexane=1/5) to give the title compound (0.42 g).

Reference Example 135 tert-Butyl N-[2-(2-dimethylamionethylcarbamoyl)-biphenyl-4-ylmethyl]carbamate tert-Butyl N-(2-methoxycarbonylbiphenyl-4-ylmethyl)-carbamate (0.42 g) was dissolved in methanol (20 mL), 5 mol/L aqueous sodium hydroxide (2.5 mL) was added, and the resulting mixture was heated under reflux for 6 hours. The reaction mixture was cooled to room temperature and then partitioned between ethyl acetate (35 mL) and 10% aqueous citric acid (10 mL). The organic layer was washed with brine (10 mL), dried over anhydrous magnesium sulfate and concentrated under reduced pressure. The residue was suspended in N,N,-dimethylformamide (10 mL), diphenylphosphoryl azide (1.24 mL), N,N-dimethylethylene-diamine (0.72 mL), triethylamine (1.6 mL) were added, and the resulting mixture was stirred at room temperature for 24 hours. Water (30 mL) was added to the reaction mixture and the whole was extracted with ethyl acetate. The organic layer was washed with brine (10 mL), dried over anhydrous magnesium sulfate and concentrated under reduced pressure. The residue obtained was purified by column chromatography on aminopropylated silica gel (eluent: ethyl acetate/hexane=1/1) to give the title compound (0.3 g).

Reference Example 136

3-Mercapt-4-phenylbenzonitrile

3-Hydroxy-4-phenylbenzonitrile (0.8 g) and 1,4-diaza-bicyclo[2,2,2]octane (0.9 g) were suspended in N,N-dimethylformamide (10 mL), dimethylthiocarbamoyl chloride (0.7 g) was added, and the resulting mixture was stirred at 70° C. for 13 hours. One mol/L hydrochloric acid was added to the reaction mixture and the insoluble material was collected by filtration. The residue obtained was dissolved at 220° C. and stirred for 13 hours. After cooling to room temperature, the residue was dissolved in ethanol (20 mL) and water (10 mL), potassium hydroxide (1.1 g) was added, and the resulting mixture was stirred at room temperature for 6 hours. One mol/L hydrochloric acid was added to the reaction mixture and the whole was extracted with ethyl acetate. The organic layer was washed with brine, dried over anhydrous sodium sulfate and concentrated under reduced pressure. The residue obtained was dissolved in tetrahydrofuran (5 mL), sodium borohydride (0.08 g) was added, and the resulting mixture was stirred at room temperature for 1 hour. One mol/L hydrochloric acid was added to the reaction mixture and the whole was extracted with ethyl acetate. The organic layer was washed with brine, dried over anhydrous sodium sulfate and concentrated under reduced pressure. The residue obtained was purified by column chromatography on silica gel (eluent: ethylacetate/hexane=1/5) to give the title compound (0.44 g).

Reference Example 137

3-[3-(tert-Butyldimethylsilyloxy)propylsulfanyl]-4-phenyl-benzonitrile

To a solution of 3-mercapto-4-phenylbenzonitrile (0.44 g) in N,N-dimethylformamide (5.0 mL) was added potassium carbonate (0.43 g). Then (3-bromopropoxy)-tert-butyldimethylsilane (0.72 mL) was added, and the resulting mixture was stirred at room temperature for 16 hours. The reaction mixture was partitioned between diethyl ether (55 mL) and water (10 mL). The organic layer was washed with water (10 mL×2) and brine (10 mL), dried over anhydrous sodium sulfate and concentrated under reduced pressure. The residue was purified by column chromatography on silica gel (eluent: hexane/ethylacetate=3/2) to give the title compound (0.8 g).

Reference Example 138

3-(3-Chloropropoxy)-4-phenylbenzonitrile

To a solution of 3-hydroxy-4-phenylbenzonitrile (3.0 g) in N,N-dimethylformamide (30.7 mL) was added potassium carbonate (6.37 g). Then 1-bromo-3-chloropropane (3.6 mL) was added, and the resulting mixture was stirred at 50° C. for 4 hours. The reaction mixture was partitioned between diethyl ether (45 mL) and water (10 mL). The organic layer was washed with water (10 mL×2) and brine (10 mL), dried over anhydrous sodium sulfate and concentrated under reduced pressure. The residue was purified by column chromatography on silica gel (eluent: hexane/ethyl acetate=15/1) to give the title compound (4.08 g).

Reference Example 139

4-Phenyl-3-(3-pyrrolidine-1-ylpropoxy)benzonitrile

To a solution of 3-(3-chloropropoxy)-4-phenyl-benzonitrile (0.3 g) in acetone (3 mL) was added potassium iodide (0.5 g), and the resulting mixture was heated under reflux for 24 hours. The reaction mixture was cooled with ice, the insoluble material was filtered out and the filtrate was concentrated under reduced pressure. The residue was dissolved in N,N-dimethylformamide (3.2 mL), pyrrolidine (0.16 mL) and potassium carbonate were added, and the resulting mixture was stirred at 80° C. for 17 hours. The reaction mixture was partitioned between diethyl ether (40 mL) and water (10 mL). The organic layer was washed with water (10 mL×2) and brine (10 mL), dried over anhydrous sodium sulfate and concentrated under reduced pressure. The residue was purified by column chromatography on aminopropylated silica gel (eluent: hexane/ethyl acetate=2/1) to give the title compound (0.26 g).

Reference Example 140

3-(3-Diethylaminopropoxy)-4-phenylbenzonitrile

The title compound was prepared in a similar manner to that described in Reference Example 139 using diethylamine instead of pyrrolidine.

Reference Example 141

4-Phenyl-3-(3-piperidine-1-ylpropoxy)benzonitrile

The title compound was prepared in a similar manner to that described in Reference Example 139 using piperidine instead of pyrrolidine.

Reference Example 142

3-(3-Bromophenylsulfanyl)propane-1-ol

3-Bromobenzenethiol (0.40 g) and potassium carbonate (0.44 g) were suspended in N,N-dimethylformamide (4.2 mL), 3-chloropropyl acetate (0.34 mL) was added, and the resulting mixture was stirred at 60° C. for 5 hours. The reaction mixture was partitioned between diethyl ether (40 mL) and water (10 mL). The organic layer was washed successively with water (10 mL×2) and brine (10 mL), dried over anhydrous sodium sulfate and concentrated under reduced pressure. The residue was dissolved in methanol (8.5 mL), 28% sodium methoxide-methanol solution (0.08 mL) was added, and the resulting mixture was stirred at room temperature for 2 hours. The reaction mixture was concentrated under reduced pressure and the residue obtained was purified by column chromatography on silica gel (eluent: hexane/ethyl acetate=3/1) to give the title compound (0.49 g).

Reference Example 143

4-(3-Hydroxypropylsulfanyl)phenylbenzonitrile 3-(3-Bromophenylsulfanyl)propane-1-ol (0.49 g) was suspended in acetonitrile (8.5 mL), 4-cyanophenylboronic acid (0.34 g), sodium carbonate (0.42 g), water (1.7 mL) and tetrakis(triphenylphosphine)palladium(0) (0.12 g) were added, and the resulting mixture was stirred at 80° C. for 7 hours. The reaction mixture was cooled to room temperature and then partitioned between ethyl acetate (35 mL) and water (10 mL). The organic layer was washed successively with water (10 mL) and brine (10 mL), dried over anhydrous sodium sulfate and concentrated under reduced pressure. The residue was purified by column chromatography on silica gel (eluent: hexane/ethyl acetate=2/1) to give the title compound (0.38 g).

Reference Example 144 tert-Butyl N-[2-(3-trifluoroacetoaminopropoxy)-biphenyl-4-ylmethyl]carbamate tert-Butyl N-[2-hydroxybiphenyl-4-ylmethyl]carbamate (2.5 g), N-(3-bromopropyl)phthalimide (2.9 g) and potassium carbonate (2.3 g) were suspended in N,N-dimethylformamide (21 mL), and the resulting mixture was stirred at 50° C. for 24 hours. The reaction mixture was cooled to room temperature and then partitioned between diethyl ether (80 mL) and water (30 mL). The organic layer was washed successively with water (30 mL) and brine (30 mL), dried over anhydrous sodium sulfate and concentrated under reduced pressure. The residue obtained was suspended in chloroform (45 mL), ethanol (9 mL) and hydrazine monohydrate (2.1 g) were added to the reaction mixture, and the resulting mixture was stirred at room temperature for 88 hours. The insoluble material was filtered out and the filtrate was partitioned between dichloromethane (35 mL) and water (15 mL). The organic layer was washed with brine (25 mL), dried over anhydrous sodium sulfate and concentrated under reduced pressure. The residue obtained was dissolved in ethanol (42 mL), ethyl trifluoroacetate (1.49 mL) was added to the reaction mixture, and the resulting mixture was stirred at room temperature for 21 hours. The reaction mixture was concentrated under reduced pressure and the residue was purified by column chromatography on silica gel (eluent: hexane/ethylacetate=3/1) to give the title compound (2.6 g).

Reference Example 145

Tert-Butyl N-[2-(3-methylaminopropoxy)biphenyl-4-yl-methyl]carbamate tert-Butyl N-[2-(3-trifluoroacetoaminopropoxy)-biphenyl-4-ylmethyl]carbamate (0.45 g) and potassium carbonate (0.55 g) were suspended in N,N-dimethylformamide (3.3 mL), methyl iodide (0.2 mL) was added, and the resulting mixture was stirred at room temperature for 25 hours. The reaction mixture was partitioned between diethyl ether (35 mL) and water (10 mL). The organic layer was washed successively with water (10 mL) and brine (10 mL), dried over anhydrous sodium sulfate and concentrated under reduced pressure. The residue obtained was dissolved in ethanol (1.8 mL), 2 mol/L aqueous sodium hydroxide (1.5 mL) was added, and the resulting mixture was stirred at 70° C. for 2 hours. The reaction mixture was partitioned between dichloromethane (35 mL) and brine (15 mL). The organic layer was dried over anhydrous sodium sulfate and concentrated under reduced pressure to give the title compound (0.36 g).

Reference Example 146 tert-Butyl N-[2-(3-ethylaminopropoxy)biphenyl-4-yl-methyl]carbamate

The title compound was prepared in a similar manner to that described in Reference Example 145 using ethyl iodide instead of methyl iodide.

Reference Example 147 tert-Butyl N-[2-(3-propylaminopropoxy)biphenyl-4-yl-methyl]carbamate

The title compound was prepared in a similar manner to that described in Reference Example 145 using 1-bromopropane instead of methyl iodide.

Reference Example 148 tert-Butyl N-{2-[3-(4-hydroxybutylamino)propoxy]biphenyl-4-ylmethyl}carbamate

The title compound was prepared in a similar manner to that described in Reference Example 145 using 4-bromobutyl acetate instead of methyl iodide.

Reference Example 149 tert-Butyl N-[3'-(3-chloropropoxy)biphenyl-4-yl-methyl]carbamate

The title compound was prepared in a similar manner to that described in Reference Example 138 using tert-butyl N-[3'-hydroxybiphenyl-4-ylmethyl]carbamate instead of 3-hydroxy-4-phenylbenzonitrile.

Reference Example 150 tert-Butyl N-[3'-(3-dimethylaminopropoxy)biphenyl-4-yl-methyl]carbamate

The title compound was prepared in a similar manner to that described in Reference Example 139 using tert-butyl N-[3'-(3-chloropropoxy)biphenyl-4-ylmethyl]carbamate instead of 3-(3-chloropropoxy)-4-phenylbenzonitrile.

Reference Example 151 tert-Butyl N-[3'-(3-piperidine-1-ylpropoxy)biphenyl-4-yl-methyl]carbamate

The title compound was prepared in a similar manner to that described in Reference Example 139 using tert-butyl N-[3'-(3-chloropropoxy)biphenyl-4-ylmethyl]carbamate instead of 3-(3-chloropropoxy)-4-phenylbenzonitrile and piperidine instead of pyrrolidine.

Reference Example 152 tert-Butyl N-[3'-(3-pyrrolidine-1-ylpropoxy)biphenyl-4-yl-methyl]carbamate

The title compound was prepared in a similar manner to that described in Reference Example 139 using tert-butyl N-[3'-(3-chloropropoxy)biphenyl-4-ylmethyl]carbamate instead of 3-(3-chloropropoxy)-4-phenylbenzonitrile.

Reference Example 153 tert-Butyl N-[2-(3-chloropropoxy)biphenyl-4-ylmethyl]carbamate

The title compound was prepared in a similar manner to that described in Reference Example 138 using tert-butyl N-[2-hydroxybiphenyl-4-ylmethyl]carbamate instead of 3-hydroxy-4-phenylbenzonitrile.

Reference Example 154 tert-Butyl N-(2-{3-[N-ethyl-N-(2-hydroxyethyl) amino]-propoxy}biphenyl-4-ylmethyl)carbamate The title compound was prepared in a similar manner to that described in Reference Example 139 using tert-butyl N-[2-(3-chloropropoxy)biphenyl-4-ylmethyl]carbamate instead of 3-(3-chloropropoxy)-4-phenylbenzonitrile and 2-ethylaminoethanol instead of pyrrolidine.

Reference Example 155 tert-Butyl N-{2-[3-(4-hydroxypiperidine-1-yl)propoxy]-biphenyl-4-ylmethyl}carbamate The title compound was prepared in a similar manner to that described in Reference Example 139 using tert-butyl N-[2-(3-chloropropoxy)biphenyl-4-ylmethyl]carbamate instead of 3-(3-chloropropoxy)-4-phenylbenzonitrile and piperidine-4-ol instead of pyrrolidine.

Reference Example 156 tert-Butyl N-{2-[3-(N-benzyloxycarbonyl-N-ethylamino)-propoxy]biphenyl-4-ylmethyl}carbamate To a solution of tert-butyl N-[2-(3-ethylaminopropoxy)-biphenyl-4-ylmethyl]carbamate (0.41 g) in tetrahydrofuran (4.0 mL) was added N-carbobenzoxyoxysuccinimide (0.260 g), and the resulting mixture was stirred at room temperature for 14 hours. The reaction mixture was concentrated under reduced pressure and the residue was purified by column chromatography on aminopropylated silica gel (eluent: hexane/ethyl acetate=2/1) to give the title compound (0.46 g).

Reference Example 157 tert-Butyl N-{2-[3-(N-benzyloxycarbonyl-N-propylamino)-propoxy]biphenyl-4-ylmethyl}carbamate The title compound was prepared in a similar manner to that described in Reference Example 156 using tert-butyl N-[2-(3-propylaminopropoxy)biphenyl-4-ylmethyl]carbamate instead of tert-butyl N-[2-(3-ethylaminopropoxy)biphenyl-4-ylmethyl]carbamate.

Reference Example 158 tert-Butyl N-(2-{3-[N-benzyloxycarbonyl-N-(4-hydroxybutyl)amino]propoxy}biphenyl-4-ylmethyl) carbamate The title compound was prepared in a similar manner to that described in Reference Example 156 using tert-butyl N-{2-[3-(4-hydroxybutylamino)propoxy]biphenyl-4-ylmethyl}-carbamate instead of tert-butyl N-[2-(3-ethylaminopropoxy)biphenyl-4-ylmethyl]carbamate.

Reference Example 159 tert-Butyl N-(3'-hydroxybiphenyl-3-ylmethyl)carbamate

The title compound was prepared in a similar manner to that described in Reference Example 2 using tert-butyl N-(3-bromobenzyl)carbamate instead of tert-butyl N-(4-bromobenzyl)carbamate and 3-hydroxyphenylboronic acid instead of 3-benzyloxyphenylboronic acid.

Reference Example 160 tert-Butyl N-(4'-hydroxybiphenyl-3-ylmethyl)carbamate

The title compound was prepared in a similar manner to that described in Reference Example 2 using tert-butyl N-(3-bromobenzyl)carbamate instead of tert-butyl N-(4-bromobenzyl)carbamate and 4-hydroxyphenylboronic acid instead of 3-benzyloxyphenylboronic acid.

Reference Example 161 tert-Butyl N-[3'-(3-benzyloxycarbonylaminopropoxy)-biphenyl-3-ylmethyl]carbamate The title compound was prepared in a similar manner to that described in Reference Example 31 using tert-butyl N-(3'-hydroxybiphenyl-3-ylmethyl)carbamate instead of tert-butyl N-(3'-hydroxybiphenyl-4-ylmethyl)carbamate and N-(3-bromopropyl)phthalimide instead of N-(4-bromobutyl) phthalimide.

Reference Example 162 tert-Butyl N-[4'-(3-benzyloxycarbonylaminopropoxy)-biphenyl-3-ylmethyl]carbamate The title compound was prepared in a similar manner to that described in Reference Example 31 using tert-butyl N-(4'-hydroxybiphenyl-3-ylmethyl)carbamate instead of tert-butyl N-(3'-hydroxybiphenyl-4-ylmethyl)carbamate and N-(3-bromopropyl)phthalimide instead of N-(4-bromobutyl)-phthalimide.

Reference Example 163 tert-Butyl N-[3'-(3-benzyloxycarbonylaminoethylcarbamoyl)-biphenyl-4-ylmethyl]carbamate The title compound was prepared in a similar manner to that described in Reference Example 33 using benzyl 2-aminoethylcarbamate instead of dimethylamine hydrochloride.

Reference Example 164

4-(3-Bromophenyl)butyronitrile 3-(3-Bromophenyl)propane-1-ol (0.59 g), triethylamine (0.57 mL) and 4-dimethylaminopyridine (0.03 g) were dissolved in dichloromethane (6.8 mL), p-toluenesulfonyl chloride (0.62 g) was added, and the resulting mixture was stirred at room temperature for 15 hours. The reaction mixture was partitioned between ethyl acetate (35 mL) and 10% aqueous citric acid (10 mL) The organic layer was washed with brine (10 mL), dried over anhydrous sodium sulfate and concentrated under reduced pressure. The residue was dissolved in dimethylsulfoxide (9.1 mL), sodium cyanide (0.17 g) was added, and the resulting mixture was stirred at 50° C. for 24 hours. The reaction mixture was partitioned between ethyl acetate (55 mL) and water (30 mL) The organic layer was washed with brine (10 mL), dried over anhydrous sodium sulfate and concentrated under reduced pressure to give the title compound (0.59 g).

Reference Example 165

[3'-(3-Cyanopropyl)biphenyl-4-yl]methanol

The title compound was prepared in a similar manner to that described in Reference Example 2 using 4-(3-bromophenyl)-butyronitrile instead of tert-butyl N-(4-bromobenzyl)-carbamate and 4-hydroxyphenylboronic acid instead of 3-benzyloxyphenylboronic acid.

Reference Example 166

[3'-(4-Benzyloxycarbonylaminobutyl)biphenyl-4-yl]methanol

[3'-(3-Cyanopropyl)biphenyl-4-yl]methanol (0.44 g) and imidazole (0.30 g) were dissolved in N,N-dimethylformamide (4.3 mL), chlorotriisopropylsilane (0.45 mL) was added, and the resulting mixture was stirred at room temperature for 4 hours. Saturated aqueous sodium hydrogen carbonate (10 mL) was added to the reaction mixture and the whole was extracted with diethyl ether (40 mL). The organic layer was washed with brine (10 mL), dried over anhydrous sodium sulfate and concentrated under reduced pressure. The residue was dissolved in tetrahydrofuran (7.3 mL) and added dropwise to a solution of lithium alminium hydride (0.1 g) in tetrahydrofuran (10 mL) under ice-cooling, and the resulting mixture was stirred at room temperature for 4 hours. The reaction was quenched by sequential addition of water (0.1 mL), 15% aqueous sodium hydroxide (0.1 mL) and water (0.1 mL). The insoluble material was filtered out and the filtrate was concentrated under reduced-pressure. The residue obtained was dissolved in tetrahydrofuran (6.9 mL), N-carbobenzoxyoxysuccinimide (0.45 g) was added, and the resulting mixture was stirred at room temperature for 3 hours. The reaction mixture was concentrated under reduced pressure and the residue was purified by column chromatography on aminopropylated silica gel (eluent: hexane/ethyl acetate=2/1) to give the title compound as triisopropylated form. The compound obtained was dissolved in tetrahydrofuran (4.1 mL), 1 mol/L tetrabutylammonium fluoride-tetrahydrofuran solution (1.1 mL) was added, and the resulting mixture was stirred at room temperature for 1.5 hours. Saturated aqueous ammonium chloride (10 mL) was added to the reaction mixture and the whole was extracted with ethyl acetate (40 mL). The organic layer was washed with brine (15 mL), dried over anhydrous sodium sulfate and concentrated under reduced pressure to give the'title compound (0.40 g).

Reference Example 167

N-[3'-(4-Benzyloxycarbonylaminobutyl)biphenyl-4-ylmethyl]-phthalimide

[3'-(4-Benzyloxycarbonylaminobutyl)biphenyl-4-yl]-methanol (0.40 g) was dissolved in tetrahydrofuran (4.1 mL). After addition of phthalimide (0.14 g) and triphenylphosphine (0.26 g) were added, diisopropyl azodicarboxylate (40% toluene solution, 0.5 g) was added dropwise, and the resulting mixture was stirred at room temperature for 6 hours. The reaction mixture was concentrated under reduced pressure. The residue was purified by column chromatography on silica gel (eluent: hexane/ethyl acetate=2/1) to give the title compound (0.4 g)

Reference Example 168

(3'-Nitrobiphenyl-4-yl)methanol

The title compound was prepared in a similar manner to that described in Reference Example 2 using 1-bromo-3-nitrobenzene instead of tert-butyl N-(4-bromobenzyl) carbamate and 4-hydroxymethylphenylboronic acid instead of 3-benzyloxyphenylboronic acid.

Reference Example 169

N-(3-Nitrobiphenyl-4-ylmethyl)phthalimide

The title compound was prepared in a similar manner to that described in Reference Example 167 using (3'-Nitrobiphenyl-4-yl)methanol instead of [3'-(4-benzyloxy-carbonylaminobutyl)biphenyl-4-yl]methanol.

Reference Example 170

N-[3-(3-Benzyloxycarbonylaminopropionylamino)biphenyl-4-ylmethyl]phthalimide A mixture of N-(3'-nitrobiphenyl-4-ylmethyl)-phthalimide (0.5 g) and 5% platinum on carbon (0.15 g) in tetrahydrofuran (7 mL) was stirred at room temperature for 12 hours under a hydrogen atmosphere. The insoluble material was filtered out and the filtrate was concentrated under reduced pressure. The residue was suspended in N,N-dimethylformamide (10 mL), triethylamine (0.21 mL), 4-dimethylaminopyridine (0.19 g), 3-benzyloxycarbonylaminopropionic acid (0.34 g) and 1-ethyl-3-(3-dimethylaminopropyl)carbodiimide (0.32 g) were added, and the resulting mixture was stirred at room temperature for 30 hours. The reaction mixture was partitioned between ethyl acetate (35 mL) and 10% aqueous citric acid (10 mL). The organic layer was washed with brine (10 mL), dried over anhydrous sodium sulfate and concentrated under reduced pressure. The residue obtained was suspended in diethyl ether and the insoluble material was collected by filtration to give'the title compound (0.53 g).

Reference Example 171

4-(Furan-3-yl)benzylamine

To a mixture of tert-butyl N-(4-bromobenzyl)carbamate (0.14 g), 2-(furan-3-yl)-4,4,5,5-tetramethyl-[1,3,2]-dioxaborolane (0.12 g), potassium carbonate (0.1 g), water (0.2 mL) and N,N-dimethylformamide (1 mL) was added tetrakis(triphenylphosphine)palladium(0) (0.03 g), and the resulting mixture was stirred at 80° C. for 12 hours. The reaction mixture was cooled to room temperature and then the insoluble material was filtered out. The filtrate was partitioned between ethyl acetate (110 mL) and water (50 mL). The organic layer was washed successively with water (50 mL) and brine (50 mL), dried over anhydrous sodium sulfate and concentrated under reduced pressure. The residue was purified by column chromatography on aminopropylated silica gel (eluent: hexane/ethyl acetate=1/1) to give tert-butyl N-[4-(furan-3-yl)benzyl]-carbamate. The compound obtained was dissolved in dichloromethane (5 mL), trifluoroacetic acid (0.57 mL) was added dropwise, and the resulting mixture was stirred at room temperature for 2 hours. Saturated aqueous sodium hydrogen carbonate (15 mL) was added dropwise and the whole was extracted with dichloromethane (30 mL). The organic layer was washed with saturated aqueous sodium hydrogen carbonate/brine (1/1, 10 mL), dried over anhydrous sodium sulfate and concentrated under reduced pressure to give the title compound (0.06 g).

Reference Example 172

4-(Thiophene-3-yl)benzylamine

The title compound was prepared in a similar manner to that described in Reference Example 171 using 3-thiopheneboronic acid instead of 2-(furan-3-yl)-4,4,5,5-tetramethyl-[1,3,2]dioxaborolane.

Reference Example 173

2-(3-Diethylaminopropoxy)biphenyl-4-ylmethylamine

The title compound was prepared in a similar manner to that described in Reference Example 93 using 3-(3-diethylamino-propoxy)-4-phenylbenzonitrile instead of 3-benzyloxy-4-phenylbenzonitrile.

Reference Example 174

2-(3-Pyrrolidine-1-ylpropoxy)biphenyl-4-ylmethylamine

The title compound was prepared in a similar manner to that described in Reference Example 93 using 4-phenyl-3-(3-pyrrolidine-1-ylpropoxy)benzonitrile instead of 3-benzyloxy-4-phenylbenzonitrile.

Reference Example 175

2-(3-Piperidine-1-ylpropoxy)biphenyl-4-ylmethylamine

The title compound was prepared in a similar manner to that described in Reference Example 93 using 4-phenyl-3-(3-piperidine-1-ylpropoxy)benzonitrile instead of 3-benzyloxy-4-phenylbenzonitrile.

Reference Example 176

3'-(3-Hydroxypropylsulfanyl)biphenyl-4-ylmethylamine

The title compound was prepared in a similar manner to that described in Reference Example 93 using 4-(3-hydroxypropylsulfanyl)phenylbenzonitrile instead of 3-benzyloxy-4-phenylbenzonitrile.

Reference Example 177

2-(3-tert-Butyldimethylsilyloxy)propylsulfanylbiphenyl-4-ylmethylamine

The title compound was prepared in a similar manner to that described in Reference Example 93 using 3-(3-tert-butyldimethylsilyloxy)propylsulfanyl-4-phenylbenzonitrile instead of 3-benzyloxy-4-phenylbenzonitrile.

Reference Example 178

2-(3-Methylaminopropoxy)biphenyl-4-ylmethylamine

The title compound was prepared in a similar manner to that described in Reference Example 34 using tert-butyl N-[2-(3-methylaminopropoxy)biphenyl-4-ylmethyl]carbamate instead of tert-butyl N-(3'-benzyloxybiphenyl-4-ylmethyl)-carbamate.

Reference Example 179

3'-(3-Dimethylaminopropoxy)biphenyl-4-ylmethylamine

The title compound was prepared in a similar manner to that described in Reference Example 34 using tert-butyl N-[3'-(3-dimethylaminopropoxy)biphenyl-4-ylmethyl]carbamate instead of tert-butyl N-(3'-benzyloxybiphenyl-4-ylmethyl)carbamate.

Reference Example 180

2-[3-(N-Benzyloxycarbonyl-N-ethylamino)propoxy]biphenyl-4-ylmethylamine

The title compound was prepared in a similar manner to that described in Reference Example 34 using tert-butyl N-{2-[3-(N-benzyloxycarbonyl-N-ethylamino)propoxy]biphenyl-4-ylmethyl}carbamate instead of tert-butyl N-(3'-benzyloxy-biphenyl-4-ylmethyl)carbamate.

Reference Example 181

2-[3-(N-Benzyloxycarbonyl-N-propylamino)propoxy]biphenyl-4-ylmethylamine

The title compound was prepared in a similar manner to that described in Reference Example 34 using tert-butyl N-{2-[3-(N-benzyloxycarbonyl-N-propylamino)propoxy]-biphenyl-4-ylmethyl}carbamate instead of tert-butyl N-(3'-benzyloxybiphenyl-4-ylmethyl)carbamate.

Reference Example 182

2-{3-[N-Benzyloxycarbonyl-N-(4-hydroxybutyl)amino]-propoxy}biphenyl-4-ylmethylamine The title compound was prepared in a similar manner to that described in Reference Example 34 using tert-butyl N-(2-{3-[N-benzyloxycarbonyl-N-(4-hydroxybutyl)amino]- propoxy}biphenyl-4-ylmethyl)carbamate instead of tert-butyl N-(3'-benzyloxybiphenyl-4-ylmethyl)carbamate.

Reference Example 183

3'-(3-Piperidine-1-ylpropoxy)biphenyl-4-ylmethylamine

The title compound was prepared in a similar manner to that described in Reference Example 34 using tert-butyl N-[3'-(3-piperidine-1-ylpropoxy)biphenyl-4-ylmethyl]carbamate instead of tert-butyl N-(3'-benzyloxybiphenyl-4-ylmethyl)carbamate.

Reference Example 184

3'-(3-Pyrrolidine-1-ylpropoxy)biphenyl-4-ylmethylamine

The title compound was prepared in a similar manner to that described in Reference Example 34 using tert-butyl N-[3'-(3-pyrrolidine-1-ylpropoxy)biphenyl-4-ylmethyl]carbamate instead of tert-butyl N-(3'-benzyloxybiphenyl-4-ylmethyl)carbamate.

Reference Example 185

4'-(3-Benzyloxycarbonylaminopropoxy)biphenyl-3-ylmethyl-amine

The title compound was prepared in a similar manner to that described in Reference Example 34 using tert-butyl N-[4'-(3-benzyloxycarbonylaminopropoxy)biphenyl-3-ylmethyl]carbamate instead of tert-butyl N-(3'-benzyloxybiphenyl-4-ylmethyl)carbamate.

Reference Example 186

3'-(3-Benzyloxycarbonylaminopropoxy)biphenyl-3-ylmethyl-amine

The title compound was prepared in a similar manner to that described in Reference Example 34 using tert-butyl N-[3'-(3-benzyloxycarbonylaminopropoxy)biphenyl-3-ylmethyl]carbamate instead of tert-butyl N-(3'-benzyloxybiphenyl-4-ylmethyl)carbamate.

Reference Example 187

3'-(2-Benzyloxycarbonylaminoethylcarbamoyl)biphenyl-4-ylmethylamine

The title compound was prepared in a similar manner to that described in Reference Example 34 using tert-butyl N-[3'-(2-benzyloxycarbonylaminoethylcarbamoyl)biphenyl-4-ylmethyl]carbamate instead of tert-butyl N-(3'-benzyloxy-biphenyl-4-ylmethyl)carbamate.

Reference Example 188

2-{3-[N-Ethyl-N-(2-hydroxyethyl)amino]propoxy}biphenyl-4-ylmethylamine

The title compound was prepared in a similar manner to that described in Reference Example 34 using tert-butyl N-(2-{3-[N-ethyl-N-(2-hydroxyethyl)amino]propoxy}biphenyl-4-ylmethyl)carbamate instead of tert-butyl N-(3'-benzyloxybiphenyl-4-ylmethyl)carbamate.

Reference Example 189

2-[3-(4-Hydroxypiperidine-1-yl)propoxy]biphenyl-4-yl-methylamine

The title compound was prepared in a similar manner to that described in Reference Example 34 using tert-butyl N-{2-[3-(4-hydroxypiperidine-1-yl)propoxy]biphenyl-4-ylmethyl}carbamate instead of tert-butyl N-(3'-benzyloxy-biphenyl-4-ylmethyl)carbamate.

Reference Example 190

3'-(3-Benzyloxycarbonylaminopropionylamino)biphenyl-4-yl-methylamine

The title compound was prepared in a similar manner to that described in Reference Example 74 using N-[3'-(3-benzyloxycarbonylaminopropionylamino)biphenyl-4-ylmethyl]-phthalimide instead of N-(2-methoxybiphenyl-4-ylmethyl)-phthalimide.

Reference Example 191

3'-(4-Benzyloxycarbonylaminobutyl)biphenyl-4-ylmethylamine

The title compound was prepared in a similar manner to that described in Reference Example 74 using N-[3'-(4-benzyloxycarbonylaminobutyl)biphenyl-4-ylmethyl]-phthalimide instead of N-(2-methoxybiphenyl-4-ylmethyl)-phthalimide.

Reference Example 192

2-Benzyloxy-3'-dimethylcarbamoylbiphenyl-4-ylmethylamine hydrochloride tert-Butyl N-(2-benzyloxy-3'-dimethylcarbamoyl-biphenyl-4-ylmethyl)carbamate (0.7 g) was suspended in 4 mol/L hydrogen chloride-1,4-dioxane solution (7.0 mL), and the resulting mixture was stirred at room temperature for 1 hour. The reaction mixture was concentrated under reduced pressure to give the title compound (0.55 g).

Reference Example 193

2-(2-Dimethylaminoethylcarbamoyl)biphenyl-4-ylmethylamine

The title compound was prepared in a similar manner to that described in Reference Example 192 using tert-butyl N-[2-(2-dimethylaminoethylcarbamoyl)biphenyl-4-ylmethyl]-carbamate instead of tert-butyl N-(2-benzyloxy-3'-dimethylcarbamoylbiphenyl-4-ylmethyl)carbamate.

Reference Example 194

3'-Benzyloxy-5'-dimethylcarbamoylbiphenyl-4-ylmethylamine hydrochloride

The title compound was prepared in a similar manner to that described in Reference Example 192 using tert-butyl N-(3'-benzyloxy-5'-dimethylcarbamoylbiphenyl-4-ylmethyl)-carbamate instead of tert-butyl N-(2-benzyloxy-3'-dimethylcarbamoylbiphenyl-4-ylmethyl)carbamate.

Reference Example 195 tert-Butyl N-[2-(3'-benzyloxybiphenyl-4-yl)ethyl] carbamate

The title compound was prepared in a similar manner to that described in Reference Example 2 using tert-butyl N-[2-(4-bromophenyl)ethyl]carbamate instead of tert-butyl N-(4-bromobenzyl)carbamate.

Reference Example 196

2-(3'-Benzyloxybiphenyl-4-yl)ethylamine hydrochloride

The title compound was prepared in a similar manner to that described in Reference Example 192 using tert-butyl N-[2-(3'-benzyloxybiphenyl-4-yl)ethyl]carbamate instead of tert-butyl N-(2-benzyloxy-3'-dimethylcarbamoylbiphenyl-4-ylmethyl)carbamate.

Reference Example 197

8-(2-Benzyloxy-3'-dimethylcarbamoylbiphenyl-4-ylmethyl-amino)-2',3',5'-tris-O-(tert-butyldimethylsilyl)adenosine The title compound was prepared in a similar manner to that described in Reference Example 112 using 2-benzyloxy-3'-dimethylcarbamoylbiphenyl-4-ylmethylamine hydrochloride instead of 3'-benzyloxybiphenyl-4-ylmethylamine.

Reference Example 198

8-(3'-Benzyloxy-5'-dimethylcarbamoylbiphenyl-4-ylmethyl-amino)-2',3',5'-tris-O-(tert-butyldimethylsilyl)adenosine The title compound was prepared in a similar manner to that described in Reference Example 112 using 3'-benzyloxy-5'-dimethylcarbamoylbiphenyl-4-ylmethylamine hydrochloride instead of 3'-benzyloxybiphenyl-4-ylmethylamine.

Reference Example 199

8-[2-(3'-Benzyloxybiphenyl-4-yl)ethylamino]-2',3',5'-tris-O-(tert-butyldimethylsilyl)adenosine The title compound was prepared in a similar manner to that described in Reference Example 112 using 2-(3'-benzyloxy-biphenyl-4-yl)ethylamine hydrochloride instead of 3'-benzyloxybiphenyl-4-ylmethylamine.

Reference Example 200

2',3',5'-Tris-O-(tert-butyldimethylsilyl)-8-(3'-hydroxy-5'-dimethylcarbamoylbiphenyl-4-ylmethylamino)adenosine The title compound was prepared in a similar manner to that described in Reference Example 113 using 8-(3'-benzyloxy-5'-dimethylcarbamoylbiphenyl-4-ylmethylamino)-2',3',5'-tris-O-(tert-butyldimethylsilyl)adenosine instead of 8-(3'-benzyloxybiphenyl-4-ylmethylamino)-2',3',5'-tris-O-(tert-butyldimethylsilyl)adenosine.

Reference Example 201

2',3',5'-Tris-O-(tert-butyldimethylsilyl)-8-(2-hydroxy-3'-dimethylcarbamoylbiphenyl-4-ylmethylamino)adenosine The title compound was prepared in a similar manner to that described in Reference Example 113 using 8-(2-benzyloxy-3'-dimethylcarbamoylbiphenyl-4-ylmethylamino)-2',3',5'-tris-O-(tert-butyldimethylsilyl)adenosine instead of 8-(3'-benzyloxybiphenyl-4-ylmethylamino)-2',3',5'-tris-O-(tert-butyldimethylsilyl)adenosine.

Reference Example 202

2',3',5'-Tris-O-(tert-butyldimethylsilyl)-8-[2-(3-chloro-propoxy)biphenyl-4-ylmethylamino]adenosine To a solution of 2',3',5'-tris-O-(tert-butyl-dimethylsilyl)-8-(2-hydroxybiphenyl-4-ylmethylamino)-adenosine (0.85 g) in N,N-dimethylformamide (5.3 mL) was added potassium carbonate (0.44 g). Then 1-bromo-3-chloropropane (0.16 mL) was added, and the resulting mixture was stirred at 40° C. for 42 hours. The reaction mixture was partitioned between diethyl ether (45 mL) and water (10 mL). The organic layer was washed successively with water (10 mL×2), and brine (10 mL), dried over anhydrous sodium sulfate and concentrated under reduced pressure to give the title compound (0.91 g).

Reference Example 203

2',3',5'-Tris-O-(tert-butyldimethylsilyl)-8-[2-(3-chloro-propoxy)-3'-dimethylcarbamoylbiphenyl-4-ylmethylamino]-adenosine The title compound was prepared in a similar manner to that described in Reference Example 202 using 2',3',5'-tris-O-(tert-butyldimethylsilyl)-8-(2-hydroxy-3'-dimethylcarbamoylbiphenyl-4-ylmethylamino)adenosine instead of 2',3',5'-tris-O-(tert-butyldimethylsilyl)-8-(2-hydroxy-biphenyl-4-ylmethylamino)adenosine.

Reference Example 204

2',3',5'-Tris-O-(tert-butyldimethylsilyl)-8-[3'-(3-chloro-propoxy)-5'-dimethylcarbamoylbiphenyl-4-ylmethylamino]-adenosine The title compound was prepared in a similar manner to that described in Reference Example 202 using 2',3',5-tris-O-(tert-butyldimethylsilyl)-8-(3'-hydroxy-5'-dimethylcarbamoylbiphenyl-4-ylmethylamino)adenosine instead of 2',3',5'-tris-O-(tert-butyldimethyl-silyl)-8-(3-hydroxybiphenyl-4-ylmethylamino)adenosine.

Reference Example 205

2',3',5'-Tris-O-(tert-butyldimethylsilyl)-8-[3'-(3-chloro-propoxy)biphenyl-4-ylmethylamino]adenosine The title compound was prepared in a similar manner to that described in Reference Example 202 using 2',3',5'-tris-O-(tert-butyldimethylsilyl)-8-(3'-hydroxybiphenyl-4-ylmethylamino)adenosine instead of 2',3',5'-tris-O-(tert-butyldimethylsilyl)-8-(3-hydroxybiphenyl-4-ylmethyl-amino)adenosine.

Reference Example 206

2',3',5'-Tris-O-(tert-butyldimethylsilyl)-8-{2-[3'-(3-chloropropoxy)biphenyl-4-yl]ethylamino}adenosine A mixture of 8-[2-(3'-benzyloxybiphenyl-4-yl)ethylamino]-2',3',5'-tris-O-(tert-butyldimethylsilyl)adenosine (0.27 g) and 10% palladium-on carbon (56.2 wt % $H_2O$, 0.12 g) in methanol (5 mL) was stirred at room temperature for 3 hours under a hydrogen atmosphere. The insoluble material was filtered out and the filtrate was concentrated under reduced pressure. To a solution of the residue obtained in N,N-dimethylformamide (3 mL) was added potassium carbonate (0.12 g). Then 1-bromo-3-chloropropane (0.07 mL) was added, and the resulting mixture was stirred at 40° C. for 42 hours. The reaction mixture was partitioned between ethyl acetate (45 mL) and water (10 mL). The organic layer was washed successively with water (10 mL×2) and brine (10 mL), dried over anhydrous sodium sulfate and concentrated under reduced pressure to give the title compound (0.19 g).

Reference Example 207

2-Nitrobiphenyl-4-carbaldehyde

4-Bromo-3-nitrobenzaldehyde (2.0 g) was suspended in N,N-dimethylformamide (30 mL), phenylboronic acid (1.3 g), sodium carbonate (1.8 g), water (6 mL) and tetrakis-(triphenylphosphine)palladium(0) (1.0 g) were added, and the resulting mixture was stirred at 90° C. for 17 hours. The reaction mixture was cooled to room temperature and then partitioned between ethyl acetate (100 mL) and water (100 mL). The organic layer was washed successively with water (50 mL) and brine (50 mL), dried over anhydrous sodium sulfate and concentrated under reduced pressure. The residue was purified by column chromatography on silica gel (eluent: hexane/ethyl acetate=2/1) to give the title compound (1.6 g).

Reference Example 208

N-(2-Nitrobiphenyl-4-ylmethyl)phthalimide

The title compound was prepared in a similar manner to that described in Reference Example 63 using 2-nitrobiphenyl-4-carbaldehyde instead of 3-methoxy-4-phenylbenzaldehyde.

Reference Example 209

N-{2-[3-(tert-Butyldimethylsilyloxy)propylamino]biphenyl-4-ylmethyl}phthalimide

A mixture of N-(2-nitrobiphenyl-4-ylmethyl) phthalimide (0.86 g) and 3% platinum on carbon (0.3 g) in a mixed solvent of tetrahydrofuran (15 mL) and ethanol (3 mL) was stirred at room temperature for 19 hours under a hydrogen atmosphere. The insoluble material was filtered out and the filtrate was concentrated under reduced pressure. The residue was suspended in N,N-dimethylformamide (10 mL) and then sodium hydride (55% purity, 0.11 g) was added under ice-cooling with stirring. Then (3-bromopropoxy)-tert-butyldimethylsilane (0.61 mL) was added, and the resulting mixture was stirred at 50° C. for 3 hours. The reaction mixture was partitioned between ethyl acetate (55 mL) and water (10 mL). The organic layer was washed successively with water (10 mL×2) and brine (10 mL), dried over anhydrous sodium sulfate and concentrated under reduced pressure. The residue was purified by column chromatography on silica gel (eluent hexane/ethyl acetate=3/2) to give the title compound (0.32 g)

Reference Example 210

2-[3-(tert-Butyldimethylsilyloxy)propylamino]biphenyl-4-ylmethylamine

The title compound was prepared in a similar manner to that described in Reference Example 74 using N-{2-[3-(tert-butyldimethylsilyloxy)propylamino]biphenyl-4-ylmethyl}phthalimide instead of N-(2-methoxybiphenyl-4-yl-methyl)phthalimide.

Example 1

8-(4'-Methylbiphenyl-4-ylmethylamino)adenosine

To a mixture of 8-(4-bromobenzylamino)adenosine (0.050 g), 4-methylphenylboronic acid (0.017 g), sodium carbonate (0.024 g), water (0.4 mL) and ethanol (2.2 mL) was added tetrakis-(triphenylphosphine)palladium(0) (0.006 g), and the resulting mixture was stirred under reflux for 22 hours. The reaction mixture was cooled to room temperature. After addition of dichloromethane/methanol (5/1, 35 mL), the insoluble material was filtered out. The filtrate was concentrated under reduced pressure. The residue was purified by preparative reverse phase column chromatography (Shiseido CAPCELL PAK C18MG80, 5 μm, 20×50 mm, flow rate 30 mL/minutes linear gradient, eluent: water/methanol=70/30-10/90) to give the title compound (0.022 g).

Examples 2 to 6

The compounds of examples 2 to 6 shown in Table 17 were prepared in a similar manner to that described in Example 1 using the corresponding materials.

Example 7

8-(3'-Ethoxybiphenyl-4-ylmethylamino)adenosine

To a mixture of tert-butyl N-(4-bromobenzyl)carbamate (0.500 g), 3-ethoxyphenylboronic acid (0.319 g), sodium carbonate (0.370 g), water (1.5 mL) and ethanol (7.5 mL) was added tetrakis(triphenylphosphine)palladium(0) (0.101 g), and the resulting mixture was stirred under reflux for 105 minutes. The reaction mixture was cooled to room temperature. After addition of ethyl acetate (30 mL), the insoluble material was filtered out. The filtrate was washed successively with water (10 mL) and brine (10 mL), dried over anhydrous sodium sulfate and concentrated under reduced pressure. The residue (0.916 g) was dissolved in dichloromethane (3.5 mL) and cooled with ice. Trifluoroacetic acid (1.33 mL) was added dropwise, and the resulting mixture was stirred at room temperature for 75 minutes. Two mol/L aqueous sodium hydroxide (10 mL) was added dropwise and the whole was extracted with dichloromethane (30 mL). The organic layer was washed with water/brine (1/1, 10 mL), dried over anhydrous sodium sulfate and concentrated under reduced pressure. A mixture of a part of the residue (0.197 g), 8-bromoadenosine (0.100 g) and N,N-diisopropylethylamine (0.202 mL) in 1-propanol (2.9 mL) was stirred under reflux for 24 hours. The reaction mixture was cooled to room temperature and then concentrated under reduced pressure. The residue was purified by column chromatography on aminopropylated silica gel (eluent: dichloromethane/methanol=10/1) to give the title compound (0.051 g).

Examples 8 to 9

The compounds of Examples 8 to 9 shown in Table 18 were prepared in a similar manner to that described in Example 7 using the corresponding materials.

Example 10

8-(3'-Benzyloxybiphenyl-4-ylmethylamino)adenosine

A mixture of a 8-bromoadenosine (0.130 g), 3'-benzyloxybiphenyl-4-ylmethylamine (0.326 g) and N,N-diisopropylethylamine (0.262 mL) in 1-propanol (3.8 mL) was stirred under reflux for 24 hours. The reaction mixture was cooled to room temperature and then concentrated under reduced pressure. The residue was purified by column chromatography on amino-propylated silica gel (eluent: dichloromethane/methanol=12/1) to give the title compound (0.120 g).

Examples 11 to 54

The compounds of examples 11 to 54 shown in Tables 18 to 25 were prepared in a similar manner to that described in Example 10 using the corresponding materials.

Example 55

8-(3'-Methoxycarbonylmethoxybiphenyl-4-ylmethylamino)-adenosine

To a solution of 2',3',5'-tris-O-(tert-butyl-dimethylsilyl)-8-(3'-methoxycarbonylmethoxybiphenyl-4-yl-methylamino)adenosine (0.269 g) in methanol (3.0 mL) was added ammonium fluoride (0.680 g), and the resulting mixture was stirred at 60° C. for 13 hours. The reaction mixture was cooled to room temperature. Dichloromethane (15 mL) was added, and the insoluble material was filtered out. The filtrate was concentrated under reduced pressure and the residue was purified by column chromatography on silica gel (eluent: dichloromethane/methanol=10/1) to give the title compound (0.134 g).

Examples 56 to 57

The compounds of Examples 56 to 57 shown in Table 26 were prepared in a similar manner to that described in Example 55 using the corresponding materials.

Example 58

8-(2'-Methoxycarbonylmethoxybiphenyl-4-ylmethylamino)-adenosine

To a solution of 2',3',5'-tris-O-(tert-butyl-dimethylsilyl)-8-(2'-hydroxybiphenyl-4-ylmethylamino)-adenosine (0.313 g) in N,N-dimethylformamide (1.9 mL) was added potassium carbonate (0.080 g). Then methyl bromoacetate (0.048 mL) was added, and the resulting mixture was stirred at room temperature for 4 hours. The reaction mixture was partitioned between diethyl ether (35 mL) and water (10 mL). The organic layer was washed successively with water (10 mL×2) and brine (10 mL), dried over anhydrous sodium sulfate and concentrated under reduced pressure. The residue (0.337 g) was dissolved in methanol (1.7 mL). Ammonium fluoride (0.379 g) was added, and the resulting mixture was stirred at 60° C. for 19 hours. The reaction mixture was cooled to room temperature. Dichloromethane (10 mL) was added, and the insoluble material was filtered out. The filtrate was concentrated under reduced pressure and the residue was purified by column chromatography on silica gel (eluent: dichloromethane/methanol=10/1) to give the title compound (0.053 g).

Examples 59 to 72

The compounds of Examples 59 to 72 shown in Tables 26 to 29 were prepared in a similar manner to that described in Example 58 using the corresponding materials.

Example 73

8-[3-(2-Benzyloxycarbonylaminoethoxy)biphenyl-4-ylmethyl-amino]adenosine

A mixture of 2',3',5'-tris-O-(tert-butyldimethyl-silyl)-8-(3-hydroxybiphenyl-4-ylmethylamino)adenosine (0.175 g), benzyl N-(2-hydroxyethyl)carbamate (0.065 g), triphenylphosphine (0.074 g) in tetrahydrofuran (1.1 mL) was stirred at 50° C. for 30 minutes. Diisopropyl azodicarboxylate (40% toluene solution, 0.143 g) was added dropwise, and the resulting mixture was stirred at 50° C. for 24 hours. The reaction mixture was concentrated under reduced pressure. The residue was purified by column chromatography on silica gel (eluent: hexane/ethyl acetate=3/2 to 1/1) to give 8-[3-(2-benzyloxycarbonylaminoethoxy)biphenyl-4-ylmethylamino]-2',3',5'-tris-O-(tert-butyldimethylsilyl)adenosine (0.146 g). To a solution of 8-[3-(2-benzyloxycarbonyl-aminoethoxy)biphenyl-4-ylmethylamino]-2',3',5'-tris-O-(tert-butyldimethylsilyl)adenosine (0.143 g) in methanol (1.5 mL) was added ammonium fluoride (0.323 g), and the resulting mixture was stirred at 60° C. for 13.5 hours. The reaction mixture was cooled to room temperature. Dichloromethane (7.5 mL) was added, and the insoluble material was filtered out. The filtrate was concentrated under reduced pressure and the residue was purified by column chromatography on aminopropylated silica gel (eluent: dichloromethane/methanol=15/1) to give the title compound (0.077 g).

Examples 74 to 75

The compounds of Examples 74 to 75 shown in Table 29 were prepared in a similar manner to that described in Example 73 using the corresponding materials.

Example 76

8-(3'-Hydroxybiphenyl-4-ylmethylamino)adenosine

A mixture of 8-(3'-benzyloxybiphenyl-4-ylmethyl-amino)adenosine (0.103 g) and 10% palladium on carbon (55.4 wt %

H₂O, 0.047 g) in methanol (7.4 mL) was stirred at room temperature for 17.5 hours under a hydrogen atmosphere. The insoluble material was filtered out and the filtrate was concentrated under reduced pressure. The residue was purified by column chromatography on silica gel (eluent: dichloromethane/methanol=8/1 to 6/1) to give the title compound (0.081 g).

Examples 77 to 92

The compounds of Examples 77 to 92 shown in Tables 29 to 32 were prepared in a similar manner to that described in Example 76 using the corresponding materials.

Example 93

8-(3'-Hydroxymethylbiphenyl-4-ylmethylamino) adenosine

To an ice-cold solution of 2',3',5'-tris-O-(tert-butyldimethylsilyl)-8-(3'-methoxycarbonylbiphenyl-4-ylmethylamino) adenosine (0.224 g) in tetrahydrofuran (2.6 mL) was added lithium aluminum hydride (0.013 g) in several portions, and the resulting mixture was stirred at room temperature for 2 hours. Lithium aluminum hydride (0.006 g) was added and stirring was continued for additional 2 hours. Ethyl acetate (1.0 mL), 0.5 mol/L sulfuric acid (1 mL) and water (9 mL) were added sequentially and the whole was extracted with ethyl acetate (35 mL). The organic layer was washed successively with 0.5 mol/L sulfuric acid/water (1/9, 10 mL×2), saturated aqueous sodium hydrogen carbonate (10 mL) and brine (10 mL), dried over anhydrous sodium sulfate and concentrated under reduced pressure. The residue (0.173 g) was dissolved in methanol (2.1 mL). Ammonium fluoride (0.468 g) was added, and the resulting mixture was stirred at 60° C. for 21 hours. The reaction mixture was cooled to room temperature. Dichloromethane (10 mL) was added and the insoluble material was filtered out. The filtrate was concentrated under reduced pressure and the residue was purified by column chromatography on aminopropylated silica gel (eluent: dichloromethane/methanol=10/1 to 6/1) to give the title compound (0.070 g).

Example 94

8-(3'-Carbamoylmethoxybiphenyl-4-ylmethylamino) adenosine 8-(3'-Methoxycarbonylmethoxybiphenyl-4-ylmethylamino)adenosine (0.080 g) was dissolved in 2.0 M ammonia methanol solution (3.0 mL), and the resulting mixture was stirred at room temperature for 18 hours. The reaction mixture was concentrated under reduced pressure to give the title compound (0.080 g).

Examples 95 to 98

The compounds of Examples 95 to 98 shown in Tables 32 to 33 were prepared in a similar manner to that described in Example 94 using the corresponding materials.

Example 99

8-[3'-(N-Methylcarbamoylmethoxy)biphenyl-4-ylmethylamino]-adenosine

The title compound was prepared in a similar manner to that described in Example 94 using 40% methylamine methanol solution instead of 2.0 M ammonia methanol solution.

Example 100

8-[3'-(N,N-Dimethylcarbamoylmethoxy)biphenyl-4-ylmethyl-amino]adenosine

The title compound was prepared in a similar manner to that described in Example 94 using 50% aqueous dimethylamine instead of 2.0 M ammonia methanol solution.

Example 101

8-[3'-(2-Hydroxyethoxy)biphenyl-4-ylmethylamino] adenosine

To a solution of 2',3',5'-tris-O-(tert-butyl-dimethylsilyl)-8-(3'-methoxycarbonylmethoxybiphenyl-4-yl-methylamino) adenosine (0.150 g) in ethanol (1.7 mL) was added sodium borohydride (0.032 g), and the resulting mixture was stirred at room temperature for 13 hours. Saturated aqueous ammonium chloride/water (1/1, 20 mL) was added dropwise and the whole was extracted with ethyl acetate (35 mL). The organic layer was washed with brine (10 mL), dried over anhydrous sodium sulfate and concentrated under reduced pressure. The residue (0.169 g) was dissolved in methanol (1.7 mL). Ammonium fluoride (0.379 g) was added, and the resulting mixture was stirred at 60° C. for 20 hours. The reaction mixture was cooled to room temperature. Dichloromethane (10 mL) was added and the insoluble material was filtered out. The filtrate was concentrated under reduced pressure and the residue was purified by column chromatography on silica gel (eluent: dichloromethane/methanol=8/1 to 6/1) to give the title compound (0.074 g).

Examples 102 to 105

The compounds of Examples 102 to 105 shown in Table 34 were prepared in a similar manner to that described in Example 101 using the corresponding materials.

Example 106

8-[3'-(N-Methylcarbamoyl)biphenyl-4-ylmethylamino]-adenosine

To a solution of 8-(3'-benzyloxycarbonylbiphenyl-4-ylmethylamino)-2',3',5'-tris-O-(tert-butyldimethylsilyl)-adenosine (0.135 g) in ethanol (1.5 mL) was added 1 mol/L aqueous sodium hydroxide (0.292 mL), and the resulting mixture was stirred at 75° C. for 1.5 hours. The reaction mixture was cooled to room temperature. One mol/L hydrochloric acid (4.46 mL) was added, and the whole was partitioned between ethyl acetate (30 mL) and water/brine (1/1, 10 mL). The organic layer was washed with water/brine (1/1, 10 mL), dried over anhydrous sodium sulfate and concentrated under reduced pressure. The residue (0.916 g) was dissolved in N,N-dimethylformamide (1.1 mL). Methlamine hydrochloride (0.011 g), diphenylphosphorylazide (0.047 mL) and triethylamine (0.046 mL) were added sequentially, and the resulting mixture was stirred at room temperature for 42.5 hours. One mol/L hydrochloric acid (10 mL) was added and the whole was extracted with ethyl acetate (30 mL). The organic layer was washed successively with saturated aqueous sodium hydrogen carbonate (10 mL×2) and brine (10 mL), dried over anhydrous sodium sulfate and concentrated under reduced pressure. The residue (0.078 g) was dissolved in methanol (2.2 mL). Ammonium fluoride (0.244 g) was added, and the resulting mixture was stirred at 60° C. for 17 hours. The reaction mixture was cooled to room temperature. Dichloromethane (10 mL) was added and the insoluble material was filtered out. The filtrate was concentrated under reduced pressure and the residue was purified by column chromatography on aminopropylated silica gel (eluent: dichloromethane/methanol=8/1) to give the title compound (0.019 g).

Example 107

8-[2-(4-Aminobutoxy)biphenyl-4-ylmethylamino]adenosine

To a solution of 8-[2-(4-aminobutoxy)biphenyl-4-yl-methylamino]-2',3',5'-tris-O-(tert-butyldimethylsilyl)-adenosine (0.083 g) in methanol (1.9 mL) was added ammonium fluoride (0.210 g), and the resulting mixture was stirred at 60° C. for 24 hours. The reaction mixture was cooled to room temperature. Dichloromethane (10 mL) was added and the insoluble material was filtered out. The filtrate was concentrated under reduced pressure and the residue was purified by column chromatography on aminopropylated silica gel (eluent: dichloromethane/methanol=8/1) to give the title compound (0.047 g).

Example 108

8-[3-(4-Carboxybutoxy)biphenyl-4-ylmethylamino]adenosine

To a solution of 8-[3-(4-ethoxycarbonylbutoxy)-biphenyl-4-ylmethylamino]adenosine (0.077 g) in methanol (1.3 mL) was added 2 mol/L aqueous sodium hydroxide (0.098 mL), and the resulting mixture was stirred at room temperature for 21 hours and then at 50° C. for 2 hours. Two mol/L aqueous sodium hydroxide (0.098 mL) was added and stirring was continued for additional 64 hours. The reaction mixture was cooled to room temperature, quenched by addition of 2 mol/L hydrochloric acid (0.227 mL) and concentrated under reduced pressure. The residue was purified by column chromatography on silica gel (eluent: dichloromethane/methanol=4/1) to give the title compound (0.083 g).

Example 109

8-[3-(5-Trifluoroacetoaminopentyloxy)biphenyl-4-ylmethyl-amino]adenosine

To a solution of 8-[ 3-(5-aminopentyloxy)biphenyl-4-ylmethylamino]adenosine (0.040 g) in ethanol (1.6 mL) was added ethyl trifluoroacetate (0.013 mL), and the resulting mixture was stirred at 30° C. for 27 hours. The reaction mixture was concentrated under reduced pressure and the residue was purified by column chromatography on silica gel (eluent: dichloromethane/methanol=10/1) to give the title compound (0.042 g).

Example 110

8-[3-(4-Carbamoylbutoxy)biphenyl-4-ylmethylamino]adenosine

To a mixture of 8-[3-(4-carboxybutoxy)biphenyl-4-yl-methylamino]adenosine (0.046 g), di-tert-butyl dicarbonate (0.030 mL), sodium hydrogen carbonate (0.019 g) and N,N-dimethyl formamide (0.820 mL) was added pyridine (0.030 mL), and the resulting mixture was stirred at room temperature for 72 hours. The reaction mixture was purified by column chromatography on aminopropylated silica gel (eluent: dichloromethane/methanol=8/1) to give the title compound (0.035 g).

Example 111

8-[2-(4-Benzyloxybutoxy)biphenyl-4-ylmethylamino]inosine

To a solution of 8-[2-(4-benzyloxybutoxy)biphenyl-4-yl-methylamino]adenosine (0.150 g) in acetic acid/water (3/1, 2.4 mL) was added sodium nitrite (0.215 g), and the resulting mixture was stirred at 25° C. for 24 hours. The reaction mixture was concentrated under reduced pressure. Methanol was added to the residue and the insoluble material was filtered out. The filtrate was concentrated under reduced pressure. The residue was purified by column chromatography on silica gel (eluent: dichloromethane/methanol=8/1 to 5/1) to give the title compound (0.096 g).

Examples 112 to 113

The compounds of Examples 112 to 113 shown in Table 35 were prepared in a similar manner to that described in Example 111 using the corresponding materials.

Example 114

8-[2-(4-Hydroxybutoxy)biphenyl-4-ylmethylamino]inosine

A mixture of 8-[2-(4-benzyloxybutoxy)biphenyl-4-yl-methylamino]inosine (0.050 g) and 10% palladium on carbon (56.2 wt % $H_2O$, 0.034 g) in methanol (1.6 mL) was stirred at 50° C. for 9 hours under a hydrogen atmosphere. The reaction mixture was cooled to room temperature. The insoluble material was filtered out and the filtrate was concentrated under reduced pressure. The residue was purified by column chromatography on silica gel (eluent: dichloromethane/methanol=7/1) to give the title compound (0.037 g).

Example 115

8-[2-(3-Diethylaminopropoxy)biphenyl-4-ylmethylamino]-adenosine

A mixture of 8-bromoadenosine (0.11 g), 3-(3-diethylaminopropoxy)biphenyl-4-ylmethylamine (0.30 g) and N,N-diisopropylethylamine (0.22 mL) in 1-propanol (3.2 mL) was stirred under reflux for 30 hours. The reaction mixture was cooled to room temperature and concentrated under reduced pressure. The residue was purified by column chromatography on aminopropylated silica gel (eluent: dichloromethane/methanol=12/1) to give the title compound (0.16 g).

Examples 116 to 137

The compounds of Examples 116 to 137 shown in Tables 36 to 39 were prepared in a similar manner to that described in Example 115 using the corresponding materials.

Example 138

8-{2-[3-Hydroxypropylsulfanyl]biphenyl-4-ylmethylamino}-adenosine

A mixture of 8-bromo-2',3',5'-tris-O-(tert-butyl-dimethylsilyl)adenosine (0.22 g), 2-(3-tert-butyldimethyl-silyloxy)propylsulfanylbiphenyl-4-ylmethylamine (0.38 g) and N,N-diisopropylethylamine (0.35 mL) in 1-propanol (10 mL) was stirred under reflux for 62 hours. The reaction mixture was cooled to room temperature and then partitioned between ethyl acetate (35 mL) and 10% aqueous citric acid (10 mL). The organic layer was washed successively with 10% aqueous citric acid (10 mL×2), saturated aqueous sodium hydrogen carbonate (10 mL) and brine (10 mL), dried over anhydrous sodium sulfate and concentrated under reduced pressure. The residue was dissolved in methanol (3.0 mL), ammonium fluoride (0.61 g) was added, and the resulting mixture was stirred at 60° C. for 13 hours. The reaction mixture was concentrated under reduced pressure and the residue obtained was purified by preparative reverse phase column chromatography (Shiseido CAPSELL PAC C18UG80, 5 μm, 20×50 mm, flow rate 30 mL/minutes linear gradient, water/methanol=70/30-10/90) to give the title compound (0.10 g).

Example 139

The compound of Example 139 shown in Table 40 was prepared in a similar manner to that described in Example 138 using the corresponding materials.

Example 140

8-(Biphenyl-4-ylmethylamino)-2'-deoxyadenosine

A mixture of 8-bromo-2'-deoxyadenosine (0.07 g), biphenyl-4-ylmethylamine (0.12 g) and N,N-diisopropyl-ethylamine (0.15 mL) in 1-propanol (2.1 mL) was stirred under reflux for 24 hours. The reaction mixture was cooled to room temperature and concentrated under reduced pressure. The residue was purified by column chromatography on aminopropylated silica gel (eluent: dichloromethane/methanol=12/1) to give the title compound (0.05 g).

Examples 141 and 142

The compounds of Examples 141 and 142 shown in Table 40 were prepared in a similar manner to that described in Example 140 using the corresponding materials.

Example 143

8-(Biphenyl-4-ylmethylamino)-9-β-D-arabinofuranosyladenine

A mixture of 8,2'-anhydro-8-hydroxy-9-β-D-arabinofuranosyladenine (0.04 g), biphenyl-4-ylmethylamine (0.08 g) and N,N-diisopropylethylamine (mL) in 1-propanol (0.10 mL) was stirred under reflux for 24 hours. The reaction mixture was cooled to room temperature and concentrated under reduced pressure. The residue was purified by column chromatography on aminopropylated silica gel (eluent: dichloromethane/methanol=12/1) to give the title compound (0.01 g).

Examples 144 and 145

The compounds of Examples 144 and 145 shown in Table 41 were prepared in a similar manner to that described in Example 143 using the corresponding materials.

Example 146

8-[2-(3-Ethylaminopropoxy)biphenyl-4-ylmethylamino]-adenosine

A mixture of 8-{3-[3-(N-benzyloxycarbonyl-N-ethylamino)propoxy]biphenyl-4-ylmethylamino}adenosine (0.18 g) and 10% palladium on carbon (43.8 wt % $H_2O$, 0.21 g) in methanol (5.3 mL) was stirred at room temperature for 24 hours under a hydrogen atmosphere. The insoluble material was filtered out and the filtrate was concentrated under reduced pressure. The residue was purified by column chromatography on amino-propylated silica gel (eluent: dichloromethane/methanol=8/1 to 6/1) to give the title compound (0.12 g).

Examples 147 to 156

The compounds of Examples 147 to 156 shown in Tables 41 to 43 were prepared in a similar manner to that described in Example 146 using the corresponding materials.

Example 157

8-[3'-(3-Guanidinopropoxy)biphenyl-4-ylmethylamino]-adenosine

8-[3'-(3-Aminopropoxy)biphenyl-4-ylmethylamino]-adenosine (0.2 g) was suspended in tetrahydrofuran (2 mL), N-benzyloxycarbonyl-1H-pyrazole-1-carboxamidine (0.47 g) was added, and the resulting mixture was stirred at 60° C. for 24 hours. The reaction mixture was concentrated under reduced pressure and the residue obtained was purified by column chromatography on aminopropylated silica gel (eluent: ethyl acetate/methanol=8/1-6/1). A mixture of the compound obtained and 10% palladium on carbon (43.8 wt % $H_2O$, 0.05 g) in methanol (2 mL) was stirred at room temperature for 4 hours under a hydrogen atmosphere. The insoluble material was filtered out and the filtrate was concentrated under reduced pressure to give the title compound (0.05 g).

Example 158

8-{2-[3-(4-Carbamoylpiperidine-1-yl)propoxy]biphenyl-4-yl-methylamino}adenosine To a solution of 2',3',5'-tris-O-(tert-butyl-dimethylsilyl)-8-[2-(3-chloropropoxy)biphenyl-4-ylmethyl-amino]adenosine (0.25 g) in N,N-dimethylformamide (2.8 mL), potassium carbonate (0.12 g) and potassium iodide (0.14 g) were added. Then isonipecotamide (0.07 g) was added, and the resulting mixture was stirred at 80° C. for 24 hours. The reaction mixture was concentrated under reduced pressure, ammonium fluoride (0.63 g) was added to a solution of the residue obtained in methanol (2.8 mL), and the resulting mixture was stirred at 60° C. for 48 hours. The reaction mixture was concentrated under reduced pressure and the residue obtained was purified by preparative reverse phase column chromatography (Shiseido CAPSELL PAC C18UG80, 5 μm, 20×50 mm, flowrate 30 mL/minutes linear gradient, water/methanol=70/30 to 10/90) to give the title compound (0.06 g).

Examples 159 to 171

The compounds of Examples 159 to 171 shown in Tables 43 to 45 were prepared in a similar manner to that described in Example 158 using the corresponding materials.

The compounds shown in Table 46 can be prepared in a similar manner to that described in Example 158 using the corresponding materials.

$^1$H-NMR data of the above Reference Example compounds 1 to 210 are shown in Tables 1 to 16, $^1$H-NMR data and the chemical structure formula of the above Example compounds 1 to 171 are shown in Tables 17 to 45, respectively.

Regarding condensation codes in Tables, "Ref No." represents the number of Reference Example, "Ex No." represents the number of Example, "Strc" represents a chemical structure formula, and "Solv" represents a measuring solvent of $^1$H-NMR respectively.

TABLE 1

| Ref No. | (Solv) δ (ppm) |
|---|---|
| 1 | (DMSO-$d_6$) 3.55-3.69(m, 2H), 3.95-4.01(m, 1H), 4.09-4.16(m, 1H), 4.46-4.62(m, 2H), 4.66-4.77(m, 1H), 5.13(d, 1H, J=3.9Hz), 5.26(d, 1H, J=6.5Hz), 5.81-5.89(m, 1H), 5.92(d, 1H, J=7.2Hz), 6.49(brs, 2H), 7.29-7.37(m, 2H), 7.47-7.60(m, 3H), 7.89(s, 1H) |
| 2 | (CDCl$_3$) 1.47(s, 9H), 4.20-4.50(m, 2H), 4.72-5.00(m, 1H), 5.12(s, 2H), 6.92-7.00(m, 1H), 7.14-7.23(m, 2H), 7.29-7.57(m, 10H) |
| 3 | (CDCl$_3$) 1.47(s, 9H), 4.14-4.58(m, 2H), 4.65-5.03(m, 1H), 5.08(s, 2H), 6.98-7.08(m, 2H), 7.22-7.39(m, 9H), 7.51-7.60(m, 2H) |
| 4 | (CDCl$_3$) 1.48(s, 9H), 4.24-4.46(m, 2H), 4.70-5.12(m, 1H), 5.46(s, 1H), 6.83-6.91(m, 2H), 7.22-7.52(m, 6H) |
| 5 | (CDCl$_3$) 1.48(s, 9H), 3.95(s, 3H), 4.22-4.52(m, 2H), 4.74-5.02(m, 1H), 7.34-7.42(m, 2H), 7.47-7.63(m, 3H), 7.72-7.81(m, 1H), 7.97-8.05(m, 1H), 8.23-8.30(m, 1H) |
| 6 | (CDCl$_3$) 1.34(s, 12H), 1.46(brs, 9H), 4.20-4.46(m, 2H), 4.64-5.00(m, 1H), 7.22-7.33(m, 2H), 7.74-7.80(m, 2H) |
| 7 | (CDCl$_3$) 0.93(t, 3H, J=7.1Hz), 1.28-1.50(m, 4H), 1.73-1.82(m, 2H), 3.93(t, 2H, J=6.7Hz), 6.79-6.85(m, 1H), 7.02-7.16(m, 3H) |
| 8 | (CDCl$_3$) 1.33(d, 6H, J=5.8Hz), 4.46-4.57(m, 1H), 6.78-6.84(m, 1H), 7.01-7.16(m, 3H) |
| 9 | (CDCl$_3$) 5.36(s, 2H), 7.28-7.48(m, 6H), 7.65-7.72(m, 1H), 7.97-8.04(m, 1H), 8.17-8.23(m, 1H) |
| 10 | (CDCl$_3$) 5.20(s, 2H), 6.65(brs, 1H), 7.12-7.44(m, 8H), 7.66(brs, 1H) |
| 11 | (CDCl$_3$) 0.94(t, 3H, J=7.2Hz), 1.32-1.54(m, 13H), 1.75-1.87(m, 2H), 4.01(t, 2H, J=6.7Hz), 4.25-4.45(m, 2H), 4.72-5.00(m, 1H), 6.84-6.92(m, 1H), 7.07-7.19(m, 2H), 7.28-7.39(m, 3H), 7.51-7.60(m, 2H) |
| 12 | (CDCl$_3$) 1.37(d, 6H, J=5.8Hz), 1.47(s, 9H), 4.22-4.50(m, 2H), 4.56-4.68(m, 1H), 4.72-5.00(m, 1H), 6.84-6.92(m, 1H), 7.06-7.20(m, 2H), 7.28-7.41(m, 3H), 7.50-7.59(m, 2H) |
| 13 | (CDCl$_3$) 1.48(s, 9H), 4.26-4.48(m, 2H), 4.76-5.00(m, 1H), 5.40(s, 2H), 7.31-7.62(m, 10H), 7.72-7.82(m, 1H), 8.02-8.09(m, 1H), 8.26-8.32(m, 1H) |
| 14 | (CDCl$_3$) 1.47(s, 9H), 3.00(s, 6H), 4.24-4.48(m, 2H), 4.70-5.02(m, 1H), 6.70-6.78(m, 1H), 6.86-6.97(m, 2H), 7.27-7.39(m, 3H), 7.52-7.60(m, 2H) |
| 15 | (CDCl$_3$) 1.47(s, 9H), 4.20-4.50(m, 2H), 4.66-5.06(m, 1H), 5.22(s, 2H), 6.65-7.70(m, 14H) |
| 16 | (CDCl$_3$) 1.47(s, 9H), 2.89-2.97(m, 2H), 3.86-3.96(m, 2H), 4.25-4.45(m, 2H), 4.72-5.00(m, 1H), 7.16-7.71(m, 8H) |
| 17 | (CDCl$_3$) 1.48(s, 9H), 4.26-4.50(m, 2H), 4.74-5.06(m, 1H), 7.32-7.46(m, 3H), 7.52-7.59(m, 2H), 7.82-7.92(m, 1H), 8.55-8.63(m, 1H), 8.80-8.88(m, 1H) |

TABLE 1-continued

| Ref No. | (Solv) δ (ppm) |
|---|---|
| 18 | (CDCl$_3$) 1.48(s, 9H), 4.18-4.54(m, 2H), 4.72-5.08(m, 1H), 5.34(brs, 1H), 6.78-6.86(m, 1H), 7.01-7.18(m, 2H), 7.23-7.40(m, 3H), 7.48-7.55(m, 2H) |

TABLE 2

| Ref No. | (Solv) δ (ppm) |
|---|---|
| 19 | (CDCl$_3$) 1.48(s, 9H), 4.26-4.50(m, 2H), 4.78-5.02(m, 1H), 5.14(s, 1H), 6.94-7.03(m, 2H), 7.19-7.30(m, 2H), 7.37-7.49(m, 4H) |
| 20 | (CDCl$_3$) 1.06(t, 3H, J=7.4Hz), 1.47(s, 9H), 1.78-1.89(m, 2H), 3.98(t, 2H, J=6.5Hz), 4.24-4.46(m, 2H), 4.73-4.97(m, 1H), 6.85-6.92(m, 1H), 7.07-7.18(m, 2H), 7.29-7.40(m, 3H), 7.52-7.58(m, 2H) |
| 21 | (CDCl$_3$) 0.99(t, 3H, J=7.4Hz), 1.44-1.59(m, 11H), 1.74-1.84(m, 2H), 4.02(t, 2H, J=6.6Hz), 4.24-4.48(m, 2H), 4.70-5.00(m, 1H), 6.85-6.91(m, 1H), 7.08-7.17(m, 2H), 7.28-7.40(m, 3H), 7.52-7.58(m, 2H) |
| 22 | (CDCl$_3$) 1.48(s, 9H), 2.06-2.17(m, 2H), 3.69(t, 2H, J=6.1Hz), 4.15(t, 2H, J=6.1Hz), 4.25-4.45(m, 2H), 4.53(s, 2H), 4.75-4.97(m, 1H), 6.84-6.93(m, 1H), 7.07-7.20(m, 2H), 7.22-7.40(m, 8H), 7.51-7.58(m, 2H) |
| 23 | (CDCl$_3$) 1.47(s, 9H), 3.47(s, 3H), 3.75-3.81(m, 2H), 4.15-4.21(m, 2H), 4.24-4.48(m, 2H), 4.74-5.00(m, 1H), 6.87-6.95(m, 1H), 7.11-7.21(m, 2H), 7.28-7.38(m, 3H), 7.50-7.58(m, 2H) |
| 24 | (CDCl$_3$) 0.96(t, 3H, J=7.4Hz), 1.48(s, 9H), 1.69-1.79(m, 2H), 3.92(t, 2H, J=6.4Hz), 4.20-4.52(m, 2H), 4.60-5.10(m, 1H), 6.92-7.06(m, 2H), 7.22-7.37(m, 4H), 7.48-7.58(m, 2H) |
| 25 | (CDCl$_3$) 0.92(t, 3H, J=7.4Hz), 1.36-1.50(m, 11H), 1.65-1.75(m, 2H), 3.96(t, 2H, J=6.4Hz), 4.18-4.54(m, 2H), 4.70-5.00(m, 1H), 6.93-7.04(m, 2H), 7.20-7.36(m, 4H), 7.47-7.55(m, 2H) |
| 26 | (CDCl$_3$) 0.89(t, 3H, J=7.1Hz), 1.25-1.43(m, 4H), 1.48(s, 9H), 1.66-1.78(m, 2H), 3.95(t, 2H, J=6.4Hz), 4.24-4.48(m, 2H), 4.70-5.00(m, 1H), 6.93-7.04(m, 2H), 7.22-7.38(m, 4H), 7.48-7.56(m, 2H) |
| 27 | (CDCl$_3$) 1.25(d, 6H, J=6.1Hz), 1.48(s, 9H), 4.23-4.51(m, 3H), 4.70-4.52(m, 1H), 6.94-7.05(m, 2H), 7.21-7.35(m, 4H), 7.48-7.56(m, 2H) |
| 28 | (CDCl$_3$) 1.47(s, 9H), 1.76-1.97(m, 4H), 3.56(t, 2H, J=6.2Hz), 4.04(t, 2H, J=6.4Hz), 4.22-4.50(m, 2H), 4.52(s, 2H), 4.72-5.00(m, 1H), 6.83-6.90(m, 1H), 7.05-7.19(m, 2H), 7.22-7.39(m, 8H), 7.50-7.58(m, 2H) |
| 29 | (CDCl$_3$) 1.47(s, 9H), 3.56-3.68(m, 2H), 4.05-4.16(m, 2H), 4.22-4.50(m, 2H), 4.78-4.98(m, 1H), 5.12(s, 2H), 5.20-5.30(m, 1H), 6.82-6.90(m, 1H), 7.05-7.12(m, 1H), 7.15-7.21(m, 1H), 7.26-7.43(m, 8H), 7.49-7.59(m, 2H) |
| 30 | (CDCl$_3$) 1.47(s, 9H), 1.96-2.10(m, 2H), 3.38-3.49(m, 2H), 4.02-4.16(m, 2H), 4.24-4.46(m, 2H), 4.70-5.20(m, 4H), 6.81-6.91(m, 1H), .04-7.22(m, 2H), 7.27-7.41(m, 8H), 7.50-7.58(m, 2H) |
| 31 | (CDCl$_3$) 1.47(s, 9H), 1.63-1.94(m, 4H), 3.19-3.39(m, 2H), 3.92-4.14(m, 2H), 4.22-4.48(m, 2H), 4.65-5.21(m, 4H), 6.79-6.92(m, 1H), 7.04-7.20(m, 2H), 7.26-7.41(m, 8H), 7.50-7.58(m, 2H) |
| 32 | (CDCl$_3$) 1.35(s, 12H), 5.38(s, 2H), 7.31-7.49(m, 6H), 7.95-8.02(m, 1H), 8.13-8.19(m, 1H), 8.47-8.52(m, 1H) |
| 33 | (CDCl$_3$) 1.47(s, 9H), 2.90-3.26(m, 6H), 4.24-4.48(m, 2H), 4.68-5.08(m, 1H), 7.32-7.50(m, 4H), 7.52-7.66(m, 4H) |
| 34 | (DMSO-$d_6$) 1.45-2.25(br, 1H), 3.74(s, 2H), 5.18(s, 2H), 6.97-7.02(m, 1H), 7.20-7.28(m, 2H), 7.32-7.44(m, 6H), 7.46-7.51(m, 2H), 7.57-7.62(m, 2H) |

TABLE 3

| Ref No. | (Solv) δ (ppm) |
|---|---|
| 35 | (CDCl$_3$) 3.91(s, 2H), 5.09(s, 2H), 6.99-7.08(m, 2H), 7.22-7.40(m, 9H), 7.53-7.62(m, 2H) |

TABLE 3-continued

| Ref No. | (Solv) δ (ppm) |
|---|---|
| 36 | (DMSO-d$_6$) 1.22-2.42(br, 2H), 3.71(s, 2H), 6.79-6.87(m, 2H), 7.32-7.38(m, 2H), 7.42-7.53(m, 4H), 9.00-10.00(br, 1H) |
| 37 | (DMSO-d$_6$) 1.48-2.28(br, 2H), 3.77(s, 2H), 3.89(s, 3H), 7.41-7.50(m, 2H), 7.58-7.68(m, 3H), 7.90-7.99(m, 2H), 8.15-8.21(m, 1H) |
| 38 | (DMSO-d$_6$) 0.90(t, 3H, J=7.2Hz), 1.30-2.80(m, 8H), 3.74(s, 2H), 4.03(t, 2H, J=6.6Hz), 6.87-6.93(m, 1H), 7.12-7.22(m, 2H), 7.30-7.43(m, 3H), 7.56-7.63(m, 2H) |
| 39 | (DMSO-d$_6$) 1.29(d, 6H, J=6.0Hz), 1.64-2.02(br, 2H), 3.74(s, 2H), 4.66-4.75(m, 1H), 6.86-6.92(m, 1H), 7.09-7.20(m, 2H), 7.30-7.43(m, 3H), 7.55-7.62(m, 2H) |
| 40 | (DMSO-d$_6$) 1.62-2.14(br, 2H), 3.76(s, 2H), 5.40(s, 2H), 7.33-7.53(m, 7H), 7.59-7.67(m, 3H), 7.92-8.01(m, 2H), 8.16-8.23(m, 1H) |
| 41 | (DMSO-d$_6$) 1.58-2.06(br, 2H), 2.95(s, 6H), 3.74(s, 2H), 6.67-6.76(m, 1H), 6.86-6.93(m, 2H), 7.20-7.28(m, 1H), 7.35-7.41(m, 2H), 7.53-7.59(m, 2H) |
| 42 | (DMSO-d$_6$) 1.50-2.22(br, 2H), 3.75(s, 2H), 5.17(s, 2H), 7.22-7.56(m, 12H), 7.76(brs, 1H), 9.83(brs, 1H) |
| 43 | (DMSO-d$_6$) 2.74-2.83(m, 2H), 3.60-3.70(m, 2H), 3.74(s, 2H), 4.64-4.70(m, 1H), 7.15-7.70(m, 8H) |
| 44 | (DMSO-d$_6$) 3.77(s, 2H), 7.43-7.51(m, 3H), 7.63-7.70(m, 2H), 8.02-8.09(m, 1H), 8.52-8.59(m, 1H), 8.85-8.91(m, 1H) |
| 45 | (DMSO-d$_6$) 1.00(t, 3H, J=7.4Hz), 1.64-1.96(m, 4H), 3.74(s, 2H), 4.00(t, 2H, J=6.7Hz), 6.86-6.94(m, 1H), 7.12-7.22(m, 2H), 7.30-7.43(m, 3H), 7.56-7.62(m, 2H) |
| 46 | (DMSO-d$_6$) 0.95(t, 3H, J=7.4Hz), 1.41-1.51(m, 2H), 1.60-2.00(m, 4H), 3.74(s, 2H), 4.04(t, 2H, J=6.5Hz), 6.86-6.94(m, 1H), 7.12-7.22(m, 2H), 7.30-7.44(m, 3H), 7.55-7.63(m, 2H) |
| 47 | (DMSO-d$_6$) 1.65-2.17(m, 4H), 3.61(t, 2H, J=6.4Hz), 3.75(s, 2H), 4.13(t, 2H, J=6.4Hz), 4.49(s, 2H), 6.87-6.95(m, 1H), 7.12-7.44(m, 10H), 7.55-7.63(m, 2H) |
| 48 | (DMSO-d$_6$) 1.60-2.18(br, 2H), 3.32(s, 3H), 3.65-3.71(m, 2H), 3.74(s, 2H), 4.13-4.20(m, 2H), 6.89-6.95(m, 1H), 7.14-7.25(m, 2H), 7.30-7.44(m, 3H), 7.56-7.64(m, 2H) |
| 49 | (DMSO-d$_6$) 0.93(t, 3H, J=7.4Hz), 1.60-2.02(m, 4H), 3.74(s, 2H), 3.93(t, 2H, J=6.4Hz), 6.97-7.11(m, 2H), 7.24-7.48(m, 6H) |
| 50 | (DMSO-d$_6$) 0.89(t, 3H, J=7.4Hz), 1.32-1.44(m, 2H), 1.59-1.2.12(m, 4H), 3.74(s, 2H), 3.97(t, 2H, J=6.4Hz), 6.96-7.03(m, 1H), 7.05-7.12(m, 1H), 7.24-7.37(m, 4H), 7.39-7.47(m, 2H) |
| 51 | (DMSO-d$_6$) 0.86(t, 3H, J=7.0Hz), 1.24-1.38(m, 4H), 1.58-2.14(m, 4H), 3.74(s, 2H), 3.96(t, 2H, J=6.5Hz), 6.96-7.03(m, 1H), 7.05-7.11(m, 1H), 7.24-7.47(m, 6H) |

TABLE 4

| Ref No. | (Solv) δ (ppm) |
|---|---|
| 52 | (DMSO-d$_6$) 1.20(d, 6H, J=6.0Hz), 1.60-2.06(br, 2H), 3.74(s, 2H), 4.50-4.62(m, 1H), 6.95-7.02(m, 1H), 7.05-7.12(m, 1H), 7.23-7.38(m, 4H), 7.40-7.47(m, 2H) |
| 53 | (DMSO-d$_6$) 1.58-2.04(m, 6H), 3.51(t, 2H, J=6.3Hz), 3.74(s, 2H), 4.05(t, 2H, J=6.5Hz), 4.47(s, 2H), 6.86-6.94(m, 1H), 7.11-7.47(m, 10H), 7.55-7.63(m, 2H) |
| 54 | (DMSO-d$_6$) 1.54-2.30(br, 2H), 3.33-3.47(m, 2H), 3.74(s, 2H), 4.02-4.12(m, 2H), 5.03(s, 2H), 6.85-6.96(m, 1H), 7.12-7.44(m, 10H), 7.46-7.66(m, 3H) |
| 55 | (DMSO-d$_6$) 1.83-1.94(m, 2H), 3.13-3.25(m, 2H), 3.75(s, 2H), 4.06(t, 2H, J=6.4Hz), 5.01(s, 2H), 6.84-6.95(m, 1H), 7.10-7.68(m, 13H) |
| 56 | (DMSO-d$_6$) 1.50-1.80(m, 4H), 3.00-3.14(m, 2H), 3.75(s, 2H), 4.03(t, 2H, J=6.4Hz), 5.01(s, 2H), 6.84-6.94(m, 1H), 7.09-7.23(m, 2H), 7.24-7.46(m, 9H), 7.54-7.64(m, 2H) |
| 57 | (DMSO-d$_6$) 1.76-2.64(br, 2H), 2.89-3.07(m, 6H), 3.77(s, 2H), 7.33-7.55(m, 4H), 7.60-7.67(m, 2H), 7.69-7.76(m, 1H) |
| 58 | (CDCl$_3$) 3.89(s, 3H), 7.35-7.59(m, 8H), 10.02(s, 1H) |
| 59 | (CDCl$_3$) 4.01(s, 3H), 7.14-7.20(m, 1H), 7.22-7.30(m, 1H), 7.38-7.53(m, 3H), 7.59-7.67(m, 2H), 7.87-7.94(m, 1H), 10.49(s, 1H) |

TABLE 4-continued

| Ref No. | (Solv) δ (ppm) |
|---|---|
| 60 | (CDCl$_3$) 7.36-7.55(m, 5H), 7.58-7.66(m, 2H), 7.90-7.98(m, 1H), 10.39(s, 1H) |
| 61 | (CDCl$_3$) 2.56(s, 3H), 7.41-7.55(m, 5H), 7.60-7.67(m, 2H), 7.85-7.92(m, 1H), 10.31(s, 1H) |
| 62 | (CDCl$_3$) 7.20-7.28(m, 2H), 7.38-7.57(m, 5H), 7.68-7.76(m, 2H), 9.91(s, 1H) |
| 63 | (CDCl$_3$) 3.81(s, 3H), 4.88(s, 2H), 7.06-7.13(m, 2H), 7.22-7.42(m, 4H), 7.44-7.50(m, 2H), 7.69-7.76(m, 2H), 7.84-7.91(m, 2H) |
| 64 | (CDCl$_3$) 3.92(s, 3H), 4.95(s, 2H), 7.03-7.13(m, 2H), 7.21-7.28(m, 1H), 7.30-7.37(m, 1H), 7.38-7.46(m, 2H), 7.51-7.58(m, 2H), 7.69-7.76(m, 2H), 7.84-7.91(m, 2H) |
| 65 | (CDCl$_3$) 5.01(s, 2H), 5.19(s, 2H), 7.07-7.17(m, 2H), 7.19-7.26(m, 1H), 7.29-7.54(m, 10H), 7.69-7.76(m, 2H), 7.82-7.89(m, 2H) |
| 66 | (DMSO-d$_6$) 4.95(s, 2H), 7.43-7.55(m, 3H), 7.80-7.96(m, 8H) |
| 67 | (CDCl$_3$) 4.98(s, 2H), 7.22-7.47(m, 6H), 7.49-7.56(m, 2H), 7.70-7.80(m, 2H), 7.84-7.92(m, 2H) |
| 68 | (CDCl$_3$) 2.58(s, 3H), 5.05(s, 2H), 7.19-7.24(m, 1H), 7.28-7.38(m, 2H), 7.39-7.56(m, 5H), 7.70-7.79(m, 2H), 7.85-7.93(m, 2H) |
| 69 | (CDCl$_3$) 3.93(s, 2H), 4.81(s, 2H), 7.10-7.29(m, 7H), 7.32-7.38(m, 2H), 7.66-7.73(m, 2H), 7.79-7.86(m, 2H) |
| 70 | (CDCl$_3$) 4.82(s, 2H), 6.90-7.02(m, 4H), 7.05-7.13(m, 1H), 7.28-7.46(m, 4H), 7.66-7.76(m, 2H), 7.82-7.90(m, 2H) |
| 71 | (CDCl$_3$) 4.78(s, 2H), 5.03(s, 2H), 6.88-6.94(m, 2H), 7.27-7.42(m, 7H), 7.66-7.72(m, 2H), 7.80-7.86(m, 2H) |

TABLE 5

| Ref No. | (Solv) δ (ppm) |
|---|---|
| 72 | (CDCl$_3$) 4.81(s, 2H), 7.20-7.40(m, 9H), 7.68-7.75(m, 2H), 7.81-7.88(m, 2H) |
| 73 | (CDCl$_3$) 4.82(s, 2H), 5.03(s, 2H), 6.84-6.93(s, 1H), 6.99-7.08(m, 2H), 7.19-7.46(m, 6H), 7.67-7.75(m, 2H), 7.81-7.90(m, 2H) |
| 74 | (DMSO-d$_6$) 1.40-2.32(br, 2H), 3.71-3.80(m, 5H), 6.93-7.01(m, 1H), 7.08-7.13(m, 1H), 7.16-7.23(m, 1H), 7.25-7.49(m, 5H) |
| 75 | (DMSO-d$_6$) 1.30-2.25(br, 2H), 3.69(s, 2H), 3.88(s, 3H), 7.15-7.23(m, 2H), 7.32-7.50(m, 4H), 7.65-7.72(m, 2H) |
| 76 | (DMSO-d$_6$) 1.70(brs, 2H), 3.75(s, 2H), 5.25(s, 2H), 7.18-7.25(m, 1H), 7.26-7.55(m, 10H), 7.63-7.69(m, 2H) |
| 77 | (DMSO-d$_6$) 1.40-2.50(br, 2H), 3.88(s, 2H), 7.39-7.56(m, 3H), 7.77-7.94(m, 4H) |
| 78 | (DMSO-d$_6$) 1.82(brs, 2H), 3.78(s, 2H), 7.34-7.61(m, 6H), 7.65-7.74(m, 2H) |
| 79 | (DMSO-d$_6$) 1.82(brs, 2H), 2.55(s, 3H), 3.75(s, 2H), 7.31-7.55(m, 6H), 7.64-7.73(m, 2H) |
| 80 | (CDCl$_3$) 1.49(brs, 2H), 3.83(s, 2H), 3.97(s, 2H), 7.13-7.31(m, 9H) |
| 81 | (CDCl$_3$) 1.53(brs, 2H), 3.85(s, 2H), 6.94-7.14(m, 5H), 7.24-7.38(m, 4H) |
| 82 | (CDCl$_3$) 1.52(brs, 2H), 3.80(s, 2H), 5.06(s, 2H), 6.90-6.98(m, 2H), 7.19-7.25(m, 2H), 7.28-7.48(m, 5H) |
| 83 | (CDCl$_3$) 1.53(brs, 2H), 3.86(s, 2H), 7.18-7.41(m, 9H) |
| 84 | (CDCl$_3$) 1.52(brs, 2H), 3.84(s, 2H), 5.07(s, 2H), 6.82-7.00(m, 3H), 7.21-7.47(m, 6H) |
| 85 | (CDCl$_3$) 3.85(s, 3H), 7.18-7.22(m, 1H), 7.30-7.54(m, 7H) |
| 86 | (CDCl$_3$) 5.50(s, 1H), 7.24-7.36(m, 3H), 7.41-7.58(m, 5H) |
| 87 | (CDCl$_3$) 5.11(s, 2H), 7.22-7.47(m, 11H), 7.52-7.59(m, 2H) |
| 88 | (CDCl$_3$) 2.29(s, 3H), 7.25-7.34(m, 3H), 7.37-7.59(m, 5H) |
| 89 | (CDCl$_3$) 2.61(s, 3H), 7.37-7.71(m, 8H) |
| 90 | (CDCl$_3$) 5.23(s, 2H), 6.97-7.05(m, 2H), 7.30-7.53(m, 6H), 7.56-7.63(m, 1H) |
| 91 | (CDCl$_3$) 7.28-7.36(m, 1H), 7.72-7.87(m, 4H), 8.08-8.16(m, 2H), 8.70-8.77(m, 1H) |
| 92 | (CDCl$_3$) 7.47-7.53(m, 2H), 7.71-7.83(m, 4H), 8.71-8.77(m, 2H) |
| 93 | (DMSO-d$_6$) 1.60-2.10(br, 2H), 3.74(s, 2H), 5.12(s, 2H), 6.97-7.04(m, 1H), 7.19-7.43(m, 10H), 7.47-7.56(m, 2H) |
| 94 | (DMSO-d$_6$) 1.80(brs, 2H), 2.21(s, 3H), 3.71(s, 2H), 7.08-7.48(m, 8H) |

TABLE 6

| Ref No. | (Solv) δ (ppm) |
|---|---|
| 95 | (DMSO-d$_6$) 1.77(brs, 2H), 2.33(s, 3H), 3.72(s, 2H), 7.29-7.51(m, 6H), 7.59-7.68(m, 2H) |
| 96 | (DMSO-d$_6$) 1.25-2.45(br, 2H), 3.71(s, 2H), 5.12(s, 2H), 6.86-6.95(m, 1H), 6.97-7.06(m, 1H), 7.11-7.23(m, 1H), 7.26-7.53(m, 6H) |
| 97 | (DMSO-d$_6$) 1.68-2.50(br, 2H), 3.77(s, 2H), 7.29-7.37(m, 1H), 7.41-7.48(m, 2H), 7.82-8.08(m, 4H), 8.62-8.68(m, 1H) |
| 98 | (DMSO-d$_6$) 3.83(s, 2H), 7.47-7.54(m, 2H), 7.66-7.82(m, 4H), 8.59-8.65(m, 2H) |
| 99 | (DMSO-d$_6$) 1.55-2.16(m, 6H), 3.42(t, 2H, J=6.3 Hz), 3.72(s, 2H), 3.99(t, 2H, J=6.2 Hz), 4.41(s, 2H), 6.93-7.00(m, 1H), 7.05-7.11(m, 1H), 7.17-7.42(m, 9H), 7.44-7.51(m, 2H) |
| 100 | (DMSO-d$_6$) 1.41(s, 9H), 4.00-4.14(m, 2H), 6.70-6.88(m, 2H), 7.14-7.43(m, 5H), 7.48-7.57(m, 2H), 9.47(s, 1H) |
| 101 | (CDCl$_3$) 1.47(s, 9H), 1.83-1.98(m, 2H), 3.19-3.33(m, 2H), 3.94-4.06(m, 2H), 4.25-4.39(m, 2H), 4.73-4.96(m, 2H), 5.05(s, 1H), 6.85-6.99(m, 2H), 7.19-7.50(m, 1H) |
| 102 | (CDCl$_3$) 1.48(s, 9H), 1.82-1.93(m, 2H), 2.19(s, 6H), 2.30-2.39(m, 2H), 4.01(t, 2H, J=6.2 Hz), 4.22-4.44(m, 2H), 4.74-5.02(m, 1H), 6.87-6.98(m, 2H), 7.24-7.43(m, 4H), 7.48-7.56(m, 2H) |
| 103 | (DMSO-d$_6$) 1.73-1.87(m, 2H), 3.05-3.21(m, 2H), 3.75(s, 2H), 4.00(t, 2H, J=6.0 Hz), 5.01(s, 2H), 6.93-7.02(m, 1H), 7.07-7.12(m, 1H), 7.18-7.55(m, 12H) |
| 104 | (DMSO-d$_6$) 1.71-1.81(m, 2H), 2.08(s, 6H), 2.27(t, 2H, J=7.1 Hz), 3.73(s, 2H), 4.00(t, 2H, J=6.3 Hz), 6.93-7.00(m, 1H), 7.06-7.12(m, 1H), 7.18-7.52(m, 6H) |
| 105 | (CDCl$_3$) 5.20(s, 2H), 7.04(d, 1H, J=8.2 Hz), 7.20-7.60(m, 7H), 9.84(s, 1H) |
| 106 | (CDCl$_3$) 5.17(s, 2H), 5.82(s, 1H), 6.96(d, 1H, J=8.3 Hz), 7.13-7.25(m, 2H), 7.35-7.50(m, 5H) |
| 107 | (CDCl$_3$) 1.70-2.10(m, 4H), 3.55(t, 2H, J=6.1 Hz), 4.04(t, 2H, J=6.5 Hz), 4.49(s, 2H), 5.17(s, 2H), 6.90(d, 1H, J=8,2 Hz), 7.08(d, 1H, J=1.9 Hz), 7.19(dd, 1H, J=1.9 Hz, 8.2 Hz), 7.24-7.45(m, 10H) |
| 108 | (CDCl$_3$) 1.90-2.05(m, 4H), 4.05-4.20(m, 2H), 4.40-4.55(m, 2H), 6.06(s, 1H), 6.98(d, 1H, J=8.3 Hz), 7.07(d, 1H, J=1.8 Hz), 7.24(dd, 1H, J=1.8 Hz, 8.3 Hz) |
| 109 | (CDCL$_3$) 1.60-1.72(m, 2H), 1.78-1.90(m, 2H), 3.62(t, 2H, J=6.5 Hz), 4.02(t, 2H, J=6.2 Hz), 5.10(s, 2H), 6.90-7.50 (m, 12H). |
| 110 | (DMSO-d$_6$) 1.44-2.25(m, 6H), 3.32-3.50(m, 2H), 3.72(s, 2H), 3.99(t, 2H, J=6.4 Hz), 4.38-4.49(m, 1H), 5.13(s, 2H), 6.90-6.98(m, 2H), 7.02-7.50(m, 10H) |
| 111 | (DMSO-d$_6$) 1.48-2.32(br, 2H), 3.73(s, 2H), 6.82-6.96(m, 2H), 7.10-7.17(m, 1H), 7.19-7.26(m, 1H), 7.30-7.37(m, 2H), 7.43-7.50(m, 2H), 9.04-9.86br, 1H |

TABLE 7

| Ref No. | (Solv) δ (ppm) |
|---|---|
| 112 | (CDCl$_3$) −0.31(s, 3H), −0.05(s, 3H), −0.01(s, 3H), 0.01(s, 3H), 0.10(s, 3H), 0.15(s, 3H), 0.75(s, 9H), 0.82(s, 9H), 0.94(s, 9H), 3.75(dd, 1H, J=2.5, 11.6Hz), 3.87(dd, 1H, J=2.6, 11.6Hz), 4.08-4.12(m, 1H), 4.28(dd, 1H, J=2.1, 4.9Hz), 4.57(dd, 1H, J=3.7, 15.7Hz), 4.84(dd, 1H, J=4.9, 6.9Hz), 4.96(dd, 1H, J=8.0, 15.7Hz), 5.04-5.26(m, 4H), 6.01(dd, 1H, J=3.7, 8.0Hz), 6.08(d, 1H, J=6.9Hz), 6.92-7.00(m, 1H), 7.15-7.22(m, 2H), 7.29-7.58(m, 10H),8.16(s, 1H) |
| 113 | (CDCl$_3$) −0.33(s, 3H), −0.06(s, 3H), 0.00(s, 3H), 0.04(s, 3H), 0.10(s, 3H), 0.15(s, 3H), 0.74(s, 9H), 0.80(s, 9H), 0.94(s, 9H), 3.78(dd, 1H, J=2.1, 11.8Hz), 3.91(dd, 1H, J=2.1, 11.8Hz), 4.11-4.16(m, 1H), 4.23(dd, 1H, J=1.5, 4.7Hz), 4.48(dd, 1H, J=4.0, 16.7Hz), 4.73(dd, 1H, J=4.7, 7.5Hz), 5.03(dd, 1H, J=8.9, 16.7Hz), 5.26(brs, 2H), 6.21(d, 1H, J=7.5Hz), 6.42(dd, 1H, J=4.0, 8.9Hz), 6.60-6.66(m, 1H), 6.77-6.85(m, 1H), 6.93-7.00(m, 1H), 7.10-7.25(m, 5H), 8.18(s, 1H) |
| 114 | (CDCl$_3$) −0.31(s, 3H), −0.05(s, 3H), −0.01(s, 3H), 0.01(s, 3H), 0.10(s, 3H), 0.15(s, 3H), 0.75(s, 9H), 0.82(s, 9H), 0.94(s, 9H), 3.75(dd, 1H, J=2.6, 11.6Hz), 3.82(s, 3H), 3.87(dd, 1H, J=2.8, 11.6Hz), 4.06-4.14(m, 1H), 4.28(dd, 1H, J=2.5, 4.7Hz), 4.57(dd, |

TABLE 7-continued

| Ref No. | (Solv) δ (ppm) |
|---|---|
| | 1H, J=3.8, 15.8Hz), 4.69(s, 2H), 4.84(dd, 1H, J=4.7, 6.9Hz), 4.97(dd, 1H, J=8.0, 15.8Hz), 5.15(brs, 2H), 6.02(d, 1H, J=3.8, 8.0Hz), 6.08(d, 1H, J=6.9Hz), 6.84-6.90(m, 1H), 7.11-7.16(m, 1H), 7.18-7.25(m, 1H), 7.32-7.44(m, 3H), 7.49-7.55(m, 2H), 8.16(s, 1H) |
| 115 | (CDCl$_3$) −0.30(s, 3H), −0.03(s, 3H), 0.05(s, 3H), 0.07(s, 3H), 0.12(s, 3H), 0.16(s, 3H), 0.76(s, 9H), 0.83(s, 9H), 0.96(s, 9H), 3.83(dd, 1H, J=2.1, 11.8Hz), 3.97(dd, 1H, J=2.1, 11.8Hz), 4.13-4.19(m, 1H), 4.27(dd, 1H, J=1.7, 5.0Hz), 4.59(dd, 1H, J=4.4, 16.7Hz), 4.81(dd, 1H, J=5.0, 7.5Hz), 4.91(dd, 1H, J=8.6, 16.7Hz), 5.39(brs, 2H), 6.23(d, 1H, J=7.5Hz), 6.38-6.56(m, 3H), 6.95-7.17(m, 6H), 8.18(s, 1H) |
| 116 | (CDCl$_3$) −0.30(s, 3H), −0.05(s, 3H), −0.02(s, 3H), 0.10(s, 3H), 0.15(s, 3H), 0.75(s, 9H), 0.81(s, 9H), 0.94(s, 9H), 3.74(dd, 1H, J=2.5, 11.7Hz), 3.82(s, 3H), 3.86(dd, 1H, J=2.8, 11.7Hz), 4.06-4.12(m, 1H), 4.27-4.31(m, 1H), 4.56(dd, 1H, J=4.2, 15.8Hz), 4.68(s, 2H), 4.85-4.90(m, 1H), 4.94(dd, 1H, J=8.1, 15.8Hz), 5.13(brs, 2H), 5.91-5.97(m, 1H), 6.05(d, 1H, J=7.2Hz), 6.94-7.00(m, 2H), 7.36-7.42(m, 2H), 7.45-7.55(m, 4H), 8.16(s, 1H) |
| 117 | (CDCl$_3$) −0.31(s, 3H), −0.05(s, 3H), −0.01(s, 3H), 0.02(s, 3H), 0.10(s, 3H), 0.15(s, 3H), 0.75(s, 9H), 0.83(s, 9H), 0.94(s, 9H), 1.47-1.68(m, 3H), 1.71-1.82(m, 2H), 3.51-3.60(m, 2H), 3.75(dd, 1H, J=2.5, 11.5Hz), 3.86(dd, 1H, J=2.8, 11.5Hz), 3.95(t, 2H, J=6.1Hz), 4.06-4.12(m, 1H), 4.30(dd, 1H, J=2.3, 4.9Hz), 4.51(dd, 1H, J=3.8, 15.6Hz), 4.88(dd, 1H, J=4.9, 7.0Hz), 4.98(dd, 1H, J=8.4, 15.6Hz), 5.01-5.17(m, 4H), 5.94(dd, 1H, J=3.8, 8.4Hz), 6.05(d, 1H, J=7.0Hz), 6.88-7.04(m, 3H), 7.07-7.13(m, 1H), 7.15-7.19(m, 1H), 7.22-7.49(m, 7H), 8.16(s, 1H) |

TABLE 8

| Ref No. | (Solv) δ (ppm) |
|---|---|
| 118 | (CDCl$_3$) −0.31(s, 3H), −0.05(s, 3H), −0.01(s, 3H), 0.02(s, 3H), 0.10(s, 3H), 0.15(s, 3H), 0.75(s, 9H), 0.83(s, 9H), 0.94(s, 9H), 1.54-1.82(m, 4H), 3.19(t, 2H, J=6.7Hz), 3.75(dd, 1H, J=2.5, 11.7Hz), 3.86(dd, 1H, J=2.5, 11.7Hz), 3.92(t, 2H, J=5.9HZ), 4.06-4.12(m, 1H), 4.30(dd, 1H, J=2.5, 4.9Hz), 4.51(dd, 1H, J=3.7, 15.6Hz), 4.88(dd, 1H, J=4.9, 6.8Hz), 4.92-5.18(m, 5H), 5.93(dd, 1H, J=3.7, 8.2Hz), 6.05(d, 1H, J=6.8Hz), 6.89-7.03(m, 3H), 7.06-7.17(m, 2H), 7.22-7.50(m, 7H), 8.17(s, 1H) |
| 119 | (CDCl$_3$) −0.32(s, 3H), −0.06(s, 3H), 0.00(s, 3H), 0.03(s, 3H), 0.10(s, 3H), 0.15(s, 3H), 0.75(s, 9H), 0.82(s, 9H), 0.94(s, 9H), 1.44(s, 9H), 1.51-1.80(m, 4H), 3.06-3.22(m, 2H), 3.70-3.96(m, 4H), 4.06-4.12(m, 1H), 4.28(dd, 1H, J=2.0, 4.7Hz), 4.49(dd, 1H, J=3.8, 15.9Hz), 4.74-4.90(m, 2H), 4.98(dd, 1H, J=8.1, 15.9Hz), 5.10(brs, 2H), 5.95-6.10(m, 2H), 6.80-6.96(m, 4H), 7.12-7.32(m, 3H), 8.16(s, 1H) |
| 120 | (CDCl$_3$) −0.31(s, 3H), −0.05(s, 3H), 0.02(s, 3H), 0.03(s, 3H), 0.10(s, 3H), 0.15(s, 3H), 0.75(s, 9H), 0.83(s, 9H), 0.94(s, 9H), 3.78(dd, 1H, J=2.5, 11.6Hz), 3.92(dd, 1H, J=2.5, 11.6Hz), 4.09-4.14(m, 1H), 4.27(dd, 1H, J=2.1, 4.8Hz), 4.52(dd, 1H, J=3.8, 16.2Hz), 4.85(dd, 1H, J=4.8, 7.1Hz), 4.95(dd, 1H, J=8.2, 16.2Hz), 5.17(brs, 2H), 6.08-6.19(m, 2H), 6.94-7.02(m, 2H), 7.18-7.43(m, 6H), 8.14(s, 1H) |
| 121 | (CDCl$_3$) −0.29(s, 3H), −0.08(s, 3H), −0.06-−0.02(m, 6H), 0.10(s, 3H), 0.15(s, 3H), 0.72-0.79(s, 18H), 0.94(s, 9H), 3.71(dd, 1H, J=2.7, 11.5Hz), 3.83(dd, 1H, J=3.0, 11.5Hz), 4.05-4.11(m, 1H), 4.30-4.36(m, 1H), 4.66(dd, 1H, J=4.2, 16.0Hz), 4.93-5.25(m, 6H), 5.85-5.95(m, 1H), 5.99(d, 1H, J=6.3Hz), 7.11-7.17(m, 2H), 7.29-7.56(m, 11H), 8.14(s, 1H) |
| 122 | (CDCl$_3$) −0.35(s, 3H), −0.07(s, 3H), 0.07-0.20(m, 12H), 0.72(s, 9H), 0.90-0.98(s, 18H), 3.81(dd, 1H, J=2.3, 11.8Hz), 3.96(dd, 1H, J=2.3, 11.8Hz), 4.05-4.11(m, 1H), 4.25-4.31(m, 1H), 4.43(dd, 1H, J=5.3, 14.8Hz), 4.65(dd, 1H, J=7.2, 14.8Hz), 4.80-4.87(m, 1H), 5.11(brs, 2H), 5.97(d, 1H, J=6.7Hz), 6.25-6.33(m, 1H), 7.06-7.12(m, 1H), 7.18-7.26(m, 1H), 7.29-7.35(m, 1H), 7.37-7.44(m, 2H), 7.53-7.59(m, 2H), 8.15(s, 1H) |
| 123 | (CDCl$_3$) −0.31(s, 3H), −0.06(s, 3H), −0.02(s, 3H), 0.01(s, 3H), 0.10(s, 3H), 0.15(s, 3H), 0.75(s, 9H), 0.81(s, 9H), 0.94(s, 9H), 3.72(dd, 1H, J=2.4, 11.7Hz), 3.80(dd, 1H, J=2.5, 11.7Hz), 4.05- |

TABLE 8-continued

| Ref No. | (Solv) δ (ppm) |
|---|---|
| | 4.11(m, 1H), 4.24-4.30(m, 1H), 4.48(dd, 1H, J=3.7, 15.8Hz), 4.81-4.88(m, 1H), 4.95-5.17(m, 5H), 5.89-6.01(m, 1H), 6.08(d, 1H, J=6.9Hz), 6.96-7.07(m, 2H), 7.16-7.43(m, 9H), 7.51-7.59(m, 2H), 8.18(s, 1H) |
| 124 | (CDCl₃) −0.44(s, 3H), −0.14(s, 3H), −0.04(s, 3H), −0.02(s, 3H), 0.10(s, 3H), 0.13(s, 3H), 0.69(s, 9H), 0.77(s, 9H), 0.96(s, 9H), 3.63-3.72(m, 2H), 3.95-4.00(m, 1H), 4.08-4.14(m, 1H), 4.33(dd, 1H, J=3.1, 16.5Hz), 4.51(dd, 1H, J=5.0, 7.7Hz), 5.04(dd, 1H, J=9.2, 16.5Hz), 5.21(s, 2H), 5.98(d, 1H, J=7.7Hz), 6.10(dd, 1H, J=3.1, 9.2Hz), 6.65-6.74(m, 2H), 7.01-7.07(m, 1H), 7.27-7.34(m, 1H), 7.37-7.49(m, 4H), 8.15(s, 1H) |

TABLE 9

| Ref No. | (Solv) δ (ppm) |
|---|---|
| 125 | (CDCl₃) −0.31(s, 3H), −0.05(s, 3H), 0.02(s, 3H), 0.10(s, 3H), 0.15(s, 3H), 0.75(s, 9H), 0.82(s, 9H), 0.94(s, 9H), 3.76(dd, 1H, J=2.4, 11.7Hz), 3.88(dd, 1H, J=2.5, 11.7Hz), 3.94(s, 3H), 4.06-4.14(m, 1H), 4.28(dd, 1H, J=2.1, 4.8Hz), 4.58(dd, 1H, J=4.1, 15.6Hz), 4.84(dd, 1H, J=4.8, 6.9Hz), 4.98(dd, 1H, J=8.1, 15.6Hz), 5.12(s, 2H), 6.04(dd, 1H, J=4.1, 8.1Hz), 6.09(d, 1H, J=6.9Hz), 7.39-7.63(m, 5H), 7.72-7.80(m, 1H), 7.97-8.05(m, 1H), 8.16(s, 1H), 8.24-8.28(m, 1H) |
| 126 | (CDCl₃) −0.30(s, 3H), −0.05(s, 3H), −0.01(s, 3H), 0.01(s, 3H), 0.10(s, 3H), 0.15(s, 3H), 0.75(s, 9H), 0.82(s, 9H), 0.94(s, 9H), 3.75(dd, 1H, J=2.5, 11.6Hz), 3.87(dd, 1H, J=2.5, 11.6Hz), 4.06-4.13(m, 1H), 4.28(dd, 1H, J=2.6, 4.9Hz), 4.57(dd, 1H, J=3.9, 15.8Hz), 4.86(dd, 1H, J=4.9, 6.8Hz), 4.97(dd, 1H, J=8.0, 15.8Hz), 5.13(brs, 2H), 5.40(s, 2H), 6.00(dd, 1H, J=3.9, 8.0Hz), 6.07(d, 1H, J=6.8Hz), 7.31-7.62(m, 10H),7.73-7.81(m, 1H), 8.00-8.08(m, 1H), 8.16(s, 1H), 8.26-8.31(m, 1H) |
| 127 | (CDCl₃) −0.32(s, 3H), −0.06(s, 3H), −0.01(s, 3H), 0.02(s, 3H), 0.10(s, 3H), 0.15(s, 3H), 0.74(s, 9H), 0.82(s, 9H), 0.94(s, 9H), 1.67-1.83(m, 4H), 3.66(t, 2H, J=6.8Hz), 3.76(dd, 1H, J=2.5, 11.6Hz), 3.87(dd, 1H, J=2.6, 11.6Hz), 3.90-3.99(m, 2H), 4.06-4.15(m, 1H), 4.29(dd, 1H, J=2.3, 4.7Hz), 4.51(dd, 1H, J=3.7, 15.5Hz), 4.85(dd, 1H, J=4.7, 7.0Hz), 4.99(dd, 1H, J=8.3, 15.5Hz), 5.10(brs, 2H), 5.98(dd, 1H, J=3.7, 8.3Hz), 6.06(d, 1H, J=7.0Hz), 6.95-7.02(m, 2H), 7.21-7.40(m, 4H), 7.44-7.53(m, 2H), 7.67-7.76(m, 2H), 7.79-7.89(m, 2H), 8.16(s, 1H) |
| 128 | (CDCl₃) −0.30(s, 3H), −0.05(s, 3H), −0.01(s, 3H), 0.02(s, 3H), 0.10(s, 3H), 0.15(s, 3H), 0.75(s, 9H), 0.82(s, 9H), 0.94(s, 9H), 1.40-1.78(m, 4H), 2.63(t, 2H, J=7.0Hz), 3.75(dd, 1H, J=2.5, 11.7Hz), 3.86(dd, 1H, J=2.8,11.7Hz), 3.93(t, 2H, J=6.4Hz), 4.05-4.12(m, 1H), 4.30(dd, 1H, J=2.5, 4.8Hz), 4.52(dd, 1H, J=4.0, 15.6Hz), 4.89(dd, 1H, J=4.8, 6.9Hz), 4.98(dd, 1H, J=8.1, 15.6Hz), 5.08(brs, 2H), 5.92(dd, 1H, J=4.0, 8.1Hz), 6.05(d, 1H, J=6.9Hz), 6.95-7.03(m, 2H), 7.23-7.42(m, 4H), 7.46-7.55(m, 2H), 8.16(s, 1H) |

TABLE 10

| Ref No. | (Solv) δ (ppm) |
|---|---|
| 129 | (DMSO-d6) 2.27(s, 3H), 5.17(s, 2H), 7.05-7.15(m, 1H), 7.20-7.50(m, 7H), 13.21(brs, 1H) |
| 130 | (DMSO-d6) 2.84(s, 3H), 2.93(s, 3H), 5.07(s, 2H), 6.25-6.50(m, 3H), 7.25-7.50(m, 5H), 9.69(s, 1H) |
| 131 | (DMSO-d6) 1.40(s, 9H), 2.91(s, 3H), 2.99(s, 3H), 4.16(d, 2H, J=6.0Hz), 5.22(s, 2H), 6.95-7.00(m, 1H), 7.21(s, 1H) 7.25-7.55(m, 9H), 7.65(d, 2H, J=8.2Hz) |
| 132 | (DMSO-d6) 2.96(s, 3H), 2.99(s, 3H), 3.66(s, 3H), 6.85(d, 1H, J=7.8Hz), 6.93(s, 1H), 7.21(d, 1H, J=7.8Hz) 7.25-7.35(m, 1H), 7.44(t, 1H, J=7.8Hz), 7.50-7.60(m, 2H) |
| 133 | (DMSO-d6) 1.41(s, 9H), 2.77(s, 3H), 2.96(s, 3H), 4.17(d, 2H, J=6.0Hz), 5.10(s, 2H), 6.94(d, 1H, J=7.6Hz), |

TABLE 10-continued

| Ref No. | (Solv) δ (ppm) |
|---|---|
| | 7.14(s, 1H), 7.25-7.40(m, 7H), 7.45(t, 2H, J=7.6Hz), 7.50-7.60(m, 2H) |
| 134 | (CDCl3) 1.48(s, 9H), 3.63(s, 3H), 4.30-4.45(m, 2H), 7.20-7.80(m, 8H) |
| 135 | (CDCl3) 1.47(s, 9H), 1.92(s, 6H), 1.96-2.06(m, 2H), 3.15-3.25(m, 2H), 4.30-4.45(m, 2H), 7.10-7.65(m, 8H) |
| 136 | (CDCl3) 3.54(s, 1H), 7.25-7.70(m, 8H) |
| 137 | (CDCl3) 0.03(s, 6H), 0.85(s, 9H), 1.70-1.85(m, 2H), 2.85-2.95(m, 2H), 3.60-3.70(m, 2H), 7.20-7.60(m, 8H) |
| 138 | (CDCl3) 2.12-2.22(m, 2H), 3.60(t, 2H, J=6.3Hz), 4.14(t, 2H, J=5.8Hz), 7.19-7.26(m, 1H), 7.31-7.51(m, 7H) |
| 139 | (CDCl3) 1.70-1.83(m, 4H), 1.88-2.00(m, 2H), 2.38-2.57(m, 6H), 4.06(t, 2H, J=6.3Hz), 7.18-7.56(m, 8H) |
| 140 | (CDCl3) 0.96(t, 6H, J=7.0Hz), 1.80-1.92(m, 2H), 2.40-2.57(m, 6H), 4.03(t, 2H, J=6.2Hz), 7.18-7.23(m, 1H), 7.28-7.56(m, 7H) |
| 141 | (CDCl3) 1.33-1.65(m, 6H), 1.83-1.98(m, 2H), 2.11-2.44(m, 6H), 4.03(t, 2H, J=6.4Hz), 7.18-7.25(m, 1H), 7.28-7.56(m, 7H) |
| 142 | (DMSO-d6) 1.65-1.75(m, 2H), 2.95-3.10(m, 2H), 3.40-3.55(m, 2H), 7.20-7.55(m, 4H) |
| 143 | (DMSO-d6) 1.65-1.80(m, 2H), 3.05-3.15(m, 2H), 3.45-3.55(m, 2H), 7.35-7.70(m, 4H), 7.85-8.00(m, 4H) |
| 144 | (CDCl3) 1.48(s, 9H), 1.91-2.04(m, 2H), 3.33-3.47(m, 2H), 3.96-4.07(m, 2H), 4.20-4.46(m, 2H), 4.70-5.10(m, 1H), 6.18-6.54(m, 1H), 6.85-7.05(m, 2H), 7.22-7.53(m, 6H) |
| 145 | (DMSO-d6) 1.70-1.85(m, 2H), 2.24(s, 3H), 2.45-2.60(m, 2H), 3.95-4.05(m, 2H), 4.14(d, 2H, J=6.2Hz), 6.80-7.05(m, 2H), 7.15-7.55(m, 6H) |

TABLE 11

| Ref No. | (Solv) δ (ppm) |
|---|---|
| 146 | (DMSO-d6) 0.96(t, 3H, J=7.1Hz), 1.41(s, 9H), 1.70-1.83(m, 2H), 2.42-2.61(m, 4H), 4.01(t, 2H, J=6.3Hz), 4.06-4.19(m, 2H), 6.81-7.05(m, 2H), 7.17-7.53(m, 6H) |
| 147 | (DMSO-d6) 0.83(t, 3H, J=7.4Hz), 1.25-1.45(m, 11H), 1.70-1.85(m, 2H), 2.35-2.45(m, 2H), 2.50-2.60(m, 2H), 3.95-4.08(m, 2H), 4.14(d, 2H, J=5.7Hz), 6.87(d, 1H, J=7.8Hz), 6.98(s, 1H), 7.15-7.55(m, 6H) |
| 148 | (DMSO-d6) 1.30-1.50(m, 13H), 1.70-1.85(m, 2H), 2.38-2.48(m, 2H), 2.50-2.60(m, 2H), 3.95-4.05(m, 2H), 4.14(d, 2H, J=6.3Hz), 6.85-7.05(m, 2H) 7.15-7.55(m, 6H) |
| 149 | (CDCl3) 1.47(s, 9H), 2.20-2.34(m, 2H), 3.77(t, 2H, J=6.3Hz), 4.18 (t, 2H, J=5.9Hz), 4.36(d, 2H, J=5.8Hz), 6.85-6.95(m, 1H), 7.11(s, 1H), 7.17(d, 1H, J=7.7Hz), 7.30-7.43(m, 3H), 7.55(d, 2H, J=8.1Hz) |
| 150 | (CDCl3) 1.47(s, 9H), 1.92-2.04(m, 2H), 2.26(s, 6H), 2.42-2.52(m, 2H), 4.07(t, 2H, J=6.5Hz), 4.21-4.51(m, 2H), 6.84-6.93(m, 1H), 7.06-7.20(m, 2H), 7.28-7.39(m, 3H), 7.51-7.59(m, 2H) |
| 151 | (CDCl3) 1.35-1.70(m, 15H), 1.90-2.10(m, 2H), 2.25-2.60(m, 6H), 4.06(t, 2H, J=6.2Hz), 4.35(d, 2H, J=5.4Hz), 6.83-6.95(m, 1H), 7.10(s, 1H), 7.14(d, 1H, J=7.7Hz), 7.25-7.40(m, 3H), 7.54(d, 2H, J=8.1Hz) |
| 152 | (CDCl3) 1.47(s, 9H), 1.70-1.90(m, 4H), 1.95-2.10(m, 2H), 2.43-2.75(m, 6H), 4.00-4.20(m, 2H), 4.35(d, 2H, J=5.5Hz), 6.85-6.95(m, 1H), 7.05-7.20(m, 2H), 7.25-7.45(m, 3H), 7.54(d, 2H, J=8.2Hz) |
| 153 | (CDCl3), 1.48(s, 9H), 2.05-2.20(m, 2H), 3.61(t, 2H, J=6.3Hz), 4.11(t, 2H, J=5.5Hz), 4.34(d, 2H, J=5.8Hz), 6.85-7.00(m, 2H), 7.20-7.60(m, 6H) |
| 154 | (CDCl3) 0.96(t, 3H, J=7.3Hz), 1.48(s, 9H), 1.75-1.90(m, 2H), 2.45-2.60(m, 6H), 3.47(t, 2H, J=5.3Hz), 3.99(t, 2H, J=6.0Hz), 4.33(d, 2H, J=6.1Hz), 6.80-7.00(m, 2H), 7.20-7.60(m, 6H) |
| 155 | (CDCl3) 1.48(s, 9H), 1.80-1.95(m, 4H), 2.00-2.15(m, 2H), 2.35-2.45(m, 2H), 2.60-2.80(m, 2H), 3.60-3.75(m, 1H), 4.00(t, 2H, J=6.2Hz), 4.33(d, 2H, J=5.6Hz), 6.85-7.00(m, 2H), 7.20-7.60(m, 6H) |

TABLE 11-continued

| Ref No. | (Solv) δ (ppm) |
|---|---|
| 156 | (CDCl3) 0.90-1.10(m, 3H), 1.48(s, 9H), 1.80-2.05(m, 2H), 3.05-3.35(m, 4H), 3.85-4.05(m, 2H), 4.20-4.40(m, 2H), 5.00-5.20(m, 2H), 6.75-7.00(m, 2H), 7.20-7.60(m, 11H) |
| 157 | (CDCl3) 0.70-0.90(m, 3H), 1.30-1.55(m, 11H), 1.80-2.05(m, 2H), 2.95-3.15(m, 2H), 3.20-3.35(m, 2H), 3.85-4.05(m, 2H), 4.20-4.40(m, 2H), 5.00-5.20(m, 2H), 6.75-7.00(m, 2H), 7.20-7.60(m, 11H) |

TABLE 12

| Ref No. | (Solv) δ (ppm) |
|---|---|
| 158 | (DMSO-d6) 1.20-1.50(m, 13H), 1.80-1.95(m, 2H), 3.05-3.15(m, 2H), 3.20-3.45(m, 4H), 3.85-4.00(m, 2H), 4.10-4.20(m, 2H), 4.95-5.10(m, 2H), 6.80-7.00(m, 2H), 7.20-7.60(m, 11H) |
| 159 | (CDCl3) 1.47(s, 9H), 4.25-4.45(m, 2H), 6.76-6.89(m, 1H), 7.00-7.54(m, 7H) |
| 160 | (CDCl3) 1.48(s, 9H), 4.25-4.45(m, 2H), 5.33(s, 1H), 6.83-6.95(m, 2H), 7.12-7.56(m, 6H) |
| 161 | (CDCl3) 1.47(s, 9H), 1.95-2.10(m, 2H), 3.35-3.50(m, 2H), 4.05-4.15(m, 2H), 4.30-4.45(m, 2H), 5.10(s, 2H), 6.80-6.95(m, 1H), 7.05-7.55(m, 12H) |
| 162 | (CDCl3) 1.47(s, 9H), 1.95-2.10(m, 2H), 3.35-3.50(m, 2H), 4.00-4.15(m, 2H), 4.30-4.45(m, 2H), 5.11(s, 2H), 6.85-7.00(m, 2H), 7.15-7.55(m, 11H) |
| 163 | (DMSO-d6) 1.40(s, 9H), 3.10-3.45(m, 4H), 4.17(d, 2H, J=6.6Hz), 5.02(s, 2H), 7.20-7.90(m, 14H), 8.11(s, 1H), 8.55-8.70(m, 1H) |
| 164 | (CDCl3) 1.90-2.05(m, 2H), 2.25-2.40(m, 2H), 2.70-2.85(m, 2H), 7.05-7.45(m, 4H) |
| 165 | (CDCl3) 1.95-2.10(m, 2H), 2.30-2.40(m, 2H), 2.80-2.90(m, 2H), 4.76(d, 2H, J=6.4Hz), 7.10-7.65(m, 8H) |
| 166 | (CDCl3) 1.45-1.85(m, 4H), 2.60-2.80(m, 2H), 3.10-3.30(m, 2H), 4.75(s, 2H), 5.09(s, 2H), 7.10-7.70(m, 13H) |
| 167 | (CDCl3) 1.45-1.70(m, 4H), 2.55-2.75(m, 2H), 3.10-3.30(m, 2H), 4.89(s, 2H), 5.08(s, 2H), 7.05-7.95(m, 17H) |
| 168 | (DMSO-d6) 4.57(d, 2H, J=5.7Hz), 5.29(t, 1H, J=5.7Hz), 7.40-7.90(m, 5H), 8.10-8.30(m, 2H), 8.43(s, 1H) |
| 169 | (CDCl3) 4.92(s, 2H), 7.40-7.95(m, 10H), 8.15-8.25(m, 1H), 8.35-8.45(m, 1H) |
| 170 | (CDCl3) 2.50-2.80(m, 2H), 3.50-3.65(m, 2H), 4.89(s, 2H), 5.09(s, 2H), 7.20-7.95(m, 17H) |
| 171 | (CDCl3) 3.88(s, 2H), 6.65-6.75(m, 1H), 7.25-7.55(m, 5H), 7.72(s, 1H) |
| 172 | (CDCl3) 3.89(s, 2H), 7.30-7.65(m, 7H) |
| 173 | (DMSO-d6) 0.80-0.95(m, 6H), 1.65-1.80(m, 2H), 2.30-2.50(m, 6H), 3.72(s, 2H), 3.90-4.10(m, 2H), 6.80-7.60(m, 8H) |
| 174 | (DMSO-d6) 1.50-1.90(m, 6H), 2.25-2.60(m, 6H), 3.73(s, 2H), 3.90-4.20(m, 2H), 6.80-7.60(m, 8H) |
| 175 | (DMSO-d6) 1.25-1.55(m, 6H), 1.70-1.85(m, 2H), 2.15-2.35(m, 6H), 3.73(s, 2H), 3.90-4.10(m, 2H), 6.80-7.60(m, 8H) |
| 176 | (DMSO-d6) 1.65-1.85(m, 2H), 3.00-3.15(m, 2H), 3.45-3.60(m, 2H), 3.66(s, 2H), 7.20-7.50(m, 8H) |

TABLE 13

| Ref No. | (Solv) δ (ppm) |
|---|---|
| 177 | (CDCl3) 0.01(s, 6H), 0.87(s, 9H), 1.60-1.85(m, 2H), 2.85(t, 2H, J=7.2Hz), 3.61(t, 2H, J=6.0Hz), 4.12(s, 2H), 7.10-7.55(m, 8H) |
| 178 | (DMSO-d6) 1.65-1.85(m, 2H), 2.22(s, 3H), 3.73(s, 2H), 3.95-4.10(m, 2H), 6.90-7.55(m, 8H) |
| 179 | (DMSO-d6) 1.70-1.95(m, 2H), 2.14(s, 6H), 2.30-2.45(m, 2H), 3.74(s, 2H), 4.00-4.15(m, 2H), 6.85-6.95(m, 1H), 7.10-7.70(m, 7H) |
| 180 | (DMSO-d6) 0.85-1.05(m, 3H), 1.75-2.00(m, 2H), 3.05-3.25(m, 2H), 3.72(s, 2H), 3.90-4.05(m, 2H), 4.90-5.15(m, 2H), 6.90-7.60(m, 13H) |

TABLE 13-continued

| Ref No. | (Solv) δ (ppm) |
|---|---|
| 181 | (DMSO-d6) 0.65-0.85(m, 3H), 1.30-1.50(m, 2H), 1.80-1.95(m, 2H), 3.00-3.15(m, 2H), 3.73(s, 2H), 3.90-4.05(m, 2H), 4.95-5.15(m, 2H), 6.85-7.60(m, 13H) |
| 182 | (DMSO-d6) 1.25-1.50(m, 4H), 1.80-1.95(m, 2H), 1.80-1.95(m, 2H), 3.05-3.20(m, 2H), 3.74(s, 2H), 3.90-4.05(m, 2H), 4.95-5.15(m, 2H), 6.85-7.60(m, 13H) |
| 183 | (DMSO-d6) 1.25-1.60(m, 6H), 1.80-1.95(m, 2H), 2.20-2.45(m, 6H), 3.74(s, 2H), 4.00-4.15(m, 2H), 6.85-6.95(m, 1H), 7.10-7.70(m, 7H) |
| 184 | (DMSO-d6) 1.60-1.75(m, 4H), 1.80-2.00(m, 2H), 2.35-2.60(m, 4H), 3.74(s, 2H), 4.00-4.15(m, 2H), 6.85-6.95(m, 1H), 7.10-7.70(m, 7H) |
| 185 | (DMSO-d6) 1.80-1.95(m, 2H), 3.10-3.25(m, 2H), 3.77(s, 2H), 3.95-4.10(m, 2H), 5.02(s, 2H), 7.00(d, 2H, J=8.4Hz), 7.20-7.65(m, 11H) |
| 186 | (DMSO-d6) 1.80-1.95(m, 2H), 3.10-3.28(m, 2H), 3.77(s, 2H), 3.99-4.12(m, 2H), 5.01(s, 2H), 6.84-6.97(m, 1H), 7.09-7.53(m, 12H), 7.58-7.67(m, 1H) |
| 187 | (DMSO-d6) 3.11-3.47(m, 4H), 3.76(s, 2H), 5.02(s, 2H), 7.24-7.87(m, 13H), 8.06-8.17(m, 1H), 8.54-8.77(m, 1H) |
| 188 | (CDCl3) 0.97(t, 3H, J=7.2Hz), 1.70-1.95(m, 2H), 2.45-2.65(m, 6H), 3.48(t, 2H, J=5.3Hz), 3.90(s, 2H), 4.02(t, 2H, J=5.9Hz), 6.90-7.05(m, 2H), 7.20-7.60(m, 6H) |
| 189 | (CDCl3) 1.45-1.75(m, 2H), 1.80-1.95(m, 4H), 2.00-2.15(m, 2H), 2.35-2.45(m, 2H), 2.60-2.80(m, 2H), 3.60-3.75(m, 1H), 3.90(s, 2H), 4.02(t, 2H, J=6.2Hz), 6.90-7.00(m, 2H), 7.20-7.60(m, 6H) |
| 190 | (DMSO-d6) 2.42-2.63(m, 2H), 3.22-3.44(m, 2H), 3.75(s, 2H), 5.02(s, 2H), 7.24-7.61(m, 13H), 7.85-7.98(m, 1H), 10.04(s, 1H) |

TABLE 14

| Ref No. | (Solv) δ (ppm) |
|---|---|
| 191 | (DMSO-d6) 1.35-1.70(m, 4H), 2.55-2.70(m, 2H), 2.95-3.10(m, 2H), 3.74(s, 2H), 4.70-4.85(m, 2H), 5.00(s, 2H), 7.10-7.70(m, 13H) |
| 192 | (DMSO-d6) 2.77(s, 3H), 2.96(s, 3H), 4.00-4.10(m, 2H), 5.15(s, 2H), 7.18(dd, 1H, J=1.4Hz, 7.72Hz), 7.25-7.60(m, 11H) |
| 193 | (DMSO-d6) 2.60-2.80(m, 2H), 2.90-3.15(m, 2H), 3.25-3.45(m, 2H), 4.00-4.15(m, 2H), 7.15-7.50(m, 8H) |
| 194 | (DMSO-d6) 2.91(s, 3H), 2.99(s, 3H), 4.08(s, 2H), 5.23(s, 2H), 7.03(s, 1H), 7.20-7.65(m, 9H), 7.78(d, 2H, J=8.2Hz) |
| 195 | (CDCl3) 1.44(s, 9H), 2.84(t, 2H, J=6.6Hz), 3.35-3.50(m, 2H), 5.12(s, 2H), 6.96(dd, 1H, J=2.1Hz, 7.7Hz), 7.15-7.60(m, 12H) |
| 196 | (DMSO-d6) 2.85-3.10(m, 4H), 5.19(s, 2H), 7.01(dd, 1H, J=2.2Hz, 7.9Hz), 7.20-7.55(m, 10H), 7.64(d, 2H, J=8.2Hz) |
| 197 | (CDCl3) −0.32(s, 3H), −0.05(s, 3H), 0.01(s, 3H), 0.03(s, 3H), 0.11(s, 3H), 0.16(s, 3H), 0.75(s, 9H), 0.83(s, 9H), 0.95(s, 9H), 2.83(s, 3H), 3.08(s, 3H), 3.65-3.90(m, 2H), 4.10(d, 1H, J=2.1Hz), 4.26(dd, 1H, J=2.1Hz, 4.9Hz) 4.49(dd, 1H, J=3.5Hz, 15.8Hz), 4.80(dd, 1H, J=4.9Hz, 7.1Hz), 4.95-5.10(m, 3H), 5.15(s, 2H), 6.05-6.20(m, 2H), 7.01(d, 1H, J=7.9Hz), 7.06(s, 1H), 7.15-7.50(m, 8H), 7.55-7.60(m, 2H), 8.19(s, 1H) |
| 198 | (CDCl3) −0.31(s, 3H), −0.05(s, 3H), −0.01(s, 3H), 0.01(s, 3H), 0.10(s, 3H), 0.15(s, 3H), 0.75(s, 9H), 0.82(s, 9H), 0.94(s, 9H), 2.97(s, 3H), 3.11(s, 3H), 3.72-3.91(m, 2H), 4.10(d, 1H, J=2.2Hz), 4.27(dd, 1H, J=2.2Hz, 4.8Hz), 4.56(dd, 1H, J=3.6Hz, 15.8Hz), 4.82(dd, 1H, J=4.8Hz, 7.1Hz), 4.97(dd, 1H, J=8.2Hz, 15.8Hz), 5.13(s, 2H), 5.16(s, 2H), 6.00-6.15(m, 2H), 6.95-7.00(m, 1H), 7.15-7.60(m, 11H), 8.16(s, 1H) |
| 199 | (CDCl3) −0.37(s, 3H), −0.09(s, 3H), 0.04(s, 3H), 0.07(s, 3H), 0.08(s, 3H), 0.13(s, 3H), 0.72(s, 9H), 0.87(s, 9H), 0.93(s, 9H), 2.90-3.20(m, 2H), 3.45-3.55(m, 1H), 3.65-3.80(m, 2H), 3.85-3.95(m, 1H), 4.00-4.10(m, 1H), 4.21(dd, 1H, J=2.1Hz, 4.9Hz), 4.74(dd, 1H, J=4.9Hz, 7.0Hz), 5.10-5.20(m, 4H), 5.65-5.85(m, 1H), 6.03(d, 1H, J=7.0Hz), 6.96(dd, 1H, J=1.9Hz, 8.2Hz), 7.15-7.55(m, 12H) 8.17(s, 1H) |
| 200 | (CDCl3) −0.35(s, 3H), −0.06(s, 3H), 0.02(s, 3H), 0.05(s, 3H), 0.10(s, 3H), 0.15(s, 3H), 0.73(s, 9H), 0.80(s, 9H), 0.95(s, 9H), 3.00(s, 3H), 3.10(s, 3H), 3.75-4.00(m, 2H), 4.10-4.25(m, 2H), 4.46(dd, 1H, J=3.5Hz, 16.8Hz), 4.68(dd, 1H, J=5.0Hz, 7.9Hz), 5.02(dd, 1H, J=8.8Hz, 16.8Hz), 5.26(s, 2H), 6.26(d, 1H, |

TABLE 14-continued

| Ref No. | (Solv) δ (ppm) |
|---|---|
| | J=7.9Hz), 6.48(s, 1H), 6.45-6.65(m, 1H), 6.83(s, 1H), 6.92(s, 1H), 6.95-7.15(m, 4H), 8.19(s, 1H) |

TABLE 15

| Ref No. | (Solv) δ (ppm) |
|---|---|
| 201 | (CDCl3) −0.47(s, 3H), −0.15(s, 3H), −0.03(s, 3H), −0.01(s, 3H), 0.10(s, 3H), 0.13(s, 3H), 0.68(s, 9H), 0.76(s, 9H), 0.97(s, 9H), 3.03(s, 3H), 3.13(s, 3H), 3.55-3.75(m, 2H), 3.90-4.10(m, 2H), 4.29(dd, 1H, J=3.0Hz, 16.8Hz), 4.43(dd, 1H, J=5.0Hz, 7.9Hz), 5.01(dd, 1H, J=9.5Hz, 16.8Hz), 5.21(s, 2H), 5.99(d, 1H, J=7.9Hz), 6.10-6.30(m, 1H), 6.60(s, 1H), 6.64(d, 1H, J=7.9Hz), 7.00(d, 1H, J=7.9Hz), 7.20-7.60(m, 4H), 8.16(s, 1H) |
| 202 | (CDCl3) −0.32(s, 3H), −0.05(s, 3H), 0.00(s, 3H), 0.02(s, 3H), 0.10(s, 3H), 0.15(s, 3H), 0.75(s, 9H), 0.83(s, 9H), 0.94(s, 9H), 2.05-2.20(m, 2H), 3.55-3.65(m, 2H), 3.70-3.95(m, 2H), 4.00-4.20(m, 3H), 4.25-4.35(m, 1H), 4.45-4.60(m, 1H), 4.80-4.90(m, 1H), 4.95-5.15(m, 3H), 5.95-6.05(m, 1H), 6.08(d, 1H, J=6.9Hz), 6.95-7.10(m, 2H), 7.20-7.55(m, 6H), 8.17(s, 1H) |
| 203 | (CDCl3) −0.32(s, 3H), −0.05(s, 3H), 0.01(s, 3H), 0.03(s, 3H), 0.10(s, 3H), 0.15(s, 3H), 0.75(s, 9H), 0.83(s, 9H), 0.94(s, 9H), 2.05-2.15(m, 2H), 3.02(s, 3H), 3.12(s, 3H), 3.59(t, 2H, J=6.3Hz), 3.70-3.95(m, 2H), 4.00-4.15(m, 3H), 4.27(dd, 1H, J=2.1Hz, 4.9Hz), 4.52(dd, 1H, J=3.6Hz, 15.8Hz), 4.81(dd, 1H, J=4.9Hz, 7.1Hz), 5.01(dd, 1H, J=8.5Hz, 15.8Hz), 5.14(s, 2H), 6.05-6.15(m, 2H), 6.95-7.05(m, 2H), 7.25-7.30(m, 1H), 7.35-7.60(m, 4H), 8.17(s, 1H) |
| 204 | (CDCl3) −0.31(s, 3H), −0.05(s, 3H), −0.00(s, 3H), 0.02(s, 3H), 0.10(s, 3H), 0.15(s, 3H), 0.75(s, 9H), 0.82(s, 9H), 0.94(s, 9H), 2.20-2.30(m, 2H), 3.01(s, 3H), 3.12(s, 3H), 3.70-3.95(m, 4H), 4.05-4.30(m, 4H), 4.56(dd, 1H, J=3.8Hz, 15.8Hz), 4.83(dd, 1H, J=4.9Hz, 7.1Hz), 4.97(dd, 1H, J=8.2Hz, 15.8Hz), 5.15(s, 2H), 6.00-6.15(m, 2H), 6.90-6.95(m, 1H), 7.10-7.15(m, 1H), 7.18(s, 1H), 7.41(d, 2H, J=8.2Hz), 7.53(d, 2H, J=8.2Hz), 8.16(s, 1H) |
| 205 | (DMSO-d6) −0.28(s, 3H), −0.08(s, 3H), −0.06(s, 3H), −0.00(s, 3H), 0.14(s, 6H), 0.76(s, 9H), 0.79(s, 9H), 0.93(s, 9H), 2.15-2.25(m, 2H), 3.60-3.75(m, 1H), 3.81(t, 2H, J=6.5Hz), 3.95-4.05(m, 2H), 4.15(t, 2H, J=6.0Hz), 4.45-4.75(m, 3H), 5.40-5.50(m, 1H), 5.84(d, 1H, J=6.0Hz) 6.49(s, 2H), 6.93(dd, 1H, J=2.5Hz, 8.2Hz), 7.15-7.25(m, 2H), 7.30-7.40(m, 2H), 7.42(d, 2H, J=8.2Hz), 7.59(d, 2H, J=8.2Hz), 7.88(s, 1H) |

TABLE 16

| Ref No. | (Solv) δ (ppm) |
|---|---|
| 206 | (CDCl3) −0.36(s, 3H), −0.08(s, 3H), 0.04(s, 3H), 0.07(s, 3H), 0.09(s, 3H), 0.14(s, 3H), 0.72(s, 9H), 0.87(s, 9H), 0.93(s, 9H), 2.20-2.30(m, 2H), 2.90-3.20(m, 2H), 3.45-3.60(m, 1H), 3.65-3.98(m, 5H), 4.00-4.05(m, 1H), 4.10-4.30(m, 3H), 4.78(dd, 1H, J=5.0Hz, 6.9Hz), 5.11(s, 2H), 5.60-5.75(m, 1H), 6.00(d, 1H, J=6.9Hz), 6.89(dd, 1H, J=2.5Hz, 7.6Hz), 7.05-7.40(m, 5H), 7.52(d, 2H, J=8.2Hz), 8.17(s, 1H) |
| 207 | (CDCl3) 7.30-7.50(m, 3H), 7.67(d, 1H, J=7.9Hz), 8.13(dd, 1H, J=1.4Hz, 7.9Hz), 8.30-8.35(m, 1H), 10.11(s, 1H) |
| 208 | (DMSO-d6) 4.92(s, 2H), 7.30-7.50(m, 5H), 7.52(d, 1H, J=7.9Hz), 7.70(dd, 1H, J=1.9Hz, 7.9Hz), 7.80-8.00(m, 5H) |
| 209 | (DMSO-d6) −0.06(s, 6H), 0.79(s, 9H), 1.60-1.70(m, 2H), 3.00-3.10(m, 2H), 3.50-3.65(m, 2H), 4.40-4.50(m, 1H), 4.73(s, 2H), 6.55-6.65(m, 2H), 6.94(d, 1H, J=7.7Hz), 7.30-7.45(m, 5H), 7.80-7.95(m, 4H) |
| 210 | (DMSO-d6) −0.03(s, 6H), 0.83(s, 9H), 1.65-1.75(m, 2H), 3.10-3.20(m, 2H), 3.55-3.65(m, 2H), 3.65(s, 2H), 4.30-4.40(m, 1H), 6.60-6.70(m, 2H), 6.90(d, 1H, J=7.6Hz), 7.30-7.50(m, 5H) |

TABLE 17

| Ex No. | Strc | (Solv) δ(ppm) |
|---|---|---|
| 1 | [structure] | (DMSO-d6) 2.33 (s, 3H), 3.56–3.71 (m, 2H), 3.96–4.03 (m, 1H), 4.10–4.18 (m, 1H), 4.55–4.69 (m, 2H), 4.70–4.80 (m, 1H), 5.17 (d, 1H, J = 3.5 Hz), 5.31 (d, 1H, J = 6.4 Hz), 5.85–5.99 (m, 2H), 6.50 (brs, 2H), 7.21–7.29 (m, 2H), 7.40–7.48 (m, 2H), 7.49–7.68 (m, 5H), 7.90 (s, 1H) |
| 2 | [structure] | (DMSO-d6) 2.36 (s, 3H), 3.56–3.71 (m, 2H), 3.92–4.21 (m, 2H), 4.50–6.10 (m, 7H), 6.50 (brs, 2H), 7.12–7.70 (m, 9H), 7.90 (s, 1H) |

TABLE 17-continued

| Ex No. | Strc | (Solv) δ(ppm) |
|---|---|---|
| 3 | | (DMSO-d$_6$) 2.22 (s, 3H), 3.56–3.71 (m, 2H), 3.95–4.04 (m, 1H), 4.09–4.19 (m, 1H), 4.58–4.82 (m, 3H), 5.96 (d, 1H, J = 7.7 Hz), 6.51 (brs, 2H), 7.14–7.68 (m, 9H), 7.90 (s, 1H) |
| 4 | | (DMSO-d$_6$) 3.54–3.79 (m, 5H), 3.96–4.04 (m, 1H), 4.10–4.18 (m, 1H), 4.55–4.82 (m, 3H), 5.16 (d, 1H, J = 4.3 Hz), 5.29 (d, 1H, J = 6.8 Hz), 5.88–6.00 (m, 2H), 6.52 (brs, 2H), 6.96–7.14 (m, 2H), 7.20–7.45 (m, 6H), 7.55–7.63 (m, 1H), 7.90 (s, 1H) |
| 5 | | (DMSO-d$_6$) 3.58–3.70 (m, 2H), 3.81 (s, 3H), 3.97–4.03 (m, 1H), 4.10–4.17 (m, 1H), 4.56–4.79 (m, 3H), 5.09–5.35 (m, 2H), 5.80–5.98 (m, 2H), 6.62 (brs, 2H), 6.88–6.95 (m, 1H), 7.12–7.24 (m, 2H), 7.30–7.50 (m, 3H), 7.55–7.70 (m, 3H), 7.93 (s, 1H) |
| 6 | | (DMSO-d$_6$) 3.57–3.70 (m, 2H), 3.78 (s, 3H), 3.96–4.03 (m, 1H), 4.10–4.18 (m, 1H), 4.54–4.80 (m, 3H), 5.15 (d, 1H, J = 3.6 Hz), 5.28 (d, 1H, J = 7.2 Hz), 5.86–5.99 (m, 2H), 6.51 (brs, 2H), 6.97–7.05 (m, 2H), 7.39–7.47 (m, 2H), 7.52–7.62 (m, 5H), 7.90 (s, 1H) |

TABLE 18
| Ex No. | Strc | (Solv) δ(ppm) |
| --- | --- | --- |
| 7 | 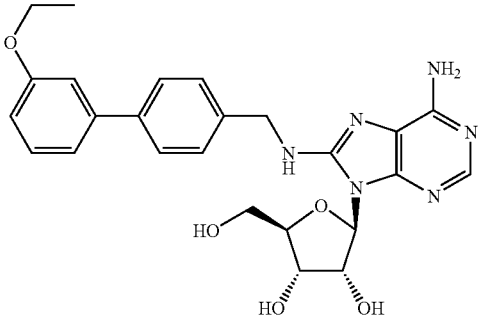 | (DMSO-d$_6$) 1.34 (t, 3H, J = 6.9 Hz), 3.57–3.72 (m, 2H), 3.97–4.02 (m, 1H), 4.05–4.16 (m, 3H), 4.56–4.69 (m, 2H), 4.71–4.79 (m, 1H), 5.14 (d, 1H, J = 4.2 Hz), 5.27 (d, 1H, J = 6.7 Hz), 5.86–5.91 (m, 1H), 5.95 (d, 1H, J = 7.5 Hz), 6.50 (brs, 2H), 6.87–6.92 (m, 1H), 7.12–7.22 (m, 2H), 7.31 –7.37 (m, 1H), 7.42–7.48 (m, 2H), 7.53–7.64 (m, 3H), 7.90 (s, 1H) |
| 8 | 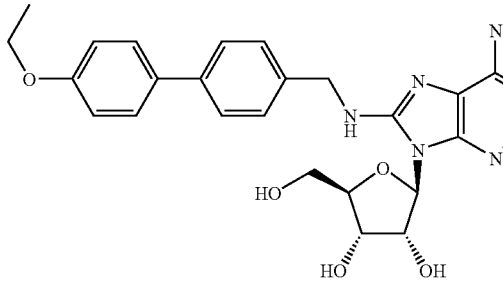 | (DMSO-d$_6$) 1.34 (t, 3H, J = 6.9 Hz), 3.57–3.72 (m, 2H), 3.94–4.17 (m, 4H), 4.54–4.79 (m, 3H), 5.14 (d, 1H, J = 4.0 Hz), 5.27 (d, 1H, J = 6.4 Hz), 5.85–5.91 (m, 1H), 5.94 (d, 1H, J = 7.5 Hz), 6.49 (brs, 2H), 6.95–7.03 (m, 2H), 7.39–7.46 (m, 2H), 7.52–7.64 (m, 5H), 7.90 (m, 1H) |
| 9 | 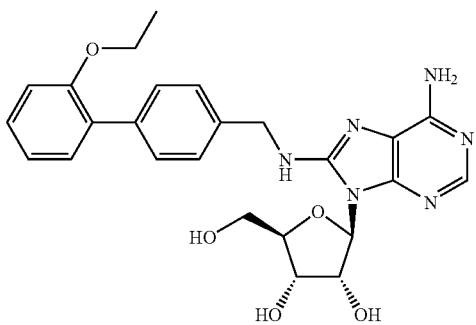 | (DMSO-d$_6$) 1.26 (t, 3H, J = 7.0 Hz), 3.54–3.74 (m, 2H), 3.97–4.07 (m, 3H), 4.11–4.17 (m, 1H), 4.56–4.70 (m, 2H), 4.72–4.81 (m, 1H), 5.18 (d, 1H, J = 4.1 Hz), 5.31 (d, 1H, J = 6.8 Hz), 5.88–6.00 (m, 2H), 6.54 (brs, 2H), 6.95–7.11 (m, 2H), 7.24–7.33 (m, 2H), 7.36–7.48 (m, 4H), 7.56–7.62 (m, 1H), 7.90 (s, 1H) |
| 10 | 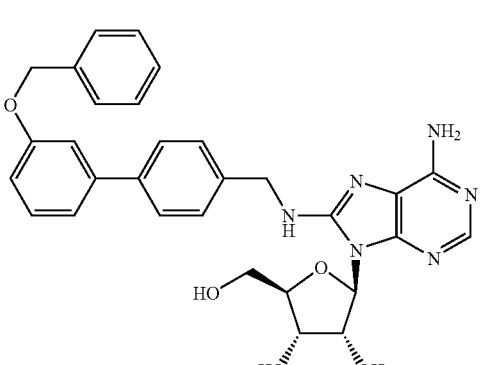 | (DMSO-d$_6$) 3.56–3.71 (m, 2H), 3.96–4.02 (m, 1H), 4.10–4.17 (m, 3H), 4.56–4.69 (m, 3H), 5.11–5.21 (m, 3H), 5.27 (d, 1H, J = 6.7 Hz), 5.86–5.92 (m, 1H), 5.95 (d, 1H, J = 7.1 Hz), 6.50 (brs, 2H), 6.96–7.02 (m, 1H), 7.18–7.65 (m, 13H), 7.90 (s, 1H) |

TABLE 18-continued

| Ex No. | Strc | (Solv) δ(ppm) |
|---|---|---|
| 11 | | (DMSO-$d_6$) 3.56–3.69 (m, 2H), 3.96–4.03 (m, 1H), 4.10–4.18 (m, 1H), 4.62 (d, 2H, J = 6.1 Hz), 4.72–4.80 (m, 1H), 5.05–5.40 (m, 4H), 5.81–6.05 (m, 2H), 6.53 (brs, 2H), 6.98–7.07 (m, 1H), 7.13–7.20 (m, 1H), 7.24–7.43 (m, 9H), 7.45–7.53 (m, 2H), 7.59 (t, 1H, J = 6.1 Hz), 7.90 (s, 1H) |
| 12 | | (DMSO-$d_6$) 3.56–3.71 (m, 2H), 3.96–4.02 (m, 1H), 4.10–4.16 (m, 1H), 4.54–4.67 (m, 2H), 4.70–4.78 (m, 1H), 5.16 (d, 1H, J = 3.8 Hz), 5.29 (d, 1H, J = 6.8 Hz), 5.86–6.01 (m, 2H), 6.52 (brs, 2H), 6.78–6.90 (m, 2H), 7.37–7.59 (m, 7H), 7.90 (s, 1H), 9.51 (brs, 1H) |

TABLE 19

| Ex No. | Strc | (Solv) δ(ppm) |
|---|---|---|
| 13 | | (DMSO-$d_6$) 3.56–3.72 (m, 2H), 3.88 (s, 3H), 3.96–4.03 (m, 1H), 4.10–4.18 (m, 1H), 4.57–4.81 (m, 3H), 5.15 (d, 1H, J = 3.9 Hz), 5.28 (d, 1H, J = 6.6 Hz), 5.85–5.92 (m, 1H), 5.96 (d, 1H, J = 7.4 Hz), 6.50 (brs, 2H), 7.46–7.72 (m, 6H), 7.87–7.99 (m, 3H), 8.14–8.21 (m, 1H) |
| 14 | | (DMSO-$d_6$) 0.90 (t, 3H, J = 7.3 Hz), 1.28–1.46 (m, 4H), 1.67–1.78 (m, 2H), 3.56–3.72 (m, 2H), 3.96–4.06 (m, 3H), 4.09–4.18 (m, 1H), 4.55–4.80 (m, 3H), 5.11–5.39 (m, 2H), 5.83–6.01 (m, 2H), 6.52 (brs, 2H), 6.86–6.94 (m, 1H), 7.11–7.22 (m, 2H), 7.30–7.38 (m, 1H), 7.41–7.49 (m, 2H), 7.54–7.68 (m, 3H), 7.90 (s, 1H) |

TABLE 19-continued

| Ex No. | Strc | (Solv) δ(ppm) |
|---|---|---|
| 15 | | (DMSO-d$_6$) 1.28 (d, 6H, J = 6.0 Hz), 3.56–3.72 (m, 2H), 3.96–4.03 (m, 1H), 4.09–4.18 (m, 1H), 4.56–4.81 (m, 4H), 5.18 (d, 1H, J = 3.5 Hz), 5.31 (d, 1H, J = 6.9 Hz), 5.81–6.01 (m, 2H), 6.52 (brs, 2H), 6.86–6.92 (m, 1H), 7.09–7.20 (m, 2H), 7.30–7.36 (m, 1H), 7.40–7.49 (m, 2H), 7.54–7.67 (m, 3H), 7.90 (s, 1H) |
| 16 | | (DMSO-d$_6$) 3.56–3.72 (m, 2H), 3.97–4.02 (m, 1H), 4.10–4.17 (m, 1H), 4.58–4.80 (m, 3H), 5.17 (d, 1H, J = 4.0 Hz), 5.30 (d, 1H, J = 6.9 Hz), 5.39 (s, 2H), 5.87–5.94 (m, 1H), 5.95 (d, 1H, J = 7.6 Hz), 6.52 (brs, 2H), 7.32–7.53 (m, 7H), 7.57–7.68 (m, 4H), 7.90 (s, 1H), 7.91–8.00 (m, 2H), 8.17–8.22 (m, 1H) |
| 17 | | (DMSO-d$_6$) 2.94 (s, 6H), 3.57–3.71 (m, 2H), 3.96–4.03 (m, 1H), 4.10–4.18 (m, 1H), 4.55–4.69 (m, 2H), 4.71–4.79 (m, 1H), 5.14 (d, 1H, J = 4.0 Hz), 5.27 (d, 1H, J = 6.7 Hz), 5.85–5.93 (m, 1H), 5.95 (d, 1H, J = 7.4 Hz), 6.49 (brs, 2H), 6.67–6.74 (m, 1H), 6.86–6.92 (m, 2H), 7.20–7.27 (m, 1H), 7.40–7.48 (m, 2H), 7.53–7.61 (m, 3H), 7.90 (s, 1H) |
| 18 | | (DMSO-d$_6$) 3.56–3.71 (m, 2H), 3.96–4.04 (m, 1H), 4.10–4.18 (m, 1H), 4.55–4.80 (m, 3H), 5.12–5.20 (m, 3H), 5.30 (d, 1H, J = 6.4 Hz), 5.84–6.00 (m, 2H), 6.52 (brs, 2H), 7.22–7.66 (m, 13H), 7.76 (brs, 1H), 7.90 (s, 1H), 9.85 (brs, 1H) |

TABLE 20

| Ex No. | Strc | (Solv) δ(ppm) |
|---|---|---|
| 19 | [structure] | (DMSO-$d_6$) 2.78 (t, 2H, J = 7.0 Hz), 3.54–3.75 (m, 4H), 3.95–4.03 (m, 1H), 4.10–4.17 (m, 1H), 4.56–4.79 (m, 4H), 5.07–5.36 (m, 2H), 5.78–6.00 (m, 2H), 6.50 (brs, 2H), 7.15–7.23 (m, 1H), 7.30–7.38 (m, 1H), 7.39–7.64 (m, 7H), 7.90 (s, 1H) |
| 20 | [structure] | (DMSO-$d_6$) 3.57–3.71 (m, 2H), 3.96–4.03 (m, 1H), 4.09–4.18 (m, 1H), 4.57–4.80 (m, 3H), 5.17 (d, 1H, J = 3.9 Hz), 5.31 (d, 1H, J = 6.5 Hz), 5.86–6.00 (m, 2H), 6.53 (brs, 2H), 7.42–7.73 (m, 6H), 7.90 (s, 1H), 8.02–8.09 (m, 1H), 8.52–8.58 (m, 1H), 8.84–8.91 (m, 1H) |
| 21 | [structure] | (DMSO-$d_6$) 0.99 (t, 3H, J = 7.4 Hz), 1.68–1.80 (m, 2H), 3.54–3.72 (m, 2H), 3.93–4.03 (m, 3H), 4.10–4.17 (m, 1H), 4.54–4.80 (m, 3H), 5.17 (d, 1H, J = 4.0 Hz), 5.30 (d, 1H, J = 6.8 Hz), 5.88–5.99 (m, 2H), 6.53 (brs, 2H), 6.86–6.94 (m, 1H), 7.10–7.23 (m, 2H), 7.29–7.49 (m, 3H), 7.54–7.66 (m, 3H), 7.90 (s, 1H) |
| 22 | [structure] | (DMSO-$d_6$) 0.94 (t, 3H, J = 7.4 Hz), 1.40–1.50 (m, 2H), 1.66–1.76 (m, 2H), 3.55–3.73 (m, 2H), 3.96–4.06 (m, 3H), 4.10–4.17 (m, 1H), 4.55–4.79 (m, 3H), 5.18 (d, 1H, J = 3.6 Hz), 5.31 (d, 1H, J = 6.5 Hz), 5.86–5.99 (m, 2H), 6.52 (brs, 2H), 6.87–6.95 (m, 1H), 7.11–7.22 (m, 2H), 7.30–7.38 (m, 1H), 7.40–7.49 (m, 2H), 7.54–7.67 (m, 3H), 7.90 (s, 1H) |

TABLE 20-continued

| Ex No. | Strc | (Solv) δ(ppm) |
|---|---|---|
| 23 | | (DMSO-$d_6$) 1.94–2.06 (m, 2H), 3.52–3.72 (m, 4H), 3.96–4.03 (m, 1H), 4.07–4.17 (m, 3H), 4.48 (s, 2H), 4.55–4.80 (m, 3H), 5.17 (d, 1H, J = 3.7 Hz), 5.30 (d, 1H, J = 6.8 Hz), 5.84–6.00 (m, 2H), 6.53 (brs, 2H), 6.87–6.94 (m, 1H), 7.11–7.49 (m, 10H), 7.54–7.66 (m, 3H), 7.90 (s, 1H) |
| 24 | | (DMSO-$d_6$) 3.31 (s, 3H), 3.56–3.73 (m, 4H), 3.96–4.03 (m, 1H), 4.08–4.23 (m, 3H), 4.56–4.80 (m, 3H), 5.03–5.40 (m, 2H), 5.76–6.04 (m, 2H), 6.50 (brs, 2H), 6.88–6.96 (m, 1H), 7.14–7.24 (m, 2H), 7.31–7.38 (m, 1H), 7.41–7.49 (m, 2H), 7.54–7.65 (m, 3H), 7.90 (s, 1H) |

TABLE 21

| Ex No. | Strc | (Solv) δ(ppm) |
|---|---|---|
| 25 | | (DMSO-$d_6$) 0.92 (t, 3H, J = 7.3 Hz), 1.58–1.72 (m, 2H), 3.56–3.72 (m, 2H), 3.86–4.04 (m, 3H), 4.10–4.17 (m, 1H), 4.56–4.82 (m, 3H), 5.17 (d, 1H, J = 3.4 Hz), 5.30 (d, 1H, J = 6.7 Hz), 5.84–6.02 (m, 2H), 6.54 (brs, 2H), 6.96–7.11 (m, 2H), 7.24–7.33 (m, 2H), 7.35–7.49 (m, 4H), 7.54–7.64 (m, 1H), 7.90 (s, 1H) |
| 26 | | (DMSO-$d_6$) 0.88 (t, 3H, J = 7.4 Hz), 1.32–1.43 (m, 2H), 1.57–1.67 (m, 2H), 3.57–3.71 (m, 2H), 3.92–4.03 (m, 3H), 4.11–4.17 (m, 1H), 4.63 (d, 2H, J = 6.1 Hz), 4.73–4.80 (m, 1H), 5.17 (d, 1H, (J = 3.6 Hz), 5.30 (d, 1H, J = 6.6 Hz), 5.86–6.00 (m, 2H), 6.53 (brs, 2H), 6.96–7.03 (m, 1H), 7.05–7.11 (m, 1H), 7.24–7.33 (m, 2H), 7.35–7.48 (m, 4H), 7.59 (t, 1H, J = 6.1 Hz), 7.90 (s, 1H) |

TABLE 21-continued

| Ex No. | Strc | (Solv) δ(ppm) |
|---|---|---|
| 27 | | (DMSO-d$_6$) 0.84 (t, 3H, J = 7.2 Hz), 1.21–1.38 (m, 4H), 1.58–1.68 (m, 2H), 3.56–3.72 (m, 2H), 3.90–4.03 (m, 3H), 4.11–4.18 (m, 1H), 4.63 (d, 2H, J = 6.2 Hz), 4.72–4.81 (m, 1H), 5.17 (d, 1H, J = 3.8 Hz), 5.29 (d, 1H, J = 6.8 Hz), 5.88–6.00 (m, 2H), 6.53 (brs, 2H), 6.95–7.11 (m, 2H), 7.24–7.33 (m, 2H), 7.35–7.48 (m, 4H), 7.59 (t, 1H, J = 6.2 Hz), 7.90 (s, 1H) |
| 28 | | (DMSO-d$_6$) 1.20 (d, 6H, J = 6.0 Hz), 3.56–3.72 (m, 2H), 3.96–4.04 (m, 1H), 4.10–4.18 (m, 1H), 4.52–4.70 (m, 3H), 4.73–4.82 (m, 1H), 5.17 (d, 1H, J = 3.7 Hz), 5.30 (d, 1H, J = 6.9 Hz), 5.88–6.00 (m, 2H), 6.53 (brs, 2H), 6.94–7.02 (m, 1H), 7.05–7.12 (m, 1H), 7.23–7.32 (m, 2H), 7.35–7.49 (m, 4H), 7.54–7.64 (m, 1H), 7.90 (s, 1H) |
| 29 | | (DMSO-d$_6$) 1.64–1.86 (m, 4H), 3.50 (t, 2H, J = 6.3 Hz), 3.57–3.70 (m, 2H), 3.96–4.08 (m, 3H), 4.11–4.17 (m, 1H), 4.46, (s, 2H), 4.56–4.80 (m, 3H), 5.06–5.36 (m, 2H), 5.78–6.00 (m, 2H), 6.50 (brs, 2H), 6.86–6.92 (m, 1H), 7.11–7.38 (m, 8H), 7.41–7.48 (m, 2H), 7.54–7.63 (m, 3H), 7.90 (s, 1H) |

TABLE 22
| Ex No. | Strc | (Solv) δ(ppm) |
|---|---|---|
| 30 | 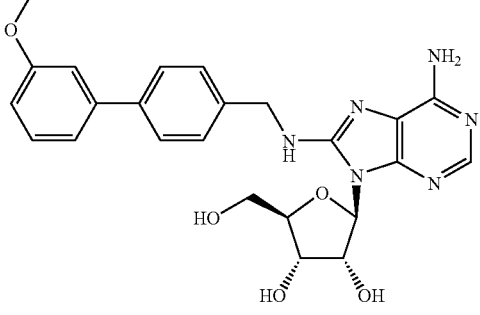 | (DMSO-d$_6$) 3.32–3.46 (m, 2H), 3.56–3.71 (m, 2H), 3.96–4.17 (m, 4H), 4.56–4.80 (m, 3H), 4.94–5.52 (m, 4H), 5.70–6.10 (m, 2H), 6.50 (brs, 2H), 6.86–6.95 (m, 1H), 7.13–7.66 (m, 14H), 7.90 (s, 1H) |
| 31 | 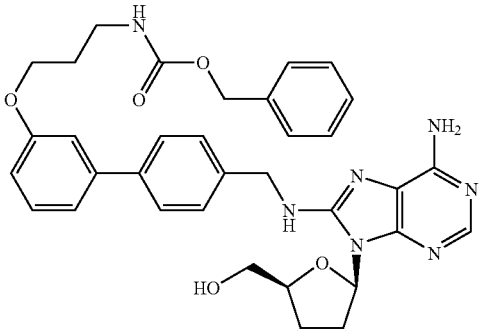 | (DMSO-d$_6$) 1.81–1.95 (m, 2H), 3.12–3.25 (m, 2H), 3.56–3.73 (m, 2H), 3.95–4.17 (m, 4H), 4.54–4.81 (m, 3H), 5.01 (s, 2H), 5.10–5.20 (m, 1H), 5.21–5.33 (m, 1H), 5.80–6.00 (m, 2H), 6.49 (s, 2H), 6.83–6.95 (m, 1H), 7.09–7.67 (m, 14H), 7.90 (s, 1H) |
| 32 | 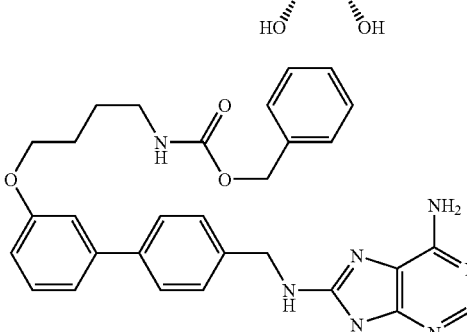 | (DMSO-d$_6$) 1.49–1.79 (m, 4H), 2.98–3.14 (m, 2H), 3.55–3.72 (m, 2H), 3.90–4.19 (m, 4H), 4.52–4.81 (m, 3H), 5.01 (s, 2H), 5.09–5.19 (m, 1H), 5.22–5.33 (m, 1H), 5.82–5.99 (m, 2H), 6.50 (brs, 2H), 6.83–6.95 (m, 1H), 7.07–7.67 (m, 14H), 7.90 (s, 1H) |
| 33 | 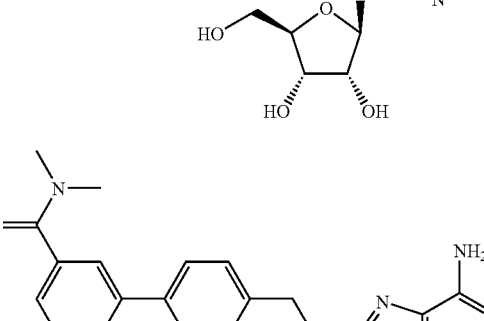 | (DMSO-d$_6$) 2.80–3.14 (m, 6H), 3.56–3.72 (m, 2H), 3.96–4.03 (m, 1H), 4.10–4.18 (m, 1H), 4.57–4.80 (m, 3H), 5.15 (d, 1H, J = 4.0 Hz), 5.28 (d, 1H, J = 6.8 Hz), 5.85–5.92 (m, 1H), 5.95 (d, 1H, J = 7.5 Hz), 6.50 (brs, 2H), 7.33–7.39 (m, 1H), 7.43–7.76 (m, 8H), 7.90 (s, 1H) |

TABLE 22-continued

| Ex No. | Strc | (Solv) δ(ppm) |
|---|---|---|
| 34 | | (DMSO-d$_6$) 3.57–3.72 (m, 2H), 3.75 (s, 3H), 3.97–4.03 (m, 1H), 4.10–4.18 (m, 1H), 4.56–4.81 (m, 3H), 5.19 (d, 1H, J = 3.9 Hz), 5.31 (d, 1H, J = 6.9 Hz), 5.89–6.01 (m, 2H), 6.54 (brs, 2H), 6.99–7.06 (m, 1H), 7.13–7.48 (m, 7H), 7.55–7.64 (m, 1H), 7.90 (s, 1H) |
| 35 | | (DMSO-d$_6$) 3.56–3.71 (m, 2H), 3.93 (s, 3H), 3.99–4.04 (m, 1H), 4.10–4.18 (m, 1H), 4.52–4.67 (m, 2H), 4.74–4.82 (m, 1H), 5.07–5.38 (m, 2H), 5.76–5.93 (m, 1H), 6.00 (d, 1H, J = 7.8 Hz), 6.49 (brs, 2H), 7.14–7.25 (m, 2H), 7.28–7.50 (m, 5H), 7.63–7.71 (m, 2H), 7.90 (s, 1H) |

TABLE 23

| Ex No. | Strc | (Solv) δ(ppm) |
|---|---|---|
| 36 | | (DMSO-d$_6$) 3.57–3.70 (m, 2H), 3.99–4.04 (m, 1H), 4.11–4.18 (m, 1H), 4.61–4.84 (m, 3H), 5.31 (s, 2H), 6.01 (d, 1H, J = 7.2 Hz), 6.48 (brs, 2H), 7.15–7.22 (m, 1H), 7.28–7.57 (m, 11H), 7.62–7.68 (m, 2H), 7.90 (s, 1H) |
| 37 | | (DMSO-d$_6$) 3.56–3.72 (m, 2H), 3.97–4.05 (m, 1H), 4.10–4.20 (m, 1H), 4.69–4.84 (m, 3H), 5.14 (d, 1H, J = 4.2 Hz), 5.31 (d, 1H, J = 6.8 Hz), 5.85–5.93 (m, 1H), 5.97 (d, 1H, J = 7.3 Hz), 6.50 (brs, 2H), 7.43–7.68 (m, 4H), 7.82–7.94 (m, 5H) |

TABLE 23-continued

| Ex No. | Strc | (Solv) δ(ppm) |
|---|---|---|
| 38 | | (DMSO-$d_6$) 3.55–3.71 (m, 2H), 3.96–4.04 (m, 1H), 4.10–4.18 (m, 1H), 4.67 (d, 2H, J = 5.9 Hz), 4.71–4.81 (m, 1H), 5.15 (d, 1H, J = 3.8 Hz), 5.29 (d, 1H, J = 6.7 Hz), 5.80–5.91 (m, 1H), 5.97 (d, 1H, J = 7.5 Hz), 6.53 (brs, 2H), 7.33–7.61 (m, 7H), 7.64–7.73 (m, 2H), 7.91 (s, 1H) |
| 39 | | (DMSO-$d_6$) 2.61 (s, 3H), 3.52–3.73 (m, 2H), 3.98–4.04 (m, 1H), 4.11–4.19 (m, 1H), 4.60 (d, 2H, J = 5.5 Hz), 4.73–4.84 (m, 1H), 4.98–5.52 (m, 2H), 5.72–6.03 (m, 2H), 6.52 (brs, 2H), 7.32–7.55 (m, 7H), 7.64–7.72 (m, 2H), 7.91 (s, 1H) |
| 40 | | (DMSO-$d_6$) 3.52–3.72 (m, 2H), 3.90 (s, 2H), 3.94–4.02 (m, 1H), 4.07–4.17 (m, 1H), 4.46–4.62 (m, 2H), 4.66–4.77 (m, 1H), 5.13 (d, 1H, J = 3.6 Hz), 5.26 (d, 1H, J = 6.7 Hz), 5.81–5.98 (m, 2H), 6.47 (brs, 2H), 7.12–7.34 (m, 9H), 7.48 (t, 1H, J = 6.2 Hz), 7.89 (s, 1H) |
| 41 | | (DMSO-$d_6$) 3.54–3.72 (m, 2H), 3.94–4.02 (m, 1H), 4.08–4.17 (m, 1H), 4.49–4.64 (m, 2H), 4.67–4.79 (m, 1H), 5.14 (d, 1H, J = 4.0 Hz), 5.27 (d, 1H, J = 6.9 Hz), 5.83–5.90 (m, 1H), 5.93 (d, 1H, J = 7.5 Hz), 6.51 (brs, 2H), 6.92–7.02 (m, 4H), 7.08–7.16 (m, 1H), 7.33–7.57 (m, 5H), 7.90 (s, 1H) |
| 42 | | (DMSO-$d_6$) 3.54–3.69 (m, 2H), 3.94–4.00 (m, 1H), 4.08–4.16 (m, 1H), 4.42–4.59 (m, 2H), 4.66–4.76 (m, 1H), 5.03–5.17 (m, 3H), 5.24 (d, 1H, J = 7.0 Hz), 5.80–5.96 (m, 2H), 6.49 (brs, 2H), 6.91–7.01 (m, 2H), 7.25–7.50 (m, 8H), 7.89 (s, 1H) |

TABLE 24

| Ex No. | Strc | (Solv) δ(ppm) |
|---|---|---|
| 43 | | (DMSO-d$_6$) 3.53–3.71 (m, 2H), 3.94–4.02 (m, 1H), 4.07–4.17 (m, 1H), 4.50–4.66 (m, 2H), 4.68–4.78 (m, 1H), 5.16 (d, 1H, J = 4.0 Hz), 5.30 (d, 1H, J = 7.0 Hz), 5.85–5.97 (m, 2H), 6.53 (brs, 2H), 7.24–7.44 (m, 9H), 7.57 (t, 1H, J = 5.9 Hz), 7.90 (s, 1H) |
| 44 | | (DMSO-d$_6$) 3.54–3.72 (m, 2H), 3.95–4.04 (m, 1H), 4.10–4.16 (m, 1H), 4.50–4.64 (m, 2H), 4.68–4.80 (m, 1H), 5.07 (s, 2H), 5.17 (d, 1H, J = 4.0 Hz), 5.30 (d, 1H, J = 6.7 Hz), 5.88–5.98 (m, 2H), 6.53 (brs, 2H), 6.82–7.08 (m, 3H), 7.18–7.45 (m, 6H), 7.50–7.58 (m, 1H), 7.90 (s, 1H) |
| 45 | | (DMSO-d$_6$) 3.58–3.72 (m, 2H), 3.98–4.05 (m, 1H), 4.11–4.20 (m, 1H), 4.62 (d, 2H, J = 6.3 Hz), 4.72–4.82 (m, 1H), 5.00–5.40 (m, 4H), 5.79–6.07 (m, 2H), 6.52 (brs, 2H), 7.00–7.08 (m, 1H), 7.20–7.43 (m, 10H), 7.47–7.62 (m, 3H), 7.91 (s, 1H) |
| 46 | | (DMSO-d$_6$) 2.21 (s, 3H), 3.56–3.72 (m, 2H), 3.96–4.04 (m, 1H), 4.08–4.18 (m, 1H), 4.52–4.67 (m, 2H), 4.69–4.81 (m, 1H), 5.19 (d, 1H, J = 4.3 Hz), 5.32 (d, 1H, J = 6.8 Hz), 5.89–6.00 (m, 2H), 6.55 (brs, 2H), 7.12–7.17 (m, 1H), 7.22–7.48 (m, 7H), 7.53–7.62 (m, 1H), 7.90 (s, 1H) |
| 47 | | (DMSO-d$_6$) 2.40 (s, 3H), 3.54–3.72 (m, 2H), 3.96–4.04 (m, 1H), 4.07–4.18 (m, 1H), 4.52–4.66 (m, 2H), 4.71–4.82 (m, 1H), 5.18 (d, 1H, J = 3.6 Hz), 5.32 (d, 1H, J = 6.6 Hz), 5.84–5.95 (m, 1H), 5.98 (d, 1H, J = 7.7 Hz), 6.54 (brs, 2H), 7.30–7.52 (m, 7H), 7.59–7.67 (m, 2H), 7.90 (s, 1H) |

TABLE 24-continued

| Ex No. | Strc | (Solv) δ(ppm) |
|---|---|---|
| 48 | | (DMSO-$d_6$) 3.53–3.71 (m, 2H), 3.96–4.05 (m, 1H), 4.08–4.20 (m, 1H), 4.58–4.84 (m, 3H), 5.00–5.52 (m, 4H), 5.72–5.96 (br, 1H), 5.99 (d, 1H, J = 7.3 Hz), 6.47 (brs, 2H), 6.86–6.94 (m, 1H), 7.02–7.11 (m, 1H), 7.15–7.46 (m, 6H), 7.48–7.54 (m, 2H), 7.90 (s, 1H) |

TABLE 25

| Ex No. | Strc | (Solv) δ(ppm) |
|---|---|---|
| 49 | | (DMSO-$d_6$) 3.55–3.72 (m, 2H), 3.94–4.04 (m, 1H), 4.07–4.17 (m, 1H), 4.57–4.81 (m, 3H), 5.10–5.41 (m, 2H), 5.80–6.02 (m, 2H), 6.53 (brs, 2H), 7.28–7.37 (m, 1H), 7.42–7.68 (m, 3H), 7.80–8.09 (m, 5H), 8.60–8.70 (m, 1H) |
| 50 | | (DMSO-$d_6$) 3.56–3.73 (m, 2H), 3.94–4.03 (m, 1H), 4.10–4.18 (m, 1H), 4.56–4.81 (m, 3H), 5.15 (d, 1H, J = 3.4 Hz), 5.29 (d, 1H, J = 6.7 Hz), 5.84–5.94 (m, 1H), 5.95 (d, 1H, J = 7.2 Hz), 6.50 (brs, 2H), 7.49–7.55 (m, 2H), 7.57–7.65 (m, 1H), 7.66–7.80 (m, 4H), 7.90 (s, 1H), 8.59–8.65 (m, 2H) |
| 51 | | (DMSO-$d_6$) 1.51–1.78 (m, 4H), 3.39 (t, 2H, J = 6.5 Hz), 3.56–3.73 (m, 2H), 3.93–4.04 (m, 3H), 4.10–4.18 (m, 1H), 4.39 (s, 2H), 4.61 (d, 2H, J = 6.0 Hz), 4.70–4.80 (m, 1H), 5.19 (d, 1H, J = 3.4 Hz), 5.31 (d, 1H, J = 7.0 Hz), 5.89–6.01 (m, 2H), 6.53 (brs, 2H), 6.98–7.05 (m, 1H), 7.11–7.17 (m, 1H), 7.20–7.42 (m, 9H), 7.43–7.51 (m, 2H), 7.54–7.62 (m, 1H), 7.90 (s, 1H) |

TABLE 25-continued

| Ex No. | Strc | (Solv) δ(ppm) |
| --- | --- | --- |
| 52 | | (DMSO-d₆) 1.72–1.84 (m, 2H), 3.05–3.17 (m, 2H), 3.58–3.70 (m, 2H), 3.93–4.04 (m, 3H), 4.11–4.17 (m, 1H), 4.61 (d, 2H, J = 6.1 Hz), 4.71–4.79 (m, 1H), 5.00 (s, 2H), 5.04–5.44 (m, 2H), 5.80–6.02 (m, 2H), 6.50 (brs, 2H), 7.00–7.06 (m, 1H), 7.10–7.62 (m, 14H), 7.90 (s, 1H) |
| 53 | | (DMSO-d₆) 1.67–1.81 (m, 2H), 2.07 (s, 6H), 2.25 (t, 2H, J = 7.1 Hz), 3.57–3.73 (m, 2H), 3.92–4.06 (m, 3H), 4.09–4.19 (m, 1H), 4.61 (d, 2H, J = 6.1 Hz), 4.69–4.81 (m, 1H), 5.12–5.41 (m, 2H), 5.91–6.02 (m, 2H), 6.55 (brs, 2H), 6.97–7.06 (m, 1H), 7.10–7.17 (m, 1H), 7.20–7.51 (m, 6H), 7.59 (t, 1H, J = 6.1 Hz), 7.90 (s, 1H) |
| 54 | | (DMSO-d₆) 3.54–3.73 (m, 2H), 3.96–4.03 (m, 1H), 4.10–4.18 (m, 1H), 4.56–4.81 (m, 3H), 5.04–5.41 (m, 2H), 5.74–6.04 (m, 2H), 6.50 (brs, 2H), 7.31–7.38 (m, 1H), 7.40–7.51 (m, 4H), 7.53–7.70 (m, 5H), 7.90 (s, 1H) |

TABLE 26

| Ex No. | Strc | (Solv) δ(ppm) |
| --- | --- | --- |
| 55 | | (DMSO-d₆) 3.57–3.72 (m, 5H), 3.97–4.02 (m, 1H), 4.10–4.17 (m, 1H), 4.56–4.80 (m, 3H), 4.87 (s, 2H), 5.14 (d, 1H, J = 4.2 Hz), 5.27 (d, 1H, J = 6.5 Hz), 5.85–5.92 (m, 1H), 5.95 (d, 1H, J = 7.5 Hz), 6.50 (brs, 2H), 6.87–6.94 (m, 1H), 7.14–7.28 (m, 2H), 7.32–7.49 (m, 3H), 7.53–7.66 (m, 3H), 7.90 (s, 1H) |

TABLE 26-continued

| Ex No. | Strc | (Solv) δ(ppm) |
| --- | --- | --- |
| 56 | | (DMSO-d$_6$) 3.56–3.74 (m, 5H), 3.94–4.05 (m, 1H), 4.09–4.17 (m, 1H), 4.54–4.68 (m, 2H), 4.70–4.79 (m, 1H), 4.84 (s, 2H), 5.16 (d, 1H, J = 4.0 Hz), 5.29 (d, 1H, J = 6.7 Hz), 5.86–6.00 (m, 2H), 6.52 (brs, 2H), 6.96–7.05 (m, 2H), 7.38–7.48 (m, 2H), 7.51–7.64 (m, 5H), 7.90 (s, 1H) |
| 57 | | (DMSO-d$_6$) 1.28–1.52 (m, 11H), 1.56–1.68 (m, 2H), 2.84–2.96 (m, 2H), 3.55–3.72 (m, 2H), 3.87–4.04 (m, 3H), 4.10–4.18 (m, 1H), 4.54–4.66 (m, 2H), 4.70–4.79 (m, 1H), 5.15 (d, 1H, J = 4.1 Hz), 5.26 (d, 1H, J = 6.7 Hz), 5.87–5.99 (m, 2H), 6.50 (brs, 2H), 6.65–6.81 (m, 2H), 6.83–6.92 (m, 2H), 6.96–7.03 (m, 1H), 7.08–7.22 (m, 3H), 7.49–7.59 (m, 1H), 7.90 (s, 1H), 9.29 (s, 1H) |
| 58 | | (DMSO-d$_6$) 3.56–3.74 (m, 5H), 3.95–4.04 (m, 1H), 4.10–4.19 (m, 1H), 4.57–4.70 (m, 2H), 4.72–4.87 (m, 3H), 5.14 (d, 1H, J = 4.2 Hz), 5.28 (d, 1H, J = 6.7 Hz), 5.86–6.02 (m, 2H), 6.51 (brs, 2H), 6.94–7.09 (m, 2H), 7.24–7.64 (m, 7H), 7.90 (s, 1H) |
| 59 | | (DMSO-d$_6$) 3.55–3.77 (m, 5H), 3.96–4.05 (m, 1H), 4.10–4.20 (m, 1H), 4.59–4.85 (m, 3H), 5.02 (s, 2H), 5.15 (d, 1H, J = 3.6 Hz), 5.32 (d, 1H, J = 6.6 Hz), 5.80–5.90 (m, 1H), 6.00 (d, 1H, J = 7.7 Hz), 6.51 (brs, 2H), 7.13–7.24 (m, 2H), 7.28–7.49 (m, 5H), 7.59–7.68 (m, 2H), 7.90 (s, 1H) |

TABLE 26-continued

| Ex No. | Strc | (Solv) δ(ppm) |
|---|---|---|
| 60 | | (DMSO-$d_6$) 3.54–3.75 (m, 5H), 3.95–4.05 (m, 1H), 4.08–4.20 (m, 1H), 4.59 (d, 2H, J = 6.1 Hz), 4.67–4.86 (m, 3H), 5.19 (d, 1H, J = 4.2 Hz), 5.29 (d, 1H, J = 6.9 Hz), 5.88–6.01 (m, 2H), 6.54 (brs, 2H), 7.00–7.10 (m, 2H), 7.22–7.44 (m, 4H), 7.50–7.64 (m, 3H), 7.90 (s, 1H) |

TABLE 27

| Ex No. | Strc | (Solv) δ (ppm) |
|---|---|---|
| 61 | | (DMSO-$d_6$) 0.89 (t, 3H, J = 7.5 Hz), 1.57-1.70 (m, 2H), 3.56-3.73 (m, 2H), 3.92 (t, 2H, J = 6.6 Hz), 3.96-4.03 (m, 1H), 4.09-4.20 (m, 1H), 4.53-4.67 (m, 2H), 4.70-4.80 (m, 1H), 5.16 (d, 1H, J = 4.0 Hz), 5.27 (d, 1H, J = 7.2 Hz), 5.86-6.00 (m, 2H), 6.51 (brs, 2H), 6.98-7.05 (m, 1H), 7.11-7.17 (m, 1H), 7.20-7.32 (m, 2H), 7.33-7.42 (m, 2H), 7.43-7.61 (m, 3H), 7.90 (s, 1H) |
| 62 | | (DMSO-$d_6$) 0.84 (t, 3H, J = 7.3 Hz), 1.28-1.39 (m, 2H), 1.55-1.65 (m, 2H), 3.57-3.71 (m, 2H), 3.92-4.05 (m, 3H), 4.10-4.19 (m, 1H), 4.61 (d, 2H, J = 6.1 Hz), 4.70-4.79 (m, 1H), 5.18 (d, 1H, J = 3.8 Hz), 5.29 (d, 1H, J = 6.7 Hz), 5.90-6.01 (m, 2H), 6.53 (brs, 2H), 6.98-7.05 (m, 1H), 7.11-7.51 (m, 7H), 7.57 (t, 1H, J = 6.1 Hz), 7.90 (s, 1H). |
| 63 | | (DMSO-$d_6$) 1.24 (t, 3H, J = 7.0 Hz), 3.56-3.72 (m, 2H), 3.95-4.08 (m, 3H), 4.10-4.18 (m, 1H), 4.54-4.68 (m, 2H), 4.70-4.79 (m, 1H), 5.11-5.35 (m, 2H), 5.82-6.01 (m, 2H), 6.50 (brs, 2H), 6.98-7.06 (m, 1H), 7.11-7.63 (m, 8H), 7.90 (s, 1H) |

TABLE 27-continued

| Ex No. | Strc | (Solv) δ (ppm) |
|---|---|---|
| 64 | | (DMSO-$d_6$) 1.83-1.97 (m, 2H), 3.48 (t, 2H, J = 6.3 Hz), 3.56-3.71 (m, 2H), 3.96-4.18 (m, 4H), 4.40 (s, 2H), 4.61 (d, 2H, J = 6.1 Hz), 4.71-4.79 (m, 1H), 5.10-5.37 (m, 2H), 5.85-6.02 (m, 2H), 6.50 (brs, 2H), 6.99-7.06 (m, 1H), 7.12-7.48 (m, 12H), 7.57 (t, 1H, J = 6.1 Hz), 7.90 (s, 1H) |
| 65 | | (DMSO-$d_6$) 1.40 (t, 3H, J = 7.0 Hz), 3.56-3.71 (m, 2H), 3.97-4.05 (m, 1H), 4.10-4.27 (m, 3H), 4.53-4.68 (m, 2H), 4.73-4.84 (m, 1H), 5.15 (d, 1H, J = 4.2 Hz), 5.32 (d, 1H, J = 6.5 Hz), 5.79-5.88 (m, 1H), 6.00 (d, 1H, J = 7.4 Hz), 6.48 (brs, 2H), 7.12-7.23 (m, 2H), 7.25-7.48 (m, 5H), 7.62-7.69 (m, 2H), 7.90 (s, 1H) |
| 66 | | (DMSO-$d_6$) 1.05 (t, 3H, J = 7.4 Hz), 1.74-1.87 (m, 2H), 3.55-3.70 (m, 2H), 3.97-4.19 (m, 4H), 4.54-4.69 (m, 2H), 4.74-4.83 (m, 1H), 5.15 (d, 1H, J = 4.0 Hz), 5.32 (d, 1H, J = 6.4 Hz), 5.80-5.88 (m, 1H), 6.00 (d, 1H, J = 7.3 Hz), 6.48 (brs, 2H), 7.12-7.22 (m, 2H), 7.24-7.48 (m, 5H), 7.60-7.72 (m, 2H), 7.90 (s, 1H) |

TABLE 28

| Ex No. | Strc | (Solv) δ (ppm) |
|---|---|---|
| 67 | | (DMSO-$d_6$) 1.12-1.22 (m, 6H), 3.56-3.72 (m, 2H), 3.97-4.03 (m, 1H), 4.10-4.19 (m, 1H), 4.48-4.65 (m, 3H), 4.69-4.80 (m, 1H), 5.16 (d, 1H, J = 4.0 Hz), 5.26 (d, 1H, J = 7.1 Hz), 5.86-6.00 (m, 2H), 6.50 (brs, 2H), 6.96-7.04 (m, 1H), 7.11-7.17 (m, 1H), 7.19-7.63 (m, 7H), 7.90 (s, 1H) |

TABLE 28-continued

| Ex No. | Strc | (Solv) δ (ppm) |
| --- | --- | --- |
| 68 | | (DMSO-d$_6$) 1.29-1.45 (m, 4H), 1.56-1.69 (m, 2H), 3.28-3.42 (m, 2H), 3.56-3.72 (m, 2H), 3.89-4.05 (m, 3H), 4.10-4.19 (m, 1H), 4.32 (t, 1H, J = 5.0 Hz), 4.61 (d, 2H, J = 6.0 Hz), 4.70-4.80 (m, 1H), 5.16 (d, 1H, J = 3.9 Hz), 5.27 (d, 1H, J = 6.7 Hz), 5.82-6.01 (m, 2H), 6.53 (brs, 2H), 6.98-7.06 (m, 1H), 7.11-7.51 (m, 7H), 7.57 (t, 1H, J = 6.0 Hz), 7.91 (s, 1H) |
| 69 | | (DMSO-d$_6$) 1.52-1.80 (m, 4H), 3.45-3.75 (m, 4H), 3.91-4.06 (m, 3H), 4.09-4.19 (m, 1H), 4.60 (d, 2H, J = 6.1 Hz), 4.70-4.80 (m, 1H), 5.14 (d, 1H, J = 3.8 Hz), 5.27 (d, 1H, J = 6.5 Hz), 5.84-6.02 (m, 2H), 6.52 (brs, 2H), 6.96-7.07 (m, 1H), 7.09-7.38 (m, 5H), 7.40-7.63 (m, 3H), 7.77-7.94 (m, 5H) |
| 70 | | (DMSO-d$_6$) 3.57-3.71 (m, 2H), 3.88-4.04 (m, 3H), 4.10-4.32 (m, 3H), 4.60 (d, 2H, J = 5.1 Hz), 4.71-4.79 (m, 1H), 5.18 (d, 1H, J = 4.0 Hz), 5.31 (d, 1H, J = 6.7 Hz), 5.90-6.00 (m, 2H), 6.55 (brs, 2H), 6.99-7.30 (m, 8H), 7.54-7.62 (m, 1H), 7.80-7.97 (m, 5H) |
| 71 | | (DMSO-d$_6$) 1.16 (t, 3H, J = 7.1 Hz), 1.53-1.69 (m, 4H), 2.22-2.31 (m, 2H), 3.57-3.72 (m, 2H), 3.92-4.07 (m, 5H), 4.09-4.18 (m, 1H), 4.61 (d, 2H, J = 6.2 Hz), 4.70-4.79 (m, 1H), 5.18 (d, 1H, J = 3.8 Hz), 5.30 (d, 1H, J = 6.6 Hz), 5.88-6.01 (m, 2H), 6.53 (brs, 2H), 6.98-7.05 (m, 1H), 7.11-7.18 (m, 1H), 7.20-7.62 (m, 7H), 7.90 (s, 1H) |

TABLE 29

| Ex No. | Strc | (Solv) δ (ppm) |
|---|---|---|
| 72 | | (DMSO-d₆) 1.15 (t, 3H, Ja.1 Hz), 1.82-1.94 (m, 2H), 2.35 (t, 2H, J = 7.4 Hz), 3.57-3.72 (m, 2H), 3.94-4.06 (m, 5H), 4.10-4.18 (m, 1H), 4.61 (d, 2H, J = 6.0 Hz), 4.70-4.79 (m, 1H), 5.18 (d, 1H, J = 4.3 Hz), 5.30 (d, 1H, J = 6.7 Hz), 5.87-6.02 (m, 2H), 6.55 (brs, 2H), 6.99-7.06 (m, 1H), 7.14 (s, 1H), 7.20-7.50 (m, 6H), 7.54-7.65 (m, 1H), 7.90 (s, 1H) |
| 73 | | (DMSO-d₆) 3.41-3.54 (m, 2H), 3.56-3.71 (m, 2H), 3.98-4.05 (m, 1H), 4.09-4.21 (m, 3H), 4.54-4.70 (m, 2H), 4.75-4.84 (m, 1H), 5.04 (s, 2H), 5.15 (d, 1H, J = 4.3 Hz), 5.33 (d, 1H, J = 6.4 Hz), 5.82-5.90 (m, 1H), 6.00 (d, 1H, J = 7.4 Hz), 6.47 (brs, 2H), 7.12-7.48 (m, 12H), 7.52-7.73 (m, 3H), 7.90 (s, 1H) |
| 74 | | (DMSO-d₆) 3.55-3.72 (m, 2H), 3.92-4.20 (m, 4H), 4.61 (d, 2H, J = 6.0 Hz), 4.70-4.80 (m, 1H), 5.03 (s, 2H), 5.18 (d, 1H, J = 4.0 Hz), 5.30 (d, 1H, J = 7.2 Hz), 5.89-6.02 (m, 2H), 6.54 (brs, 2H), 7.01-7.07 (m, 1H), 7.15 (s, 1H), 7.21-7.65 (m, 13H), 7.90 (s, 1H) |
| 75 | | (DMSO-d₆) 1.24-1.45 (m, 4H), 1.53-1.69 (m, 2H), 2.90-3.02 (m, 2H), 3.57-3.72 (m, 2H), 3.86-4.04 (m, 3H), 4.09-4.17 (m, 1H), 4.61 (d, 2H, J = 6.2 Hz), 4.69-4.80 (m, 1H), 5.00 (s, 2H), 5.19 (d, 1H, J = 4.1 Hz), 5.30 (d, 1H, J = 7.0 Hz), 5.90-6.00 (m, 2H), 6.54 (brs, 2H), 6.97-7.05 (m, 1H), 7.09-7.51 (m, 13H), 7.53-7.63 (m, 1H), 7.90 (s, 1H) |

TABLE 29-continued

| Ex No. | Strc | (Solv) δ (ppm) |
|---|---|---|
| 76 | | (DMSO-d$_6$) 3.56-3.70 (m, 2H), 3.97-4.02 (m, 1H), 4.10-4.17 (m, 1H), 4.54-4.60 (m, 3H), 5.17 (d, 1H, J = 3.9 Hz), 5.31 (d, 1H, J = 6.3 Hz), 5.84-5.99 (m, 2H), 6.52 (brs, 2H), 6.70-6.78 (m, 1H), 6.96-7.08 (m, 2H), 7.19-7.27 (m, 1H), 7.39-7.68 (m, 5H), 7.90 (s, 1H), 9.51 (brs, 1H) |
| 77 | | (DMSO-d$_6$) 3.56-3.72 (m, 2H), 3.96-4.04 (m, 1H), 4.10-4.18 (m, 1H), 4.55-4.68 (m, 2H), 4.71-4.80 (m, 1H), 5.16 (d, 1H, J = 4.1 Hz), 5.30 (d, 1H, J = 6.7 Hz), 5.90-5.98 (m, 2H), 6.52 (brs, 2H), 6.80-6.95 (m, 2H), 7.09-7.17 (m, 1H), 7.19-7.25 (m, 1H), 7.34-7.64 (m, 5H), 7.90 (s, 1H), 9.47 (s, 1H) |

TABLE 30

| Ex No. | Strc | (Solv) δ (ppm) |
|---|---|---|
| 78 | | (DMSO-d$_6$) 3.54-3.72 (m, 2H), 3.96-4.03 (m, 1H), 4.10-4.18 (m, 1H), 4.57-4.80 (m, 3H), 4.94-5.50 (m, 2H), 5.76-6.02 (m, 2H), 6.50 (brs, 2H), 7.44-7.70 (m, 6H), 7.85-8.19 (m, 4H) |
| 79 | | (DMSO-d$_6$) 3.55-3.72 (m, 2H), 3.95-4.03 (m, 1H), 4.10-4.18 (m, 1H), 4.54-4.80 (m, 3H), 5.00-5.22 (m, 3H), 5.27 (d, 1H, J = 6.9 Hz), 5.84-5.99 (m, 2H), 6.38-6.62 (m, 3H), 6.71-6.84 (m, 2H), 7.03-7.11 (m, 1H), 7.34-7.64 (m, 5H), 7.90 (s, 1H) |

TABLE 30-continued

| Ex No. | Strc | (Solv) δ (ppm) |
|---|---|---|
| 80 | | (DMSO-$d_6$) 1.83-1.92 (m, 2H), 3.51-3.71 (m, 4H), 3.96-4.19 (m, 4H), 4.53 (t, 1H, J = 5.2 Hz), 4.56-4.79 (m, 3H), 5.14 (d, 1H, J = 4.0 Hz), 5.27 (d, 1H, J = 6.8 Hz), 5.85-5.93 (m, 1H), 5.95 (d, 1H, J = 7.2 Hz), 6.50 (brs, 2H), 6.86-6.95 (m, 1H), 7.11-7.23 (m, 2H), 7.30-7.38 (m, 1H), 7.41-7.50 (m, 2H), 7.53-7.65 (m, 3H), 7.90 (s, 1H) |
| 81 | | (DMSO-$d_6$) 1.52-1.63 (m, 2H), 1.71-1.81 (m, 2H), 3.41-3.50 (m, 2H), 3.56-3.71 (m, 2H), 3.96-4.19 (m, 4H), 4.43 (t, 1H, J = 5.0 Hz), 4.57-4.69 (m, 2H), 4.71-4.79 (m, 3H), 5.14 (d, 1H, J = 4.0 Hz), 5.27 (d, 1H, J = 6.6 Hz), 5.85-5.92 (m, 1H), 5.95 (d, 1H, J = 7.4 Hz), 6.50 (brs, 2H), 6.87-6.93 (m, 1H), 7.12-7.22 (m, 2H), 7.30-7.37 (m, 1H), 7.41-7.49 (m, 2H), 7.53-7.64 (m, 3H), 7.90 (s, 1H) |
| 82 | | (DMSO-$d_6$) 1.42-1.54 (m, 2H), 1.60-1.72 (m, 2H), 3.30-3.43 (m, 2H), 3.58-3.72 (m, 2H), 3.92-4.04 (m, 3H), 4.10-4.18 (m, 1H), 4.41 (t, 1H, J = 4.9 Hz), 4.61 (d, 2H, J = 6.0 Hz), 4.70-4.79 (m, 1H), 5.18 (d, 1H, J = 3.9 Hz), 5.30 (d, 1H, J = 6.7 Hz), 5.91-6.00 (m, 2H), 6.53 (brs, 2H), 6.98-7.05 (m, 1H), 7.12-7.18 (m, 1H), 7.20-7.42 (m, 4H), 7.44-7.51 (m, 2H), 7.58 (t, 1H, J = 6.0 Hz), 7.90 (s, 1H) |
| 83 | | (DMSO-$d_6$) 3.55-3.72 (m, 2H), 3.95-4.03 (m, 1H), 4.10-4.18 (m, 1H), 4.47-4.64 (m, 2H), 4.72-4.80 (m, 1H), 5.95 (d, 1H, J = 7.1 Hz), 6.49 (brs, 2H), 6.81-6.99 (m, 2H), 7.14-7.42 (m, 4H), 7.46-7.59 (m, 3H), 7.90 (s, 1H) |

TABLE 31

| Ex No. | Strc | (Solv) δ (ppm) |
| --- | --- | --- |
| 84 | | (DMSO-d$_6$) 1.72-1.83 (m, 2H), 3.41-3.53 (m, 2H), 3.58-3.72 (m, 2H), 3.94-4.20 (m, 4H), 4.47 (t, 1H, J = 5.4 Hz), 4.61 (d, 2H, J = 5.9 Hz), 4.70-4.79 (m, 1H). 5.16 (d, 1H, J = 4.3 Hz), 5.28 (d, 1H, J = 6.9 Hz), 5.86-6.00 (m, 2H), 6.50 (brs, 2H), 6.98-7.06 (m, 1H), 7.12-7.62 (m, 8H), 7.90 (s, 1H) |
| 85 | | (DMSO-d$_6$) 1.64-1.76 (m, 2H), 2.60 (t, 2H, J = 6.5 Hz), 3.58-3.72 (m, 2H), 3.96-4.19 (m, 4H), 4.54-4.68 (m, 2H), 4.70-4.79 (m, 1H), 5.96 (d, 1H, J = 7.5 Hz), 6.51 (brs, 2H), 6.98-7.05 (m, 1H), 7.12-7.63 (m, 8H), 7.90 (s, 1H). |
| 86 | | (DMSO-d$_6$) 1.24-1.88 (br, 2H), 2.88 (t, 2H, J = 5.9 Hz), 3.56-3.72 (m, 2H), 3.92-4.03 (m, 3H), 4.09-4.18(m, 1H), 4.56-4.80 (m, 3H), 5.16 (d, 1H, J = 4.0 Hz), 5.29 (d, 1H, J = 6.7 Hz), 5.85-5.99 (m, 2H), 6.50 (brs, 2H), 6.88-6.95 (m, 1H), 7.14-7.22 (m, 2H), 7.30-7.38 (m, 1H), 7.41-7.49 (m, 2H), 7.54-7.64 (m, 3H), 7.90 (s, 1) |
| 87 | | (DMSO-d$_6$) 3.57-3.72(m, 2H), 3.96-4.04 (m, 1H), 4.10-4.18 (m, 1H), 4.47-4.61 (m, 2H), 4.71-4.81 (m, 1H), 5.15 (d, 1H, J = 3.5 Hz), 5.30 (d, 1H, J = 6.6 Hz), 5.84-5.93 (m, 1H), 5.96 (d, 1H, J = 7.0 Hz), 6.51 (brs, 2H), 7.01-7.10 (m, 2H), 7.23-7.70 (m, 7H), 7.92 (s, 1H), 10.19 (brs, 1H) |

TABLE 31-continued

| Ex No. | Strc | (Solv) δ (ppm) |
|---|---|---|
| 88 | | (DMSO-d$_6$) 2.89-2.99 (m, 2H), 3.57-3.71 (m, 2H), 3.97-4.03 (m, 1H), 4.08-4.20 (m, 3H), 4.61 (d, 2H, J = 5.9 Hz), 4.65-4.77 (m, 1H), 5.97 (d, 1H, J = 7.5 Hz), 6.68 (brs, 2H), 7.12-7.26 (m, 2H), 7.30-7.52 (m, 4H), 7.61-7.74 (m, 3H), 7.88 (s, 1H) |
| 89 | | (DMSO-d$_6$) 2.78 (t, 2H, J = 5.8 Hz), 3.56-3.73 (m, 2H), 3.92 (t, 2H, J = 5.8 Hz), 3.97-4.05 (m, 1H), 4.09-4.19 (m, 1H), 4.54-4.82 (m, 3H), 5.08-5.51 (m, 2H), 5.86-6.06 (m, 2H), 6.54 (brs, 2H), 6.99-7.06 (m, 1H), 7.12-7.18 (m, 1H), 7.21-7.66 (m, 7H), 7.90 (s, 1H) |

TABLE 32

| Ex No. | Strc | (Solv) δ (ppm) |
|---|---|---|
| 90 | | (DMSO-d$_6$) 1.23-1.39 (m, 4H), 1.51-1.70 (m, 2H), 2.40-2.54 (m, 2H), 3.56-3.71 (m, 2H), 3.87-4.19 (m, 4H), 4.54-4.80 (m, 3H), 5.96 (d, 1H, J = 7.3 Hz), 6.54 (brs, 2H), 6.97-7.05 (m, 1H), 7.11-7.17 (m, 1H), 7.20-7.42 (m, 4H), 7.44-7.51 (m, 2H), 7.55-7.63 (m, 1H), 7.90 (s, 1H) |
| 91 | | (DMSO-d$_6$) 1.73-1.85 (m, 2H), 2.70 (t, 2H, J = 6.7 Hz), 3.56-3.72 (m, 2H), 3.96-4.18 (m, 4H), 4.55-4.82 (m, 3H), 5.03-5.46 (m, 2H), 5.82-6.00 (m, 2H), 6.50 (brs, 2H), 6.87-6.95 (m, 1H), 7.12-7.23 (m, 2H), 7.28-7.38 (m, 1H), 7.40-7.70 (m, 5H), 7.90 (s, 1H) |

TABLE 32-continued

| Ex No. | Strc | (Solv) δ (ppm) |
|---|---|---|
| 92 | | (DMSO-$d_6$) 1.43-1.55 (m, 2H), 1.67-1.80 (m, 2H), 2.59 (t, 2H, J = 6.9 Hz), 3.56-3.72 (m, 2H), 3.96-4.07 (m, 3H), 4.10-4.18 (m, 1H), 4.55-4.80 (m, 3H), 5.02-5.48 (m, 2H), 5.82-6.02 (m, 2H), 6.49 (brs, 2H), 6.86-6.94 (m, 1H), 7.11-7.23 (m, 2H), 7.29-7.38 (m, 1H), 7.41-7.49 (m, 2H), 7.53-7.67 (m, 3H), 7.90 (s, 1H) |
| 93 | | (DMSO-$d_6$) 3.55-3.73 (m, 2H), 3.96-4.03 (m, 1H), 4.10-4.18 (m, 1H), 4.51-4.80 (m, 5H), 5.14 (d, 1H, J = 3.8 Hz), 5.21 (t, 1H, J = 5.6 Hz), 5.28 (d, 1H, J = 6.8 Hz), 5.84-5.93 (m, 1H), 5.95 (d, 1H, J = 7.5 Hz), 6.50 (brs, 2H), 7.25-7.33 (m, 1H), 7.35-7.66 (m, 8H), 7.90 (s, 1H) |
| 94 | | (DMSO-$d_6$) 3.56-3.72 (m, 2H), 3.96-4.04 (m, 1H), 4.10-4.18 (m, 1H), 4.49 (s, 2H), 4.56-4.80 (m, 3H), 5.17 (d, 1H, J = 4.0 Hz), 5.30 (d, 1H, J = 6.7 Hz), 5.88-6.00 (m, 2H), 6.53 (brs, 2H), 6.90-6.96 (m, 1H), 7.18-7.28 (m, 2H), 7.32-7.74 (m, 8H), 7.90 (s, 1H) |
| 95 | | (DMSO-$d_6$) 3.56-3.70 (m, 2H), 3.96-4.02 (m, 1H), 4.10-4.16 (m, 1H), 4.46 (s, 2H), 4.54-4.80 (m, 3H), 5.16 (d, 1H, J = 3.9 Hz), 5.29 (d, 1H, J = 7.1 Hz), 5.86-5.99 (m, 2H), 6.52 (brs, 2H), 6.98-7.05 (m, 2H), 7.34-7.63 (m, 9H), 7.90 (s, 1H) |

TABLE 33

| Ex No. | Strc | (Solv) δ (ppm) |
| --- | --- | --- |
| 96 | | (DMSO-d$_6$) 3.54-3.75 (m, 2H), 3.94-4.06 (m, 1H), 4.08-4.20 (m, 1H), 4.43 (s, 2H), 4.56-4.83 (m, 3H), 5.17 (d, 1H, J = 4.2 Hz), 5.31 (d, 1H, J = 6.7 Hz), 5.88-6.02 (m, 2H), 6.54 (brs, 2H), 6.93-7.66 (m, 11H), 7.90 (s, 1H) |
| 97 | | (DMSO-d$_6$) 3.54-3.70 (m, 2H), 3.97-4.04 (m, 1H), 4.10-4.18 (m, 1H), 4.61-4.82 (m, 5H), 5.14 (d, 1H, J = 3.9 Hz), 5.31 (d, 1H, J = 6.9 Hz), 5.85-5.93 (m, 1H), 5.98 (d, 1H, J = 7.7 Hz), 6.49 (brs, 2H), 7.11-7.25 (m, 2H), 7.31-7.68 (m, 9H), 7.90 (s, 1H) |
| 98 | | (DMSO-d$_6$) 3.53-3.75 (m, 2H), 3.94-4.04 (m, 1H), 4.09-4.20 (m, 1H), 4.43 (s, 2H), 4.52-4.66 (m, 2H), 4.69-4.79 (m, 1H), 5.18 (d, 1H, J = 3.9 Hz), 5.31 (d, 1H, J = 6.7 Hz), 5.88-6.00 (m, 2H), 6.55 (brs, 2H), 7.00-7.16 (m, 3H), 7.21-7.65 (m, 8H), 7.90 (s, 1H) |
| 99 | | (DMSO-d$_6$) 2.66 (d, 3H, J = 4.9 Hz), 3.56-3.71 (m, 2H), 3.96-4.03 (m, 1H), 4.10-4.17 (m, 1H), 4.53 (s, 2H), 4.57-4.69 (m, 2H), 4.70-4.80 (m, 1H), 5.15 (d, 1H, J = 4.1 Hz), 5.28 (d, 1H, J = 6.6 Hz), 5.85-5.93 (m, 1H), 5.95 (d, 1H, J = 7.0 Hz), 6.50 (brs, 2H), 6.91-6.97 (m, 1H), 7.19-7.28 (m, 2H), 7.34-7.40 (m, 1H), 7.43-7.50 (m, 2H), 7.52-7.66 (m, 3H), 7.90 (s, 1H), 7.98-8.09 (m, 1H) |

TABLE 33-continued

| Ex No. | Strc | (Solv) δ (ppm) |
|---|---|---|
| 100 | | (DMSO-d$_6$) 2.84 (s, 3H), 3.01 (s, 3H), 3.56-3.70 (m, 2H), 3.96-4.03 (m, 1H), 4.10-4.18 (m, 1H), 4.56-4.80 (m, 3H), 4.85 (s, 2H), 5.09-5.40 (m, 2H), 5.83-6.00 (m, 2H), 6.50 (brs, 2H), 6.85-6.92 (m, 1H), 7.14-7.24 (m, 2H), 7.29-7.38 (m, 1H), 7.41-7.50 (m, 2H), 7.53-7.64 (m, 3H), 7.90 (s, 1H) |
| 101 | | (DMSO-d$_6$) 3.56-3.77 (m, 4H), 3.95-4.18 (m, 4H), 4.55-4.80 (m, 3H), 4.85 (t, 1H, J = 5.5 Hz), 5.14 (d, 1H, J = 4.0 Hz), 5.27 (d, 1H, J = 6.7 Hz), 5.86-5.92 (m, 1H), 5.95 (d, 1H, J = 7.4 Hz), 6.50 (brs, 2H), 6.87-6.95 (m, 1H), 7.13-7.24 (m, 2H), 7.30-7.38 (m, 1H), 7.41-7.49 (m, 2H), 7.54-7.64 (m, 3H), 7.90 (s, 1H) |

TABLE 34

| Ex No. | Strc | (Solv) δ (ppm) |
|---|---|---|
| 102 | | (DMSO-d$_6$) 3.54-3.77 (m, 4H), 3.96-4.04 (m, 3H), 4.09-4.18 (m, 1H), 4.55-4.68 (m, 2H), 4.70-4.79 (m, 1H), 4.82-4.89 (m, 1H), 5.14 (d, 1H, J = 3.8 Hz), 5.27 (d, 1H, J = 6.8 Hz), 5.84-5.92 (m, 1H), 5.95 (d, 1H, J = 7.2 Hz), 6.49 (brs, 2H), 6.96-7.05 (m, 2H), 7.37-7.47 (m, 2H), 7.49-7.62 (m, 5H), 7.90 (s, 1H) |
| 103 | | (DMSO-d$_6$) 3.56-3.73 (m, 4H), 3.96-4.06 (m, 3H), 4.11-4.18 (m, 1H), 4.57-4.83 (m, 4H), 5.14 (d, 1H, J = 3.9 Hz), 5.28 (d, 1H, J = 7.0 Hz), 5.86-5.99 (m, 2H), 6.51 (brs, 2H), 6.96-7.04 (m, 1H), 7.06-7.14 (m, 1H), 7.24-7.43 (m, 4H), 7.46-7.64 (m, 3H), 7.90 (s, 1H) |

TABLE 34-continued

| Ex No. | Strc | (Solv) δ (ppm) |
|---|---|---|
| 104 | | (DMSO-d$_6$) 3.57-3.86 (m, 4H), 3.98-4.05 (m, 1H), 4.10-4.24 (m, 3H), 4.56-4.82 (m, 3H), 5.10-5.40 (m, 3H), 5.86-5.92 (m, 1H), 5.99 (d, 1H, J = 7.2 Hz), 6.54 (brs, 2H), 7.13-7.26 (m, 2H), 7.29-7.55 (m, 5H), 7.61 -7.70 (m, 2H), 7.90 (s, 1H) |
| 105 | | (DMSO-d$_6$) 3.57-3.72 (m, 4H), 3.96-4.06 (m, 3H), 4.10-4.19 (m, 1H), 4.61(d, 2H, J = 5.9 Hz), 4.68-4.80 (m, 2H), 5.15 (d, 1H, J = 4.0 Hz), 5.27 (d, 1H, J = 6.7 Hz), 5.85-6.00 (m, 2H), 6.51 (brs, 2H), 6.99-7.06 (m, 1H), 7.12-7.19 (m, 1H), 7.20-7.42 (m, 4H), 7.49-7.62 (m, 3H), 7.90 (s, 1H) |
| 106 | | (DMSO-d$_6$) 2.80 (d, 3H, J = 4.6 Hz), 3.56-3.72 (m, 2H), 3.96-4.03 (m, 1H), 4.10-4.18 (m, 1H), 4.57-4.81 (m, 3H), 5.16 (d, 1H, J = 3.6 Hz), 5.29 (d, 1H, J = 6.3 Hz), 5.83-6.00 (m, 2H), 6.50 (brs, 2H), 7.44-7.86 (m, 8H), 7.90 (s, 1H), 8.06-8.12 (m, 1H), 8.46-8.57 (m, 1H) |
| 107 | | (DMSO-d$_6$) 1.33-1.45 (m, 2H), 1.58-1.70 (m, 2H), 3.57-3.71 (m, 2H), 3.91-4.03 (m, 3H), 4.10-4.18 (m, 1H), 4.54-4.68 (m, 2H), 4.70-4.79 (m, 1H), 5.96 (d, 1H, J = 7.4 Hz), 6.51 (brs, 2H), 6.97-7.06 (m, 1H), 7.12-7.42 (m, 5H), 7.44-7.51 (m, 2H), 7.53-7.60 (m, 1H), 7.90 (s, 1H) |

TABLE 35

| Ex No. | Strc | (Solv) δ (ppm) |
|---|---|---|
| 108 | | (DMSO-d$_6$) 1.51-1.72 (m, 4H), 2.21 (t, 2H, J = 7.3 Hz), 3.60-3.72 (m, 2H), 3.92-4.06 (m, 3H), 4.09-4.20 (m, 1H), 4.58-4.76 (m, 3H), 5.09-5.50 (m, 2H), 5.78-6.20 (m, 2H), 6.80-7.52 (m, 10H), 7.60-8.10 (m, 2H) 12.02 (brs, 1H) |
| 109 | | (DMSO-d$_6$) 1.27-1.52 (m, 4H), 1.57-1.70 (m, 2H), 3.07-3.21 (m, 2H), 3.57-3.72 (m, 2H), 3.88-4.05 (m, 3H), 4.09-4.19 (m, 1H), 4.61 (d, 2H, J = 6.1 Hz), 4.70-4.79 (m, 1H), 5.18 (d, 1H, J = 4.0 Hz), 5.29 (d, 1H, J = 6.7 Hz), 5.90-6.01 (m, 2H), 6.53 (brs, 2H), 6.98-7.06 (m, 1H), 7.11-7.18 (m, 1H), 7.20-7.50 (m, 6H), 7.52-7.63 (m, 1H), 7.90 (s, 1H), 9.32-9.46 (m, 1H) |
| 110 | | (DMSO-d$_6$) 1.44-1.74 (m, 4H), 2.04 (t, 2H, J= 7.0 Hz), 3.56-3.73 (m, 2H), 3.89-4.06 (m, 3H), 4.10-4.20(m, 1H), 4.54-4.68 (m, 2H), 4.70-4.81 (m, 1H), 5.16 (d, 1H, J = 4.0 Hz), 5.28 (d, 1H, J = 7.2 Hz), 5.87-6.00 (m, 2H), 6.51 (brs, 2H), 6.69 (brs, 1H), 6.97-7.06 (m, 1H), 7.09-7.62 (m, 9H), 7.90 (s, 1H) |
| 111 | | (DMSO-d$_6$) 1.52-1.80 (m, 4H), 3.40 (t, 2H, J = 6.3 Hz), 3.62-3.73 (m, 2H), 3.92-4.05 (m, 3H), 4.09-4.19(m, 1H), 4.40 (s, 2H), 4.54 (d, 2H, J = 6.1 Hz), 4.62-4.71 (m, 1H), 5.12-5.24 (m, 1H), 5.35 (d, 1H, J = 6.3 Hz), 5.69-5.79 (m, 1H), 5.94 (d, 1H, J = 7.5 Hz), 6.96-7.02 (m, 1H), 7.05-7.12 (m, 1H), 7.19-7.58 (m, 12H), 7.82 (s, 1H), 11.50-12.70 (br, 1H) |

TABLE 35-continued

| Ex No. | Strc | (Solv) δ (ppm) |
|---|---|---|
| 112 | | (DMSO-d$_6$) 3.60-3.74 (m, 2H), 3.96-4.06 (m, 1H), 4.09-4.20 (m, 1H), 4.48-4.72 (m, 3H), 5.12-5.22 (m, 1H), 5.32-5.40 (m, 1H), 5.67-5.76 (m, 1H), 5.89-6.00 (m, 1H), 7.30-7.72 (m, 10H), 7.78-7.88 (m, 1H), 12.09 (brs, 1H) |
| 113 | | (DMSO-d$_6$) 3.60-3.72 (m, 2H), 3.98-4.02 (m, 1H), 4.11-4.16 (m, 1H), 4.61-4.77 (m, 3H), 5.13-5.20 (m, 1H), 5.37 (d, 1H, J = 6.6 Hz), 5.66-5.74 (m, 1H), 5.95 (d, 1H, J = 7.5 Hz), 7.42-7.64 (m, 4H), 7.78-7.92 (m, 5H), 11.94-12.20 (br, 1H) |

TABLE 36

| Ex No. | Strc | (Solv) δ (ppm) |
|---|---|---|
| 114 | | (DMSO-d$_6$) 1.43-1.54 (m, 2H), 1.61-1.73 (m, 2H), 3.33-3.43 (m, 2H), 3.60-3.74 (m, 2H), 3.92-4.04 (m, 3H), 4.10-4.18 (m, 1H), 4.37-4.45 (m, 1H), 4.54 (d, 2H, J = 5.9 Hz), 4.62-4.70 (m, 1H), 5.20 (d, 1H, J = 4.4 Hz), 5.38 (d, 1H, J = 6.6 Hz), 5.77 (t, 1H, J = 4.4 Hz), 5.94 (d, 1H, J = 7.7 Hz), 6.94-7.03 (m, 1H), 7.06-7.13 (m, 1H), 7.19-7.62 (m, 7H), 7.83 (s, 1H), 12.10 (brs, 1H) |
| 115 | | (DMSO-d$_6$) 0.86 (t, 6H, J = 7.3 Hz), 1.60-1.81 (m, 2H), 2.29-2.45 (m, 6H), 3.56-3.74 (m, 2H), 3.91-4.07 (m, 3H), 4.10-4.18 (m,1H), 4.61 (d, 2H, J = 6.1 Hz), 4.69-4.80 (m, 1H), 5.18 (d, 1H, J = 3.8 Hz), 5.30 (d, 1H, J = 6.6 Hz), 5.87-6.07 (m, 2H), 6.53 (brs, 2H), 6.97-7.06 (m, 1H), 7.09-7.16 (m, 1H), 7.19-7.67 (m, 7H), 7.90 (s, 1H) |

TABLE 36-continued

| Ex No. | Strc | (Solv) δ (ppm) |
|---|---|---|
| 116 | | (DMSO-d$_6$) 1.68-1.82 (m, 2H), 2.21 (s, 3H), 3.56-3.73 (m, 2H), 3.94-4.22 (m, 4H), 4.55-4.81 (m, 3H), 4.95-5.70 (m, 2H), 5.80-6.10 (m, 2H), 6.51 (brs, 2H), 6.96-7.07 (m, 1H), 7.11-7.65 (m, 8H), 7.90 (s, 1H) |
| 117 | | (DMSO-d$_6$) 1.77-1.93 (m, 2H), 2.14 (s, 6H), 2.36 (t, 2H, J = 7.1 Hz), 3.55-3.74 (m, 2H), 3.93-4.19 (m, 4H), 4.56-4.80 (m, 3H), 5.15 (d, 1H, J = 4.4 Hz), 5.28 (d, 1H, J = 7.1 Hz), 5.85-6.00 (m, 2H), 6.50 (brs, 2H), 6.86-6.95 (m, 1H), 7.09-7.25 (m, 2H), 7.28-7.67 (m, 6H), 7.90 (s, 1H) |
| 118 | | (DMSO-d$_6$) 0.94 (t, 3H, J = 7.0 Hz), 1.74-1.94 (m, 2H), 3.13 (q, 2H, J = 7.0 Hz), 3.18-3.32 (m, 2H), 3.54-3.74 (m, 2H), 3.87-4.06 (m, 3H), 4.10-4.19 (m, 1H), 4.61 (d, 2H, J = 5.9 Hz), 4.69-4.81 (m, 1H), 4.91-5.20 (m, 3H), 5.27 (d, 1H, J = 6.7 Hz), 5.85-6.01 (m, 2H), 6.50 (brs, 2H), 6.98-7.63 (m, 14H), 7.90 (s, 1H) |
| 119 | | (DMSO-d$_6$) 0.62-0.82 (m, 3H), 1.28-1.44 (m, 2H), 1.75-1.96 (m, 2H), 2.97-3.12 (m, 2H), 3.56-3.72 (m, 2H), 3.86-4.06 (m, 3H), 4.08-4.21 (m, 1H), 4.55-4.68 (m, 2H), 4.70-4.80 (m, 1H), 4.92-5.20 (m, 3H), 5.27 (d, 1H, J = 7.2 Hz), 5.85-6.02 (m, 2H), 6.50 (brs, 2H), 6.98-7.71 (m, 14H), 7.90 (s, 1H) |

TABLE 37
| Ex No. | Strc | (Solv) δ (ppm) |
|---|---|---|
| 120 | 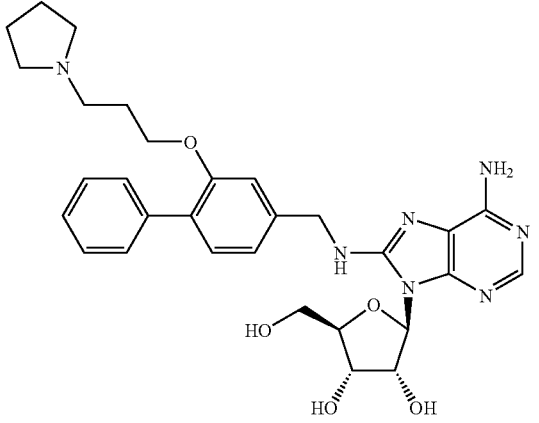 | (DMSO-d$_6$) 1.55-1.86 (m, 6H), 2.20-2.50 (m, 6H), 3.55-3.74 (m, 2H), 3.93-4.08 (m, 3H), 4.10-4.19 (m, 1H), 4.61 (d, 2H, J=6.3Hz), 4.69-4.82 (m, 1H), 5.04-5.46 (m, 2H), 5.85-6.04 (m, 2H), 6.51 (brs, 2H), 6.97-7.07 (m, 1H), 7.10-7.66 (m, 8H), 7.90 (s, 1H) |
| 121 | 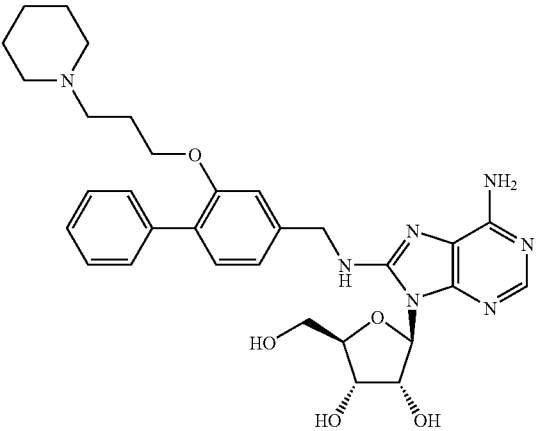 | (DMSO-d$_6$) 1.24-1.52 (m, 6H), 1.66-1.84 (m, 2H), 2.24-2.40 (m, 6H), 3.57-3.75 (m, 2H), 3.90-4.06 (m, 3H), 4.10-4.19 (m, 1H), 4.61 (m, 2H, J=6.1Hz), 4.69-4.81 (m, 1H), 5.07-5.40 (m, 2H), 5.87-6.02 (m, 2H), 6.50 (brs, 2H), 6.96-7.06 (m, 1H), 7.09-7.64 (m, 8H), 7.90 (s, 1H) |
| 122 | 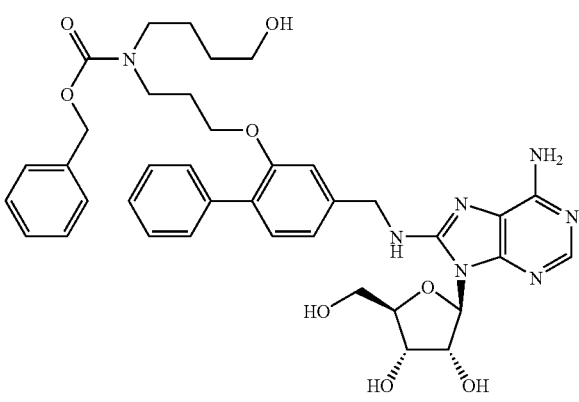 | (DMSO-d$_6$) 1.15-1.48 (m, 4H), 1.77-1.93 (m, 2H), 2.98-3.40 (m, 4H), 3.53-3.75 (m, 2H), 3.84-4.24 (m, 4H), 4.34-4.45 (m, 1H), 4.53-4.82 (m, 3H), 4.90-5.42 (m, 4H), 5.88-6.04 (m, 2H), 6.53 (brs, 2H), 6.97-7.65 (m, 14H), 7.90 (s, 1H) |
| 123 | 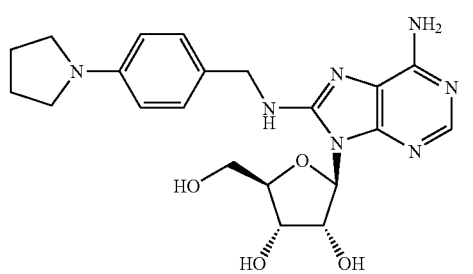 | (DMSO-d$_6$) 1.86-1.99 (m, 4H), 3.10-3.25 (m, 4H), 3.52-3.70 (m, 2H), 3.91-4.01 (m, 1H), 4.05-4.16 (m, 1H), 4.32-4.54 (m, 2H), 4.62-4.75 (m, 1H), 5.15 (d, 1H, J=4.2Hz), 5.24 (d, 1H, J=6.9Hz), 5.79-5.95 (m, 2H), 6.36-6.64 (m, 4H), 7.14-7.24 (m, 2H), 7.26-7.42 (m, 1H), 7.88 (s, 1H) |

TABLE 37-continued

| Ex No. | Strc | (Solv) δ (ppm) |
|---|---|---|
| 124 | | (DMSO-$d_6$) 1.09-1.85 (m, 10H), 2.35-2.56 (m, 1H), 3.53-3.71 (m, 2H), 3.94-4.03 (m, 1H), 4.06-4.18 (m, 1H), 4.44-4.79 (m, 3H), 5.16 (d, 1H, J = 4.2 Hz), 5.27 (d, 1H, J = 6.9 Hz), 5.84-5.98 (m, 2H), 6.51 (brs, 2H), 7.10-7.33 (m, 4H), 7.44-7.56 (m, 1H), 7.89 (s, 1H) |
| 125 | | (DMSO-$d_6$) 1.26-1.59 (m, 6H), 1.78-1.94 (m, 2H), 2.10-2.54 (m, 6H), 3.53-3.74 (m, 2H), 3.94-4.18 (m, 4H), 4.54-4.81 (m, 3H), 5.06-5.38 (m, 2H), 5.83-6.03 (m, 2H), 6.51 (brs, 2H), 6.84-6.96 (m, 1H), 7.08-7.24 (m, 2H), 7.28-7.70 (m, 6H), 7.90 (s, 1H) |

TABLE 38

| Ex No. | Strc | (Solv) δ (ppm) |
|---|---|---|
| 126 | | (DMSO-$d_6$) 1.57-1.77 (m, 4H), 1.80-1.98 (m, 2H), 2.32-2.61 (m, 6H), 3.53-3.75 (m, 2H), 3.94-4.20 (m, 4H), 4.54-4.82 (m, 3H), 5.07-5.39 (m, 2H), 5.85-6.01 (m, 2H), 6.52 (brs, 2H), 6.84-6.96 (m, 1H), 7.09-7.70 (m, 8H), 7.90 (s, 1H) |
| 127 | | (DMSO-$d_6$) 1.79-1.96 (m, 2H), 3.10-3.26 (m, 2H), 3.52-3.75 (m, 2H), 3.90-4.24 (m, 4H), 4.52-4.85 (m, 3H), 4.93-5.48 (m, 4H), 5.70-6.10 (m, 2H), 6.50 (brs, 2H), 6.89-7.09 (m, 2H), 7.22-7.74 (m, 13H), 7.89 (s, 1H) |

TABLE 38-continued

| Ex No. | Strc | (Solv) δ (ppm) |
| --- | --- | --- |
| 128 | | (DMSO-d$_6$) 2.44-2.58 (m, 2H), 3.23-3.39 (m, 2H), 3.52-3.76 (m, 2H), 3.93-4.20 (m, 2H), 4.52-4.82 (m, 3H), 5.02 (s, 2H), 5.18 (d, 1H, J=3.8Hz), 5.32 (d, 1H, J=6.7Hz), 5.82-6.05 (m, 2H), 6.53 (brs, 2H), 7.22-7.68 (m, 14H), 7.85-7.98 (m, 2H), 10.04 (s, 1H) |
| 129 | | (DMSO-d$_6$) 3.12-3.41 (m, 4H), 3.53-3.75 (m, 2H), 3.95-4.19 (m, 2H), 4.55-4.83 (m, 3H), 5.01 (s, 2H), 5.20 (d, 1H, J=3.9Hz), 5.32 (d, 1H, J=6.4Hz), 5.87-6.02 (m, 2H), 6.54 (brs, 2H), 7.21-8.16 (m, 16H), 8.55-8.74 (m, 1H) |
| 130 | | (CD$_3$OD) 0.94 (t, 3H, J=7.4Hz), 1.73-1.90 (m, 2H), 2.40-2.65 (m, 6H), 3.53 (t, 2H, J=6.5Hz), 3.60-3.90 (m, 2H), 4.01 (t, 2H, J=5.9Hz), 4.10-4.35 (m, 2H), 4.60-4.70 (m, 2H), 4.80 (dd, 1H, J=5.8Hz, 7.8Hz), 6.11 (d, 1H, J=7.5Hz), 6.98-7.50 (m, 8H), 7.98 (s, 1H) |
| 131 | | (DMSO-d$_6$) 1.33-1.70 (m, 4H), 2.54-2.70 (m, 2H), 2.94-3.10 (m, 2H), 3.53-3.74 (m, 2H), 3.95-4.04 (m, 1H), 4.08-4.17 (m, 1H), 4.53-4.83 (m, 3H), 4.93-5.07 (m, 4H), 5.77-6.09 (m, 2H), 6.54 (brs, 2H), 7.07-7.69 (m, 15H), 7.90 (s, 1H) |

TABLE 39

| Ex No. | Strc | (Solv) δ (ppm) |
|---|---|---|
| 132 | | (CD$_3$OD) 3.70-3.90 (m, 2H), 4.10-4.20 (m, 1H), 4.23-4.35 (m, 1H), 4.55-4.75 (m, 2H), 6.09 (d, 1H, J=7.5Hz), 7.35-7.75 (m, 7H), 7.98 (s, 1H) |
| 133 | | (CD$_3$OD) 3.70-3.90 (m, 2H), 4.10-4.20 (m, 1H), 4.23-4.35 (m, 1H), 4.55-4.75 (m, 2H), 6.08 (d, 1H, J=7.5Hz), 6.73-6.82 (m, 1H), 7.30-7.60 (m, 5H), 7.80-7.90 (m, 1H), 7.97 (s, 1H) |
| 134 | | (DMSO-d$_6$) 2.06 (s, 6H), 2.10 (t, 2H, J=7.0Hz), 3.05-3.20 (m, 2H), 3.55-3.75 (m, 2H), 3.95-4.05 (m, 1H), 4.10-4.20 (m, 1H), 4.64 (d, 2H, J=5.5Hz), 4.70-4.83 (m, 1H), 5.15-5.25 (m, 1H), 5.31 (d, 1H, J=5.5Hz), 5.85-6.00 (m, 2H), 6.53 (brs, 2H), 7.25-7.55 (m, 8H), 7.60-7.70 (m, 1H), 7.80-7.95 (m, 2H) |
| 135 | | (CD$_3$OD) 1.40-1.60 (m, 2H), 1.70-1.90 (m, 4H), 1.95-2.15 (m, 2H), 2.30-2.45 (m, 2H), 2.60-2.80 (m, 2H), 3.50-3.65 (m, 1H), 3.73-3.90 (m, 2H), 3.99 (t, 2H, J=5.8Hz), 4.13-4.22 (m, 1H), 4.25-4.35 (m, 1H), 4.58-4.73 (m, 2H), 4.75-4.85 (m, 1H), 6.11 (d, 1H, J=7.7Hz), 6.98-7.50 (m, 8H), 7.97 (s, 1H) |
| 136 | | (DMSO-d$_6$) 1.63-1.83 (m, 2H), 2.96-3.15 (m, 2H), 3.40-3.75 (m, 4H), 3.94-4.21 (m, 2H), 4.46-4.86 (m, 4H), 5.03-5.56 (m, 2H), 5.78-6.10 (m, 2H), 6.54 (brs, 2H), 7.22-7.70 (m, 9H), 7.90 (s, 1H) |

TABLE 39-continued
| Ex No. | Strc | (Solv) δ (ppm) |
|---|---|---|
| 137 | 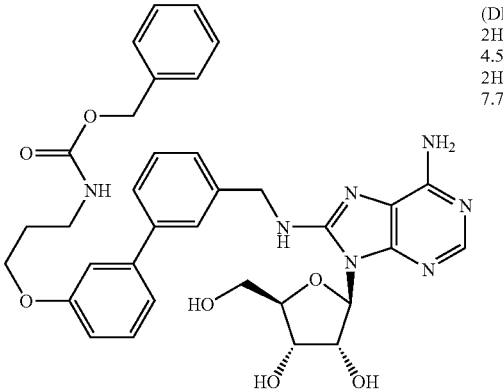 | (DMSO-d$_6$) 1.80-1.95 (m, 2H), 3.08-3.26 (m, 2H), 3.54-3.74 (m, 2H), 3.92-4.19 (m, 4H), 4.56-4.81 (m, 3H), 5.01 (s, 2H), 5.80-6.00 (m, 2H), 6.50 (brs, 2H), 6.82-6.98 (m, 1H), 7.08-7.74 (m, 14H), 7.89 (s, 1H) |
TABLE 40
| Ex No. | Strc | (Solv) δ (ppm) |
|---|---|---|
| 138 | 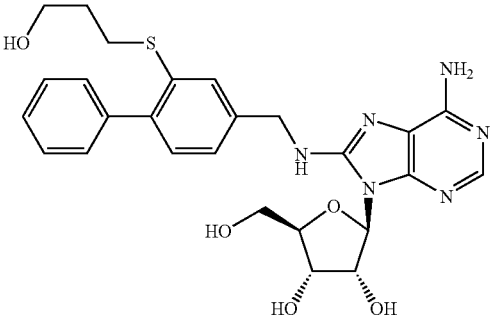 | (DMSO-d$_6$) 1.50-1.65 (m, 2H), 2.80-2.90 (m, 2H), 3.55-3.75 (m, 2H), 3.90-4.05 (m, 1H), 4.10-4.20 (m, 1H), 4.61 (d, 2H, J=6.2Hz), 4.70-4.80 (m, 1H), 5.90-6.00 (m, 2H), 6.54 (s, 2H), 7.10-7.55 (m, 8H), 7.60-7.70 (m, 1H), 7.90 (s, 1H) |
| 139 | 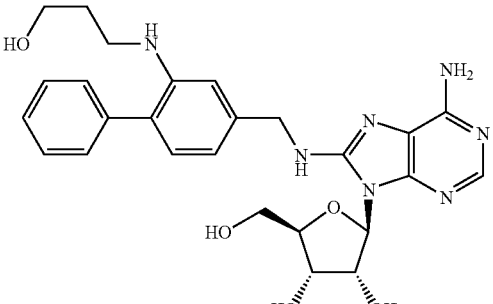 | (DMSO-d$_6$) 1.55-1.65 (m, 2H), 3.05-3.15 (m, 2H), 3.35-3.45 (m, 2H), 3.55-3.70 (m, 2H), 3.95-4.20 (m, 2H), 4.40-4.60 (m, 4H), 4.70-4.80 (m, 1H), 5.15 (d, 1H, J=4.1Hz), 5.25 (d, 1H, J=6.6Hz), 5.85-5.95 (m, 1H), 5.96 (d, 1H, J=6.9Hz), 6.49 (s, 2H), 6.67 (d, 1H, J=7.7Hz), 6.73 (s, 1H), 6.91 (d, 1H, J=7.9Hz), 7.30-7.55 (m, 6H), 7.90 (s, 1H) |
| 140 | 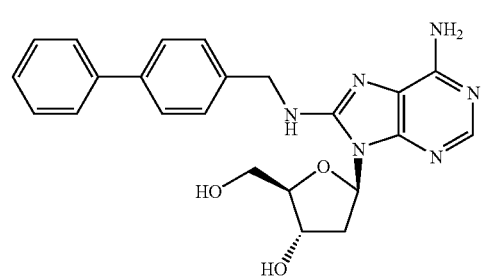 | (DMSO-d$_6$) 2.00-2.10 (m, 1H), 2.72-2.84 (m, 1H), 3.57-3.73 (m, 2H), 3.89-3.97 (m, 1H), 4.38-4.48 (m, 1H), 4.53-4.71 (m, 2H), 5.32 (d, 1H, J=3.9Hz), 5.78-5.87 (m, 1H), 6.36-6.64 (m, 3H), 7.31-7.50 (m, 5H), 7.55-7.74 (m, 5H), 7.90 (s, 1H) |

TABLE 40-continued

| Ex No. | Strc | (Solv) δ (ppm) |
| --- | --- | --- |
| 141 | | (DMSO-d$_6$) 1.71-1.85 (m, 2H), 1.99-2.13 (m, 1H), 2.71-2.84 (m, 1H), 3.05-3.18 (m, 2H), 3.58-3.73 (m, 2H), 3.90-4.05 (m, 3H), 4.39-4.48 (m, 1H), 4.52-4.69 (m, 2H), 5.00 (s, 2H), 5.33 (d, 1H, J=4.0Hz), 5.80-5.89 (m, 1H), 6.37-6.66 (m, 3H), 6.97-7.06 (m, 1H), 7.10-7.17 (m, 1H), 7.19-7.54 (m, 12H), 7.61-7.73 (m, 1H), 7.90 (s, 1H) |
| 142 | | (DMSO-d$_6$) 1.80-1.94 (m, 2H), 1.99-2.10 (m, 1H), 2.70-2.84 (m, 1H), 3.12-3.26 (m, 2H), 3.58-3.73 (m, 2H), 3.89-3.97 (m, 1H), 4.04 (t, 2H, J=6.2Hz), 4.38-4.48 (m, 1H), 4.53-4.71 (m, 2H), 5.01 (s, 2H), 5.32 (d, 1H, J=3.8Hz), 5.78-5.88 (m, 1H), 6.40 (dd, 1H, J=5.6Hz, 9.2Hz), 6.52 (brs, 2H), 6.84-6.95 (m, 1H), 7.09-7.75 (m, 14H), 7.90 (s, 1H) |
| 143 | | (DMSO-d$_6$) 3.63-3.78 (m, 3H), 4.16-4.26 (m, 2H), 4.58 (dd, 1H, J=6.4Hz, 15.8Hz), 4.67 (dd, 1H, J=5.7Hz, 15.8Hz), 5.46-5.55 (m, 2H), 5.76 (d, 1H, J=4.8Hz), 6.27 (d, 1H, J=5.5Hz), 6.43 (brs, 2H), 7.21-7.53 (m, 6H), 7.55-7.68 (m, 4H), 7.89 (s, 1H) |

TABLE 41

| Ex No. | Strc | (Solv) δ (ppm) |
| --- | --- | --- |
| 144 | | (DMSO-d$_6$) 1.69-1.85 (m, 2H), 3.04-3.17 (m, 2H), 3.62-3.80 (m, 3H), 3.90-4.04 (m, 2H), 4.18-4.29 (m, 2H), 4.53 (dd, 1H, J=6.9Hz, 16.1Hz), 4.69 (dd, 1H, J=5.5Hz, 16.1Hz), 5.00 (s, 2H), 5.46-5.61 (m, 2H), 5.70-5.81 (m, 1H), 6.28 (d, 1H, J=5.7Hz), 6.44 (brs, 2H), 7.00-7.09 (m, 1H), 7.14-7.56 (m, 14H), 7.89 (s, 1H) |

TABLE 41-continued

| Ex No. | Strc | (Solv) δ (ppm) |
|---|---|---|
| 145 | | (DMSO-$d_6$) 1.80-1.96 (m, 2H), 3.11-3.27 (m, 2H), 3.59-3.81 (m, 3H), 4.05 (t, 2H, J=6.2Hz), 4.14-4.29 (m, 2H), 4.57 (dd, 1H, J=6.1Hz, 16.0Hz), 4.66 (dd, 1H, J=5.5Hz, 16.0Hz), 5.01 (s, 2H), 5.40-5.88 (m, 3H), 6.26 (d, 1H, J=5.2Hz), 6.42 (brs, 2H), 6.83-6.95 (m, 1H), 7.09-7.66 (m, 14H), 7.89 (s, 1H) |
| 146 | | (DMSO-$d_6$) 0.90-0.98 (m, 3H), 1.68-1.82 (m, 2H), 2.38-2.60 (m, 4H), 3.56-3.74 (m, 2H), 3.96-4.07 (m, 3H), 4.10-4.20 (m, 1H), 4.61 (d, 2H, J=6.5Hz), 4.68-4.82 (m, 1H), 5.00-5.58 (m, 2H), 5.81-6.08 (m, 2H), 6.51 (brs, 2H), 6.97-7.06 (m, 1H), 7.11-7.66 (m, 8H), 7.90 (s, 1H) |
| 147 | | (DMSO-$d_6$) 0.82 (t, 3H, J=7.4Hz), 1.26-1.42 (m, 2H), 1.66-1.84 (m, 2H), 2.33-2.60 (m, 4H), 3.55-3.75 (m, 2H), 3.93-4.21 (m, 4H), 4.61 (d, 2H, J=5.9Hz), 4.69-4.81 (m, 1H), 5.04-5.53 (m, 2H), 5.84-6.10 (m, 2H), 6.51 (brs, 2H), 6.98-7.05 (m, 1H), 7.11-7.68 (m, 8H), 7.90 (s, 1H) |
| 148 | | (DMSO-$d_6$) 1.26-1.47 (m, 4H), 1.66-1.81 (m, 2H), 2.35-2.59 (m, 4H), 3.56-3.72 (m, 2H), 3.88-4.20 (m, 4H), 4.53-4.80 (m, 3H), 5.10-5.52 (m, 2H), 5.88-6.10 (m, 2H), 6.53 (brs, 2H), 6.92-7.67 (m, 9H), 7.90 (s, 1H) |

TABLE 41-continued

| Ex No. | Strc | (Solv) δ (ppm) |
|---|---|---|
| 149 | | (DMSO-d$_6$) 1.70-1.90 (m, 2H), 2.64-2.76 (m, 2H), 3.53-3.76 (m, 2H), 3.94-4.24 (m, 4H), 4.57-4.85 (m, 3H), 5.02-5.50 (m, 2H), 5.78-6.10 (m, 2H), 6.50 (brs, 2H), 6.95-7.07 (m, 2H), 7.26-7.70 (m, 7H), 7.89 (s, 1H) |

TABLE 42

| Ex No. | Strc | (Solv) δ (ppm) |
|---|---|---|
| 150 | | (DMSO-d$_6$) 2.40 (t, 2H, J=6.6Hz), 2.84 (t, 2H, J=6.6Hz), 3.50-3.76 (m, 2H), 3.92-4.20 (m, 2H), 4.52-4.84 (m, 3H), 5.08-5.45 (m, 2H), 5.84-6.06 (m, 2H), 6.54 (brs, 2H), 7.23-7.67 (m, 8H), 7.85-7.97 (m, 2H), 10.14 (brs, 1H) |
| 151 | | (DMSO-d$_6$) 2.69 (t, 2H, J=6.4Hz), 3.14-3.75 (m, 4H), 3.94-4.20 (m, 2H), 4.52-4.85 (m, 3H), 5.10-5.44 (m, 2H), 5.85-6.06 (m, 2H), 6.54 (brs, 2H), 7.40-7.98 (m, 9H), 8.05-8.17 (m, 1H), 8.44-8.60 (m, 1H) |
| 152 | | (DMSO-d$_6$) 1.28-1.71 (m, 4H), 2.44-2.70 (m, 4H), 3.52-3.75 (m, 2H), 3.93-4.20 (m, 2H), 4.53-4.83 (m, 3H), 4.99-5.64 (m, 2H), 5.82-6.11 (m, 2H), 6.54 (brs, 2H), 7.11-7.24 (m, 1H), 7.28-7.74 (m, 8H), 7.90 (s, 1H) |

TABLE 42-continued

| Ex No. | Strc | (Solv) δ (ppm) |
| --- | --- | --- |
| 153 | | (DMSO-$d_6$) 1.62-1.78 (m, 2H), 2.62 (t, 2H, J=6.6Hz), 3.63-3.79 (m, 3H), 3.96-4.10 (m, 2H), 4.20-4.32 (m, 2H), 4.44-4.57 (m, 1H), 4.67-4.83 (m, 1H), 6.30 (d, 1H, J = 6.1 Hz), 6.43 (brs, 2H), 6.98-7.06 (m, 1H), 7.17-7.52 (m, 8H), 7.89 (s, 1H) |
| 154 | | (DMSO-$d_6$) 1.73-1.87 (m, 2H), 2.70 (1, 2H, J=6.7Hz), 3.61-3.81 (m, 3H), 4.02-4.13 (m, 2H), 4.15-4.31 (m, 2H), 4.58 (dd, 1H, J=6.5Hz, 15.7Hz), 4.66 (dd, 1H, J=5.4Hz, 15.7Hz), 5.35-5.88 (m, 3H), 6.26 (d, 1H, J=5.3Hz), 6.39 (brs, 2H), 6.85-6.94 (m, 1H), 7.11-7.40 (m, 4H), 7.44-7.65 (m, 4H), 7.89 (s, 1H) |
| 155 | | (DMSO-$d_6$) 1.65-1.77 (m, 2H), 2.00-2.12 (m, 1H), 2.61 (t, 2H, J=6.7Hz), 2.70-2.84 (m, 1H), 3.59-3.73 (m, 2H), 3.90-3.96 (m, 1H), 4.03 (t, 2H, J=6.3Hz), 4.39-4.49 (m, 1H), 4.52-4.68 (m, 2H), 6.37-6.68 (m, 3H), 6.97-7.05 (m, 1H), 7.13-7.52 (m, 7H), 7.63-7.73 (m, 1H), 7.90 (s, 1H) |

TABLE 43

| Ex No. | Strc | (Solv) δ (ppm) |
| --- | --- | --- |
| 156 | | (DMSO-$d_6$) 1.69-1.91 (m, 2H), 2.71 (t, 2H, J=6.8Hz), 3.52-3.74 (m, 2H), 3.94-4.20 (m, 4H), 4.54-4.83 (m, 3H), 5.96 (d, 1H, J=7.2Hz), 6.53 (brs, 2H), 6.85-6.96 (m, 1H), 7.06-7.77 (m, 8H), 7.89 (s, 1H) |

| Ex No. | Strc | (Solv) δ (ppm) |
|---|---|---|
| 157 | | (CD₃OD) 2.00-2.15 (m, 2H), 3.35-3.50 (m, 2H), 3.70-3.90 (m, 2H), 4.00-4.35 (m, 4H), 4.60-4.85 (m, 3H), 6.10 (d, 1H, J=7.6Hz), 6.80-7.00 (m, 1H), 7.10-7.65 (m, 7H), 7.98 (s, 1H) |
| 158 | | (DMSO-d₆) 1.40-2.10 (m, 9H), 2.20-2.35 (m, 2H), 2.70-2.85 (m, 2H), 3.55-3.75 (m, 2H), 3.90-4.20 (m, 4H), 4.61 (d, 1H, J=6.3Hz), 4.70-4.80 (m, 1H), 5.17 (d, 1H, J=4.3Hz), 5.29 (d, 1H, 6.9Hz), 5.90-6.00 (m, 2H), 6.52 (s, 2H), 6.70 (s, 1H), 6.98-7.65 (m, 10H), 7.90 (s, 1H) |
| 159 | | (DMSO-d₆) 1.09 (s, 6H), 1.65-1.85 (m, 2H), 2.40-2.50 (m, 2H), 3.55-3.75 (m, 2H), 3.95-4.20 (m, 4H), 4.61 (d, 2H, J=6.0Hz), 4.70-4.80 (m, 1H), 5.18 (d, 1H, J=3.7Hz), 5.25-5.40 (m, 1H), 5.88-6.02 (m, 2H), 6.53 (s, 2H), 6.85 (s, 1H), 6.95-7.65 (m, 10H), 7.90 (s, 1H) |
| 160 | | (DMSO-d₆) 1.80-1.90 (m, 2H), 2.18 (s, 3H), 2.40 (t, 2H, J=6.5Hz), 2.45-2.55 (m, 2H), 3.45 (t, 2H, J=6.3Hz), 3.55-3.70 (m, 2H), 3.90-4.20 (m, 4H), 4.55-4.80 (m, 3H), 5.96 (d, 1H, J=7.6Hz), 6.53 (s, 2H), 6.90 (dd, 1H, J=2.5Hz, 8.2 Hz), 7.14 (s, 1H), 7.19 (d, 1H, J=8.2Hz), 7.30-7.40 (m, 1H), 7.45 (d, 2H, J=8.2 Hz), 7.55-7.70 (m, 3H), 7.90 (s, 1H) |

TABLE 43-continued

| Ex No. | Strc | (Solv) δ (ppm) |
|---|---|---|
| 161 | | (DMSO-d$_6$) 1.45-1.70 (m, 4H), 1.80-1.90 (m, 4H), 1.95-2.10 (m, 1H), 2.40 (t, 2H, J=7.3Hz), 2.80-2.95 (m, 2H), 3.55-3.70 (m, 2H), 3.95-4.20 (m, 4H), 4.50-4.80 (m, 3H), 5.96 (d, 1H, J=7.6Hz), 6.54 (s, 2H), 6.72 (s, 1H), 6.90 (dd, 1H, J=2.2Hz, 8.2Hz), 7.10-7.40 (m, 4H), 7.45 (d, 2H, J=8.2Hz), 7.55 -7.70 (m, 3H), 7.90 (s, 1H) |

TABLE 44

| Ex No. | Strc | (Solv) δ (ppm) |
|---|---|---|
| 162 | | (CD$_3$OD) 1.90-2.10 (m, 2H), 2.60-2.90 (m, 4H), 3.60-3.90 (m, 4H), 4.00-4.35 (m, 4H), 4.55-4.85 (m, 3H), 6.10 (d, 1H, J=7.6Hz), 6.89 (dd, 1H, J=2.1Hz, 8.0Hz), 7.05-7.20 (m, 2H), 7.31 (t, 1H, J=8.0Hz), 7.45 (d, 2H, J=8.2Hz), 7.58 (d, 2H, J=8.2Hz), 7.98 (s, 1H) |
| 163 | | (CD$_3$OD) 1.30 (s, 6H), 1.90-2.05 (m, 2H), 2.68 (t, 2H, J=6.9Hz), 3.70-3.90 (m, 2H), 4.05-4.20 (m, 3H), 4.28 (dd, 1H, J =1.6Hz, 5.4Hz), 4.60 - 4.85 (m, 3H), 6.10 (d, 1H, J=7.6Hz), 6.80-6.95 (m, 1H), 7.10-7.20 (m, 2H), 7.25-7.55 (m, 1H), 7.45 (d, 2H, J=8.3Hz), 7.58 (d, 2H, J=8.3Hz), 7.97 (s, 1H) |

TABLE 44-continued
| Ex No. | Strc | (Solv) δ (ppm) |
|---|---|---|
| 164 | 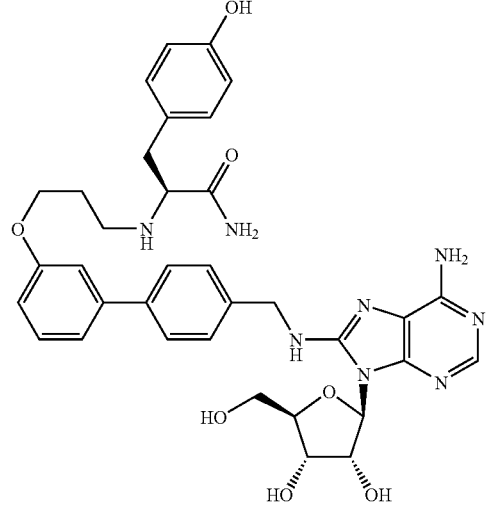 | (CD$_3$OD) 1.85-1.95 (m, 2H), 2.55-2.95 (m, 5H), 3.70-3.90 (m, 2H), 3.95-4.05 (m, 2H), 4.10 - 4.35 (m, 2H), 4.55-4.85 (m, 3H), 6.10 (d, 1H, J = 7.6 Hz), 6.67 (d, 2H, J = 8.5 Hz), 6.75-6.90 (m, 1H), 6.95-7.20 (m, 4H), 7.25-7.35 (m, 1H), 7.45 (d, 2H, J = 8.2 Hz), 7.57 (d, 2H, J = 8.2 Hz), 7.97 (s, 1H) |
| 165 | 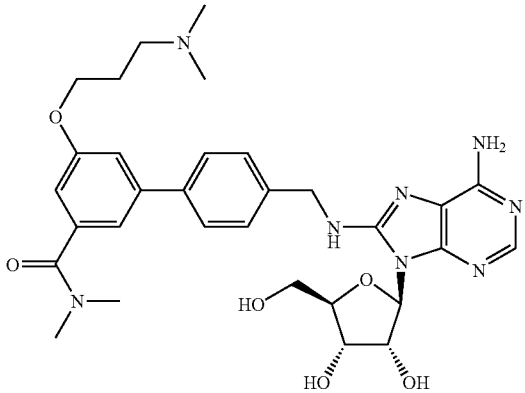 | (DMSO-d$_6$) 1.80-1.95 (m, 2H), 2.17 (s, 6H), 2.40 (t, 2H, J=7.1Hz), 2.93 (s, 3H), 2.98 (s, 3H), 3.55-3.70 (m, 2H), 3.95-4.20 (m, 4H), 4.55-4.80 (m, 3H), 5.85-6.00 (m, 2H), 6.53 (s, 2H), 6.89 (s, 1H), 7.15-7.25 (m, 2H), 7.46 (d, 2H, J=8.2Hz), 7.55-7.70 (m, 3H), 7.90 (s, 1H) |
| 166 | 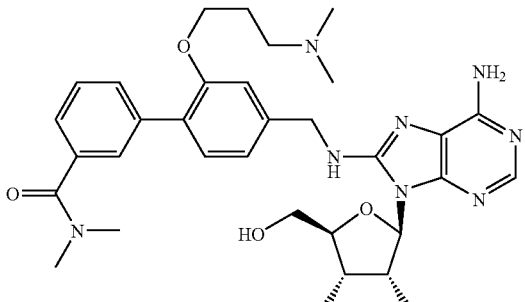 | (DMSO-d$_6$) 1.70-1.80 (m, 2H), 2.08 (s, 6H), 2.26 (t, 2H, J=6.9Hz), 2.94 (s, 3H), 2.97 (s, 3H), 3.55-3.70 (m, 2H), 3.95-4.20 (m, 4H), 4.62 (d, 2H, J=5.7Hz), 4.75 (dd, 1H, J=5.4Hz, 7.3Hz) 5.90-6.00 (m, 2H), 6.54 (s, 2H), 6.95-7.65 (m, 8H), 7.90 (s, 1H) |

TABLE 44-continued

| Ex No. | Strc | (Solv) δ (ppm) |
| --- | --- | --- |
| 167 | | (CD$_3$OD) 2.25-2.35 (m, 2H), 3.19 (s, 9H), 3.55-3.65 (m, 2H), 3.75-3.90 (m, 2H), 4.10-4.20 (m, 3H), 4.25-4.35 (m, 1H), 4.60-4.75 (m, 2H), 6.10 (d, 1H, J=7.6Hz), 6.92 (dd, 1H, J=2.4Hz, 8.0Hz), 7.10-7.25 (m, 2H), 7.34 (t, 1H, J=7.9Hz), 7.46 (d, 2H, J=8.2Hz), 7.57 (d, 2H, J=8.2Hz), 7.98 (s, 1H) |

TABLE 45

| Ex No. | Strc | (Solv) δ (ppm) |
| --- | --- | --- |
| 168 | | (CD$_3$OD) 1.75-1.90 (m, 2H), 2.11 (s, 3H), 2.40-2.55 (m, 2H), 3.75-3.95 (m, 2H), 4.00-4.40 (m, 4H), 4.60-4.90 (m, 3H), 6.10 (d, 1H, J=7.6Hz), 7.00-7.55 (m, 8H), 7.98 (s, 1H) |
| 169 | | (CD$_3$OD) 1.80-1.95 (m, 2H), 2.55-2.70 (m, 2H), 2.81 (s, 3H), 2.89 (s, 3H), 3.75-3.90 (m, 2H), 4.00-4.10 (m, 2H), 4.15-4.35 (m, 2H), 4.60-4.90 (m, 3H), 6.10 (d, 1H, J=7.6Hz), 7.00-7.50 (m, 8H), 7.98 (s, 1H) |

TABLE 45-continued

| Ex No. | Strc | (Solv) δ (ppm) |
|---|---|---|
| 170 | | (CD$_3$OD) 1.55-2.05 (m, 8H), 2.30-2.45 (m, 2H), 2.55-2.70 (m, 1H), 2.80-3.00 (m, 5H), 3.09 (s, 3H), 3.70-3.95 (m, 2H), 4.01 (t, 2H, J=5.9Hz), 4.15-4.22 (m, 1H), 4.25-4.35 (m, 1H), 4.60-4.75 (m, 2H), 4.80 (dd, 1H, J=5.6Hz, 7.6Hz), 6.10 (d, 1H, J=7.6Hz), 6.98-7.50 (m, 8H), 7.98 (s, 1H) |
| 171 | | (DMSO-d$_6$) 1.80-1.95 (m, 2H), 2.16 (s, 6H), 2.38 (t, 2H, J=7.3Hz), 2.90-3.05 (m, 2H), 3.50-3.70 (m, 4H), 3.95-4.00 (m, 1H), 4.06 (t, 2H, J=6.5Hz), 4.12 (d, 1H, J=4.4Hz), 4.60-4.75 (m, 1H), 5.05-5.30 (m, 2H), 5.85-5.95 (m, 2H), 6.51 (s, 2H), 6.90 (dd, 1H, J=1.9Hz, 8.2Hz), 7.00-7.25 (m, 3H), 7.30-7.40 (m, 3H), 7.60 (d, 2H, J=8.2Hz), 7.90 (s, 1H) |

TABLE 46

| Strc |
|---|
| |
| |

TABLE 46-continued

| Strc |
|---|
| 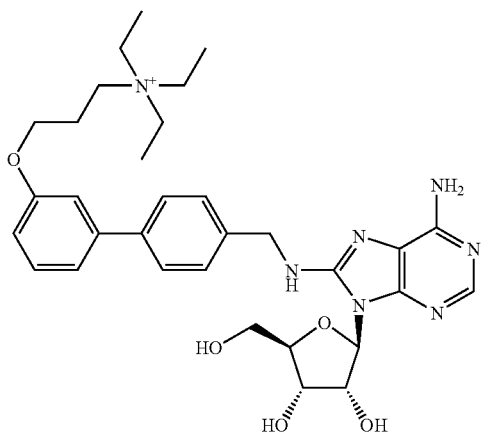 |
| 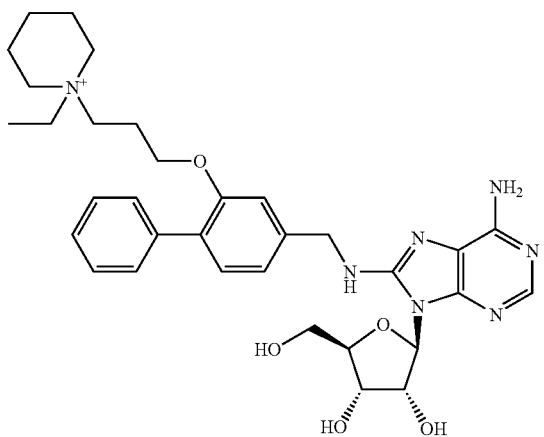 |
| 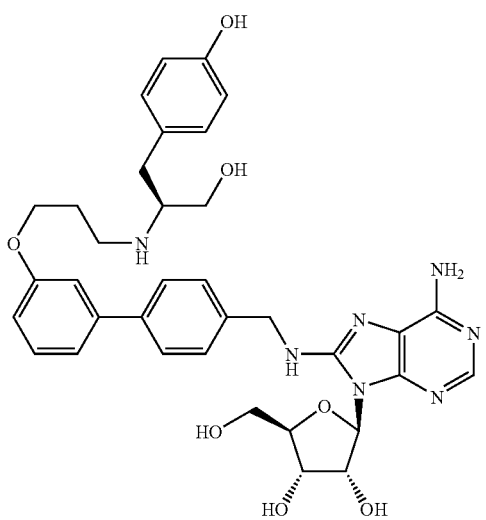 |

TABLE 46-continued

| Strc |
|---|
| 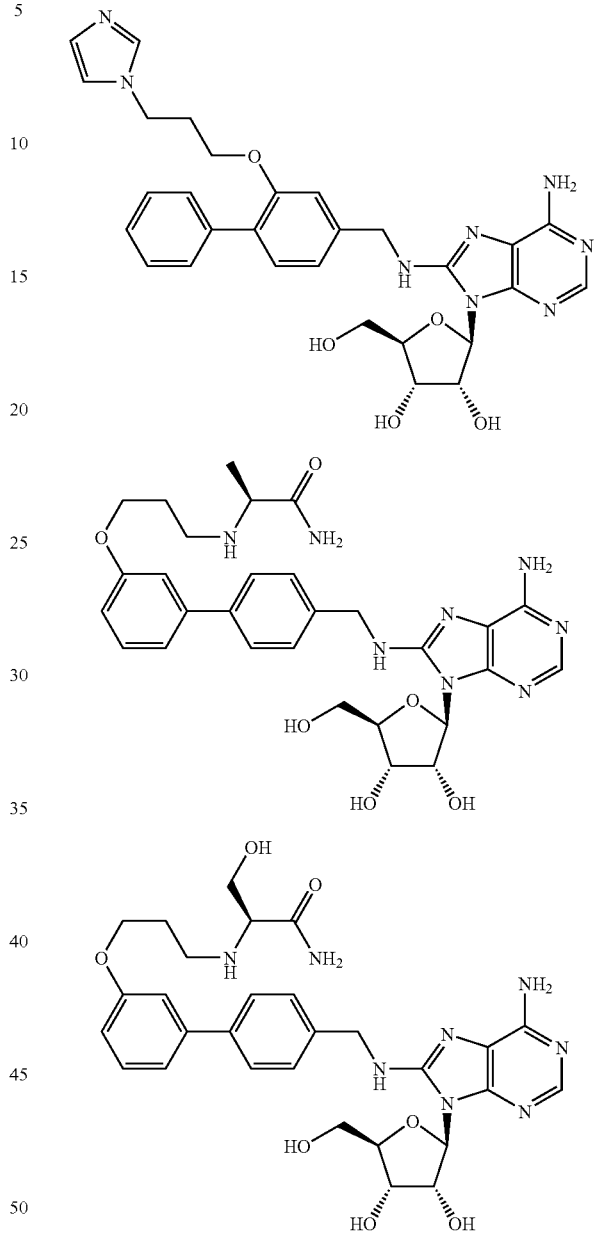 |

Test Example 1

Human CNT1 cDNA Cloning

Human CNT1 cDNA was obtained by PCR amplification of human kidney cDNA (Origene). PCR reaction solution contained 1 μL cDNA, 2 units Platinum taq DNA polymerase high fidelity (Invitrogen), 1 μM primers (Forward: 5'-TGC ACT GCA TGG TTG CTG CT-3', Reverse: 5'-GTC TAA GTC CTG TGG CTT CC-3'). Amplifications for 1 cycle at 94° C. for 2 minutes and 32 cycles at 94° C. for 30 seconds, 58° C. for 30 seconds and 68° C. for 3 minutes were performed and PCR products were ligated into PCR-II-TOPO vector (Invitrogen). The amino acid sequence of cloned human CNT1 was substituted at G34E (codon, GGA to GAA), Q462R (codon, CAG to CGG) and R511C (codon, CGC to TGC) compared to a reported amino acid sequence for human CNT1 (NCBI Accession No. AAB53837.1).

Test Example 2

Human CNT2 cDNA Cloning and Construction of Expression Plasmid

Human CNT2 cDNA was obtained by PCR amplification of human kidney cDNA (CLONTECH). PCR reaction solution contained 1 µL cDNA, 2 units Platinum taq DNA polymerase high fidelity (Invitrogen), 1 µM primers (Forward: 5'-AGG AGC CAG AGG GAA TCA AT-3', Reverse: 5'-ACA TCT TGG TGA GTG AGT TG-3'). Amplifications for 1 cycle at. 94° C. for 2 minutes, 32 cycles at 94° C. for 30 seconds, 58° C. for 30 seconds and 68° C. for 3 minutes were performed and PCR products were ligated into PCR-II-TOPO vector (Invitrogen). PCR reaction was performed with primers containing restriction enzyme sites and the constructed plasmid as a template. PCR reaction solution contained 100 ng plasmid, 2 units Pyrobest DNA polymerase (Takara), 330 nM primers (Forward: 5'-CCG CTC GAG AGG AGC CAG AGG GAA TCA AT-3', Reverse: 5'-CGT CTA GAA CAT CTT GGT GAG TGA GTT G-3'). Amplifications for 1 cycle at 95° C. for 3 minutes, 15 cycles at 98° C. for 10 seconds, 60° C. for 30 seconds and 72° C. for 1 minute and 1 cycle at 72° C. for 7 minutes were performed, and the PCR products were ligated into PCI-neo mammalian expression vector (Promega). The amino acid sequence of cloned human CNT2 was substituted at P22L (codon, CCG to CTG), S45C (codon, AGC to TGC) and I160M (codon, ATA to ATG) compared to a reported amino acid sequence for human CNT2 (NCBI Accession No. AAC51930).

Test Example 3

Human CNT3 cDNA Cloning

Human CNT3 cDNA was obtained by PCR amplification of human small intestine cDNA (CLONTECH). PCR reaction solution contained 0.2 µL cDNA, Expand long template PCR system (Roche), 0.5 µM primers (Forward: 5'-GCC AGC CAG CAG CAA AAA-3', Reverse: 5'-TGG AGA AGT GGC TGA CCT-3'). Amplifications for 1 cycle at 94° C. for 2 minutes and 33 cycles at 94° C. for 10 seconds, 58° C. for 30 seconds and 68° C. for 2 minutes were performed, and PCR products were ligated into PCR-II-TOPO vector (Invitrogen) Nucleotide sequence of cloned human CNT3 was identical to a reported nucleotide sequence for human CNT3 (NCBI Accession No. NM 022127) from position 1130 to 1215.

Test Example 4

Distribution Pattern of Human CNTs in Human Tissues

1) Synthesis of cDNA

Total RNAs derived from human liver, colon, testis, pancreas, lung, small intestine, stomach, placenta and muscle were purchased from Sawady Technology, and total RNAs of trachea, brain, kidney and heart were purchased from CLONTECH. Total RNA concentration was determined by RiboGreen RNA quantification reagent and kit (Molecular Probe). cDNAs were synthesized (reverse transcription). A reaction solution (16.5 µL) contained 1.5 µg total RNA and 1.5 µL random hexamer at 500 ng/µL (Invitrogen). The reaction solution was incubated at 70° C. for 5 minutes, then at room temperature for 5 minutes. A reaction solution (13.5 µL) containing 6 µL 5×BRL 1st strand buffer (Invitrogen), 3.25 µL distilled water (Nippongene), 1.5 µL of 10 mM dNTP mix (Invitrogen), 0.75 µL RNase inhibitor (Invitrogen) and 2 µL Superscript II (Invitrogen) was added to the reaction solution described above. Another reaction solution containing distilled water (Nippongene) instead of Superscript II was also added to the solution described above. After all mixtures were incubated at room temperature for 10 minutes and 42° C. for 1 hour. To inactivate Superscript II, the resulting solutions were incubated at 95° C. for 10 minutes and transferred to ice immediately. Next, 1.5 µL of RNase H (Invitrogen) was added and the solutions were incubated at 37° C. for 30 minutes. At the end of the reaction, 170 µL of distilled water was added. The synthesized cDNAs were extracted with 200 µL of a mixture (phenol: chloroform: isoamylalcohol=25:24:1) (Invitrogen) and furthermore extracted with 200 µL of a mixture (chloroform: isoamylalcohol=24:1). After ethanol precipitation, cDNAs were dissolved in 100 µL of distilled water (Nippongene).

2) Determination of Human CNTs Gene Expression by Quantitative Real-Time PCR

For human CNT1 in quantitative real-time PCR, forward: 5'-ATT TAC CAG TGC TGC CGT GAG-3' and reverse: 5'-AAA CCG ACA GCA GTT GTC CAG-3' as primers and 5'-AGA GCG TCA ATC CAG AGT TCA GCC CA-3' as a probe were used. For human CNT2, forward: 5'-GGC AGC TTG CAT CTT GAA TTT C-3' and reverse: 5'-CAA AAA CGA GTG AAC CAG GAC A-3' as primers and 5'-CCT TGT TTG TCA TCA CCT GCT TGG TGA TCT-3' as a probe were used. Probes were labeled with fluorescence dye, FAM at 5' terminal and TAMRA at 3' terminal. A reaction solution (25 µL) contained 2.5 ng cDNA synthesized above, 1× Taqman Universal master mix (Applied Biosystems), 500 nM forward and reverse primers and 200 nM probe. PCR protocol was as follows. One cycle at 50° C. for 2 minutes, 1 cycle at 95° C. for 10 minutes and 40 cycles at 95° C. for 15 seconds and at 60° C. for 1 minute. Assays were performed using GeneAmp 5500 Sequence detection system (Applied Biosystems), MicroAmp optical 96-well reaction plates (Applied Biosystems) and MicroAmp optical caps (Applied Biosystems). Signals were detected according to manufacturer's instruction (See Genome Research, 1996, vol. 6, pp. 986-994). Samples were analyzed with serially (1:10) diluted plasmid DNAs as standard curve. As shown in FIG. 1, human CNT1 was expressed in kidney and liver abundantly and expressed in small intestine weakly. It was not detected that CNT1 was expressed in the other tissues. On the other hand, human CNT2 was expressed in small intestine and stomach abundantly and expressed in colon, kidney and testis weakly.

Test Example 5

Distribution Pattern of Human CNTs in Stomach and Intestine

Determination of Human CNTs Gene Expression by Quantitative Real-Time PCR

Figure 2:
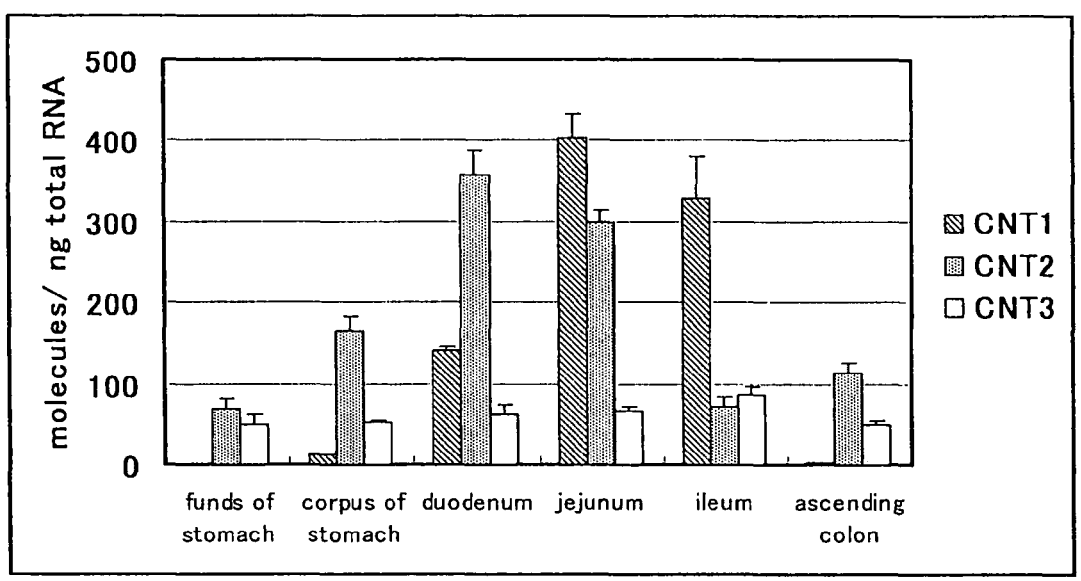
FIG. 2 is a graph showing the pattern of CNT1 to CNT3 distribution in human stomach and intestines. The vertical axis is the number of molecular per 1 ng total RNA (molecular number/ng total RNA). The horizontal axis is the name of part. The left bar graph shows CNT1, the central bar graph shows CNT2 and the right bar graph shows CNT3.

Total RNAs derived from funds of stomach, corpus of stomach, duodenum, jejunum, ileum and ascending colon were purchased from BIOCHAIN. Total RNA concentration was determined by RiboGreen RNA quantification reagent and kit (Molecular Probe). Primers and probes for human CNT1, 2 were the same in Test Example 4. For human CNT3, forward: 5'-GCT GGT CCG ACC ATA TTT ACC TTA C-3' and reverse: 5'-CGC TTC CAG CAATGG TAGAGA-3' as primers and 5'-TCA CCA AGT CTG AAC TCC ACG CCA TC-3' as a probe were used. Probe was labeled with fluorescence dye, FAM at 5' terminal and TAMRA at 3' terminal. Reaction solution (25 µL) contained Taqman EZ RT-PCR kit (Applied Biosystems), 500 nM forward and reverse primer and 200 nM probe. PCR protocol was as follows. One cycle at 50° C. for 2 minutes, 1 cycle at 60° C. for 30 minutes, 1 cycle at 95° C. for 5 minutes and 40 cycles at 94° C. for 20 seconds and at 62° C. for 1 minute. Assays were performed using DNA Engine Opticon (MJ Japan) and 96 well low multiple-plates (MJ Japan). Signals were detected according to manufacturer's instruction (See Genome Research, 1996, vol. 6, pp. 986-994). Samples were analyzed with serially (1:10) diluted plasmid DNAs as standard curve. As shown in FIG. 2, human CNT1 was expressed in jejunum and ileum strongly. On the other hand, human CNT2 was expressed in duodenum and jejunum strongly. Human CNT3 was expressed weakly in all tissues but expressed at the same quantity as CNT2 in ileum. And then, CNT2 was the most expressed, next CNT3 was expressed in stomach and ascending colon.

Test Example 6

Preparation of Cells Transiently Expressing Human CNT2

Expression plasmid of human CNT2 was transfected into COS-7 cells (RIKEN CELL BANK RCB0539) by lipofection method. LIPOFECTAMINE 2000 (Invitrogen) was used as a lipofection reagent. COS-7 cells were diluted in D-MEM (Invitrogen) containing 10% fetal calf serum (Sanko Junyaku) at $5 \times 10^5$/1 mL, and seeded into collagen-coated 96-well plates (IWAKI) at 100 µL/well and cultured at 37° C. for 2 hours with 5% $CO_2$ condition. For each well, 0.6 µL of LIPOFECTAMINE 2000 (Invitrogen) was diluted in 25 µL of OPTI-MEM (Invitrogen), and incubated for 7 minutes at room temperature (hereinafter referred to as Lipo 2000-OPTI). For each well, 0.3 µg of plasmid was diluted in 25 µL of OPTI-MEM (Invitrogen), and the solution was added to the Lipo 2000-OPTI and mixed gently and incubated for 30 minutes at room temperature, and was transferred 50 µL for each well to culture medium. The cells were incubated at 37° C. with 5% $CO_2$ condition for 2 days, and used for the uptake assays.

Test Example 7

(1) Measurement of Inhibitory Activity against Uptake of Adenosine through Human CNT2

An Uptake buffer was prepared by addition of a mixture of non-radioisotope labeled (Sigma) and $^{14}C$-labeled (Amersham Biosciences) adenosine at the final concentration of 10 µM into a buffer, pH 7.4, containing 140 mM sodium chloride, 2 mM potassium chloride, 1 mM calcium chloride, 1 mM magnesium chloride, 10 mM HEPES 2-[4-(2-hydroxyethyl)-1-piperazinyl]ethane sulfonic acid, 5 mM tris(hydroxy-methyl)aminomethane and 5 mM glucose. For measurement of basal uptake, Basal uptake measurement buffer, which contained 140 mM choline chloride instead of sodium chloride was prepared. In uptake assays, NBMPR was added to Uptake buffer and Basal uptake measurement buffer at the final concentration of 10 µM. In the case of measurement of inhibitory activity of test compounds, test compounds were dissolved in dimethyl sulfoxide, and then appropriately diluted with Uptake buffer as to prepare Measurement buffers. After removing culture medium of human CNT2 transiently expressing cells, Pretreatment buffer (Basal uptake measurement buffer without adenosine and glucose) was added to wells at 200 µL/well and incubated at 37° C. for 10 minutes. After repeating the same step again, Pretreatment buffer was removed and Measurement buffers and Basal uptake measurement buffer were added at 75 µL/well and incubated at 37° C. After incubation for 30 minutes, Measurement buffers and Basal uptake measurement buffer were removed, and the cells were washed with Washing buffer (Basal uptake measurement buffer with non-radioisotope labeled adenosine at 10 µM) at 200 µL/well twice. The cells were solubilized with 0.2 mol/L sodium hydroxide at 75 µL/well, and the cell lysates were transferred into PicoPlates (Perkin Elmer). After mixing with 150 µL of MicroScint-40 (Perkin Elmer), radioactivity was measured by means of scintillation counter (Perkin Elmer). One hundred % was set to the difference between the uptake in the control group and the basal uptake, and the uptake of adenosine at each test compound concentration was calculated. The test compound concentration inhibiting 50% uptake of adenosine ($IC_{50}$ value) was calculated using logit plot. The results are shown in Table 47.

TABLE 47

| Test compound | $IC_{50}$ (nM) |
|---|---|
| Example 82 | 297 |

(2) Measurement of Inhibitory Activity against Uptake of Inosine through Human CNT2

An Uptake buffer was prepared by addition of a mixture of non-radioisotope labeled (WAKO) and $^{14}C$-labeled (Muromachi Yakuhin) inosine at the final concentration of 10 µM into a buffer, pH7.4, containing 140 mM sodium chloride, 2 mM potassium chloride, 1 mM calcium chloride, 1 mM magnesium chloride, 10 mM HEPES 2-[4-(2-hydroxyethyl)-1-piperazinyl]ethane sulfonic acid, 5 mM tris(hydroxymethyl) aminomethane and 5 mM glucose. For measurement of basal uptake, Basal uptake measurement buffer, which contained 140 mM choline chloride instead of sodium chloride was prepared. In uptake assays, NBMPR was added to Uptake buffer and Basal uptake measurement buffer at the final concentration of 0 µM. In the case of measurement of inhibitory activity of test compounds, test compounds were dissolved in dimethyl sulfoxide, and then appropriately diluted with Uptake buffer as to prepare Measurement buffers. After removing culture medium of human CNT2 transiently expressing cells, Pretreatment buffer (Basal uptake measurement buffer without inosine and glucose) was added to wells at 200 µL/well and incubated at 37° C. for 10 minutes. After repeating the same step again, Pretreatment buffer was removed and Measurement buffers and Basal uptake measurement buffer were added at 75 µL/well and incubated at 37° C. After incubation for 30 minutes, Measurement buffers and Basal uptake measurement buffer were removed, and the cells were washed with Washing buffer (Basal uptake measurement buffer with non-radioisotope labeled inosine at 10 µM) at 200 µL/well twice. The cells were solubilized with 0.2 mol/L sodium hydroxide at 75 µL/well, and the cell lysates were transferred into PicoPlates (Perkin Elmer). After mixing with 150 µL of MicroScint-40 (Perkin Elmer), radioactivity was measured by means of scintillation counter (Perkin Elmer). One hundred % was set to the difference between the uptake in the control group and the basal uptake, and the uptake of inosine at each test compound concentration was calculated. The test compound concentration inhibiting 50% uptake of inosine ($IC_{50}$ value) was calculated using logit plot. The results are shown in Table 48.

TABLE 48

| Test compound | $IC_{50}$ (nM) |
|---|---|
| Example 115 | 378 |
| Example 117 | 378 |
| Example 120 | 444 |
| Example 125 | 528 |
| Example 130 | 223 |
| Example 132 | 649 |
| Example 147 | 321 |
| Example 149 | 176 |
| Example 153 | 1608 |
| Example 154 | 7148 |
| Example 155 | 266 |
| Example 157 | 234 |
| Example 164 | 85 |
| Example 167 | 412 |
| Example 171 | 2434 |

Test Example 8

Effects of CNT Inhibitor on Plasma Uric Acid Level

Male SD-IGS rats (5 weeks old) which were fasted overnight, were subcutaneously treated with oxonic acid (Aldrich; 100 mg/kg), and after 1 hour, purine mix (Adenosine: Inosine: Guanosine=1:1:1 (Adenosine (Sigma), Inosine (WAKO), Guanosine (ICN); 50 mg/kg) and test compounds (50 mg/kg) were orally administrated simultaneously. A control group was treated with oxonic acid and the purine mix, and a group administrated only oxonic acid represented endogenous plasma uric acid value. After 1 hour, blood was collected from the abdominal aorta under ether anesthesia, and the plasma was collected with Venoject II vacuum blood collecting tube (Terumo, VP-FH052). According to the method described in Journal of Chromatography B, Vol. 744 (2000), pp. 129-138, plasma uric acid level was measured by using HPLC method mentioned below. The difference between plasmauric acid value in each study group and endogenous plasma uric acid value was calculated on the basis of 100% in the control group. The results are shown in Table 49.

TABLE 49

| Test compound | Percentage of increment of plasma uric acid level (%) |
|---|---|
| Example 82 | 44.1 ($p < 0.05$) |

Determination of Plasma Uric Acid Level by High-Performance Liquid Chromatography (HPLC)

Theophylline (10 μg) as an internal standard substance was added to 0.1 mL of plasma collected with the above method, and then the samples were deproteinized with 1 mL of methanol. After the samples were centrifuged, the methanol layers were evaporated to dryness under a stream of nitrogen. The residues were dissolved in 300 μL of mobile phase, and 40 μL of the portion was injected into HPLC. Plasma uric acid concentration was determined by HPLC method according to the condition described below. Calibration curves were constructed by addition of theophylline as an internal standard substance and several concentrations of uric acid to 0.1 mL of distilled water appropriately.

HPLC Analytical Condition
Column: Inertsil ODS-2 (4.6×250 mm)
Mobile phase
   A solution: acetonitrile
   B solution: 10 mM phosphate buffer (pH 3.0)
A linear gradient elution method: A solution 2% to A solution 22% (25 minutes)
Column temperature: 40° C.
Flow rate: 0.5 mL/minute
Detection absorbance: 284 nm

INDUSTRIAL APPLICABILITY

The 8-modified purinenucleoside derivatives represented by the above general formula (I) of the present invention or prodrugs thereof, or pharmaceutically acceptable salts thereof, or hydrates or solvates thereof can markedly inhibit the elevation of plasma uric acid level. Therefore, they are useful as agents for the prevention or treatment of diseases associated with an abnormality of plasma uric acid level.

The invention claimed is:

1. An 8-modified purinenucleoside derivative represented by the general formula:

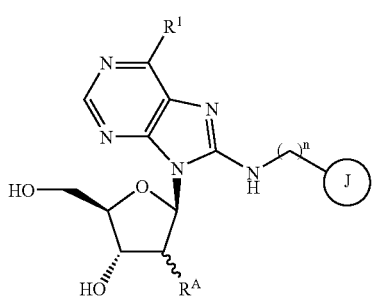

[Chem. 1]

wherein n represents 1 or 2;

$R^A$ represents a hydrogen atom or a hydroxyl group;

$R^1$ represents a hydrogen atom, a hydroxyl group, a thiol group, an amino group or a chlorine atom;

ring J represents an optionally substituted 2-naphthyl group, or a group represented by the general formula:

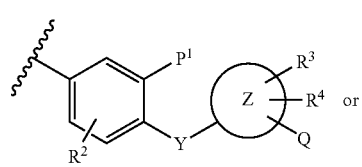

[Chem. 2]

or

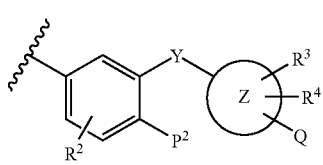

[Chem. 3]

Y represents a single bond or a connecting group;

ring Z represents an aryl group, a heteroaryl group, a cycloalkyl group or a heterocycloalkyl group;

$R^2$ to $R^4$, $P^1$, $P^2$ and Q independently represents a halogen atom, a cyano group, -AH group or -A-D-E-G group, in which A represents a single bond, —O—, —S—, —$NR^5$—, —COO—, —$CONR^6$—, —$NR^7CO$— or —$NR^8COO$— wherein $R^5$ to $R^8$ independently represents a hydrogen atom or a lower alkyl group;

D represents an optionally substituted lower alkylene group, an optionally substituted lower alkenylene group or an optionally substituted lower alkynylene group;

E represents a single bond, —O—, —S—, —$NR^9$—, —COO—, —$CONR^{10}$—, —$NR^{11}CO$—, —$NR^{12}COO$—, an optionally substituted lower cycloalkylene group, an optionally substituted heterocycloalkylene group, an optionally substituted arylene group or an optionally substituted heteroarylene group in which $R^9$ to $R^{12}$ independently represents a hydrogen atom or a lower alkyl group;

G represents a hydrogen atom, an optionally substituted lower alkyl group, an optionally substituted lower alkenyl group or an optionally substituted lower alkynyl group or an aryl(lower alkyl) group;

or a prodrug thereof, or a pharmaceutically acceptable salt thereof, or a hydrate or solvate thereof.

2. An 8-modified purinenucleoside derivative as claimed in claim 1 wherein the ring J represents a group represented by the general formula:

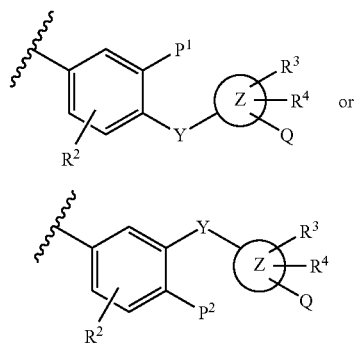

[Chem.4]

[Chem.5]

in which ring Z represents an aryl group or a heteroaryl group;
$R^2$ to $R^4$ independently represents a hydrogen atom, a halogen atom, a hydroxyl group, a cyano group, a lower alky group, a a lower alkylthio group, a lower alkoxy group which may have an aryl group, an amino group or a mono- or di-(lower alkyl)amino group; or a prodrug thereof, or a pharmaceutically acceptable salt thereof, or a hydrate or solvate thereof.

3. An 8-modified purinenucleoside derivative as claimed in claim 1 or 2 wherein the substituent:

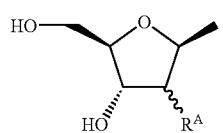

[Chem. 6]

represents a D-ribofranosyl group, or a prodrug thereof, or a pharmaceutically acceptable salt thereof, or a hydrate or solvate thereof.

4. An 8-modified purinenucleoside derivative as claimed in claim 1 wherein $R^1$ represents a hydrogen atom, a hydroxy group or an amino group, or a prodrug thereof, or a pharmaceutically acceptable salt thereof, or a hydrate or solvate thereof.

5. An 8-modified purinenucleoside derivative as claimed in claim 1 wherein n represents 1, or a prodrug thereof, or a pharmaceutically acceptable salt thereof, or a hydrate or solvate thereof.

6. An 8-modified purinenucleoside derivative as claimed in claim 1 wherein Y represents a single bond, or a prodrug thereof, or a pharmaceutically acceptable salt thereof, or a hydrate or solvate thereof.

7. A pharmaceutical composition comprising as an active ingredient a 8-modified purinenucleoside derivative as claimed in claim 1, or a prodrug thereof, or a pharmaceutically acceptable salt thereof, or a hydrate or solvate thereof.

8. A pharmaceutical composition as claimed in claim 7 comprising in combination as an active ingredient at least one agent selected from a group consisting of colchicine, a nonsteroidal anti-inflammatory agent, a steroid, a uric acid synthesis inhibitor, a uricosuric drug, a urinary alkalinizer and a uric acid oxidase.

9. A method for the treatment of a disease associated with an increased plasma uric acid level, which comprises administering of an effective amount of an 8-modified purinenucleoside derivative as claimed in claim 1, or a prodrug thereof, or a pharmaceutically acceptable salt thereof, or a hydrate or solvate thereof.

10. A method for the treatment as claimed in claim 9 wherein the disease is a disease selected from a group consisting of gout, hyperuricemia, urinary lithiasis, hyperuricemic nephropathy and acute uric acid nephropathy.

11. A method for the treatment as claimed in claim 10 wherein the disease is gout.

12. A method for the treatment as claimed in claim 10 wherein the disease is hyperuricemia.

13. A method for the treatment as claimed in claim 9, which comprises administering in combination an effective amount of at least one agent selected from a group consisting of colchicine, a nonsteroidal anti-inflammatory agent, a steroid, a uric acid synthesis inhibitor, a uricosuric drug, a urinary alkalinizer and a uric acid oxidase.

14. A sodium-dependent nucleoside transporter 2 inhibitor comprising as an active ingredient an 8-modified purinenucleoside derivative represented by the general formula:

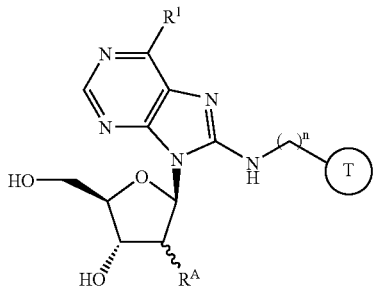

[Chem.7]

wherein
n represents 1 or 2;
$R^A$ represents a hydrogen atom or a hydroxyl group;
$R^1$ represents a hydrogen atom, a hydroxyl group, a thiol group, an amino group or a chlorine atom;
ring T represents an aryl group;
or a prodrug thereof, or a pharmaceutically acceptable salt thereof, or a hydrate or solvate thereof.

* * * * *

SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 1
tgcactgcat ggttgctgct                                               20

<210> SEQ ID NO 2
<211> LENGTH: 20
<212> TYPE: DNA
<213> ORGANISM: Artificial Sequence

```
<220> FEATURE:
<223> OTHER INFORMATION: Description of Artificial Sequence: primer

<400> SEQUENCE: 2
gtctaagtcc tgtggcttcc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
aggagccaga gggaatcaat                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
acatcttggt gagtgagttg                                              20

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 5
ccgctcgaga ggagccagag ggaatcaat                                    29

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 6
cgtctagaac atcttggtga gtgagttg                                     28

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 7
gccagccagc agcaaaaa                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 8
tggagaagtg gctgacct                                                18
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
atttaccagt gctgccgtga g                                         21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
aaaccgacag cagttgtcca g                                         21

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 11
agagcgtcaa tccagagttc agccca                                    26

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 12
ggcagcttgc atcttgaatt tc                                        22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 13
caaaaacgag tgaaccagga ca                                        22

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 14
ccttgtttgt catcacctgc ttggtgatct                                30

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: primer
```

```
<400> SEQUENCE: 15
gctggtccga ccatatttac cttac                                              25

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16
cgcttccagc aatggtagag a                                                  21

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 17
tcaccaagtc tgaactccac gccatc                                             26
```